US010612053B2

(12) United States Patent
Muller et al.

(10) Patent No.: US 10,612,053 B2
(45) Date of Patent: Apr. 7, 2020

(54) ISOLATED GENES AND TRANSGENIC ORGANISMS FOR PRODUCING BIOFUELS

(71) Applicants: THE TRANSLATIONAL GENOMICS RESEARCH INSTITUTE, Phoenix, AZ (US); UNIVERSITÉ DU LUXEMBOURG, Luxembourg (LU); Emilie Muller, Esch-sur-Alzette (LU); Paul Wilmes, Bettembourg (LU); Paul S. Keim, Flagstaff, AZ (US); John D. Gillece, Flagstaff, AZ (US); James M. Schupp, Flagstaff, AZ (US); Lance B. Price, Flagstaff, AZ (US); David M. Engelthaler, Flagstaff, AZ (US)

(72) Inventors: Emilie Muller, Esch-sur-Alzette (LU); Paul Wilmes, Bettembourg (LU); Paul S. Keim, Flagstaff, AZ (US); John D. Gillece, Flagstaff, AZ (US); James M. Schupp, Flagstaff, AZ (US); Lance B. Price, Flagstaff, AZ (US); David M. Engelthaler, Flagstaff, AZ (US)

(73) Assignees: The Translational Genomics Research Institute, Phoenix, AZ (US); Arizona Board of Regents on behalf of Northern Arizona University, Flagstaff, AZ (US); Universite du Luxembourg, Luxembourg (LU)

( * ) Notice: Subject to any disclaimer, the term of this patent is extended or adjusted under 35 U.S.C. 154(b) by 43 days.

(21) Appl. No.: 14/429,287

(22) PCT Filed: Sep. 18, 2013

(86) PCT No.: PCT/US2013/060285
§ 371 (c)(1),
(2) Date: Mar. 18, 2015

(87) PCT Pub. No.: WO2014/047103
PCT Pub. Date: Mar. 27, 2014

(65) Prior Publication Data

US 2015/0232896 A1 Aug. 20, 2015

Related U.S. Application Data

(60) Provisional application No. 61/702,659, filed on Sep. 18, 2012.

(51) Int. Cl.
*C12P 7/64* (2006.01)

(52) U.S. Cl.
CPC ............. *C12P 7/649* (2013.01); *C12P 7/6463* (2013.01)

(58) Field of Classification Search
None
See application file for complete search history.

(56) References Cited

U.S. PATENT DOCUMENTS

2003/0106091 A1 6/2003 Agarwal et al.
2011/0250658 A1 10/2011 Franklin et al.
2012/0184003 A1 7/2012 Chen et al.
2013/0040340 A1 * 2/2013 Dauner ................. C12P 7/6436 435/42

OTHER PUBLICATIONS

Dufreche, S., et al. 2007 J Amer Oil Chem Soc 84: 181-187.*
Nielsen, P.H., et al. 2002 Water Sci Technol 46(1-2): 73-80.*
Levantesi et al., "Phylogeny, physiology and distribution of 'Candidatus Microthrix calida', a new Microthrix species isolated from industrial activated sludge wastewater treatment plants", Environ Microbiol. 8(9):1552-1563 (2006).
Rossetti et al., "Microthrix parvicella, a filamentous bacterium causing bulking and foaming in activated sludge systems: a review of current knowledge", FEMS Microbiol Rev., 29(1):49-64 (2005).
Muller et al., "Genome Sequence of 'Candidatus Microthrix parvicella' Bio17-1, a Long-Chain-Fatty-Acid-Accumulating Filamentous Actinobacterium from a Biological Wastewater Treatment Plant", J. Bacteriol., 194 (23):6670-6671 (Dec. 2012).
International Search Report and Written Opinion of the International Searching Authority for PCT/US2013/060285 dated Apr. 16, 2014.

* cited by examiner

*Primary Examiner* — Marsha Tsay
(74) *Attorney, Agent, or Firm* — Rodney J. Fuller; Booth Udall Fuller, PLC

(57) ABSTRACT

Methods for the production of lipids and biofuels with a culture of *Candidatus Microthrix* spp. grown on a medium such as wastewater or sewage sludge are provided. The *Candidatus Microthrix* spp. may be cultured with additional microorganisms that contribute to the accumulation of lipids from the growth medium such as Zoog!oea spp., *Rhizobacter* spp., *Blautia* spp., *Hydrolatea* spp., ODI genera incertae sedis. Further discloses are transformed organisms comprising genes isolated from *Candidatus Microthrix parvicella*, as well as methods and processes for producing lipids, fatty acids, or biofuels in vitro using the protein products of the isolated genes.

12 Claims, 21 Drawing Sheets

Specification includes a Sequence Listing.

| | | Subset 01 | Subset 02 | Subset 03 | Subset 04 | Subset 05 | Subset 06 | Subset 07 | Subset 08 | Subset 09 |
|---|---|---|---|---|---|---|---|---|---|---|
| Subset size (kbp) | | 2045 | 1626 | 5091 | 2634 | 2861 | 1783 | 1304 | 6641 | 334 |
| Number of contigs | | 1155 | 997 | 2578 | 1254 | 1465 | 1152 | 595 | 1820 | 116 |
| Number of features | | 1704 | 1657 | 4840 | 2268 | 2722 | 2023 | 1419 | 6619 | 422 |
| Metabolic scenarios[a] | | 41 | 56 | 87 | 61 | 77 | 20 | 51 | 152 | 0 |
| 40 COGs completeness[b] | count | 22 | 9 | 36 | 36 | 34 | 30 | 30 | 40 | 0 |
| | sum | 22 | 9 | 63 | 39 | 56 | 55 | 32 | 83 | 0 |

[a] Number of predicted scenarios on the 287 present in RAST.

[b] Prediction of the genome completeness according to 40 COGs (Aziz et al. (2008) BMC Genomics 9:75).

b

ISOLATED GENES AND TRANSGENIC ORGANISMS FOR PRODUCING BIOFUELS

CROSS-REFERENCE TO RELATED APPLICATIONS

The present application is the U.S. National Stage of International Application No. PCT/US2013/060285 filed on Sep. 18, 2013, which claims the benefit of U.S. Provisional Application No. 61/702,659 filed on Sep. 18, 2012, the contents of each of which are hereby incorporated by reference in their entireties for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 315,413 byte ASCII (text) file named "Seq_List" created on Sep. 18, 2013.

FIELD OF THE INVENTION

The present invention relates to biofuel production using cultures of *Candidatus Microthrix* spp. on a growth medium that may comprise wastewater or sewage sludge. Also provided in the present invention are isolated genes and peptides from a strain of *Candidatus Microthrix parvicella* Bio 17-1 that are associated with a lipid accumulating phenotype.

BACKGROUND OF THE INVENTION

There is an ever-increasing demand for renewable biofuels and bioenergy products as an alternative to fossil fuels. Biofuels are currently produced from, for example, various cellulosic materials and sugar-based plants, including sugarcane, beets, corn, rice, potatoes (among others), as well as wood chips. While the process is straight forward, producing biofuels and bioenergy products from these materials is, overall, inefficient and expensive given the cost of the source materials, and tends to drive up the price of food. Further, the current raw material sources for production of biofuel will not be sufficient to meet the escalating demands.

The U.S. population generates around 8.6 million dry metric tons of sludge annually, that is, approximately 13 billion pounds (dry basis) of sludge. Disposal of this enormous amount of sludge without substantial impact on the environment is an ongoing challenge.

Moreover, in the United States approximately 230 million tons (dry matter) of animal waste (manure) are generated every year. Unsafe and improper disposal of decomposable animal waste causes substantial environmental pollution, including surface and groundwater contamination, odors, dust, and methane and ammonia emission. Processing and/or disposal of municipal, industrial, and farm sewage waste (e.g., sludge) is costly, and has an enormous impact on the environment as well as on the public health.

*Candidatus Microthrix* are deeply branching filamentous actinobacteria occurring at the water-air interface of biological wastewater treatment plants where they are often responsible for foaming and bulking *Candidatus Microthrix* are notoriously difficult to grow in culture owing to their slow growth rate and unique growth medium requirements. This has long-delayed study of their genetic content. FEMS Microbiology Reviews 29 (2005) 49-64. In wastewater treatment plants, however, *Candidatus Microthrix* rapidly dominate the environment based on a competitive advantage which is likely conferred by their uptake of long-chain-fatty-acids (LCFA) that are accumulated as neutral lipids under anaerobic conditions and converted into phospholipids for cell division under aerobic conditions.

Lipid storing organisms are useful for the production of biofuel. The stored lipids may be extracted and processed directly into, for example, biodiesel as in algae biofuels. Additionally, organisms with complex lipid storing mechanisms, such as *Candidatus Microthrix*, may possess novel lipid processing and storage enzymes that can be introduced into transformed organisms for the direct production of biofuel or biofuel precursors.

Alternatively, proteins associated with lipid processing and storage could be used to produce biofuels in vitro. Suitable enzymes for commercial production of biofuels that can assemble and process alkyl chains into biofuel or biofuel precursors have been difficult to isolate.

Methods and systems are needed for recovering valuable components of sewage sludge to help satisfy energy needs, while simultaneously reducing the impact of such waste on the environment and the health of the population. Therefore, there is a need to increase the lipid production and storage from sewage sludge with an organism or community of organisms to serve as a suitable feedstock for biofuels production. Additionally, the isolation of novel lipid storage and processing proteins, and the genes encoding them, is desirable.

BRIEF SUMMARY OF THE INVENTION

The invention is directed to a method of producing a lipid comprising: culturing *Candidatus Microthrix* spp. in a culture system suitable for maintaining the viability and proliferation of the *Candidatus Microthrix* spp. wherein the culture system provides a carbon source or lipid material in a growth medium; isolating the *Candidatus Microthrix* spp. from the culture system; and extracting the lipid from the *Candidatus Microthrix* spp. In certain implementations, the method further comprises producing a biofuel from the extracted lipid.

In certain embodiments, the *Candidatus Microthrix* spp. are cultured at a temperature below 20° C. or below 15° C. The growth medium may comprise wastewater or sewage sludge. In other embodiments, the *Candidatus Microthrix* spp. are cultured together with a microorganism selected from the group consisting of *Zoogloea* spp., *Rhizobacter* spp., *Blautia* spp., *Hydrolatea* spp., OD1 *genera incertae sedis*, and combinations thereof. These microorganisms as well as the *Candidatus Microthrix* spp. may be isolated from wastewater, sewer sludge, soil, or other environmental sources.

The invention also provides a method of producing a lipid comprising: transforming a microorganism with a nucleic acid encoding an enzyme selected from the group consisting of a long-chain-fatty-acid-CoA-ligase, an enoyl-CoA hydratase, a lipase, a 3-ketoacyl-CoA thiolase, an acyl-CoA thioesterase, a 3-hydroxyacyl-CoA dehydrogenase, and combinations thereof; culturing the microorganism in a culture system suitable for maintaining the viability and proliferation of the microorganism wherein the culture system provides a carbon source or lipid material in a growth medium; isolating the microorganism from the culture system; and extracting the lipid from the microorganism. In certain aspects, the method further comprises producing a biofuel from the extracted lipid.

In one embodiment, the present invention is directed to an isolated '*Candidatus Microthrix parvicella*,' strain Bio17-1 and to 57 newly isolated genes and peptides that have been identified that are involved in the lipid accumulating phenotype. These include:

28 genes encoding Long-chain-fatty-acid-CoA ligases (EC 6.2.1.3);

17 genes encoding Enoyl-CoA hydratases (EC 4.2.1.17);

2 genes encoding Lipases (EC 3.1.1.5 and/or EC 3.1.1.23);

8 genes encoding 3-ketoacyl-CoA thiolases (EC 2.3.1.16);

1 gene encoding an esterase (EC 3.1.2.-); and 1 gene encoding a 3-hydroxyacyl-CoA dehydrogenase (EC 1.1.1.35).

The present invention is further directed to a system and method that utilizes these genes and the gene products to produce or process lipids, fatty acids, and biofuel. Additionally, the invention is directed to transgenic organisms that have one or more of isolated genes. The transgenic organisms are useful in producing biofuel or biofuel precursors.

BRIEF DESCRIPTION OF THE DRAWINGS

FIG. 7 depicts a summary of the composite genomes.

DETAILED DESCRIPTION OF THE INVENTION

Figure 1:
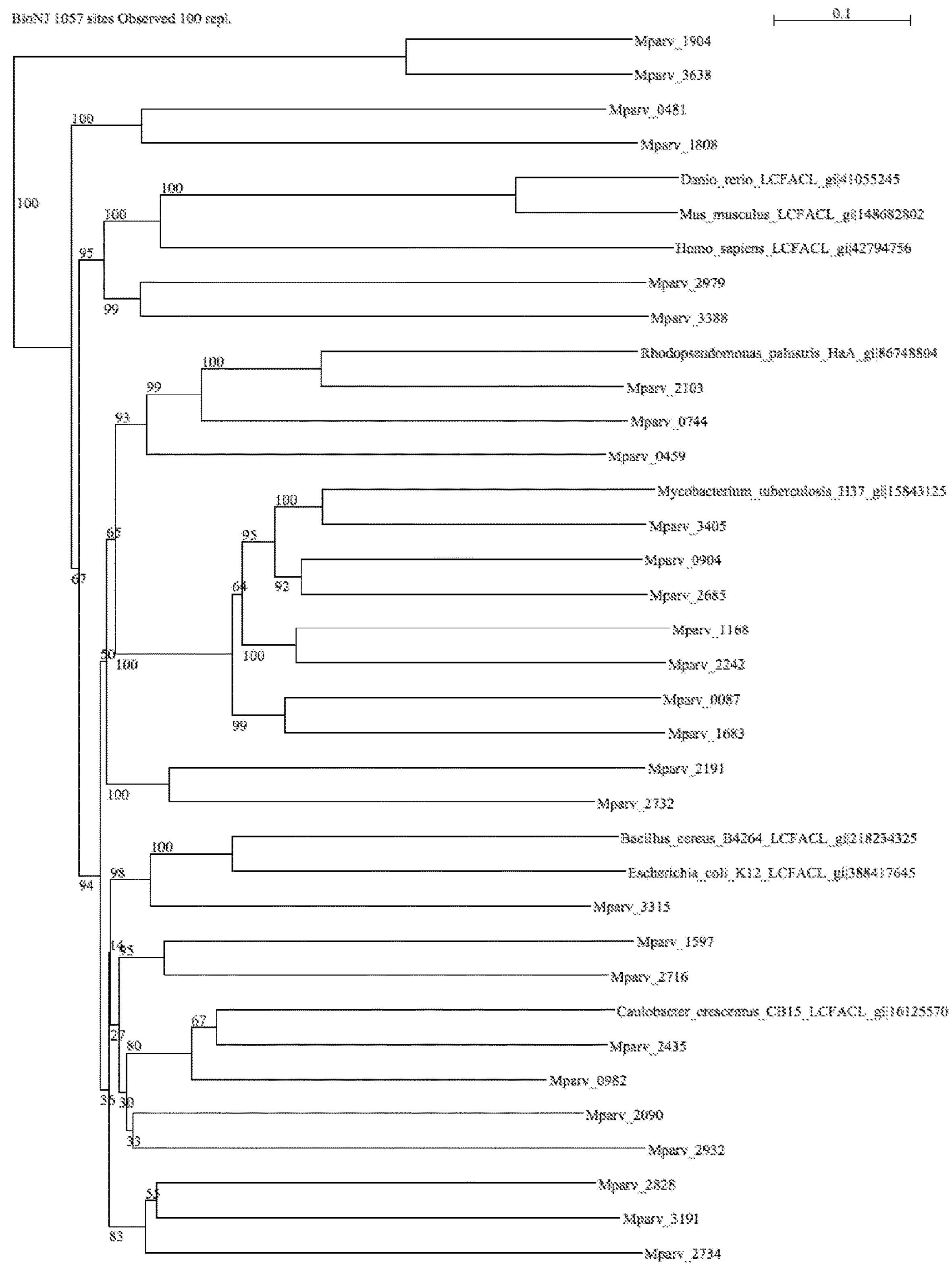
FIG. 1 depicts a phylogenetic tree of the 28 long-chain-fatty-CoA ligase homologues. The phylogenetic tree was constructed by Bio-Neighbor Joining at all position (including gaps) after ClustalW2 alignment with default parameters of the amino-acid sequences of '*Candidatus Microthrix parvicella*' strain Bio17-1 and of some reference sequences (GenBank GI number indicated after the organism name).

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the invention. It will be understood, however, by those skilled in the relevant arts, that the present invention may be practiced without these specific details. It should be noted that there are many different and alternative configurations, devices and technologies to which the disclosed inventions may be applied. The full scope of the inventions is not limited to the examples that are described below.

The singular forms "a," "an," and "the" include plural referents unless the context clearly dictates otherwise. Thus, for example, reference to "a step" includes reference to one or more of such steps.

As used herein, a "biofuel" refers to any fuel, fuel additive, aromatic, and/or aliphatic compound derived from a biomass starting material such sewage sludge, wastewater, or the like.

The term "culture system" as used herein refers to a system of water retaining, filtering, heating/cooling, and circulating systems, and structures that are typically employed in the maintenance of a culture medium under conditions suitable for supporting the viability and reproduction of a desired organism(s).

The terms "culture medium" and "growth medium" as used herein refer to an aqueous or agar-based medium designed to support the growth of microorganisms.

The term "carbon source" as used herein refers to a nutrient (e.g., sugar) that provides carbon skeletons needed for synthesis of new organic molecules (i.e., anabolism).

The term "viability" as used herein refers to "capacity for survival" and is more specifically used to mean a capacity for living, developing, or reproducing under favorable conditions.

The term "lipid" and "lipid material" as used herein refers to naturally-occurring molecules which includes fats, waxes, sterols, fat-soluble vitamins (such as vitamins A, D, E and K), monoglycerides, diglycerides, triglycerides, phospholipids, fatty acids and the like. The main biological functions of lipids include energy storage, as structural components of cell membranes, and as important signaling molecules. Lipids may be broadly defined as hydrophobic or amphiphilic small molecules; the amphiphilic nature of some lipids allows them to form structures such as vesicles, liposomes, or membranes in an aqueous environment.

The term "chemical extraction method" as used herein refers to a use of chemicals other than organic solvents to isolate lipids from undesirable components. The Babcock, Gerber and Detergent methods are examples of non-solvent liquid extraction methods for isolation of lipid content, and are well known to one of skill in the art.

The term "enzymatic extraction method" as used herein refers to a method of isolating lipids from undesirable components using enzymes such as hydrolases, proteinases, lipases and the like to break down complexes of polysaccharides, proteins, and lipids to release the desired lipids from cells. Lipids can then be extracted using organic solvents, mechanical methods, or combinations thereof The term "mechanical extraction method" as used herein refers to the disruption of cells by physical methods such as homogenization, crushing, filtration, sedimentation, and the like, to extract the lipids from cells.

The term "solvent extraction method" as used herein refers to the isolation of lipids using organic solvents and centrifugation methods. The fact that lipids are soluble in organic solvents, but insoluble in water, provides a convenient method of separating the lipid components from water-soluble components, such as proteins, carbohydrates and minerals.

The term "steam extraction methods" as used herein refers to heated water extraction which is a technique based on the use of steam heat as an extractant, at elevated temperatures, and at a pressure high enough to convert and maintain lipids in a liquid state.

As used herein, "transesterify," "transesterifying," and "transesterification" refer to a process of exchanging an alkoxy group of an ester by another alcohol and more specifically, of converting a lipid, e.g. triglycerides, to biodiesel, e.g. fatty acid alkyl esters, and glycerol. Transesterification can be accomplished by using traditional chemical processes such as acid or base catalyzed reactions, or by using enzyme-catalyzed reactions.

The present invention arises from the discovery of a genus of filamentous bacteria, *Candidatus Microthrix* spp., that accumulate lipids and predominate among a community of microorganisms when cultured on wastewater or sewage sludge. An isolated strain, *Candidatus Microthrix parvicella* Bio 17-1, was genetically characterized and found to have an abundance of genes involved in lipid metabolism including a number of long-chain-fatty-acid-CoA-ligases, enoyl-CoA hydratases, lipases, and 3-ketoacyl-CoA thiolases along with at least one acyl-CoA thioesterase and 3-hydroxyacyl-CoA dehydrogenase.

The present invention is directed to a method of producing a biofuel in some embodiments. The method comprises one or more steps selected from culturing *Candidatus Microthrix* spp. in a culture system suitable for maintaining the viability and proliferation of the *Candidatus Microthrix* spp. wherein the culture system provides lipids in a growth medium; isolating the *Candidatus Microthrix* spp. from the culture system; extracting the lipids from the *Candidatus Microthrix* spp.; and/or producing a biofuel from the extracted lipids. In one embodiment, the method of producing a biofuel further comprises measuring depletion of the lipids in the growth medium prior to isolating the *Candidatus Microthrix* spp. from the culture system.

In certain aspects, the *Candidatus Microthrix* spp. culture used for producing biofuels is maintained at a temperature of about 25° C., about 24° C., about 23° C., about 22° C., about 21° C., about 20° C., about 19° C., about 18° C., about 17° C., about 16° C., about 15° C., about 14° C., about 13° C., about 12° C., about 11° C., about 10° C., about 9° C., about 8° C., about 7° C., about 6° C., about 5° C., about 4° C., about 3° C., about 2° C., or about 1° C.

In other embodiments, the temperature of the culture containing the *Candidatus Microthrix* spp. is maintained below about 25° C., about 24° C., about 23° C., about 22° C., about 21° C., about 20° C., about 19° C., about 18° C., about 17° C., about 16° C., about 15° C., about 14° C., about 13° C., about 12° C., about 11° C., about 10° C., about 9° C., about 8° C., about 7° C., about 6° C., about 5° C., or about 4° C.

In yet other embodiments, the *Candidatus Microthrix* spp. culture used for producing biofuels is preferably maintained at a temperature of 4° C. to 25° C.; e.g., any range within 4° C. to 25° C. such as 4° C. to 10° C., 4° C. to 15° C., 10° C. to 15° C., 10° C. to 20° C., 15° C. to 25° C., 20° C. to 25° C., 4° C. to 20° C., 10° C. to 25° C., etc.

In some embodiments, the growth medium for the culture may be wastewater or sewage sludge. The wastewater or sewage sludge may belong to a class selected from sanitary, commercial, industrial, agricultural and surface runoff. The wastewater from residences and institutions, carrying body wastes, washing water, food preparation wastes, laundry wastes, and other waste products of normal living, are classed as domestic or sanitary sewage. Liquid-carried wastes from stores and service establishments serving the immediate community, termed commercial wastes, are included in the sanitary or domestic sewage category if their characteristics are similar to household flows. Wastes that result from an industrial process or the production or manufacture of goods are classed as industrial wastewater. Their flows and strengths are usually more varied, intense, and concentrated than those of sanitary sewage. Surface runoff, also known as storm flow or overland flow, is that portion of precipitation that runs rapidly over the ground surface to a defined channel. Precipitation absorbs gases and particulates from the atmosphere, dissolves and leaches materials from vegetation and soil, suspends matter from the land, washes spills and debris from urban streets and highways, and carries all these pollutants as wastes in its flow to a collection point. Any of these types of wastewater or sewage may be used as growth medium in the present invention.

In one implementation, the *Candidatus Microthrix* spp. are cultured with one or more additional microorganisms that contribute to the production of biofuels by assisting with the accumulation and production of lipids. The *Candidatus Microthrix* spp. may be cultured in a culture system together with *Zoogloea* spp., *Rhizobacter* spp., *Blautia* spp., *Hydrolatea* spp., OD1 genera incertae sedis, *Perlucidibaca* spp., *Brevibacterium* spp., *Mycobacterium* spp., *Nocardia* spp., *Rhodococcus* spp., *Micromonospora* spp., *Dietzia* spp., and *Gordonia* spp., *Acinetobacter* spp., *Saccharomyces* spp., *Rhodotorula* spp., *Chlorella* spp., and combinations thereof. In a preferred embodiment, the *Candidatus Microthrix* spp. are cultured with a microorganism selected from the group consisting of *Zoogloea* spp., *Rhizobacter* spp., *Blautia* spp., *Hydrolatea* spp., OD1 genera incertae sedis, and combinations thereof. In other embodiments, the *Candidatus Microthrix* spp. are cultured with a consortium of strains from wastewater or sewer sludge.

In yet other implementations, the *Candidatus Microthrix* spp. are environmental strain isolated from wastewater or sewer sludge. Various methods may be used to isolate *Candidatus Microthrix* spp. or other microorganisms from environmental sources including laser microdissection, single cell encapsulation combined with flow cytometry, manipulation with optical tweezers, and segregation with a micromanipulator (See Pham et al. (2012) Trends in Biotechnology 30:475).

Laser microdissection involves visualization of the cells of interest via microscopy, transfer of laser energy to a thermolabile polymer with formation of a polymercell composite (IR system) or photovolatilization of cells surrounding a selected area (UV system), and removal of the cells of interest from a heterogeneous sample (See Frohlich et al. (2000) FEMS Microbiol. Rev. 24:567).

In single cell encapsulation combined with flow cytometry, by emulsifying a mixture of diluted cell suspension and preheated agarose gel microdroplets (GMDs) including single cells are formed and incubated in media. This method allows low nutrient flux into GMDs and creates proper conditions for slow-growing microorganisms. Then, GMDs containing colonies are separated from free-living cells and empty GMDs using a flow cytometer (See Alain et al. (2009) Extremophiles 13:583; Zengler et al. (2002) Proc. Natl. Acad. Sci. U.S.A. 99:15681; and Zengler et al. (2005) Methods Enzymol. 397:124).

Manipulation with optical tweezers uses a highly focused laser beam to trap and manipulate microscopic neutral objects such as microbial cells. Using this method, a single cell can be isolated from a mixture of cells (See Frohlich et al. (2000) FEMS Microbiol. Rev. 24:567; and Zhang et al. (2008) J. R. Soc. Interface 5:671).

Segregation of cells with a micromanipulator entails the use of a capillary tube or a microneedle to pick up a single cell out of a mixed community under visual control with an inverse microscope (See Frohlich et al. (2000) FEMS Microbiol. Rev. 24:567).

In some aspects, the culture system is inoculated with a ratio of *Candidatus Microthrix* spp. cells to one or more additional microorganism cells of from about 1,000:1 to about 1:1,000; e.g., any range within from about 1,000:1 to about 1:1,000 such as from about 750:1 to about 1:750, from about 500:1 to about 1:500, from about 250:1 to about 1:250, from about 100:1 to about 1:100, from about 1:1 to about 1:100, from about 5:1 to about 20:1, from about 50:1 to about 1:50, from about 25:1 to about 1:25, etc.

In other aspects, the *Candidatus Microthrix* spp. is *Candidatus Microthrix parvicella* or *Candidatus Microthrix calida*. (See Levantesi et al. (2006) Environ. Microbiol. 8:1552-1563). Also included within the scope of the present invention are *Candidatus Microthrix* spp. strains that are phylogenetically closely related. The strain of *Candidatus Microthrix parvicella* may be *Candidatus Microthrix parvicella*, strain Bio 17-1; *Candidatus Microthrix parvicella*, strain Ben 43; *Candidatus Microthrix parvicella*, strain DAN1-3; *Candidatus Microthrix parvicella*, strain RN1; *Candidatus Microthrix parvicella*, clone 17; or *Candidatus Microthrix parvicella*, clone 6.

In another aspect, the present invention is directed to a method of producing a biofuel comprising: transforming a microorganism with a nucleic acid encoding an enzyme selected from the group consisting of a long-chain-fatty-acid-CoA-ligase, an enoyl-CoA hydratase, a lipase, a 3-ketoacyl-CoA thiolase, an acyl-CoA thioesterase, a 3-hydroxyacyl-CoA dehydrogenase, and combinations thereof; culturing the microorganism in a culture system suitable for maintaining the viability and proliferation of the microorganism wherein the culture system provides lipids in a growth medium; isolating the microorganism from the culture system; extracting the lipids from the microorganism; and producing a biofuel from the extracted lipids. The microorganism may be any one of *Candidatus Microthrix* spp., *Bacillus* spp., *Saccharomyces cerevisiae, Escherichia coli*, a *cyanobacterium*, and an alga.

Other host cells useful for the methods and compositions described herein include archae, prokaryotic, or eukaryotic cells.

Suitable prokaryotic hosts include, but are not limited, to any of a variety of gram-positive, gram-negative, or gram-variable bacteria. Examples include, but are not limited to, cells belonging to the genera: *Agrobacterium, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizoblum, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphylococcus, Strepromyces, Synnecoccus*, and *Zymomonas*. Examples of prokaryotic strains include, but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei*, and *Staphylococcus aureus*. In a particular embodiment, the host cell is an *Escherichia coli* cell.

Suitable archae hosts include, but are not limited to, cells belonging to the genera: *Aeropyrum, Archaeglobus, Halobacterium, Methanococcus, Methanobacterium, Pyrococcus, Sulfolobus*, and *Thermoplasma*. Examples of archae strains include, but are not limited to: *Archaeoglobus fulgidus, Halobacterium* sp., *Methanococcus jannaschii, Methanobacterium thermoautotrophicum, Thermoplasma acidophilum, Thermoplasma volcanium, Pyrococcus horikoshii, Pyrococcus abyssi*, and *Aeropyrum pernix*.

Suitable eukaryotic hosts include, but are not limited to, fungal cells, algal cells, insect cells, and plant cells. In some embodiments, yeasts useful in the present methods include yeasts that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botrvozyma, Brettannomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomnyces, Waltomyces, Wickerhamia, Wickerhamiella, Williopsis, Yamadazyma, Yarrowia, Zygoascus, Zygosaccharomyces, Zygowilliopsis*, and *Zygozyma*, among others.

In some embodiments, the host microbe is *Saccharomyces cerevisiae, Pichia pastoris, Schizosaccharomyces pombe, Dekkera bruxellensis, Kluyveromyces lactis* (previously called *Saccharomyces lactis*), *Kluveromyces marxianus, Arxula adeninivorans*, or *Hansenula polymorpha* (now known as *Pichia angusta*). In some embodiments, the host microbe is a strain of the genus *Candida*, such as *Candida lipolytica, Candida guilliermondii, Candida krusei, Candida pseudotropicalis*, or *Candida utilis*.

As used herein, “transform” and “transformation” refer to the transfer of a nucleic acid molecule into a host organism. The nucleic acid molecule may be a plasmid that replicates autonomously, for example, or, it may integrate into the genome of the host organism. Host organisms containing the transformed nucleic acid fragments are referred to as “transgenic” or “recombinant” or “transformed” or “transformant” organisms.

“Stable transformation” refers to the transfer of a nucleic acid fragment into the genome of a host organism, including both nuclear and organellar genomes, resulting in genetically stable inheritance (i.e., the nucleic acid fragment is “stably integrated”). In contrast, “transient transformation” refers to the transfer of a nucleic acid fragment into the nucleus, or DNA-containing organelle, of a host organism resulting in gene expression without integration or stable inheritance.

The terms “plasmid” and “vector” refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction that is capable of introducing an expression cassette(s) into a cell.

The term “expression cassette” refers to a fragment of DNA comprising the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence [“ORF”]; and, 3) a 3' untranslated region (i.e., a terminator) that, in eukaryotes, usually contains a polyadenylation site. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

Standard resource materials that are useful to make recombinant constructs describe, inter alia: 1) specific conditions and procedures for construction, manipulation and isolation of macromolecules, such as DNA molecules, plasmids, etc.; 2) generation of recombinant DNA fragments and recombinant expression constructs; and, 3) screening and isolation of clones. See, Sambrook, J., Fritsch, E. F. and Maniatis, T., Molecular Cloning: A Laboratory Manual, 2nd ed., Cold Spring Harbor Laboratory: Cold Spring Harbor, N.Y. (1989) (hereinafter “Maniatis”); by Silhavy, T. J., Bennan, M. L. and Enquist, L. W., Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience, Hoboken, N.J. (1987).

In general, the choice of sequences included in the construct depends on the desired expression products, the nature of the host cell and the proposed means of separating transformed cells versus non-transformed cells. The skilled artisan is aware of the genetic elements that must be present on the plasmid vector to successfully transform, select and propagate host cells containing the chimeric gene. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation, i.e., a promoter, the gene coding sequence, and a region 3' of the DNA fragment that controls transcriptional termination, i.e., a terminator. It is most preferred when both control regions are derived from genes from the transformed host cell, although they need not be derived from genes native to the production host.

Transcription initiation regions or promoters useful for driving expression of heterologous genes or portions of them in the desired host cell are numerous and well known. These control regions may comprise a promoter, enhancer, silencer, intron sequences, 3' UTR and/or 5' UTR regions, and protein and/or RNA stabilizing elements. Such elements may vary in their strength and specificity. Virtually any promoter, i.e., native, synthetic, or chimeric, capable of directing expression of these genes in the selected host cell is suitable, although transcriptional and translational regions from the host species are particularly useful. Expression in a host cell can occur in an induced or constitutive fashion. Induced expression occurs by inducing the activity of a regulatable promoter operably linked to the gene of interest, while constitutive expression occurs by the use of a constitutive promoter.

3' non-coding sequences encoding transcription termination regions may be provided in a recombinant construct and may be from the 3' region of the gene from which the initiation region was obtained or from a different gene. A large number of termination regions are known and function satisfactorily in a variety of hosts when utilized in both the same and different genera and species from which they were derived. Termination regions may also be derived from various genes native to the preferred hosts. The termination region is usually selected more for convenience rather than for any particular property.

Particularly useful termination regions for use in yeast are derived from a yeast gene, particularly *Saccharomyces, Schizosaccharomyces, Candida, Yarrowia* or *Kluyveromyces*. The 3'-regions of mammalian genes encoding γ-interferon and α-2 interferon are also known to function in yeast. The 3'-region can also be synthetic, as one of skill in the art can utilize available information to design and synthesize a 3'-region sequence that functions as a transcription terminator. A termination region may be unnecessary, but is highly preferred.

The vector may also comprise a selectable and/or scorable marker, in addition to the regulatory elements described above. Preferably, the marker gene is an antibiotic resistance gene such that treating cells with the antibiotic results in growth inhibition, or death, of untransformed cells and uninhibited growth of transformed cells. For selection of yeast transformants, any marker that functions in yeast is useful with resistance to kanamycin, hygromycin and the amino glycoside G418 and the ability to grow on media lacking uracil, lysine, histidine or leucine being particularly useful.

Merely inserting a gene into a cloning vector does not ensure its expression at the desired rate, concentration, amount, etc. In response to the need for a high expression rate, many specialized expression vectors have been created by manipulating a number of different genetic elements that control transcription, RNA stability, translation, protein stability and location, oxygen limitation, and secretion from the host cell. Some of the manipulated features include: the nature of the relevant transcriptional promoter and terminator sequences, the number of copies of the cloned gene and whether the gene is plasmid-borne or integrated into the genome of the host cell, the final cellular location of the synthesized protein, the efficiency of translation and correct folding of the protein in the host organism, the intrinsic stability of the mRNA and protein of the cloned gene within the host cell and the codon usage within the cloned gene, such that its frequency approaches the frequency of preferred codon usage of the host cell. Each of these may be used in the methods and host cells described herein to further optimize expression of disclosed genes.

For example, gene expression can be increased at the transcriptional level through the use of a stronger promoter (either regulated or constitutive) to cause increased expression, by removing/deleting destabilizing sequences from either the mRNA or the encoded protein, or by adding stabilizing sequences to the mRNA (U.S. Pat. No. 4,910,141). Alternately, additional copies of the genes may be introduced into the recombinant host cells to thereby increase lipid production and accumulation, either by cloning additional copies of genes within a single expression construct or by introducing additional copies into the host cell by increasing the plasmid copy number or by multiple integration of the cloned gene into the genome.

After a recombinant construct is created comprising at least one chimeric gene comprising a promoter, an open reading frame ["ORF"], and a terminator, it is placed in a plasmid vector capable of autonomous replication in the host cell or is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

When two or more genes are expressed from separate replicating vectors, each vector may have a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired lipid products.

Constructs comprising the gene(s) of interest may be introduced into a host cell by any standard technique. These techniques include transformation, e.g., lithium acetate transformation (Methods in Enzymology, 194:186-187 (1991)), biolistic impact, electroporation, microinjection, vacuum filtration or any other method that introduces the gene of interest into the host cell.

For convenience, a host cell that has been manipulated by any method to take up a DNA sequence, for example, in an expression cassette, is referred to herein as "transformed" or "recombinant" or "transformant". The transformed host will have at least one copy of the expression construct and may have two or more, depending upon whether the gene is integrated into the genome, amplified, or is present on an extrachromosomal element having multiple copy numbers.

The transformed host cell can be identified by selection for a marker contained on the introduced construct. Alternatively, a separate marker construct may be co-transformed with the desired construct, as many transformation techniques introduce many DNA molecules into host cells.

Typically, transformed hosts are selected for their ability to grow on selective media, which may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. Additional selection techniques are described in U.S. Pat. Nos. 7,238,482 and 7,259,255.

Regardless of the selected host or expression construct, multiple transformants must be screened to obtain a strain displaying the desired expression level and pattern. Such screening may be accomplished by Southern analysis of DNA blots (Southern, J. Mol. Biol., 98:503 (1975)), Northern analysis of mRNA expression (Kroczek, J. Chromatogr. Biomed. Appl., 618(1-2):133-145 (1993)), Western analysis of protein expression, phenotypic analysis or GC analysis of the lipid products.

The lipids produced by the methods of the present invention may be converted into biofuels by transesterification. Transesterification of lipids yields long-chain fatty acid esters useful as biodiesel.

In particular embodiments, the present application describes genetically engineering strains with one or more exogenous genes. For example, cells that produce high levels of triacylglycerides (TAGs) suitable for biodiesel can be engineered to express a lipase, which can facilitate transesterification of TAGs. The lipase can optionally be expressed using an inducible promoter, so that the cells can first be grown to a desirable density in a culture system and then harvested, followed by induction of the promoter to express the lipase, optionally in the presence of sufficient alcohol to drive conversion of TAGs to fatty acid esters.

Some lipid is sequestered in cell membranes and other non-aqueous parts of the cell. Therefore, to increase the yield of the transesterification reaction, it can be beneficial to lyse the cells to increase the accessibility of the lipase to the lipid. Cell disruption can be performed, for example, mechanically, through addition of pressurized steam, or by employing a virus that lyses the cells, expressing a gene to produce a lytic protein in the cell, or treating the culture with an agent that lyses cells.

Optionally, the lipase can be expressed in an intracellular compartment, where it remains separate from the majority of the lipid until transesterification. Generally, it is preferable to carry out transesterification after water has been substantially removed from the preparation and/or an excess of alcohol has been added. Lipases can use water, as well as alcohol, as a substrate in transesterification. With water, the lipid is conjugated to a hydroxyl moiety to produce a polar fatty acid, rather than an ester. With an alcohol, such as methanol, the lipid is conjugated to a methyl group, producing a non-polar fatty acid ester, which is typically preferable for a transportation fuel. To limit exposure of the lipase to intracellular lipids until conditions are suitable for transesterification to produce fatty acid esters, the lipase can be expressed, for example, in the chloroplast, mitochondria, or other cellular organelle. This compartmentalized expression results in sequestration of the lipase from the majority of the cellular lipid until after the cells have been disrupted.

In one embodiment, the invention provides an isolated strain comprising *Candidatus Microthrix parvicella* Bio 17-1 as described herein.

The invention also includes isolated nucleic acids that comprise a nucleotide sequence having at least 80% homology, more preferably at least 90% homology, and most preferably at least 95% homology to a sequence selected from the group consisting of: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, and SEQ ID NO 113. In a preferred embodiment, the sequence includes one or more the isolated sequences.

The invention also encompasses a nucleic acid having a sequence that encodes a peptide having at least 80% homology, more preferably at least 90% homology, and most preferably at least 95% homology to a sequence selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, and SEQ ID NO 114.

The invention also encompasses a transgenic cell and/or organism that comprises any of the nucleotide sequences set forth above. A method of producing a transformed biofuel or biofuel precursor-producing cell or organism is also included. The method comprises: selecting an organism or cell suitable for growth on a suitable medium; and transforming the cell or organism with a nucleic acid molecule above.

According to some embodiments, a method of producing biofuels comprises: contacting the transformed organism, comprising a nucleic acid molecule that comprises the nucleotide sequence of any one of SEQ ID NO 1-114, to a suitable medium; and, harvesting the lipids or fatty acids produced by the transformed organism.

In some embodiments, the organism suitable for growth on a medium is selected from the group consisting of: *Candidatus Microthrix, Candidatus Microthrix parvicella* Bio 17-1, *Saccharomyces cerevisiae, Escherichia coli*, a cyanobacteria, and an alga. In some embodiments, the suitable medium is wastewater. In some embodiments, the method further comprises: modifying the lipids by transesterification.

According to some embodiments, a method of producing biofuels comprises: growing an organism containing at least one of the nucleic acid molecules set forth herein; growing the organism on a suitable medium; and harvesting the lipids or fatty acids produced by the organism.

In some embodiments, the organism is selected from: *Candidatus Microthrix, Candidatus Microthrix parvicella* Bio 17-1, *Saccharomyces cerevisiae, Escherichia coli*, a cyanobacteria, and an alga. The method preferably further comprises: modifying the lipids by transesterification.

In yet other embodiments, the *Candidatus Microthrix* spp. is selected from the group consisting of *Candidatus Microthrix parvicella* and *Candidatus Microthrix calida. Candidatus Microthrix calida* is described in Levantesi C et al. (2006) Eniviron. Microbiol. 8:1552.

According to some embodiments, an isolated peptide comprises a sequence having at least 80% homology, more preferably at least 90% homology, and most preferably at least 95% homology to a sequence selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, and SEQ ID NO 114.

According to some embodiments, a method of producing or modifying lipids and fatty acids comprises: adding to a suitable feedstock, a peptide identified herein; and collecting and/or purifying the resulting lipid or fatty acid product.

The invention also encompasses an isolated 14-24 base pair nucleic acid sequence comprises a sequence complimentary to the sense or antisense sequence of a sequential 14 base pair sequence present in a sequence selected from: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, and SEQ ID NO 113.

In certain aspects, the present invention is directed to the production of biofuels and biofuel precursors in transformed organisms.

As was described in U.S. Publication No. 2011/0223641 to Stephanopoulos et al., biofuel and biofuel precursor production using transformed, or engineered, microorganisms is known in the art. In Stephanopoulus, the transformed microorganism, *Y. lipolytica*, was modified to upregulate lipid production and accumulation by genetic manipulation which also conferred increased resistance to feedstock toxicity.

According to the results of the present disclosure, the genes isolated from Bio 17-1 are related to a lipid-accumulating phenotype. Specifically, the novel genes identified from Bio 17-1 can be introduced in specific "cassettes" that allow any transformed organism to increase lipid production, modification, purification or storage. Using methods known in the art, these genes or cassettes of genes can be transformed into organisms such as *Candidatus Microthrix, Candidatus Microthrix parvicella* Bio 17-1, *Saccharomyces cerevisiae, Escherichia coli*, cyanobacteria, and algae as these organisms are capable of being grown in liquid-phase media in large batches with high density of cells. (See for example, Kawai et al., Transformation of *Saccharomyces cerevisiae* and other fungi: methods and possible underlying mechanism.) The use of such organisms allows for the production, modification, or purification of large amounts of biofuel or biofuel precursors at economical costs. Other organisms would be suitable as one having skill in the art would recognize from the present disclosure.

As can be determined by one having skill in the art by the present disclosures, some modification of the genes may be necessary to produce the desired function of the genes or gene products introduced into a transformed organism. The function of the gene products is disclosed above in each section. For example, the gene products of the odd-numbered sequences of SEQ ID NO: 1-55 (SEQ ID NO: 1, 3, 5 . . . 55) perform the function of catalyzing the reaction:

ATP+ a long-chain carboxylate+CoA=AMP+diphosphate+an acyl-CoA The functions of the other genes and gene products are set forth herein.

To ensure that the gene product performs the same function in a transformed microorganism, an assay may need to be conducted that ensures that the gene product is enzymatically active. For example, the function of long-chain fatty acid:CoA ligases can be assayed using the method set forth in Bierbach, Studies on long chain fatty acid:CoA ligase from human small intestine. Gut. 1980 August; 21(8) 689-954. Assays for the functionality of the other above-mentioned enzymes are routine and well-known in the art.

Modifications that might be necessary to ensure functionality in a transformed organism may include: changing the nucleotide sequence to produce a homologous peptide with a different codon sequence; adding, deleting, or modifying promoter and repressor sequences depending on the specific regulation mechanisms of the transformed organism, modifying the nucleic acid sequence for greater translational or transcriptional efficiency, adding a sequence encoding a poly-adenosine tail, adding a fluorescent marker or identifying sequence, or the like. Additionally, conservative amino acid encoding substitutions may be made to create a sequence that encodes a similar peptide but with slightly increased or decreased functionality as can be readily determined by the above-mentioned assay and others well-known in the art.

A modified nucleic acid would comprise a sequence having preferably 80% homology to a sequence located in the sequence listing, more preferably 95% homology, and most preferably, 100% homology. A transgenic cell could be created according to the above disclosures using a sequence comprising any of these sequences. Such a transgenic cell may be useful for producing biofuel or biofuel precursors by selecting an organism based on the desired growth medium (for example nutrient broth, agar, wastewater, or any other desired media) and then transforming the organism with any of the above mentioned sequences. Additionally, the biofuel or biofuel precursor could be collected by contacting the transformed organism to the desired media and then harvesting the lipids or fatty acids produced by the transformed organism. Methods of harvesting lipids or fatty acids from transformed organisms are well-known in the art, and are discussed in U.S. Publication No. 2011/0223641 to Stephanopoulos et al.

In addition to using a transformed cell, an organism containing the above-mentioned nucleotide sequences could also be used to produce biofuel. Locating an organism containing the above mentioned nucleotide sequences can be readily determined through PCR, LAMP, or other DNA amplification and identification techniques based on the sequences disclosed herein. For example, a PCR primer consists, typically, of a 14-24 base pair sequence being complementary to the 3' ends of a sense and antisense strand of the desired gene. Using the sequences set forth herein, one having skill in the art would readily be able to design primers to locate the genes herein disclosed and additionally genes having similar functionality based on sequence modifications. For example, other *Candidatus Microthrix* species may have similar genes that would be useful for the production of biofuels and these genes could be readily isolated using the disclosed sequences. Additionally, nucleotide sequences that encode the peptide sequences described could also be used to design primers that will locate genes that disclose genes having a conserved amino acid sequence but that contain conservative mutations.

In some embodiment, the present invention is directed to the production of biofuels using peptide enzymes. The peptide sequences disclosed herein (and the modified versions disclosed having 80%, 95%, and 100% homology) may be used in vitro to produce biofuel or biofuel precursors. In vitro biofuel production has several advantages over in vivo production, not least of which are not having to protect the in vivo organism from disease or deadly changes in environmental conditions. Therefore, the peptides and modified versions disclosed may be used to produce biofuel or biofuel precursors by adding them to a suitable feedstock (such as wastewater, a lipid or fatty acid-enriched medium, or other ligand, substrate, or product of the disclosed enzymes, or other such material containing a suitable chemical). Thereafter, the resulting product of the reaction may be collected, or collected and purified to result in a biofuel or biofuel precursor.

Related publications containing teachings that may be used in practicing the present invention include U.S. Publication No. 2012/01599839 to Koskinen et al., U.S. Publication No. 2005/0112735 to Zappi et al., and U.S. Publication No. 2011/0223641 to Stephanopoulos et al.

U.S. Publication No. 2012/01599839 to Koskinen et al. discloses an integrated process for producing biofuels using various feedstock materials using microorganisms that may directly process the feedstock into biofuels or biofuel precursors, or may produce enzymes useful in converting feedstock into biofuels or biofuel precursors.

U.S. Publication No. 2005/0112735 to Zappi et al. describes a method for producing biofuels in large-scale commercial amounts using lipids extracted from sludge generated from wastewater treatment. The lipid extraction is performed in vitro by chemical extraction with generation of biofuel from transesterification of collected lipids.

U.S. Publication No. 2011/0223641 to Stephanopoulos et al. describes biofuel and biofuel precursor production using transformed, or engineered, microorganisms. The transformed microorganism, *Y. lipolytica*, was modified to upregulate lipid production and accumulation by genetic manipulation which also conferred increased resistance to feedstock toxicity.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Example 1

Genome Sequence of "*Candidatus Microthrix Parvicella*" Bio17-1, a Long-Chain-Fatty-Acid-Accumulating Filamentous Actinobacterium from a Biological Wastewater Treatment Plant Methods A draft genome sequence of '*Candidatus M. parvicella*' Bio17-1 was produced and genes related to lipid storage and processing were identified according to the following method.

The Bio17-1 strain was isolated from a Dutch wastewater treatment plant serving fish industries. First, two sequencing libraries were prepared with mean insert lengths of 350 basepairs (bp) (paired-end) or 2,750 bp (mated pairs) and sequenced on an Illumina Genome Analyzer II. Raw 100-bp reads were error corrected with Quake. (Kelley et al. 2010. Quake: quality-aware detection and correction of sequencing errors. Genome Biology 11:R116) $5.84\times10^6$ paired and $1.12\times10^6$ single-end reads with minimum mean quality value (QV) of 30 and a minimum length of 70 bp were used for assemblies. Second, 24,031 SMRT sequence reads were obtained on a Pacific Biosciences PacBio RS using C1 chemistry. Error correction yielded 2,625 reads (232-1984 bp) from this run.

Using the Illumina sequence reads, two preliminary assemblies were obtained with Velvet (Zerbino et al. 2008. Velvet: algorithms for de novo short read assembly using de Bruijn graphs. Genome Res. 18:821-829) and Edena (Hernandez et al. 2008. De novo bacterial genome sequencing: Millions of very short reads assembled on a desktop computer. Genome Res.), and merged with the minimus2 utility (Treangen et al. 2011. Next generation sequence assembly with AMOS. Curr Protoc Bioinformatics Chapter 11:Unit 11.8). The resulting 27 contigs were scaffolded with SSPACE (Boetzer et al. 2011. Scaffolding pre-assembled contigs using SSPACE. Bioinformatics 27:578-579) and gaps filled with GapFiller (Boetzer et al. 2012. Toward almost closed genomes with GapFiller. Genome biology 13:R56). Additional assemblies were obtained using SOAPdenovo (Li et al. 2009. De novo assembly of human genomes with massively parallel short read sequencing. Genome Res.) (kmer values between 65-81, steps of 2) and CABOG (Miller et al. 2008. Aggressive assembly of pyrosequencing reads with mates. Bioinformatics 24:2818-2824). Error corrected PacBio reads (Koren et al. 2012. Hybrid error correction and de novo assembly of single-molecule sequencing reads. Nature Biotechnology 30:693-700) and the additional assemblies, were mapped onto the preliminary assemblies. Draft contigs were broken where discrepancies among assemblies or PacBio reads suggested misassemblies. Conversely, contigs were joined where contig ends overlapped with perfect identity for at least 500 bp. Manual curation and manipulation of the assemblies were performed using consed (Gordon et al. 1998. Consed: a graphical tool for sequence finishing. Genome Res. 8:195-202). Automatic annotation and draft metabolic reconstruction were performed by the RAST server (Aziz et al. 2008. The RAST Server: rapid annotations using subsystems technology. BMC Genomics 9:75). CRISPR loci were identified using CRISPRFinder (Grissa et al. 2007. CRISPRFinder: a web tool to identify clustered regularly interspaced short palindromic repeats. Nucleic acids research 35:W52-7).

Results

The draft assembly consists of 4,202,850 bp, arranged in 13/16 scaffolds/contigs, with a mean GC % of 66.4. Automated annotation identified 4,063 coding sequences, in addition to 1 rRNA operon and 46 tRNAs covering all amino-acids. A complete pentose phosphate pathway and TCA cycle are encoded in the genome. As previously hypothesized for '*M. parvicella*' strain RN1, a nitrate reductase is encoded by the genome, but no nitrite reductase appears to be present. The strain is also predicted to be a prototroph for all amino-acids and to be able to polymerize/depolymerize polyhydroxybutyrate. No genes are annotated as related to photosynthesis, plasmid, prophage or phage elements. The draft sequence contains one CRISPR locus with 88 spacers.

'*M. parvicella*' Bio17-1's ability to accumulate excessive amounts of fatty acids is also highlighted by its gene content. The genome encodes 28 homologs of long-chain-fattyacyl-CoA ligase and 17 homologs of enoyl-CoA hydratase. The genetic inventory of '*M. parvicella*' makes it of particular interest for future wastewater treatment strategies based around the comprehensive reclamation of nutrients and chemical energy-rich biomolecules.

The genome sequence of "*Candidatus Microthrix parvicella*" strain Bio17-1 has been deposited at DDBJ/EMBL/GenBank under accession number AMPG00000000; the version described in this paper is the first version, AMPG01000000. A provisional annotation is available upon request. Raw sequence reads were deposited in the Sequence Read Archive under accession number SRA058866.

The following are classifications of the identified enzymes. Nucleic acid sequences are listed in the Sequence Listing and the resulting protein encoded by each nucleic acid sequence is listed immediately after the nucleic acid sequence which encodes it.

Long-Chain-Fatty-Acid CoA Ligase (EC 6.2.1.3)

According to the IUBMB nomenclature, these enzymes catalyze the reaction:

ATP+a long-chain carboxylate+CoA=AMP+diphosphate+an acyl-CoA '*Candidatus Microthrix parvicella*' Bio17-1 genome contains 28 homologues of this enzyme (FIG. 1) and (Table 1).

TABLE 1

| SEQ ID NOS | FIG Number (GenBank GI Number) |
|---|---|
| SEQ ID NO: 1 | fig \| 340363.9.peg.87 (Mparv_0087) |
| SEQ ID NO: 3 | fig \| 340363.9.peg.459 (Mparv_0459) |
| SEQ ID NO: 5 | fig \| 340363.9.peg.481 (Mparv_0481) |
| SEQ ID NO: 7 | fig \| 340363.9.peg.744 (Mparv_0744) |
| SEQ ID NO: 9 | fig \| 340363.9.peg.904 (Mparv_0904) |
| SEQ ID NO: 11 | fig \| 340363.9.peg.982 (Mparv_0982) |
| SEQ ID NO: 13 | fig \| 340363.9.peg.1168 (Mparv_1168) |
| SEQ ID NO: 15 | fig \| 340363.9.peg.1597 (Mparv_1597) |
| SEQ ID NO: 17 | fig \| 340363.9.peg.1683 (Mparv_1683) |
| SEQ ID NO: 19 | fig \| 340363.9.peg.1808 (Mparv_1808) |
| SEQ ID NO: 21 | fig \| 340363.9.peg.1904 (Mparv_1904) |
| SEQ ID NO: 23 | fig \| 340363.9.peg.2090 (Mparv_2090) |
| SEQ ID NO: 25 | fig \| 340363.9.peg.2103 (Mparv_2103) |
| SEQ ID NO: 27 | fig \| 340363.9.peg.2191 (Mparv_2191) |
| SEQ ID NO: 29 | fig \| 340363.9.peg.2242 (Mparv_2242) |
| SEQ ID NO: 31 | fig \| 340363.9.peg.2435 (Mparv_2435) |
| SEQ ID NO: 33 | fig \| 340363.9.peg.2685 (Mparv_2685) |
| SEQ ID NO: 35 | fig \| 340363.9.peg.2716 (Mparv_2716) |
| SEQ ID NO: 37 | fig \| 340363.9.peg.2732 (Mparv_2732) |
| SEQ ID NO: 39 | fig \| 340363.9.peg.2734 (Mparv_2734) |
| SEQ ID NO: 41 | fig \| 340363.9.peg.2828 (Mparv_2828) |
| SEQ ID NO: 43 | fig \| 340363.9.peg.2932 (Mparv_2932) |
| SEQ ID NO: 45 | fig \| 340363.9.peg.2979 (Mparv_2979) |
| SEQ ID NO: 47 | fig \| 340363.9.peg.3191 (Mparv_3191) |
| SEQ ID NO: 49 | fig \| 340363.9.peg.3315 (Mparv_3315) |
| SEQ ID NO: 51 | fig \| 340363.9.peg.3388 (Mparv_3388) |
| SEQ ID NO: 53 | fig \| 340363.9.peg.3405 (Mparv_3405) |
| SEQ ID NO: 55 | fig \| 340363.9.peg.3638 (Mparv_3638) |

Enoyl-CoA Hydratase (EC 4.2.1.17)

According to the IUBMB nomenclature, these enzymes catalyze the reaction:

(3S)-3-hydroxyacyl-CoA=trans-2(or 3)-enoyl-CoA+$H_2O$

Figure 2:
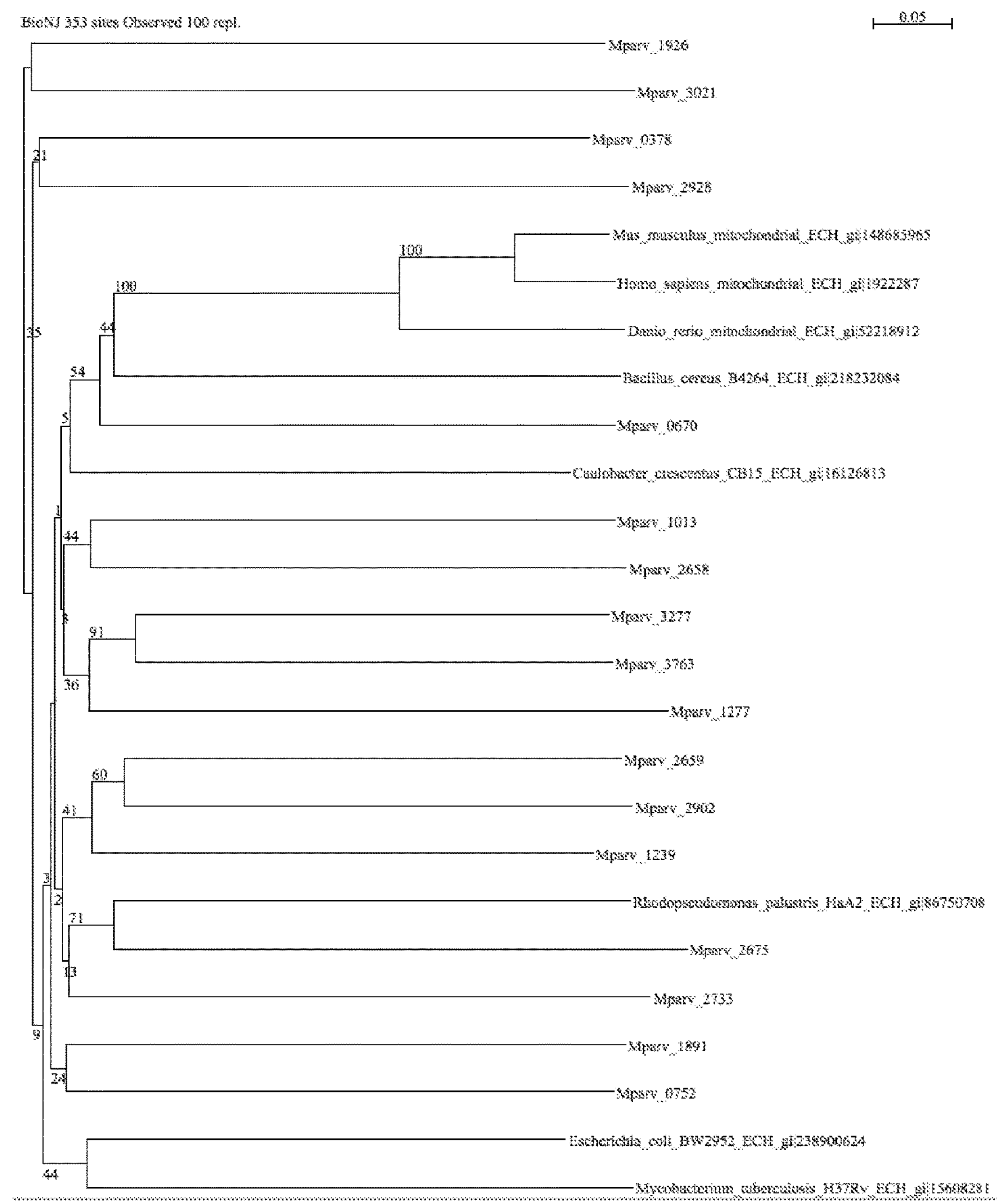
FIG. 2 depicts a phylogenetic tree of the 17 enoyl-CoA hydratase homologues. The phylogenetic tree was constructed by Bio-Neighbor Joining at all position (including gaps) after ClustalW2 alignment with default parameters of the amino-acid sequences of '*Candidatus Microthrix parvicella*' strain Bio17-1 and of some reference sequences (GenBank GI number indicated after the organism name).

'*Candidatus Microthrix parvicella*' Bio17-1 genome contains 17 homologues of this enzyme (FIG. 2) and (Table 2).

TABLE 2

| SEQ ID NOS | FIG Number (GenBank GI Number) |
|---|---|
| SEQ ID NO: 57 | fig \| 340363.9.peg.378 (Mparv_0378) |
| SEQ ID NO: 59 | fig \| 340363.9.peg.670 (Mparv_0670) |
| SEQ ID NO: 61 | fig \| 340363.9.peg.752 (Mparv_0752) |
| SEQ ID NO: 63 | fig \| 340363.9.peg.1013 (Mparv_1013) |
| SEQ ID NO: 65 | fig \| 340363.9.peg.1239 (Mparv_1239) |
| SEQ ID NO: 67 | fig \| 340363.9.peg.1277 (Mparv_1277) |
| SEQ ID NO: 69 | fig \| 340363.9.peg.1891 (Mparv_1891) |
| SEQ ID NO: 71 | fig \| 340363.9.peg.1926 (Mparv_1926) |
| SEQ ID NO: 73 | fig \| 340363.9.peg.2658 (Mparv_2658) |
| SEQ ID NO: 75 | fig \| 340363.9.peg.2659 (Mparv_2659) |
| SEQ ID NO: 77 | fig \| 340363.9.peg.2675 (Mparv_2675) |
| SEQ ID NO: 79 | fig \| 340363.9.peg.2733 (Mparv_2733) |
| SEQ ID NO: 81 | fig \| 340363.9.peg.2902 (Mparv_2902) |
| SEQ ID NO: 83 | fig \| 340363.9.peg.2928 (Mparv_2928) |
| SEQ ID NO: 85 | fig \| 340363.9.peg.3021 (Mparv_3021) |
| SEQ ID NO: 87 | fig \| 340363.9.peg.3277 (Mparv_3277) |
| SEQ ID NO: 89 | fig \| 340363.9.peg.3763 (Mparv_3763) |

Lipase (EC 3.1.1.5 and/or EC 3.1.1.23)

According to the IUBMB nomenclature, these enzymes hydrolyze glycerol monoesters of long-chain fatty acids (Table 3).

TABLE 3

| SEQ ID NOS | FIG Number (GenBank GI Number) |
|---|---|
| SEQ ID NO: 91 | fig \| 340363.9.peg.1413 (Mparv_1413) |
| SEQ ID NO: 93 | fig \| 340363.9.peg.3991 (Mparv_3991) |

3-Ketoacyl-CoA Thiolase (EC 2.3.1.16)

According to the IUBMB nomenclature, these enzymes catalyze the reaction:

acyl-CoA+acetyl-CoA=CoA+3-oxoacyl-CoA

'*Candidatus Microthrix parvicella*' Bio17-1 genome contains 8 homologues of this enzyme (Table 4).

TABLE 4

| SEQ ID NOS | FIG Number (GenBank GI Number) |
|---|---|
| SEQ ID NO: 95 | fig \| 340363.9.peg.358 (Mparv_0358) |
| SEQ ID NO: 97 | fig \| 340363.9.peg.972 (Mparv_0972) |
| SEQ ID NO: 99 | fig \| 340363.9.peg.1007 (Mparv_1007) |
| SEQ ID NO: 101 | fig \| 340363.9.peg.1376 (Mparv_1376) |
| SEQ ID NO: 103 | fig \| 340363.9.peg.2792 (Mparv_2792) |
| SEQ ID NO: 105 | fig \| 340363.9.peg.2924 (Mparv_2924) |
| SEQ ID NO: 107 | fig \| 340363.9.peg.2925 (Mparv_2925) |
| SEQ ID NO: 109 | fig \| 340363.9.peg.3387 (Mparv_3387) |

Acyl-CoA Thioesterase (EC 3.1.2.-)

This enzyme is predicted by automatic annotation to catalyze the reaction:

acyl-CoA=CoA+free fatty acid

*Candidatus Microthrix parvicella*' Bio17-1 genome contains 1 type of this enzyme (Table 5).

TABLE 5

| SEQ ID NOS | FIG Number (GenBank GI Number) |
|---|---|
| SEQ ID NO: 111 | fig \| 340363.9.peg.3949 (Mparv_3949) |

3-Hydroxyacyl-CoA Dehydrogenase (EC 1.1.1.35)

According to the IUBMB nomenclature, this enzyme catalyzes the reaction:

(S)-3-hydroxyacyl-CoA+NAD$^+$=3-oxoacyl-CoA+NADH+H$^+$

*Candidatus Microthrix parvicella*' Bio17-1 genome contains 1 type of this enzyme (Table 6).

TABLE 6

| SEQ ID NOS | FIG Number (GenBank GI Number) |
|---|---|
| SEQ ID NO: 113 | fig \| 340363.9.peg.1591 (Mparv_1591) |

The protein products of the above mentioned genes were also determined. These proteins are listed in the Sequence Listing where each protein sequence follows immediately the nucleic acid sequence that encodes it.

Example 2

Systematic Molecular Measurements Reveal Key Microbial Populations Driving Community-Wide Phenotype Introduction Natural microbial communities are heterogeneous and dynamic. Therefore, a major consideration for multiple omic data studies is the sample-to-sample heterogeneity, which can lead to inconsistent results if the different biomolecular fractions are obtained from distinct sub-samples. Conversely, systematic omic measurements, i.e. the standardized, reproducible and simultaneous measurement of multiple features from a single undivided sample, result in fully integrable datasets.

Our objective was to prove the feasibility and benefits of such systematic measurements in the study of the respective contributions of different populations to a community-wide phenotype (here, the lipid accumulation of microbial community naturally present at the air-water interface of certain biological wastewater treatment systems).

Methods

Figure 3:
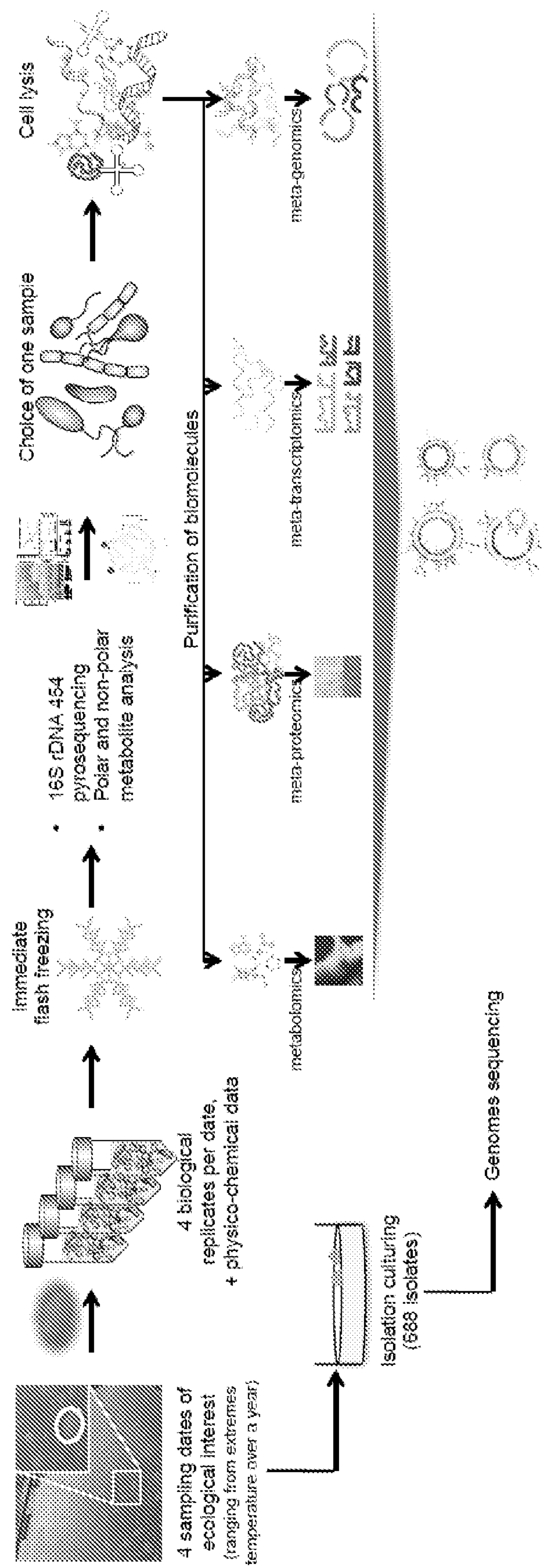
FIG. 3 depicts a workflow overview. 16 distinct samples were chosen for their temporally, spatially and ecological differences. Community structure and lipid were analyzed to choose one time point of particular interest. The chosen undivided sample undergoes a comprehensive biomolecular extraction (DNA, RNA, proteins and metabolites as described in Roume et al. (2013) The ISME Journal 7:110) and analyzed by high-throughput technologies.

The experimental methods used for this study are outlined in FIG. 3.

Results

Figure 4:
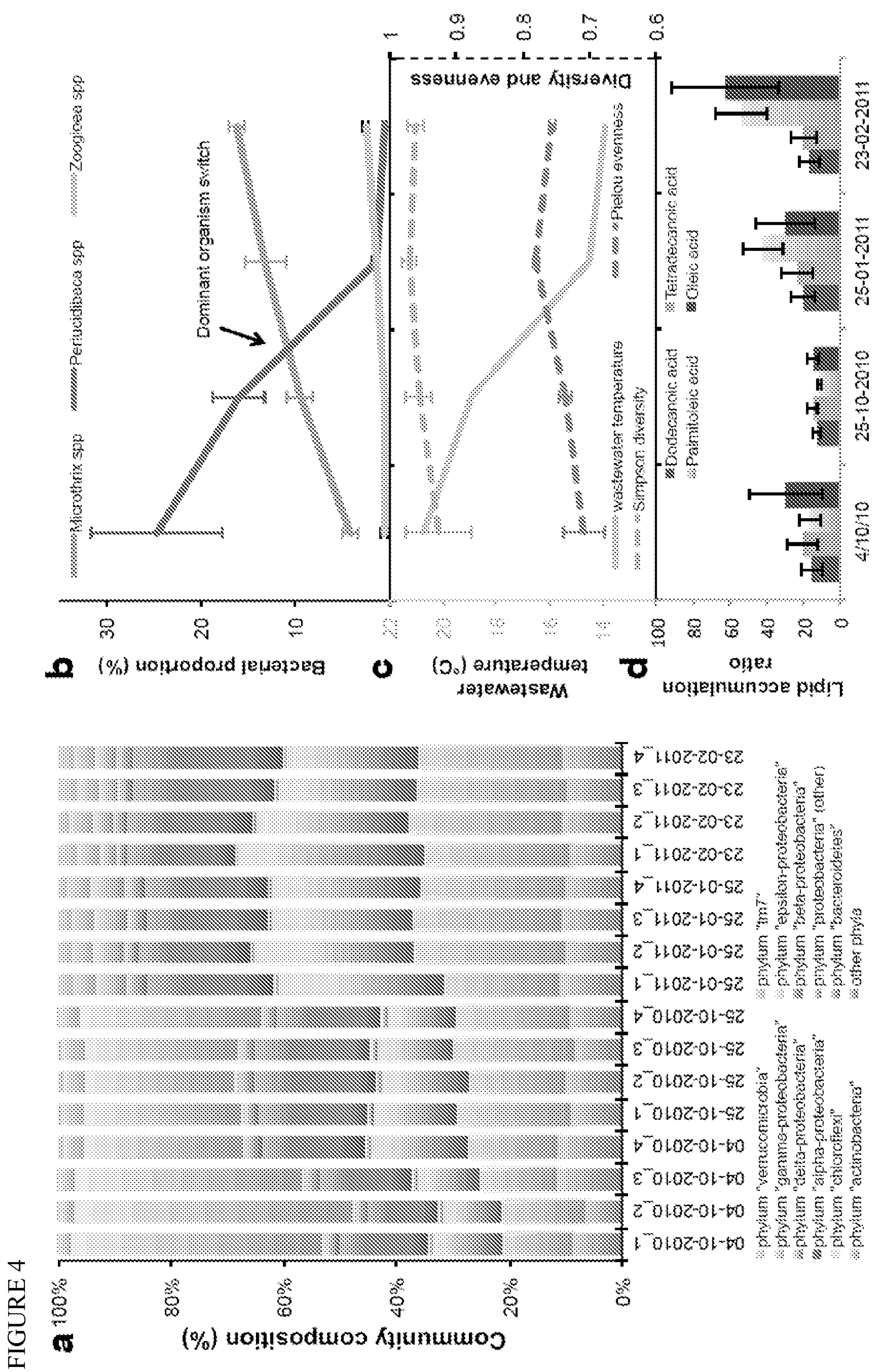
FIG. 4 depicts lipid accumulating community dynamics. (a) 16S phylotyping at the phylum-level of the community at 4 different time points for 4 biological replicates. (b) Dynamics of the 2 most abundant organisms and of a potential keystone species (see FIG. 5) of the community. (c) Wastewater temperature, Simpson diversity and Pielou evenness over time. (d) Cellular accumulation of some long chain fatty acids, calculated by comparing the intracellular to the extracellular concentration (by GCMS Single Ion Monitoring).

The lipid accumulating community was studied in quadruplicate at 4 different time points in term of composition (FIG. 4*a,b*), diversity, evenness (FIG. 4*c*) and long chain fatty acid contents. It was observed that biological replicates sampled the same day are highly heterogeneous, and community structure changes significantly over time, leading to a switch in the dominant organism. Biomass lipid accumulation increased when *Microthrix* spp. dominated the community (this also corresponded with low wastewater temperature). During the transition, there was a time point (25/01/11) when the diversity and the evenness of the community were maximal. This time point (25/01/11) was chosen to show the benefits of systematic measurements on the understanding of a community-wide phenotype (see FIG. 4).

Figure 5:
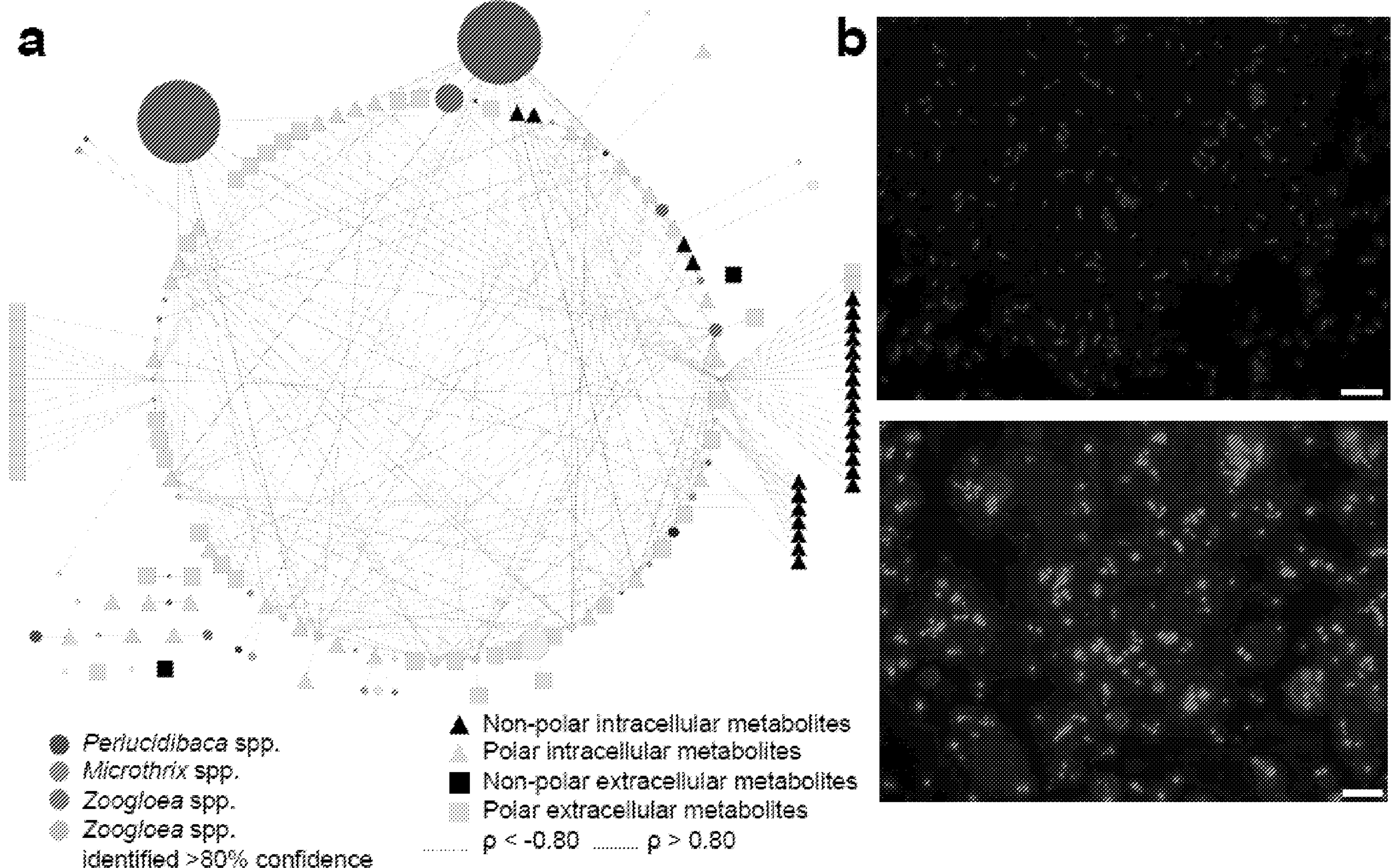
FIG. 5 depicts *Zooglea* spp., a potential keystone species. (a) Spearman correlations of normalized abundances of conserved bacterial genera and metabolites. Node size is proportional to the average abundance of the taxa. p-value<0.001. (b) 2 isolated *Zoogloea* strains observed in epifluorescence after Nile Red staining (non-polar granules are fluorescent). Scale bare: 10 μm.

The abundance of a population identified as *Zoogloea* spp. with a confidence above 80% correlated with the abundance of numerous nonpolar metabolites, some of them identified as long-chain fatty acids. *Zoogloea* species accumulate intracellular non-polar granules. Correlations between bacterial abundances and metabolite abundances allowed the identification of low abundance species playing an essential role in the community as so called "keystone species" (see FIG. 5).

Figure 6:
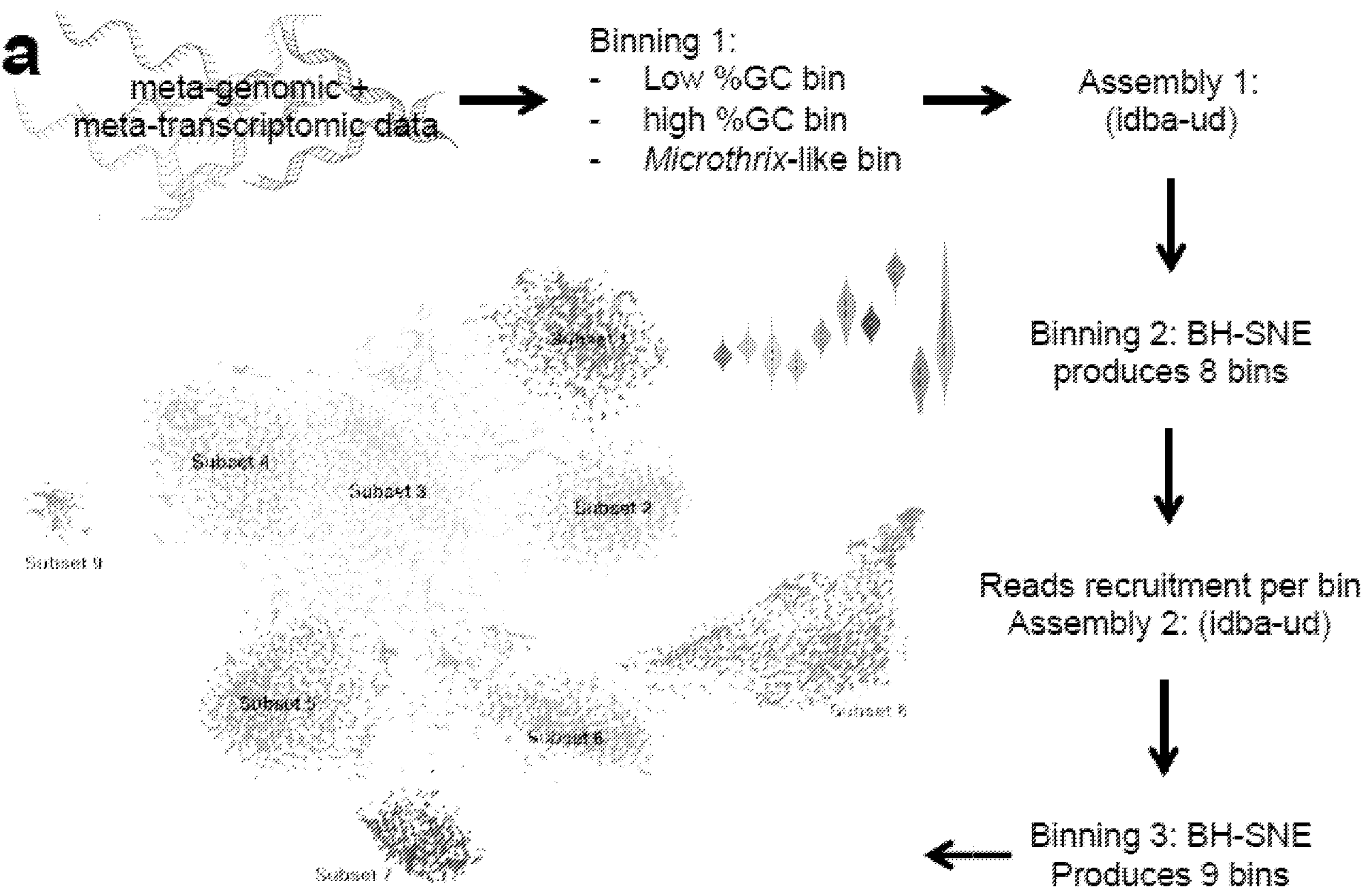
FIG. 6 depicts microbial community clustering into 9 composite genomes and identification. (a) Meta-genomic and meta-transcriptomic data treatment workflow. (b) Predicted proteins identity between the 9 subsets and *Microthrix* Bio17-1 isolate genome. From outside to inside, concentric circles represent the percentage identity of subset 01 to subset 09.
Figure 6:
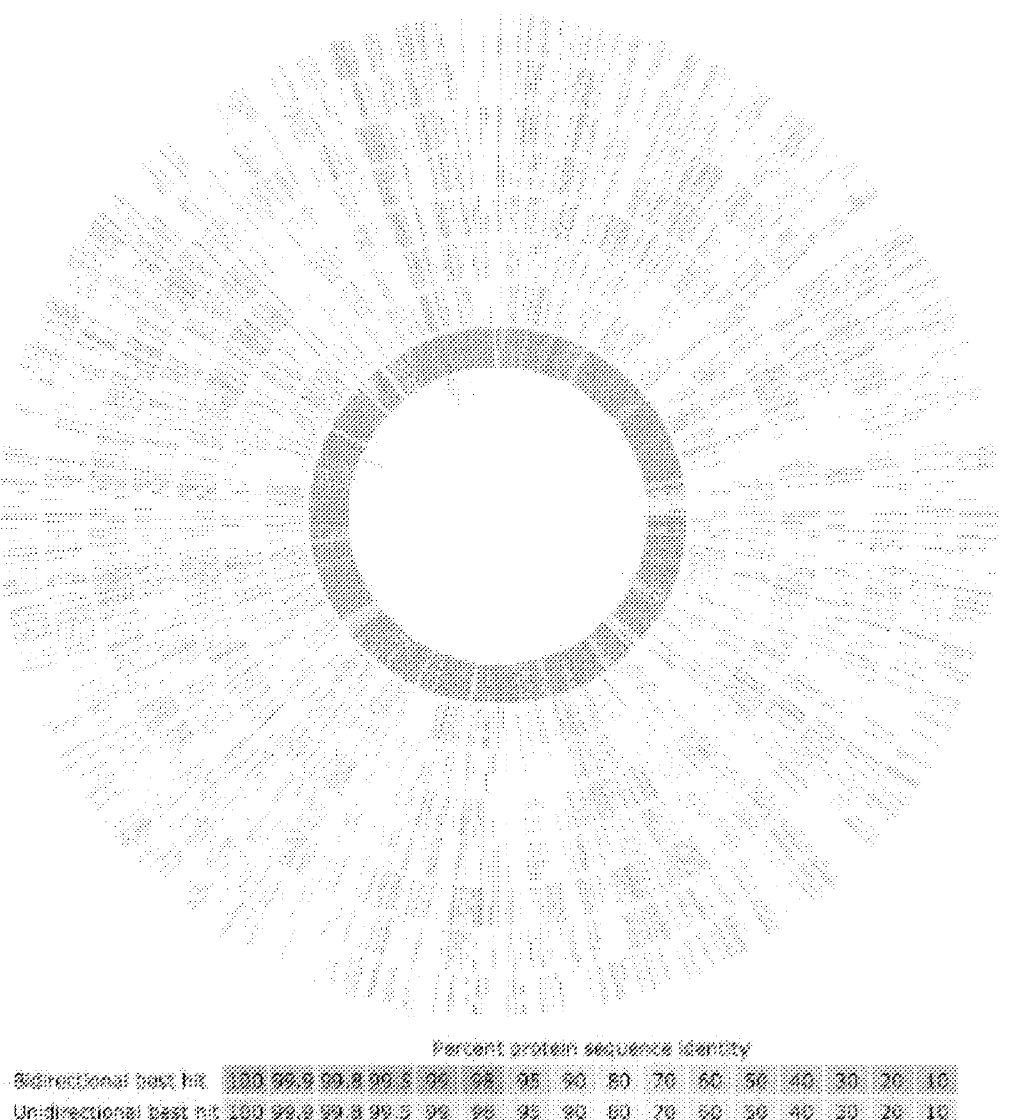
Figure 8:
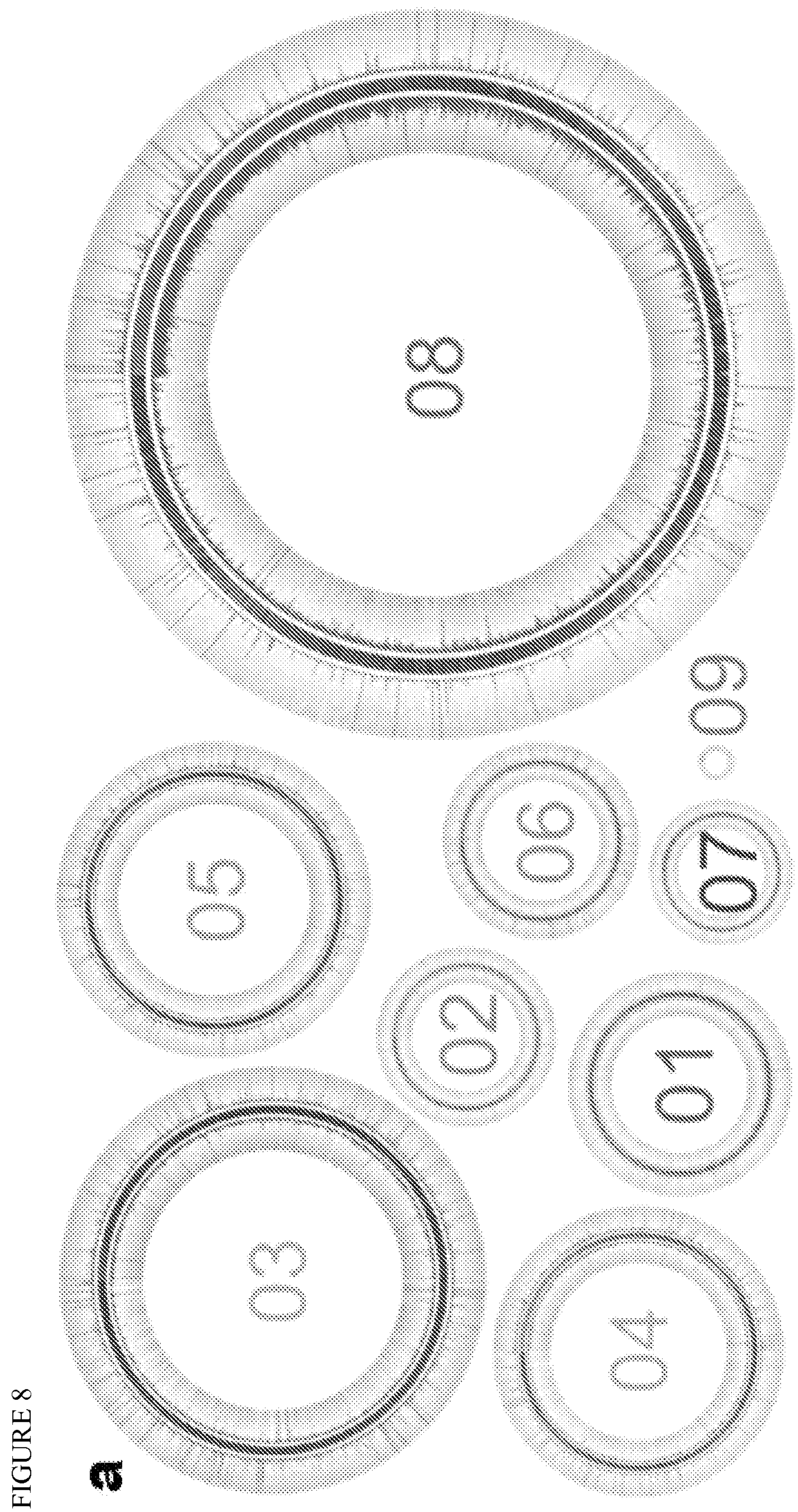
FIG. 8 depicts the subset coverage and expression. (a) The inner blue plots show the DNA coverage and the outer blue plots represents the RNA expression levels (windows of 100 pb excepted for subset09, 50 bp). (b) Normalized metagenome coverage. (c) Normalized metatranscriptome coverage.
Figure 8:
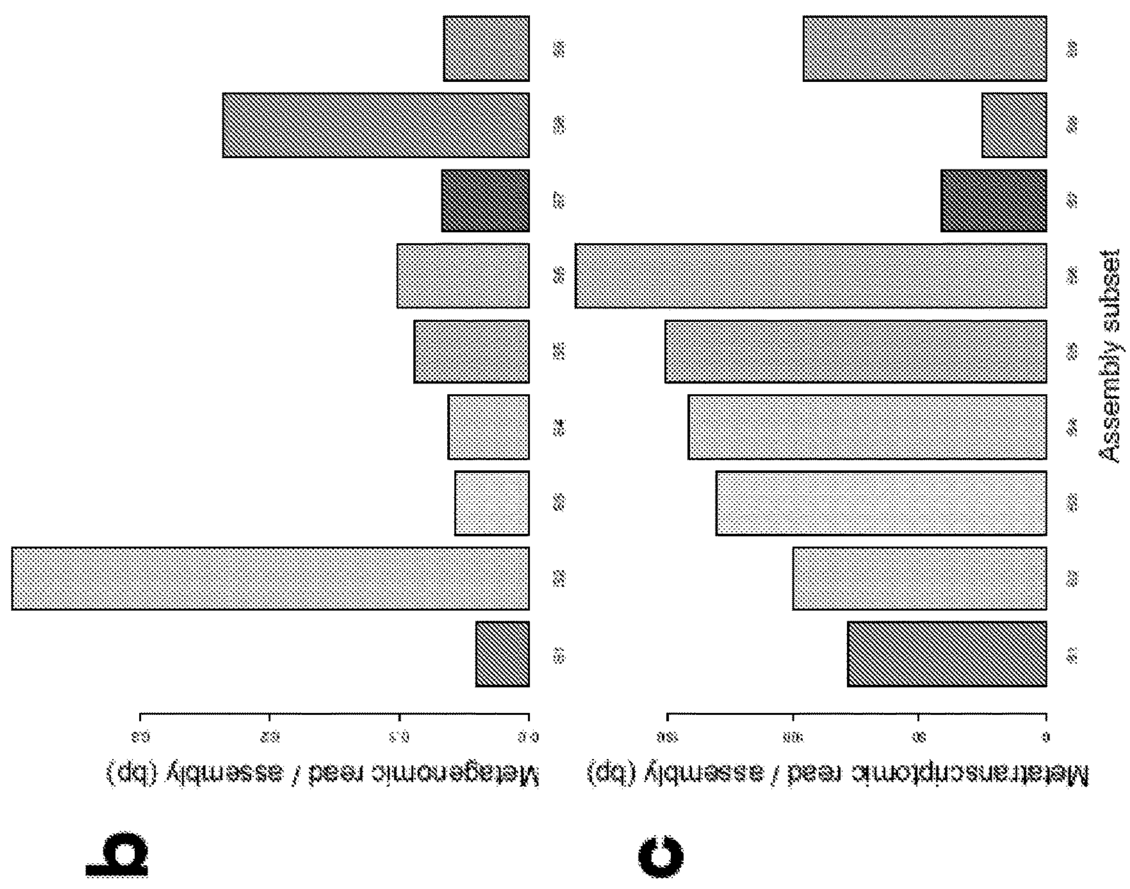

Subset 08 was identified as a *Microthrix* population following comparison of the protein sequence with the proteome sequences of an isolate genome (see FIGS. 6-8).

Example 3

Linking Mixed Microbial Community Phenotype to Individual Genotypes

Introduction

Figure 15:
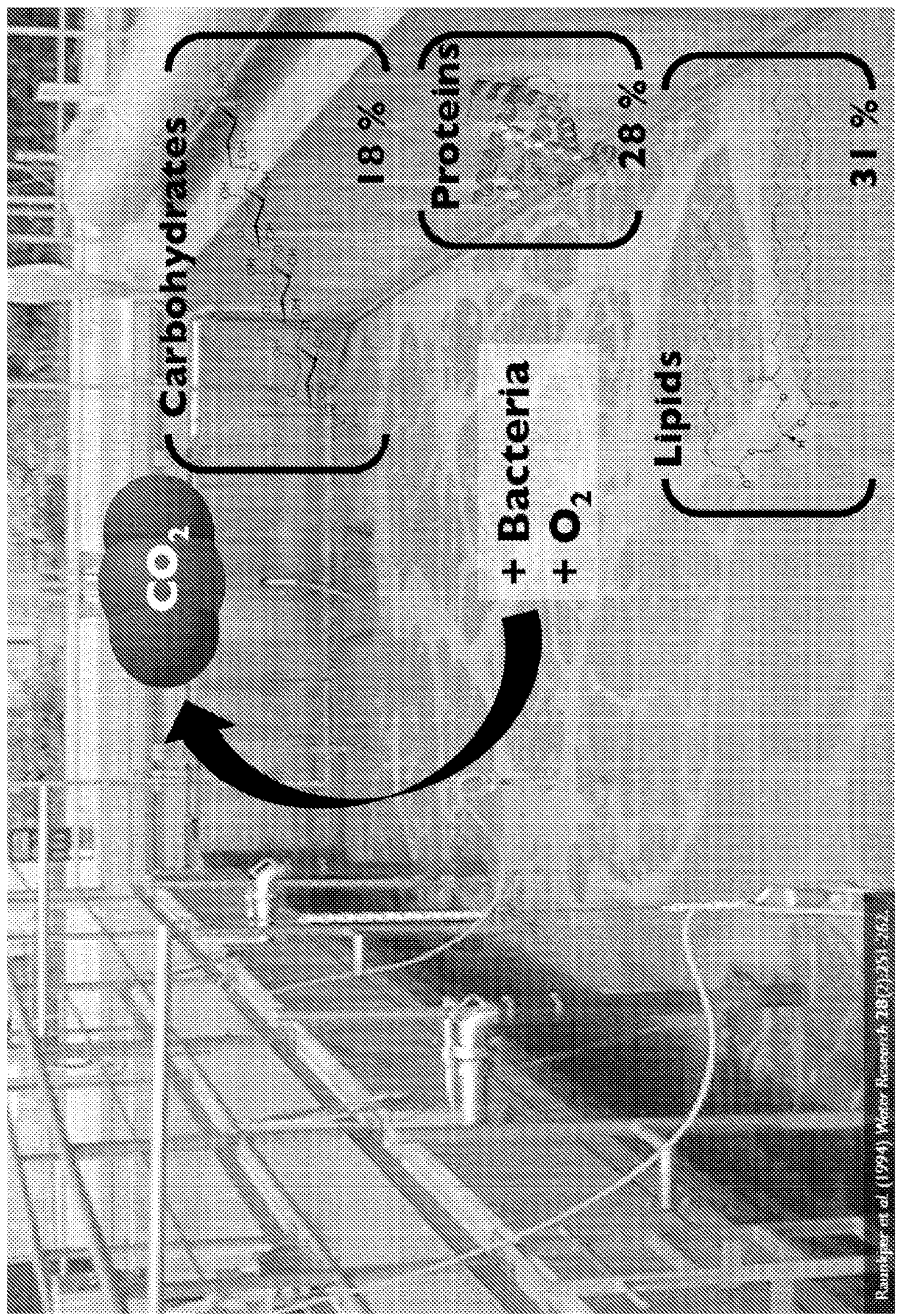
FIG. 15 depicts a typical organic composition of wastewater.
Figure 16:
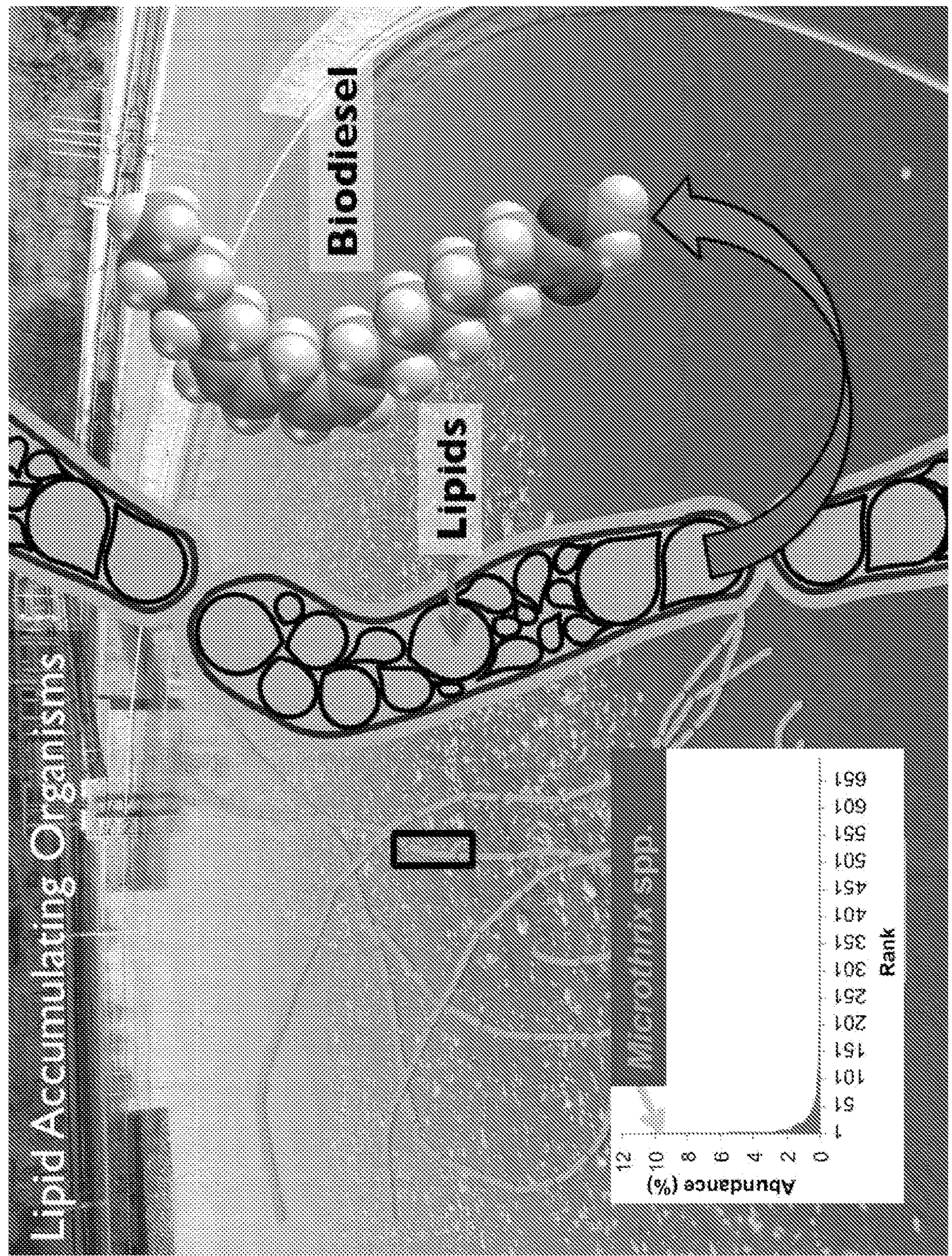
FIG. 16 depicts lipid accumulating organisms present in wastewater and highlights the importance of the filamentous bacteria *Microthrix* spp. among such organisms.
Figure 17:
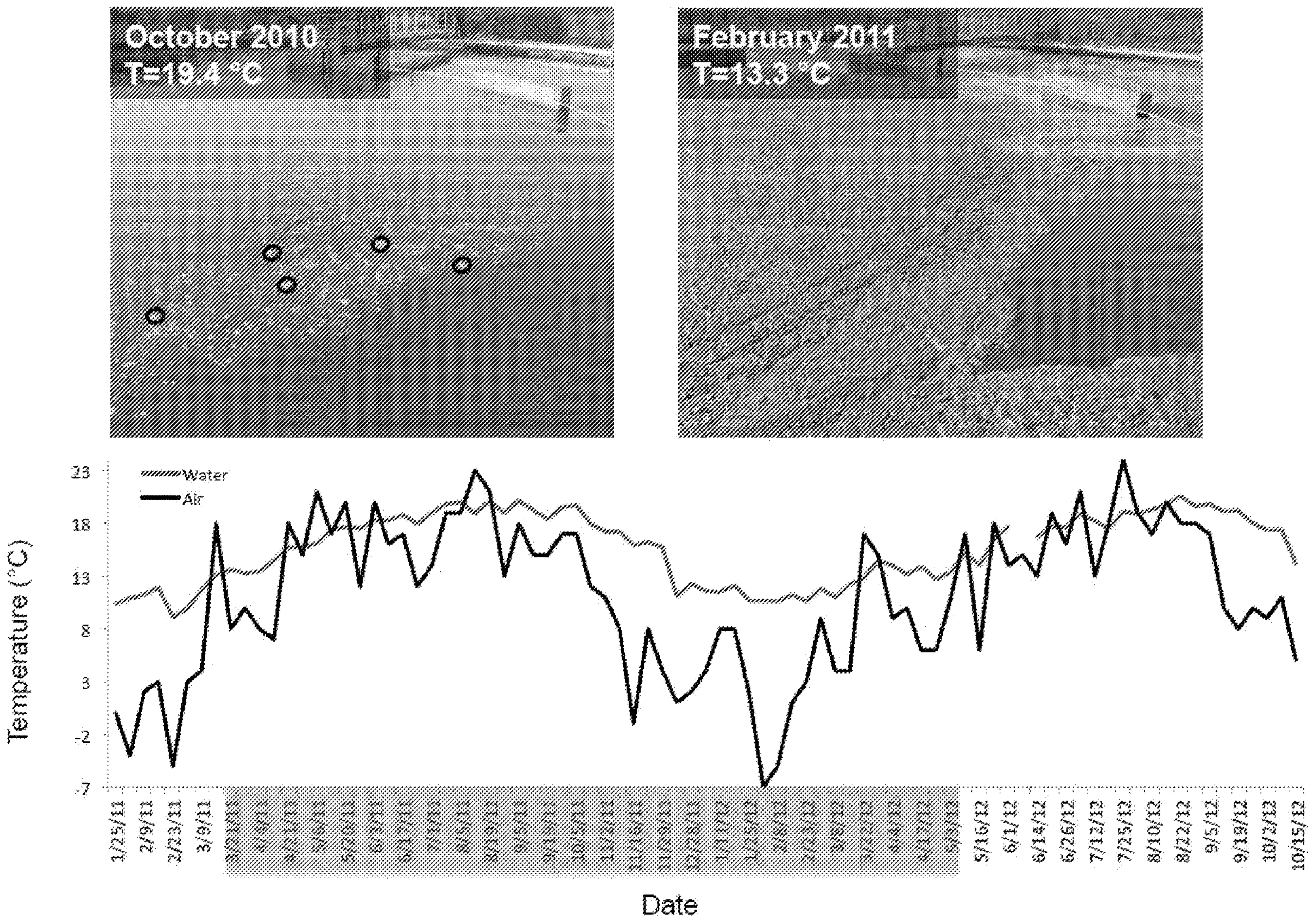
FIG. 17 depicts a model community of lipid accumulating organisms present in wastewater and the water and air temperatures in this community's environment over a period of about 9 months.

Biological wastewater treatment is arguably the most widely used biotechnological process on Earth. Wastewater also represents a valuable energy commodity that is currently not being harnessed comprehensively. Mixed microbial communities that naturally occur at the air-water interface of certain biological wastewater treatment systems accumulate excess long-chain-fatty-acids intracellularly (see FIGS. 15-17). This phenotypic trait may potentially be exploited for the transformation of wastewater into biodiesel (fatty acid methyl esters).

Using a molecular Eco-Systems Biology approach, we studied which organisms and genes contribute to the community-wide lipid accumulation phenotype and, thus, overall community function.

Methods

Figure 9:
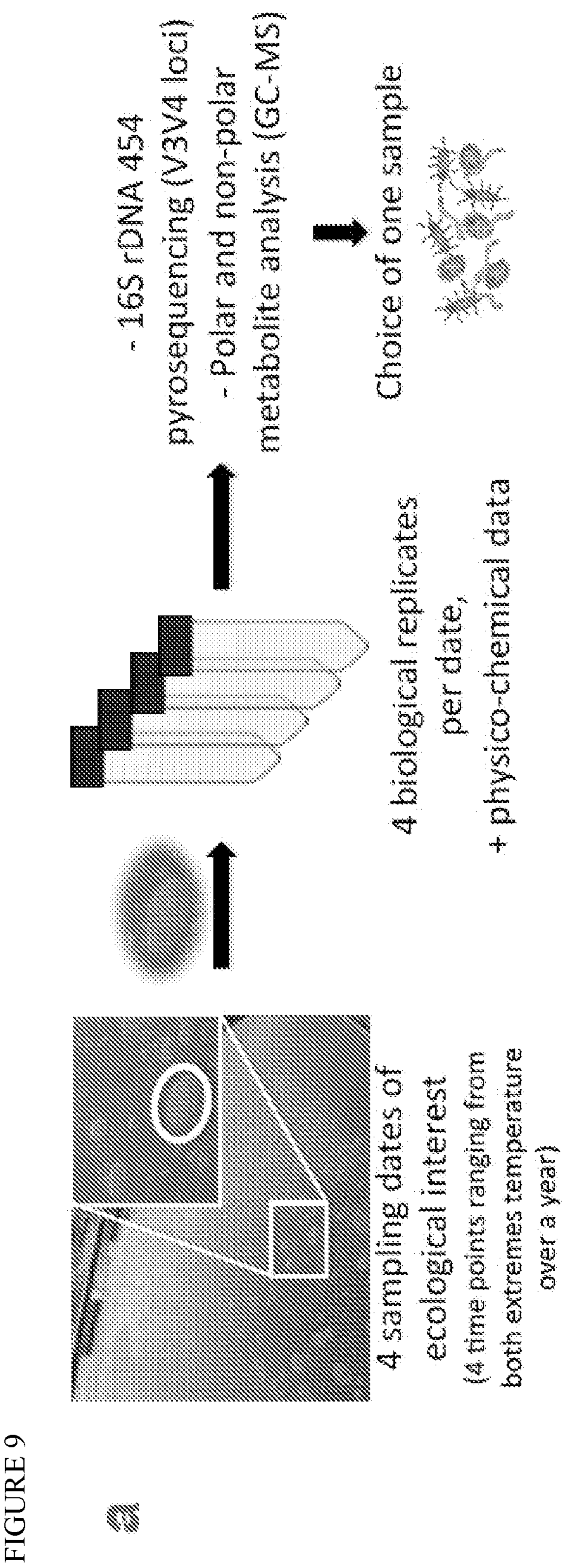
FIG. 9 depicts a workflow overview. (a) DNA and metabolites were extracted from 16 samples chosen for a representation of temporally, spatially and ecological distinct samples (4 time points ranging from both extremes temperatures over a year). (b) All biomolecular fractions were obtained from a single unique subsample (in house developed protocol; see Roume et al. (2013) The ISME Journal 7:110) and analyzed by high-throughput technologies.
Figure 9:
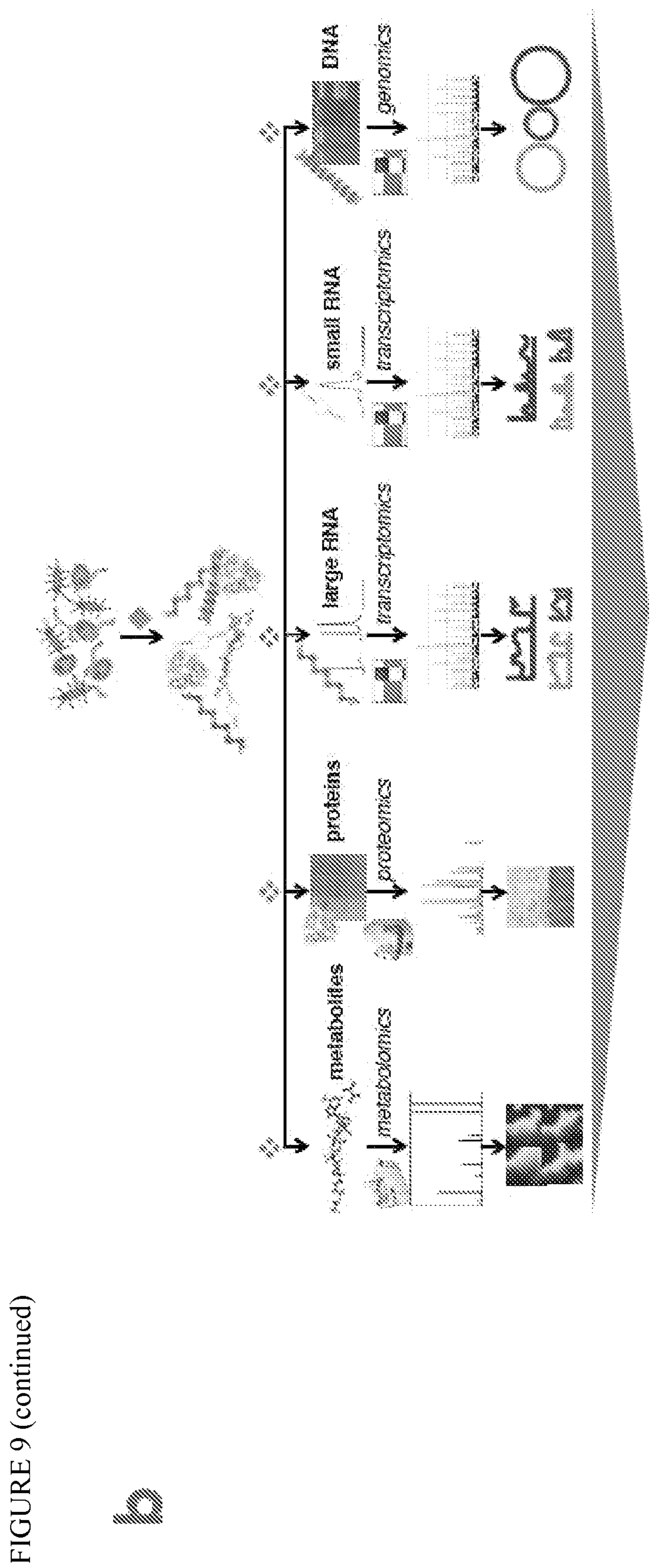

The experimental methods used for this study are outlined in FIG. 9.

Results

Figure 10:
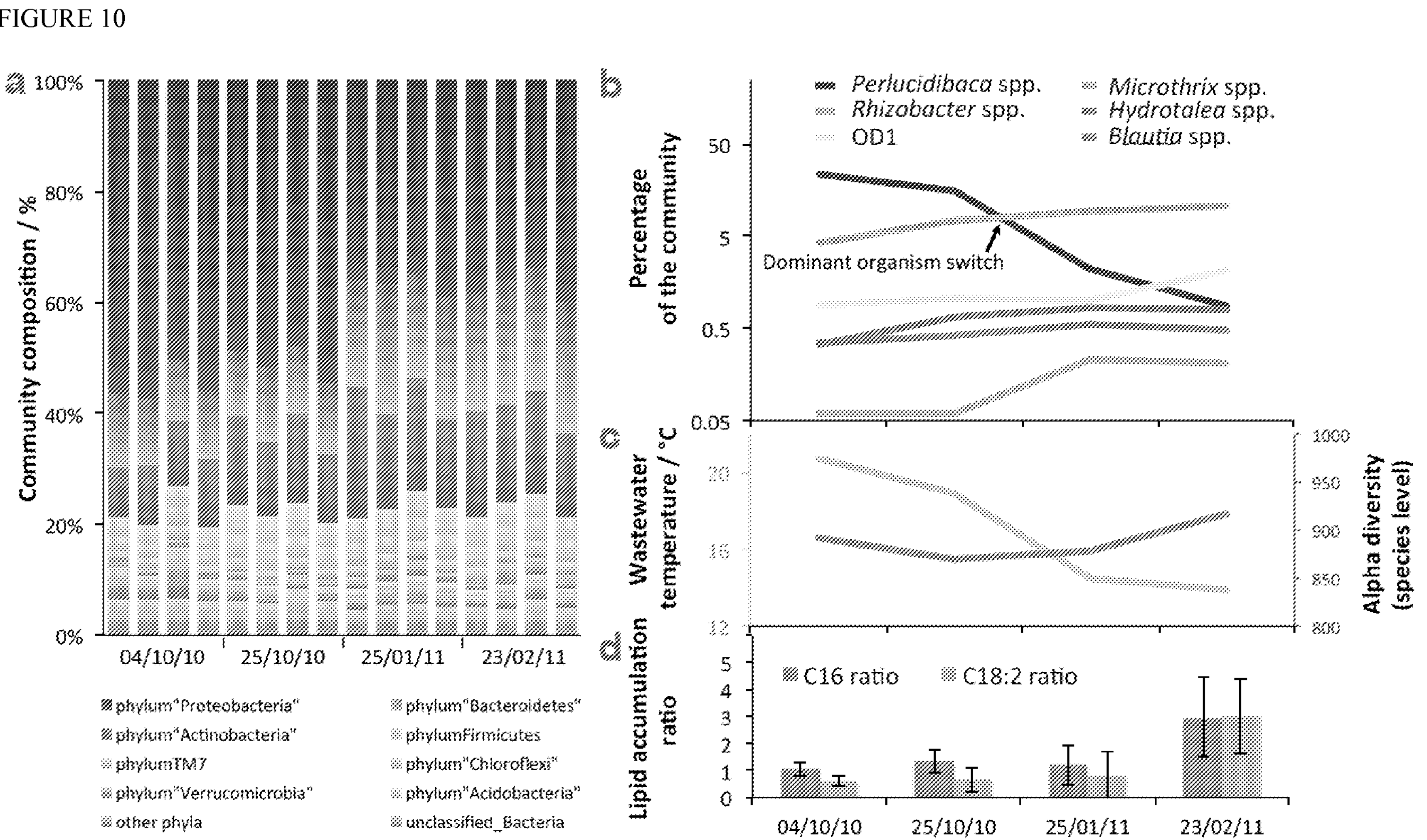
FIG. 10 depicts lipid accumulating community dynamics. (a) 16S phylotyping at the phylum-level of the community at 4 different time points for 4 biological replicates. (b) Dynamics of the 2 most abundant organisms and of 4 potential keystone species (see FIG. 11) of the community. (c) Wastewater temperature and alpha diversity over time. (d) Cellular accumulation of the 2 most abundant long chain fatty acids of the system, calculated by comparing the intracellular lipid concentration to the extracellular concentration.

It was observed that the community structure changes significantly over time, leading to a switch in the dominant organism, and biological replicates sampled the same day are highly heterogeneous. Biomass lipid accumulation was maximal when *Microthrix* spp. dominated the community (this corresponded with cold wastewater temperature) (see FIG. 10).

Figure 11:
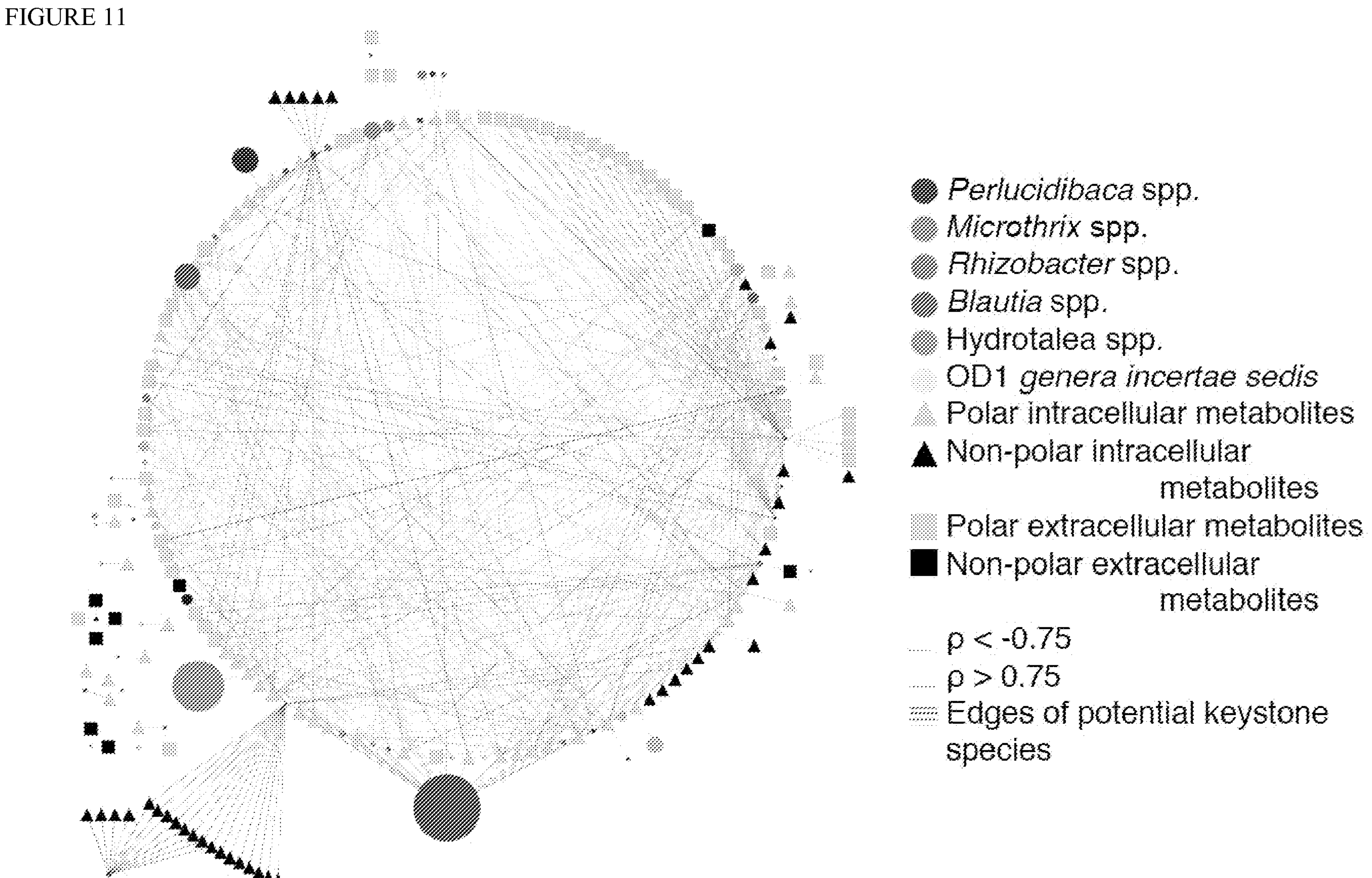
FIG. 11 depicts a 16S rRNA amplicon and intracellular/extracellular metabolites correlation network. Spearman correlations were calculated based on normalized abundances of conserved genus and metabolites. 4 species of low abundance (see FIG. 10*b*) show numerous edges with non-polar metabolites and particular long chain fatty acids, namely *Rhizobacter, Blautia, Hydrotalea* and OD1. The size of nodes are proportional to the average abundance of the taxa on the 16 samples, rho>0.75 or <−0.75, p<0.001.

Four species of low abundance (see FIG. 10*b*) predominated among those producing non-polar metabolites and particular long chain fatty acids, namely *Rhizobacter, Blautia, Hydrotalea* and OD1 (see FIG. 11).

Figure 12:
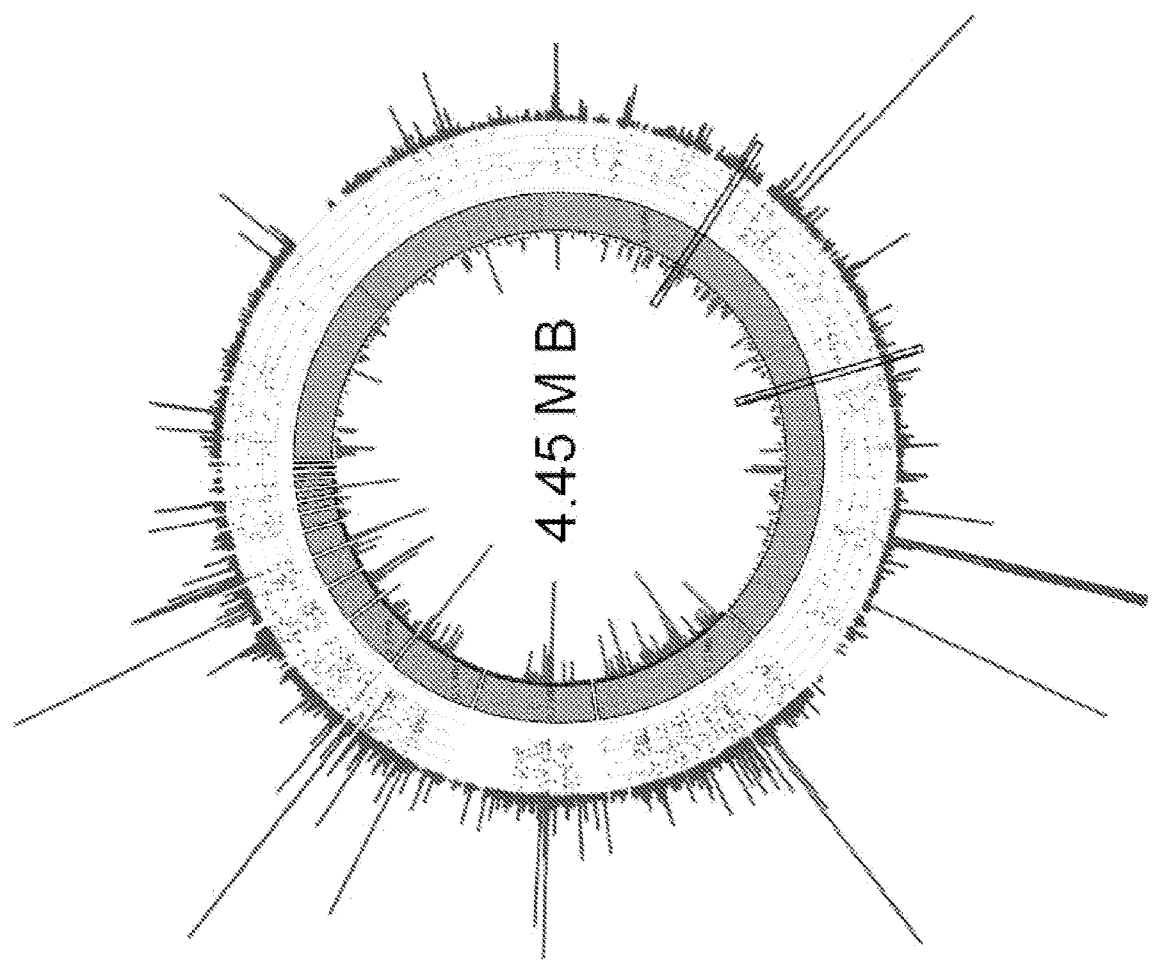
FIG. 12 depicts the *Microthrix parvicella* Bio17-1 genome with mapped variations as well as transcripts and protein abundances. The genome of the isolated strain Bio17-1 was sequenced (Illumina and PacBio) and assembled into 15 contigs (green) and automatically annotated through RAST. Orange bands represent the 25 homologs of long-chain-fatty-acid acyl-CoA ligase (named in orange) and black bands show other features annotated to belong to fatty acid/lipid metabolism subsystem. The size scale of contig 1 is different than for other contigs. The outer plot in blue represents the metatranscriptome (Illumina RNAseq reads mapped with bwa). Line height represents the average coverage (<=20 bp windows, scale 0-500). The red dots show SNP frequencies in the metatranscriptome (from 0 to 1, 0 being closer to the chromosome, phred >=20). The inner plot in red shows the peptide spectra mapping to the annotation feature (scale 0-250). Black rectangles highlight examples of long-chain-fatty-acid acyl-CoA ligase variant expression.
Figure 13:
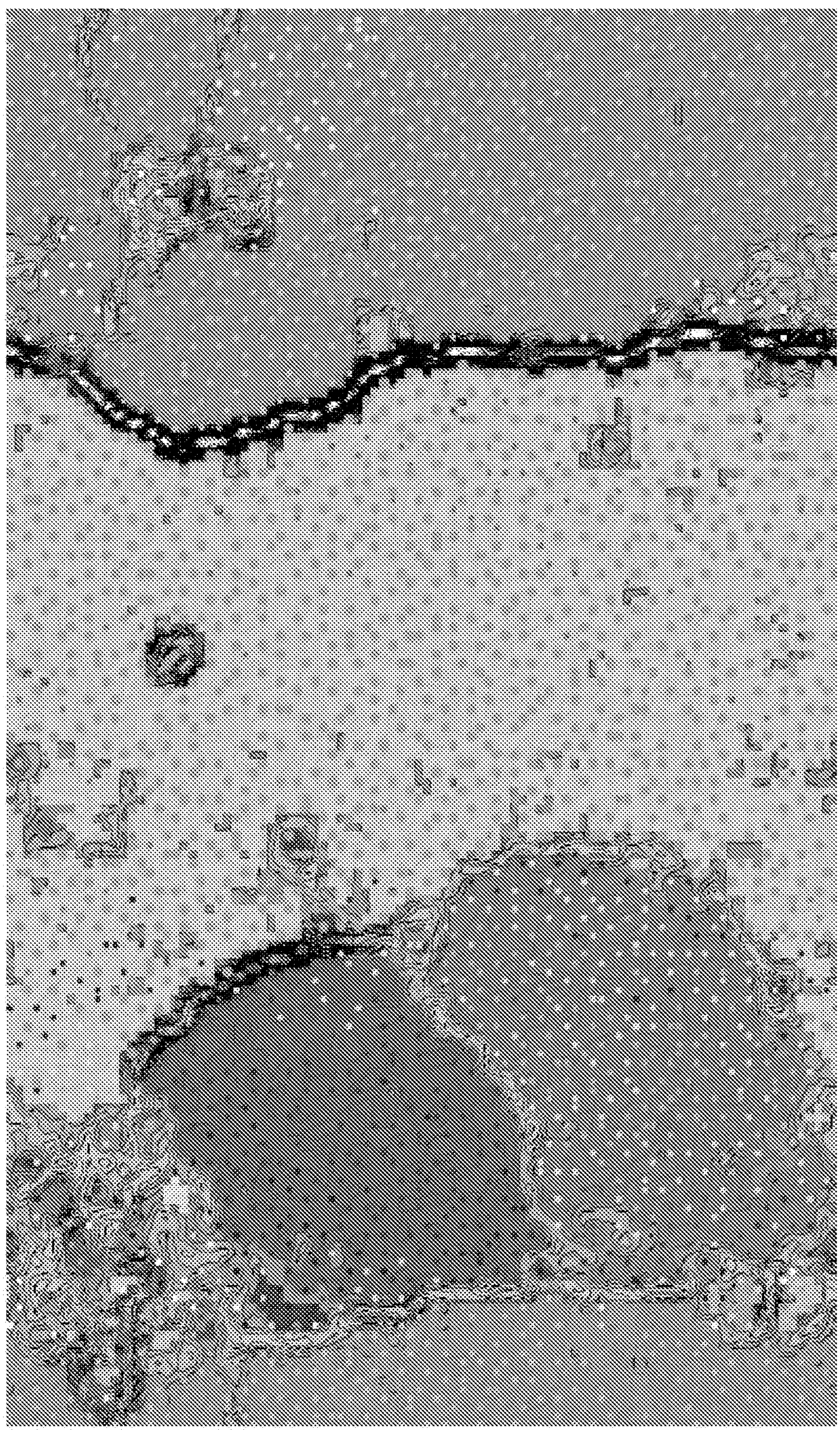
FIG. 13 depicts an emergent self-organizing map of metagenomic contigs (training set). Tetranucleotide frequencies were determined in order to cluster together reads belonging to the same organism. The different bins are color coded according to the topography. *Microthrix parvicella* Bio17-1 reads tetranucleotide frequencies are mapped with large violet dots in the training map. They all clustered with the yellow bin that can be defined as *Microthrix* spp. pangenome.
Figure 14:
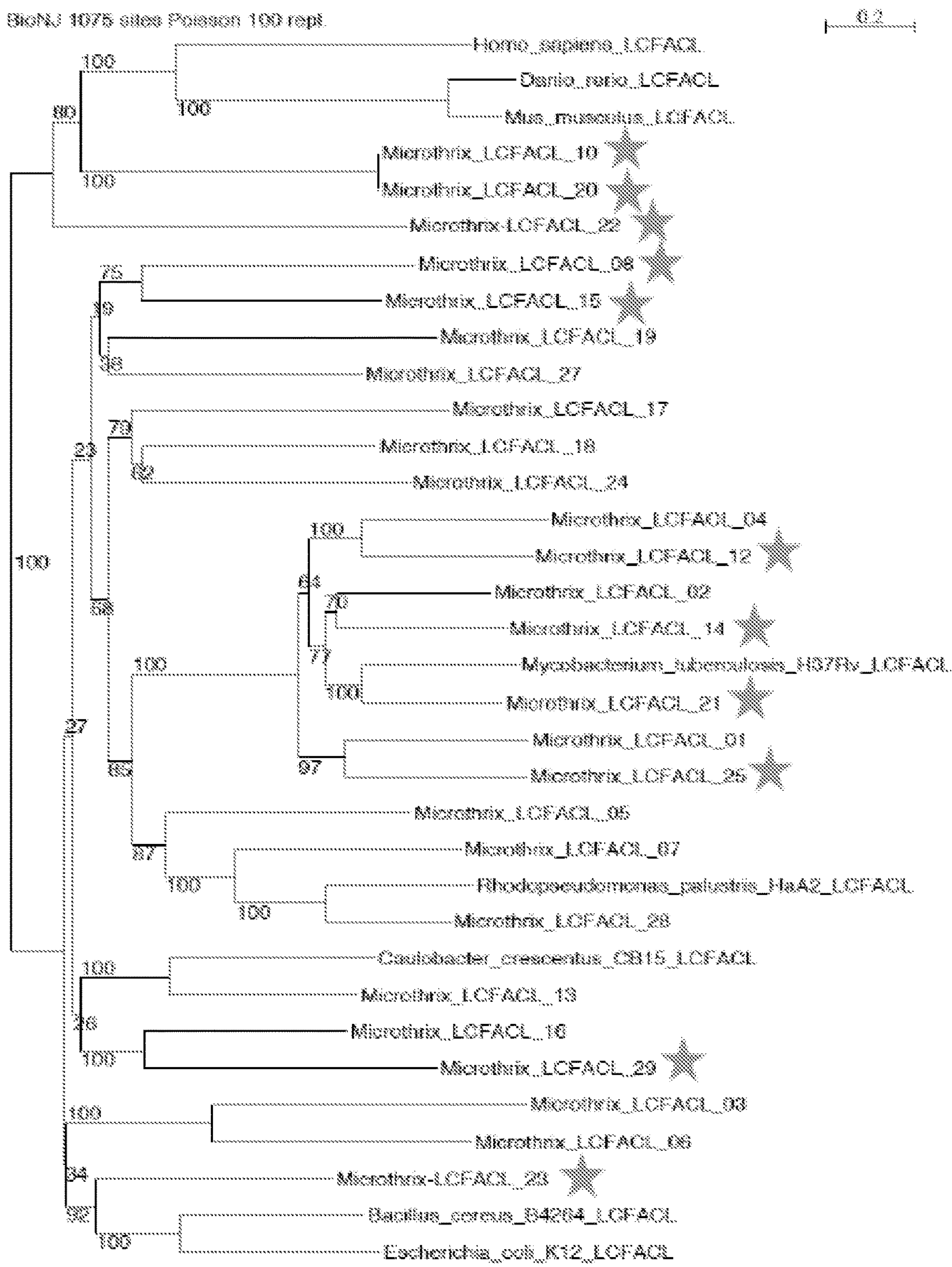
FIG. 14 depicts *Microthrix parvicella* Bio17-1 long-chain-fattyCoA ligase homologs. The phylogenetic tree was constructed by Bio-Neighbor Joining after ClustalW2 alignment of the amino-acid sequences. Homologs detected by metaproteomics are indicated with orange stars.
Figure 18:
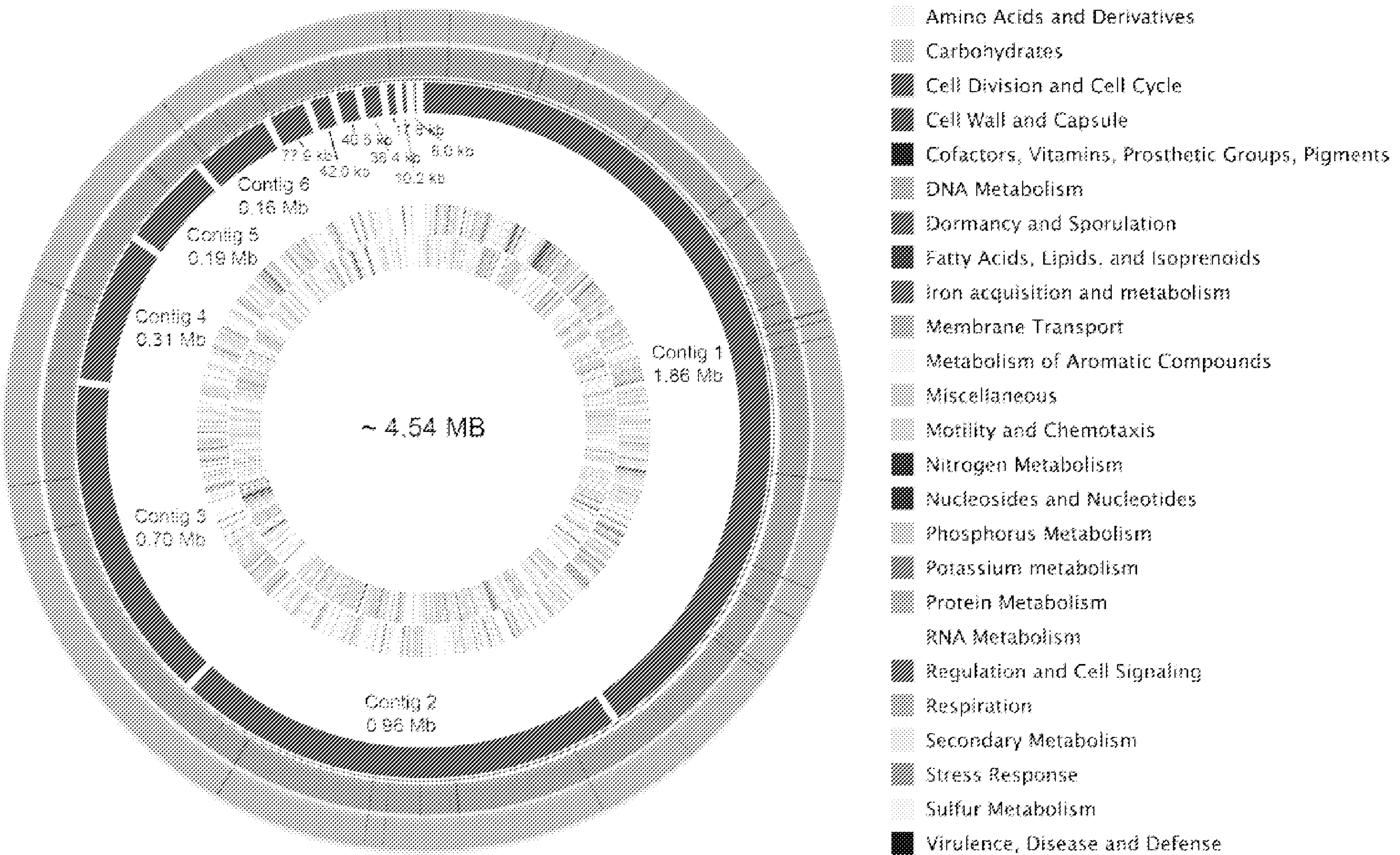
FIG. 18 depicts the *Candidatus Microthrix parvicella* Bio17-1 genome. Groups of genes are identified by their biological function, and their location in the genome is indicated with the various colors.

*Microthrix* spp. were key players within the community in the lipid accumulating phenotype (see FIG. 13). Sequencing of the *Microthrix parvicella* Bio17-1 genome uncovered 25 homologs of long-chain-fatty-acid acyl-CoA ligase (see FIGS. 11-12 and 18).

Conclusion

Functional meta-omic analyses offer exciting prospects for elucidating the genetic blueprints and the functional relevance of specific populations within microbial communities (if the biomolecular fractions used for high-throughput omics are coming from a single undivided sample). Connecting the overall community phenotype to specific genotypes allows much needed fundamental ecological understanding of microbial community and population dynamics, particularly in relation to environment-driven demography changes leading to tipping points and catastrophic bifurcations.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method of modifying a lipid or fatty acid comprising:

adding to a suitable feedstock a long-chain-fatty-acid-CoA-ligase, wherein the long-chain-fatty-acid-CoA-ligase facilitates processing of the lipid or fatty acid; and collecting and purifying the resulting lipid or fatty acid product;

wherein the long-chain-fatty-acid-CoA-ligase comprises a sequence selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, and SEQ ID NO: 56;

and the long-chain-fatty-acid-CoA-ligase is expressed in a culture of cells with the suitable feedstock at a temperature below 16° C.

2. The method of claim 1, wherein the suitable feedstock comprises wastewater or sewage sludge.

3. The method of claim 1, wherein the suitable feedstock is enriched in lipid material.

4. The method of claim 1, wherein the resulting lipid or fatty acid product comprises a fatty acid alkyl ester.

5. The method of claim 1, wherein the long-chain-fatty-acid-CoA-ligase is expressed in a culture of cells with the suitable feedstock at a temperature of 4° C. to 15° C.

6. A method of producing a biofuel or biofuel precursor, comprising:

adding to a suitable feedstock a long-chain-fatty-acid-CoA-ligase, wherein the long-chain-fatty-acid-CoA-ligase facilitates processing of a lipid or fatty acid into the biofuel or biofuel precursor; and collecting the biofuel or biofuel precursor;

wherein the long-chain-fatty-acid-CoA-ligase comprises a sequence selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, and SEQ ID NO: 56;

and the long-chain-fatty-acid-CoA-ligase is expressed in a culture of cells with the suitable feedstock at a temperature below 16° C.

7. The method of claim 6, wherein the suitable feedstock comprises wastewater or sewage sludge.

8. The method of claim 6, wherein the suitable feedstock is enriched in lipid material.

9. The method of claim 6, wherein the biofuel or biofuel precursor comprises a fatty acid alkyl ester.

10. The method of claim 6, wherein the long-chain-fatty-acid-CoA-ligase is expressed in a culture of cells with the suitable feedstock at a temperature of 4° C. to 15° C.

11. The method of claim 1, wherein the long-chain-fatty-acid-CoA-ligase is expressed by a genetically engineered recombinant host cell.

12. The method of claim 6, wherein the long-chain-fatty-acid-CoA-ligase is expressed by a genetically engineered recombinant host cell.

* * * * *

```
SEQUENCE LISTING

<160> NUMBER OF SEQ ID NOS: 114

<210> SEQ ID NO 1
<211> LENGTH: 1674
<212> TYPE: DNA
<213> ORGANISM: Candidatus Microthrix parvicella

<400> SEQUENCE: 1

atgcccagct tgcagaccaa catcgccgag gtgttcgagt cgttggccac tgccataccc      60

gaccgagagt gcatcgtgtt tcgggacctc cgcctcacct acgcccaggt gcaggatcgc     120

tgccatcagt tggcaaacgt cctgaccgat gcaggtttgg gcgtccagac cgaacgtggc     180

gaactggcca gccacgaaat cggccaggat gccctggcgc tgtacctcca caacggcaac     240

gaatacctgg agggcatgat cggcgcctac atggcccgca ccgccccctt caacgtcaac     300

taccgctacg tggccgagga gttgctgtac ctgctgaggg acagcggcgc ccgggccatc     360

atctaccact cggcgttcgc cccacactg gcagcggtat tgccgcagct cccccatctg      420

acggtgctgt tgcaggtgga cgacgactcg ggcaacgcgc tgttggacgg tgcccgttgg     480

tatgaggcgg ctttggcaga cgcatcgacc gacctcgacc cggcgcttcg cgcctcgtgg     540

tcgccggacg acctctacat cctctacacc ggtggcacca ccggcatgcc caagggcgtg     600

atgtggcgcc aggccgacat ttacgtctcc tcgcttggcg gcaggccctt cggcgcaccc     660

gaggaatggg aatcggttga cgccctcgtg gcggccgcag cagccgccaa ccccaccaag     720

acggtgcccg caccgccgtt catgcacggc gcggcacact gggcggcatt caccgccttc     780

tccaatgggg gaaccgtggt ggtgaccgac gtggtcgacc gcttcgatgc gccctcggtg     840

gtcgacctgc tcgcacggga gcaggccaac gtgctgctgc tggtgggcga cgcgtttgcc     900

cgccccctgc tggacgccgt cgatgcctcg gctgcgagcg gcaaacccgc cgacctgagc     960

gcgttgttcg tcctcacatc cggtggtgcc atcctgtcgg cgcccatcaa ggagcgtctg    1020

ttggagtcgc tcccaaacat catgttgatc gatgggctgg gaagctccga gacgggcacc    1080

caggccggac aggtttcgag cgccggcggc gatgtttcca ccgggcgctt ctcgccccac    1140
```

```
cccggcatgg tcgtgctcaa cgaggacctc acccgggtcc tcgaacccgg cgacgacgag   1200

atgggatggc tgggacagcg aaaccgagtg ccgctgggct atctgggcga cgaggccaag   1260

accgcccgca cgttccccga actggacggc gtccgctatg cggtgccggg ggatcgcagc   1320

cgcatcctgg ccgacggaac gctcgagctg tacggccgcg attcggtgac gatcaactcc   1380

ggcggcgaga agatcttcgc cgaggaggtg gagcaggcca tctccgccca tccgggggtc   1440

atcgacgtgg tggtgtgcgg gcgaccctcg gagcgctggg gcaacgaggt ggtcgccatc   1500

gtcaagctga ccgagggcgc gtcggccacc gaggacgagt tgctcaccga ggccgccaag   1560

cacgtggccc gatacaagtt gcccaaggcg atcgtttgga gagacgagat cgtgcgctcc   1620

cccgccggca aggccgacta ccgctgggcc aaagcgcagg cgaccgaggg ctga         1674
```

```
<210> SEQ ID NO 2
<211> LENGTH: 557
<212> TYPE: PRT
<213> ORGANISM: Candidatus Microthrix parvicella

<400> SEQUENCE: 2

Met Pro Ser Leu Gln Thr Asn Ile Ala Glu Val Phe Glu Ser Leu Ala
1               5                   10                  15

Thr Ala Ile Pro Asp Arg Glu Cys Ile Val Phe Arg Asp Leu Arg Leu
            20                  25                  30

Thr Tyr Ala Gln Val Gln Asp Arg Cys His Gln Leu Ala Asn Val Leu
        35                  40                  45

Thr Asp Ala Gly Leu Gly Val Gln Thr Glu Arg Gly Glu Leu Ala Ser
    50                  55                  60

His Glu Ile Gly Gln Asp Ala Leu Ala Leu Tyr Leu His Asn Gly Asn
65                  70                  75                  80

Glu Tyr Leu Glu Gly Met Ile Gly Ala Tyr Met Ala Arg Thr Ala Pro
                85                  90                  95

Phe Asn Val Asn Tyr Arg Tyr Val Ala Glu Glu Leu Leu Tyr Leu Leu
            100                 105                 110

Arg Asp Ser Gly Ala Arg Ala Ile Ile Tyr His Ser Ala Phe Ala Pro
        115                 120                 125

Thr Leu Ala Ala Val Leu Pro Gln Leu Pro His Leu Thr Val Leu Leu
    130                 135                 140

Gln Val Asp Asp Asp Ser Gly Asn Ala Leu Leu Asp Gly Ala Arg Trp
145                 150                 155                 160

Tyr Glu Ala Ala Leu Ala Asp Ala Ser Thr Asp Leu Asp Pro Ala Leu
                165                 170                 175

Arg Ala Ser Trp Ser Pro Asp Asp Leu Tyr Ile Leu Tyr Thr Gly Gly
            180                 185                 190

Thr Thr Gly Met Pro Lys Gly Val Met Trp Arg Gln Ala Asp Ile Tyr
        195                 200                 205

Val Ser Ser Leu Gly Gly Arg Pro Phe Gly Ala Pro Glu Glu Trp Glu
    210                 215                 220

Ser Val Asp Ala Leu Val Ala Ala Ala Ala Ala Ala Asn Pro Thr Lys
225                 230                 235                 240

Thr Val Pro Ala Pro Pro Phe Met His Gly Ala Ala His Trp Ala Ala
                245                 250                 255

Phe Thr Ala Phe Ser Asn Gly Gly Thr Val Val Val Thr Asp Val Val
            260                 265                 270

Asp Arg Phe Asp Ala Pro Ser Val Val Asp Leu Leu Ala Arg Glu Gln
```

```
        275                 280                 285

Ala Asn Val Leu Leu Leu Val Gly Asp Ala Phe Ala Arg Pro Leu Leu
    290                 295                 300

Asp Ala Val Asp Ala Ser Ala Ala Ser Gly Lys Pro Ala Asp Leu Ser
305                 310                 315                 320

Ala Leu Phe Val Leu Thr Ser Gly Gly Ala Ile Leu Ser Ala Pro Ile
                325                 330                 335

Lys Glu Arg Leu Leu Glu Ser Leu Pro Asn Ile Met Leu Ile Asp Gly
            340                 345                 350

Leu Gly Ser Ser Glu Thr Gly Thr Gln Ala Gly Gln Val Ser Ser Ala
        355                 360                 365

Gly Gly Asp Val Ser Thr Gly Arg Phe Ser Pro His Pro Gly Met Val
    370                 375                 380

Val Leu Asn Glu Asp Leu Thr Arg Val Leu Glu Pro Gly Asp Asp Glu
385                 390                 395                 400

Met Gly Trp Leu Gly Gln Arg Asn Arg Val Pro Leu Gly Tyr Leu Gly
                405                 410                 415

Asp Glu Ala Lys Thr Ala Arg Thr Phe Pro Glu Leu Asp Gly Val Arg
            420                 425                 430

Tyr Ala Val Pro Gly Asp Arg Ser Arg Ile Leu Ala Asp Gly Thr Leu
        435                 440                 445

Glu Leu Tyr Gly Arg Asp Ser Val Thr Ile Asn Ser Gly Gly Glu Lys
    450                 455                 460

Ile Phe Ala Glu Glu Val Glu Gln Ala Ile Ser Ala His Pro Gly Val
465                 470                 475                 480

Ile Asp Val Val Val Cys Gly Arg Pro Ser Glu Arg Trp Gly Asn Glu
                485                 490                 495

Val Val Ala Ile Val Lys Leu Thr Glu Gly Ala Ser Ala Thr Glu Asp
            500                 505                 510

Glu Leu Leu Thr Glu Ala Ala Lys His Val Ala Arg Tyr Lys Leu Pro
        515                 520                 525

Lys Ala Ile Val Trp Arg Asp Glu Ile Val Arg Ser Pro Ala Gly Lys
    530                 535                 540

Ala Asp Tyr Arg Trp Ala Lys Ala Gln Ala Thr Glu Gly
545                 550                 555
```

<210> SEQ ID NO 3
<211> LENGTH: 1353
<212> TYPE: DNA
<213> ORGANISM: Candidatus Microthrix parvicella

<400> SEQUENCE: 3

```
atgacggcag cagttgtgca gcgcgccggt ctggccgacg atgcccaggc gcggtcggcg      60

gggtggctga tcaacacggg gttgcgccct ggcgaccgcc tcgccatctc ggctcccagc     120

agtctcgact atctcaacgt ggccctgggt gcgctgcgca gcgggatgat accggtgttg     180

atcaacacgt cgctcctgaa ggacgaggtc gagtacatcc tgagcgacgc ccggcccgcc     240

atcgtaatgg gagaacacga ggtggttgca gccaccaaac atcaccggcg tgccgccttg     300

tcacggtggc ccctggggcg gccgatggcc tacacgtccg gcaccaccgg acagcccaaa     360

ggcgtctact cgggggtcct cagcgagacg gaggcccagt cgctctgggc cgaggaaatc     420

gatctgtggg gcatcaccgc cgcagacacc tacgtacaga tcggtccgct ctatcactcc     480

gctccgctgc gcttcgcagc ctgcgtgcaa ctggcgggcg ggtccgtggt cgttccgggc     540
```

-continued

```
ccgttccaag cggaacgcac cctgaaggcc atcctggagc actccccctc ggtcggtttc    600

gctgcaccca tccatctcaa aaggttgttc gccgtcgacc ctgacgatgc ctggaccgac    660

atgcgtctgc tggcccacgc cggcgcgccg tgcccaccgg aggtgtctgc ggaagccagg    720

cgacgctttg gagacgaagc ggtttgggag ttctatggca gcaccgaggg tcagttcacc    780

gtgtgctcgc cggccgatcg gctggctgcg cccgggtcgg ttggtcgagc tcgacccaac    840

cgcaggctcc ggctggacga cgacggccac atctggtgca ccgccccgcc cgccgccgcc    900

ttcacctact gggacgaccc ggagcgcacc aagctcgcat ggcgaaccac gtcggatggc    960

cacgccgaat tcaccgtggg tgatctgggc cgcctggtgg atggttacct gtacctggac   1020

gggcggcggg acgacctgat catctcgggt ggggtcaacg tctacccggc cgaggtcgag   1080

cgggtgttgc gccaggtgga cggcgtggag gacgtcgcag tgttcggcgt cgccgatgat   1140

gagtggggcg aggcggtcaa cgccgtggtg gtgccgcgct cacccgccga tcacaccgca   1200

gacaccacct tgatcgacgc cgtcaacgcg cacgcccacg cttccttggc gccctacaag   1260

cgccccaagc gggttctggt gcgcgcctcg atccccgtga gctcgaccgg aaaggtacgt   1320

cgctcgaccc tgtcgagcga gttggcccgt tag                                1353


<210> SEQ ID NO 4
<211> LENGTH: 450
<212> TYPE: PRT
<213> ORGANISM: Candidatus Microthrix parvicella

<400> SEQUENCE: 4

Met Thr Ala Ala Val Val Gln Arg Ala Gly Leu Ala Asp Asp Ala Gln
1               5                   10                  15

Ala Arg Ser Ala Gly Trp Leu Ile Asn Thr Gly Leu Arg Pro Gly Asp
            20                  25                  30

Arg Leu Ala Ile Ser Ala Pro Ser Ser Leu Asp Tyr Leu Asn Val Ala
        35                  40                  45

Leu Gly Ala Leu Arg Ser Gly Met Ile Pro Val Leu Ile Asn Thr Ser
    50                  55                  60

Leu Leu Lys Asp Glu Val Glu Tyr Ile Leu Ser Asp Ala Arg Pro Ala
65                  70                  75                  80

Ile Val Met Gly Glu His Glu Val Val Ala Ala Thr Lys His His Arg
                85                  90                  95

Arg Ala Ala Leu Ser Arg Trp Pro Leu Gly Arg Pro Met Ala Tyr Thr
            100                 105                 110

Ser Gly Thr Thr Gly Gln Pro Lys Gly Val Tyr Ser Gly Val Leu Ser
        115                 120                 125

Glu Thr Glu Ala Gln Ser Leu Trp Ala Glu Glu Ile Asp Leu Trp Gly
    130                 135                 140

Ile Thr Ala Ala Asp Thr Tyr Val Gln Ile Gly Pro Leu Tyr His Ser
145                 150                 155                 160

Ala Pro Leu Arg Phe Ala Ala Cys Val Gln Leu Ala Gly Gly Ser Val
                165                 170                 175

Val Val Pro Gly Pro Phe Gln Ala Glu Arg Thr Leu Lys Ala Ile Leu
            180                 185                 190

Glu His Ser Pro Ser Val Gly Phe Ala Ala Pro Ile His Leu Lys Arg
        195                 200                 205

Leu Phe Ala Val Asp Pro Asp Asp Ala Trp Thr Asp Met Arg Leu Leu
    210                 215                 220

Ala His Ala Gly Ala Pro Cys Pro Pro Glu Val Ser Ala Glu Ala Arg
```

```
225                 230                 235                 240

Arg Arg Phe Gly Asp Glu Ala Val Trp Glu Phe Tyr Gly Ser Thr Glu
                245                 250                 255

Gly Gln Phe Thr Val Cys Ser Pro Ala Asp Arg Leu Ala Ala Pro Gly
            260                 265                 270

Ser Val Gly Arg Ala Arg Pro Asn Arg Arg Leu Arg Leu Asp Asp Asp
        275                 280                 285

Gly His Ile Trp Cys Thr Ala Pro Pro Ala Ala Ala Phe Thr Tyr Trp
    290                 295                 300

Asp Asp Pro Glu Arg Thr Lys Leu Ala Trp Arg Thr Thr Ser Asp Gly
305                 310                 315                 320

His Ala Glu Phe Thr Val Gly Asp Leu Gly Arg Leu Val Asp Gly Tyr
                325                 330                 335

Leu Tyr Leu Asp Gly Arg Arg Asp Asp Leu Ile Ile Ser Gly Gly Val
            340                 345                 350

Asn Val Tyr Pro Ala Glu Val Glu Arg Val Leu Arg Gln Val Asp Gly
        355                 360                 365

Val Glu Asp Val Ala Val Phe Gly Val Ala Asp Asp Glu Trp Gly Glu
    370                 375                 380

Ala Val Asn Ala Val Val Val Pro Arg Ser Pro Ala Asp His Thr Ala
385                 390                 395                 400

Asp Thr Thr Leu Ile Asp Ala Val Asn Ala His Ala His Ala Ser Leu
                405                 410                 415

Ala Pro Tyr Lys Arg Pro Lys Arg Val Leu Val Arg Ala Ser Ile Pro
            420                 425                 430

Val Ser Ser Thr Gly Lys Val Arg Arg Ser Thr Leu Ser Ser Glu Leu
        435                 440                 445

Ala Arg
    450
```

<210> SEQ ID NO 5
<211> LENGTH: 1677
<212> TYPE: DNA
<213> ORGANISM: Candidatus Microthrix parvicella

<400> SEQUENCE: 5

```
gtgcacagcc tgatctcccg aatcgaacgc gcggccgaaa gcgatgccac cctcacggtg      60

gcctcgccgg aaggctacga caccaccacc tgggcacaga cccattccgc cgctcgatcg     120

ctggctgcgg ggctgcagac ttacggggtg acgccgggga cccacgtggc gctgctgggg     180

cccaccaccc ggccgttgat cacggcgatc caggccacct ggctcaccgg tggttgcctg     240

gtgatgttgc cgttaccgat gcgcctggga tcgattgagg cgttcgtcga acagaccaga     300

agccgaattc gcgccgctga ctgctcgctg gtgttgatcg acgagcagtt cgctgctttt     360

gttgaacgcg ccgaaggcga tccgcccttc gtggtcctgc aggatctggt ggcccgttcc     420

tccgagttgg cgccggccga ttggaagcgc cccgacgacg atcctgacgc gcttgcagtg     480

ctgcagttca cttcgggatc caccgccgag cccaaggggg tcatgctgcc ccatcgcacc     540

atctgcgcca accttgacgc ctgcacccag gccggaggcc tgatcgacga cgaggtgttc     600

gtctcgtggc tgccgctgta tcacgacatg gggttggtcg gcctgttgac cattccgatg     660

acgaccggtc gcaacctcgt gcaggcggcg cctcaagatt tcctgtcccg acctgcacga     720

tggatgcagt ggatctccga ctacggcggc acgatgacgg ccggacccaa cttcgcgtac     780

gcgctggctg ccagggcgtt gcggcgggcc gaggaactcg acctgtcgtc gctcgaggtg     840
```

```
ttgctgaatg gggccgagcc catcgacgcc gacgtattcc gtcggttcct cgcggcgggg    900

gagccgttcg ggctccgtcc cggtgcggcg tttcccgcct tcgggatggc cgaagttggc    960

attggtggcg ccttttctcg ccgctgggac ggctttcgta ccgatgtggt cgatgccgat   1020

gcattggagc acgagcacgt cgccaggccg ccgagtgagg atggcgcacc ggagggtgaa   1080

aagaccacca cgcgggaact ggcgctgctg ggccgggcgg tgcccgggct ggagatgcgc   1140

gtcgtcgatc gttccagtgg gcaggaactg ggtgaccgcc aggtgggtga gctgctgatt   1200

cgcggcacct cggtgacgcc gggctattac aagaaccccg aggcgaccgc cgaactgctg   1260

gtggacggat ggctgcacac cggtgacctt gcgtatctgc tggacggcga gctcgtggtg   1320

tgcggacgta tcaaggacgt gatcatcgtc ggtggccgca acatctaccc acaggacatc   1380

gagcgttcgg ccggtgacgt ggccggcgtg cggcccggca atgtgatcgc ctttggcgcc   1440

gacggtcggg cgggcgcgca atcgatcgtt gtggtggccg agttgggcga tgccgaggca   1500

gcgacggtgc gagacctcct gaccgagcgg atcaccagcg acatcggggt gccccccaag   1560

gaggtggtca tggtggccaa gggaacggtg cccaagacct cctccggcaa gctacagcgc   1620

tcactggcca agtcccggtg gctgaacggc gaactggaga ccgccggaac cagttag      1677
```

<210> SEQ ID NO 6
<211> LENGTH: 558
<212> TYPE: PRT
<213> ORGANISM: Candidatus Microthrix parvicella

<400> SEQUENCE: 6

```
Met His Ser Leu Ile Ser Arg Ile Glu Arg Ala Ala Glu Ser Asp Ala
1               5                   10                  15

Thr Leu Thr Val Ala Ser Pro Glu Gly Tyr Asp Thr Thr Thr Trp Ala
            20                  25                  30

Gln Thr His Ser Ala Ala Arg Ser Leu Ala Ala Gly Leu Gln Thr Tyr
        35                  40                  45

Gly Val Thr Pro Gly Thr His Val Ala Leu Leu Gly Pro Thr Thr Arg
    50                  55                  60

Pro Leu Ile Thr Ala Ile Gln Ala Thr Trp Leu Thr Gly Gly Cys Leu
65                  70                  75                  80

Val Met Leu Pro Leu Pro Met Arg Leu Gly Ser Ile Glu Ala Phe Val
                85                  90                  95

Glu Gln Thr Arg Ser Arg Ile Arg Ala Ala Asp Cys Ser Leu Val Leu
            100                 105                 110

Ile Asp Glu Gln Phe Ala Ala Phe Val Glu Arg Ala Glu Gly Asp Pro
        115                 120                 125

Pro Phe Val Val Leu Gln Asp Leu Val Ala Arg Ser Ser Glu Leu Ala
    130                 135                 140

Pro Ala Asp Trp Lys Arg Pro Asp Asp Asp Pro Asp Ala Leu Ala Val
145                 150                 155                 160

Leu Gln Phe Thr Ser Gly Ser Thr Ala Glu Pro Lys Gly Val Met Leu
                165                 170                 175

Pro His Arg Thr Ile Cys Ala Asn Leu Asp Ala Cys Thr Gln Ala Gly
            180                 185                 190

Gly Leu Ile Asp Asp Glu Val Phe Val Ser Trp Leu Pro Leu Tyr His
        195                 200                 205

Asp Met Gly Leu Val Gly Leu Leu Thr Ile Pro Met Thr Thr Gly Arg
    210                 215                 220
```

```
Asn Leu Val Gln Ala Ala Pro Gln Asp Phe Leu Ser Arg Pro Ala Arg
225                 230                 235                 240

Trp Met Gln Trp Ile Ser Asp Tyr Gly Gly Thr Met Thr Ala Gly Pro
                245                 250                 255

Asn Phe Ala Tyr Ala Leu Ala Ala Arg Ala Leu Arg Arg Ala Glu Glu
            260                 265                 270

Leu Asp Leu Ser Ser Leu Glu Val Leu Leu Asn Gly Ala Glu Pro Ile
        275                 280                 285

Asp Ala Asp Val Phe Arg Arg Phe Leu Ala Ala Gly Glu Pro Phe Gly
    290                 295                 300

Leu Arg Pro Gly Ala Ala Phe Pro Ala Phe Gly Met Ala Glu Val Gly
305                 310                 315                 320

Ile Gly Gly Ala Phe Ser Arg Arg Trp Asp Gly Phe Arg Thr Asp Val
                325                 330                 335

Val Asp Ala Asp Ala Leu Glu His Glu His Val Ala Arg Pro Pro Ser
            340                 345                 350

Glu Asp Gly Ala Pro Glu Gly Glu Lys Thr Thr Thr Arg Glu Leu Ala
        355                 360                 365

Leu Leu Gly Arg Ala Val Pro Gly Leu Glu Met Arg Val Val Asp Arg
    370                 375                 380

Ser Ser Gly Gln Glu Leu Gly Asp Arg Gln Val Gly Glu Leu Leu Ile
385                 390                 395                 400

Arg Gly Thr Ser Val Thr Pro Gly Tyr Tyr Lys Asn Pro Glu Ala Thr
                405                 410                 415

Ala Glu Leu Leu Val Asp Gly Trp Leu His Thr Gly Asp Leu Ala Tyr
            420                 425                 430

Leu Leu Asp Gly Glu Leu Val Val Cys Gly Arg Ile Lys Asp Val Ile
        435                 440                 445

Ile Val Gly Gly Arg Asn Ile Tyr Pro Gln Asp Ile Glu Arg Ser Ala
    450                 455                 460

Gly Asp Val Ala Gly Val Arg Pro Gly Asn Val Ile Ala Phe Gly Ala
465                 470                 475                 480

Asp Gly Arg Ala Gly Ala Gln Ser Ile Val Val Val Ala Glu Leu Gly
                485                 490                 495

Asp Ala Glu Ala Ala Thr Val Arg Asp Leu Leu Thr Glu Arg Ile Thr
            500                 505                 510

Ser Asp Ile Gly Val Pro Pro Lys Glu Val Val Met Val Ala Lys Gly
        515                 520                 525

Thr Val Pro Lys Thr Ser Ser Gly Lys Leu Gln Arg Ser Leu Ala Lys
    530                 535                 540

Ser Arg Trp Leu Asn Gly Glu Leu Glu Thr Ala Gly Thr Ser
545                 550                 555
```

<210> SEQ ID NO 7
<211> LENGTH: 2235
<212> TYPE: DNA
<213> ORGANISM: Candidatus Microthrix parvicella

<400> SEQUENCE: 7

```
atggccgtcc tgctcaacga catcgtggca acgcgaggcg acgaaccggc catcgtagat     60

ggccggggca cccgcacctg ggtccaactc aacgagcggg tcgaacgtct ggtgcacgcc    120

cttcgtgatc gcggcctcaa ctcgggcgac tgcgtgatgg ccatgctggg caaccaggcc    180

gaggccatcg aggtcgcgct cgcctgcgcc cacgggggct ggctgctcgt cccggtgaac    240
```

```
tggcactggg tggccgacga ggtcgcctac gtgctgggcg acaccgatgc ggcggccgtc    300

gtggtcgatg cccgctgggt cgaagtggtg accgctgccc tcgcccttgc gggcgccacc    360

gaagcagcgt tgccctcggt gcgcctgccg tcggtgcgcg tcctggtcga cggcccggac    420

gggcacggtg ccgatgaccc gcccgatggg ttcgagggat acgaggagct cgtcgcctcg    480

ggcgttccag gcgaaatcgc cgacgccgaa cggggcggcc cgatgtttta cacctcgggc    540

acgaccgggc gccccaaagg tgtgcgatcg gtgctgggca cggtcggcgg gcccccccgag    600

gtgctcaccc tgatcgccca ctcgctggca cccgcgatgg agctgcggat cacgagcgcc    660

tctgatcaac aagcggtcca ggccatttgt ggccccatct accactccgc gcaatgggtg    720

ttcgcccact tctcgctgtt gtgcggcaac gccgtcgtgc tccaacaccg cttcgatccg    780

gacgaactgt tgtcgttgat cgacgagcac caggtgacca acatccatct ggtcccaacc    840

caaatgatgc ggctgctgga ccttgacgat gagcgctggg ccgcgttctc aggtgactcg    900

ttgcgttcgg tcatccacgg cgccgccgcc tgcccgcccc agacaaagcg cgacctcatc    960

gatgccctcg gtcccatcgt caccgagtac tacgggggca cggagggcgg gttcatctcc   1020

gtgatcacct ccgacgagtg gctggaacga ccaggcagcg tcggcaagcc gttacccagc   1080

ttcgagcttg ccctgctcga cgacctgggc gagccggtgc cccagggcca acccgggcag   1140

gtctggtttc gcagcctgct gggcagcgac ttcgagtacc acaacgcacc ggacaagacg   1200

gcctcggcgc accgcaacgg ttttgggacg ttgggcgatg tcggctacct ggacgacgag   1260

ggttacctct tcctgtccgg ccgcaccatc gacatgatcg tgtcgggagg cgtcaacatc   1320

tacccggccg agatcgaggc ggtgttggcc gaccacccgg cgatctcaga cgtcgccgtg   1380

ttcgccgtgc cccatgccga gatgggcgag tcggtacacg ccgccgtttc gctggccgaa   1440

ggcctcgctt gggacgaggc gttggaggcc gacgtggtgg cctggtgtcg agaacgaatg   1500

gccggctata agtgcccccg cagcttcgag gtgcacgacg agcttccccg ctcggccgca   1560

ggcaagctgc tgaagtcgcc gctgcgcaag ccgtggtggc cggatacccc cgcccagacc   1620

ccgacccaat actgggaggc ccgctacctc gaccgcccac aggtgtggag cggcaaggtg   1680

aacccggtgc tggcggccga ggcggcgggc cggcatcccg gcacggccct cgaccttggt   1740

tgcggcgagg gcggcgacgc cctgtggctg gccgagcggg gctggaccgt gaccgccgtc   1800

gatatctcac agaccgcact cgaccgaggc gccgcccagg ccgctgaacg tggcctttca   1860

acgagcatcg tctggcagcg acacgagctg ggatcgtcgt ttccgacagg ggagtacgac   1920

ctggtgtcag cccagttcct ccactcccaa gtggcattgg cacgcgccga gatccttcag   1980

caggcgatgg gtgcggtggc gcccgggggc acgctgctga tcgtcagcca cgccgagttt   2040

ccgccgtggg ccgacgtggc agacgacgct ccggcgatgc catcacccga cgacgaactc   2100

gccgacctga gcgttgatcg ggcccggtgg gaggtgcagc gctgcgagac cgcagcgcgc   2160

ctggcaaccg gcccaggagg ccaggaggcc accctggtgg acggcatcat caagcttcgg   2220

cgcctcgacg cctga                                                    2235
```

<210> SEQ ID NO 8
<211> LENGTH: 744
<212> TYPE: PRT
<213> ORGANISM: Candidatus Microthrix parvicella

<400> SEQUENCE: 8

```
Met Ala Val Leu Leu Asn Asp Ile Val Ala Thr Arg Gly Asp Glu Pro
1               5                   10                  15
```

-continued

```
Ala Ile Val Asp Gly Arg Gly Thr Arg Thr Trp Val Gln Leu Asn Glu
            20                  25                  30

Arg Val Glu Arg Leu Val His Ala Leu Arg Asp Arg Gly Leu Asn Ser
        35                  40                  45

Gly Asp Cys Val Met Ala Met Leu Gly Asn Gln Ala Glu Ala Ile Glu
    50                  55                  60

Val Ala Leu Ala Cys Ala His Gly Gly Trp Leu Leu Val Pro Val Asn
65                  70                  75                  80

Trp His Trp Val Ala Asp Glu Val Ala Tyr Val Leu Gly Asp Thr Asp
                85                  90                  95

Ala Ala Ala Val Val Val Asp Ala Arg Trp Val Glu Val Val Thr Ala
            100                 105                 110

Ala Leu Ala Leu Ala Gly Ala Thr Glu Ala Ala Leu Pro Ser Val Arg
        115                 120                 125

Leu Pro Ser Val Arg Val Leu Val Asp Gly Pro Asp Gly His Gly Ala
    130                 135                 140

Asp Asp Pro Pro Asp Gly Phe Glu Gly Tyr Glu Glu Leu Val Ala Ser
145                 150                 155                 160

Gly Val Pro Gly Glu Ile Ala Asp Ala Glu Arg Gly Gly Pro Met Phe
                165                 170                 175

Tyr Thr Ser Gly Thr Thr Gly Arg Pro Lys Gly Val Arg Ser Val Leu
            180                 185                 190

Gly Thr Val Gly Gly Pro Pro Glu Val Leu Thr Leu Ile Ala His Ser
        195                 200                 205

Leu Ala Pro Ala Met Glu Leu Arg Ile Thr Ser Ala Ser Asp Gln Gln
    210                 215                 220

Ala Val Gln Ala Ile Cys Gly Pro Ile Tyr His Ser Ala Gln Trp Val
225                 230                 235                 240

Phe Ala His Phe Ser Leu Leu Cys Gly Asn Ala Val Val Leu Gln His
                245                 250                 255

Arg Phe Asp Pro Asp Glu Leu Leu Ser Leu Ile Asp Glu His Gln Val
            260                 265                 270

Thr Asn Ile His Leu Val Pro Thr Gln Met Met Arg Leu Leu Asp Leu
        275                 280                 285

Asp Asp Glu Arg Trp Ala Ala Phe Ser Gly Asp Ser Leu Arg Ser Val
    290                 295                 300

Ile His Gly Ala Ala Ala Cys Pro Pro Gln Thr Lys Arg Asp Leu Ile
305                 310                 315                 320

Asp Ala Leu Gly Pro Ile Val Thr Glu Tyr Tyr Gly Gly Thr Glu Gly
                325                 330                 335

Gly Phe Ile Ser Val Ile Thr Ser Asp Glu Trp Leu Glu Arg Pro Gly
            340                 345                 350

Ser Val Gly Lys Pro Leu Pro Ser Phe Glu Leu Ala Leu Leu Asp Asp
        355                 360                 365

Leu Gly Glu Pro Val Pro Gln Gly Gln Pro Gly Gln Val Trp Phe Arg
    370                 375                 380

Ser Leu Leu Gly Ser Asp Phe Glu Tyr His Asn Ala Pro Asp Lys Thr
385                 390                 395                 400

Ala Ser Ala His Arg Asn Gly Phe Gly Thr Leu Gly Asp Val Gly Tyr
                405                 410                 415

Leu Asp Asp Glu Gly Tyr Leu Phe Leu Ser Gly Arg Thr Ile Asp Met
            420                 425                 430

Ile Val Ser Gly Gly Val Asn Ile Tyr Pro Ala Glu Ile Glu Ala Val
```

```
        435                 440                 445

Leu Ala Asp His Pro Ala Ile Ser Asp Val Ala Val Phe Ala Val Pro
    450                 455                 460

His Ala Glu Met Gly Glu Ser Val His Ala Ala Val Ser Leu Ala Glu
465                 470                 475                 480

Gly Leu Ala Trp Asp Glu Ala Leu Glu Ala Asp Val Val Ala Trp Cys
                485                 490                 495

Arg Glu Arg Met Ala Gly Tyr Lys Cys Pro Arg Ser Phe Glu Val His
            500                 505                 510

Asp Glu Leu Pro Arg Ser Ala Ala Gly Lys Leu Leu Lys Ser Pro Leu
        515                 520                 525

Arg Lys Pro Trp Trp Pro Asp Thr Pro Ala Gln Thr Pro Thr Gln Tyr
    530                 535                 540

Trp Glu Ala Arg Tyr Leu Asp Arg Pro Gln Val Trp Ser Gly Lys Val
545                 550                 555                 560

Asn Pro Val Leu Ala Ala Glu Ala Ala Gly Arg His Pro Gly Thr Ala
                565                 570                 575

Leu Asp Leu Gly Cys Gly Glu Gly Gly Asp Ala Leu Trp Leu Ala Glu
            580                 585                 590

Arg Gly Trp Thr Val Thr Ala Val Asp Ile Ser Gln Thr Ala Leu Asp
        595                 600                 605

Arg Gly Ala Ala Gln Ala Ala Glu Arg Gly Leu Ser Thr Ser Ile Val
    610                 615                 620

Trp Gln Arg His Glu Leu Gly Ser Ser Phe Pro Thr Gly Glu Tyr Asp
625                 630                 635                 640

Leu Val Ser Ala Gln Phe Leu His Ser Gln Val Ala Leu Ala Arg Ala
                645                 650                 655

Glu Ile Leu Gln Gln Ala Met Gly Ala Val Ala Pro Gly Gly Thr Leu
            660                 665                 670

Leu Ile Val Ser His Ala Glu Phe Pro Pro Trp Ala Asp Val Ala Asp
        675                 680                 685

Asp Ala Pro Ala Met Pro Ser Pro Asp Asp Glu Leu Ala Asp Leu Ser
    690                 695                 700

Val Asp Arg Ala Arg Trp Glu Val Gln Arg Cys Glu Thr Ala Ala Arg
705                 710                 715                 720

Leu Ala Thr Gly Pro Gly Gly Gln Glu Ala Thr Leu Val Asp Gly Ile
                725                 730                 735

Ile Lys Leu Arg Arg Leu Asp Ala
            740
```

<210> SEQ ID NO 9
<211> LENGTH: 1593
<212> TYPE: DNA
<213> ORGANISM: Candidatus Microthrix parvicella

<400> SEQUENCE: 9

```
gtggagttca acttggccga tctcttcgag agcgtggtgg ccacggtgcc cgaggccgac      60

gccctggtcg caggcgaccg gcgacttacc taccgagcgc tcgacgaccg ggcaaaccgc     120

ctggccaatc acctcgccgc agcgggcgtc ggccgtgacg acttcgtcgg cctgcacctg     180

tccaacggca ccgagtacat cgaggcgatg ctcgcctgtt tcaagctgcg ggcggtgccg     240

gtcaacatca attggcgtta tgtcagcgcc gagttgcggt acctctacga ggacgccggg     300

ctggtgggcc tcatcgtgca ccgacgcttc ggcgaggcgg cgggtggggc gctcgacgcc     360
```

```
atcgccgatg cccgggtggt gctcgacgtc gacgacggaa ccgacgcccc acccatcggc    420

gaggactacg aggccgccct ggcatcctcg agcgttgagc cgtccttcgg cccacgctcg    480

gccgacgatc tctactgcgt ctacacgggt ggcacgacgg gcatgccaaa gggtgtgctg    540

tggcgccatg aggacatctt ctttgccgcc atgggaggcg gcgacccgat gcagttcggc    600

aacgtcatcg ccgagcccgg cgaactcgcc gatcgggtgc tcagcccggg tcttgtcgag    660

ctgccggtgc cgccgctgat gcacgccagt gcccagtggc tcgccttcca cacgttcttt    720

ggtggcggca aactggtgtt gtcgccgggt ggaacgttcg atcccgccgc catttggcgc    780

ctggtggcgg acgagggcgt gaacatcctg gtcatcgtcg gagacgccat ggcccggccc    840

cttctggatc atttggatga gtttggtggc gacgacgagt tgtcctcgtt gatggcgctc    900

ggatcgggcg gagcgatcct gtctccatcc accaagtcac gtctcagggg gcggttcaag    960

gatctggtga tcgtcgatgc ctttggtgca tccgagaccg gccagcttgg gggaaagcct   1020

cccgaggccg acccattcgg cgcccccgagg ctgacggcca acgagcacac gacggtcttc   1080

gacgatgagt ttcgtccggt gcaaccgggg tccggcgtca tcgggctcct cgcccgtgga   1140

gggcgggtcc cccttcgcta ccacggcgac cccgccaaga cggcggccac gttcgtggag   1200

gtcgacggcg tgcgctggtc gctgccaggc gacgaggcca ccatcgcctc cgacggcacc   1260

atcgaactgc tgggccgctc cgcccagtgc atcaacaccg gcggtgagaa ggtctatgcg   1320

gaggaggtcg agactgtcct cttggggcat cccgacatcg aggacgtggt cgtggtcggc   1380

gtgcccgacg atcggtgggg tcaccgggtg gtcgccgtcg cctccgcacg tgccggccgc   1440

agcgtgagtc tcgacgacct gcgccggcac ggccaagccg acctcgcctc ctacaagctg   1500

ccccgagatc tggtggtggt cgacgagatc gttcgacaac ccagcggaaa gcccgactac   1560

cggtgggcgg tcggcgtcgc cgaggagaac tga                                1593
```

<210> SEQ ID NO 10
<211> LENGTH: 530
<212> TYPE: PRT
<213> ORGANISM: Candidatus Microthrix parvicella

<400> SEQUENCE: 10

```
Met Glu Phe Asn Leu Ala Asp Leu Phe Glu Ser Val Val Ala Thr Val
1               5                   10                  15

Pro Glu Ala Asp Ala Leu Val Ala Gly Asp Arg Arg Leu Thr Tyr Arg
            20                  25                  30

Ala Leu Asp Asp Arg Ala Asn Arg Leu Ala Asn His Leu Ala Ala Ala
        35                  40                  45

Gly Val Gly Arg Asp Asp Phe Val Gly Leu His Leu Ser Asn Gly Thr
    50                  55                  60

Glu Tyr Ile Glu Ala Met Leu Ala Cys Phe Lys Leu Arg Ala Val Pro
65                  70                  75                  80

Val Asn Ile Asn Trp Arg Tyr Val Ser Ala Glu Leu Arg Tyr Leu Tyr
                85                  90                  95

Glu Asp Ala Gly Leu Val Gly Leu Ile Val His Arg Arg Phe Gly Glu
            100                 105                 110

Ala Ala Gly Gly Ala Leu Asp Ala Ile Ala Asp Ala Arg Val Val Leu
        115                 120                 125

Asp Val Asp Asp Gly Thr Asp Ala Pro Pro Ile Gly Glu Asp Tyr Glu
    130                 135                 140

Ala Ala Leu Ala Ser Ser Ser Val Glu Pro Ser Phe Gly Pro Arg Ser
145                 150                 155                 160
```

```
Ala Asp Asp Leu Tyr Cys Val Tyr Thr Gly Gly Thr Thr Gly Met Pro
                165                 170                 175

Lys Gly Val Leu Trp Arg His Glu Asp Ile Phe Phe Ala Ala Met Gly
            180                 185                 190

Gly Gly Asp Pro Met Gln Phe Gly Asn Val Ile Ala Glu Pro Gly Glu
        195                 200                 205

Leu Ala Asp Arg Val Leu Ser Pro Gly Leu Val Glu Leu Pro Val Pro
    210                 215                 220

Pro Leu Met His Ala Ser Ala Gln Trp Leu Ala Phe His Thr Phe Phe
225                 230                 235                 240

Gly Gly Gly Lys Leu Val Leu Ser Pro Gly Gly Thr Phe Asp Pro Ala
                245                 250                 255

Ala Ile Trp Arg Leu Val Ala Asp Glu Gly Val Asn Ile Leu Val Ile
            260                 265                 270

Val Gly Asp Ala Met Ala Arg Pro Leu Leu Asp His Leu Asp Glu Phe
        275                 280                 285

Gly Gly Asp Asp Glu Leu Ser Ser Leu Met Ala Leu Gly Ser Gly Gly
    290                 295                 300

Ala Ile Leu Ser Pro Ser Thr Lys Ser Arg Leu Arg Gly Arg Phe Lys
305                 310                 315                 320

Asp Leu Val Ile Val Asp Ala Phe Gly Ala Ser Glu Thr Gly Gln Leu
                325                 330                 335

Gly Gly Lys Pro Pro Glu Ala Asp Pro Phe Gly Ala Pro Arg Leu Thr
            340                 345                 350

Ala Asn Glu His Thr Thr Val Phe Asp Asp Glu Phe Arg Pro Val Gln
        355                 360                 365

Pro Gly Ser Gly Val Ile Gly Leu Leu Ala Arg Gly Gly Arg Val Pro
    370                 375                 380

Leu Arg Tyr His Gly Asp Pro Ala Lys Thr Ala Ala Thr Phe Val Glu
385                 390                 395                 400

Val Asp Gly Val Arg Trp Ser Leu Pro Gly Asp Glu Ala Thr Ile Ala
                405                 410                 415

Ser Asp Gly Thr Ile Glu Leu Leu Gly Arg Ser Ala Gln Cys Ile Asn
            420                 425                 430

Thr Gly Gly Glu Lys Val Tyr Ala Glu Glu Val Glu Thr Val Leu Leu
        435                 440                 445

Gly His Pro Asp Ile Glu Asp Val Val Val Val Gly Val Pro Asp Asp
    450                 455                 460

Arg Trp Gly His Arg Val Val Ala Val Ala Ser Ala Arg Ala Gly Arg
465                 470                 475                 480

Ser Val Ser Leu Asp Asp Leu Arg Arg His Gly Gln Ala Asp Leu Ala
                485                 490                 495

Ser Tyr Lys Leu Pro Arg Asp Leu Val Val Val Asp Glu Ile Val Arg
            500                 505                 510

Gln Pro Ser Gly Lys Pro Asp Tyr Arg Trp Ala Val Gly Val Ala Glu
        515                 520                 525

Glu Asn
    530
```

<210> SEQ ID NO 11
<211> LENGTH: 369
<212> TYPE: DNA
<213> ORGANISM: Candidatus Microthrix parvicella

<400> SEQUENCE: 11
gtgtccaggc tacgacggct cgacgccgac gggtacatga cgctcaccga ccgcatcaag 60
gacatgatca tcaccggcgg gcacaacgtc tactcgatcg aggtggagaa cgccctggcc 120
gcacaccccg acgtcgccga ctgcgccatc gtggcgaggc cgcacctcac ctacggcgag 180
agcatcgtcg caatcatcac cccggtcgag ggtgcaacga tcaccctccc ccaggtccag 240
gagttctgtc gggaacgcct ctcgcactac aaggtgcccc acgacctgat cgtccgtccg 300
atccctcgca acccgtccgg aaagatcatg aagcacgtca gccgaaccga gatggccgac 360
gccgactga 369

<210> SEQ ID NO 12
<211> LENGTH: 122
<212> TYPE: PRT
<213> ORGANISM: Candidatus Microthrix parvicella

<400> SEQUENCE: 12

Met Ser Arg Leu Arg Arg Leu Asp Ala Asp Gly Tyr Met Thr Leu Thr
1 5 10 15

Asp Arg Ile Lys Asp Met Ile Ile Thr Gly Gly His Asn Val Tyr Ser
20 25 30

Ile Glu Val Glu Asn Ala Leu Ala Ala His Pro Asp Val Ala Asp Cys
35 40 45

Ala Ile Val Ala Arg Pro His Leu Thr Tyr Gly Glu Ser Ile Val Ala
50 55 60

Ile Ile Thr Pro Val Glu Gly Ala Thr Ile Thr Leu Pro Gln Val Gln
65 70 75 80

Glu Phe Cys Arg Glu Arg Leu Ser His Tyr Lys Val Pro His Asp Leu
85 90 95

Ile Val Arg Pro Ile Pro Arg Asn Pro Ser Gly Lys Ile Met Lys His
100 105 110

Val Ser Arg Thr Glu Met Ala Asp Ala Asp
115 120

<210> SEQ ID NO 13
<211> LENGTH: 1737
<212> TYPE: DNA
<213> ORGANISM: Candidatus Microthrix parvicella

<400> SEQUENCE: 13
atggggttca acgagaattt tgcgaccgtg tgggaggcga ttgcggatga actggtcgac 60
gcaccggcgc tgtcgcacgg cccgctgacg cggagttggg ccgagctgga tactcgcgcc 120
gctcggtttg ccggagcgct cgccgcgttc ggcgtcggcg cagaagccaa ggtggggttg 180
gcgttgtaca acggcccggc ctacaccgag gtcacctacg gcgcgttcaa ggcccgggcg 240
gtgccgttca acgtgaacta ccggtatcgc gaagccgagc tggcctacct gctggacaac 300
gccgattgcg aggtggtggt ggcccacccc gagttggtgg agcgcatcga ggccgttcgc 360
gatcaggtgc cgtcgatccg gcttctggtg gtggtgggcg gcgagaccga tgcgtcacct 420
tcacccgaac cacccgacgg ctgggtccac tacgagcgtc tgttggccga cgctgaacca 480
gcgcgccgca tcgagcgctc cggtgacgac ctgtggttcc tctacaccgg tggcaccacc 540
ggtatgccca agggggtgat gtggcctcat cgctcgctgc tgggggtgtt tgcccccaca 600
tggaagggct tgaagcagcc gctgccaacc accccggtgg aggcggcagc gaccgctcga 660
cgacttcgtg atcagtcggc cgagcagcga ctgatacctg cggcgccgat gatgcacggc 720

```
acctcgtcgc agctgacgct gggcgggctg agcgcgggcg cccacgtcat caccctgccg    780
tcgcgcagct ttgatgcagc tcggctgtgg gcgacggtgg aggaccgatc cgccagtcac    840
ctctgcatcg tcggcgacgc gttctgtcga ccgatgatcg ccgaactgga agccgccgag    900
gctgcgggga cgccctacaa cctggcatcg ctgaaggtgg tgacgtcgtc gggcgccatg    960
tggtcgtcgg cccaaaagga ggcgctgctg gaacgggcgc cggcgctgct gatcgacctg   1020
ctgggctcgt cggagggcaa cggatttggt gcgtcggtgg cccgacgggg gcgcagcgcc   1080
gggaccgccc ggtttcagct gggtgatcat gcggcggtgt ttaccgaaga cggccgaagg   1140
gtggagcccg gttcgggga gcgcggcatg ctggccaccg gcggacacct cccgcttggc    1200
tactacaaag acccggtgaa gaccgctgcg acctatccgg tctacgaggg acggcgttgg   1260
gccgtgcccg gcgactacgc caccgtcgag agcgacaaca ccatcacgct gctggggcgg   1320
ggttcggtgt gcatcaacac cgctggagag aaggtgtttc ccgaagaggt ggaggaggcg   1380
accaagtcgc tcgactgggt gatcgatgcc accgtggtcg gcgtgcccga caaaaagtgg   1440
ggcagcgcag tgacagccgt cgtctccctg gggtcgaaca ggcccgccgg ggtggcttcg   1500
ccgcccgccg ggtcgggaac gctcgctgcg tcggacctcc tcggacaggt tcgcgaacac   1560
gtcaaagatc agctggctgc ttacaaggcg ccccgacacg tggtggtggt ggacgccgtg   1620
aagcgtggtc ctaacggcaa ggctgactac cgctgggcca ccgagatcgc cgaggttgcg   1680
ctgggccatg gcacgtccgc accctcggcc gagcctgtgc gctccggtcg tccgtga      1737
```

```
<210> SEQ ID NO 14
<211> LENGTH: 578
<212> TYPE: PRT
<213> ORGANISM: Candidatus Microthrix parvicella

<400> SEQUENCE: 14

Met Gly Phe Asn Glu Asn Phe Ala Thr Val Trp Glu Ala Ile Ala Asp
1               5                   10                  15

Glu Leu Val Asp Ala Pro Ala Leu Ser His Gly Pro Leu Thr Arg Ser
            20                  25                  30

Trp Ala Glu Leu Asp Thr Arg Ala Ala Arg Phe Ala Gly Ala Leu Ala
        35                  40                  45

Ala Phe Gly Val Gly Ala Glu Ala Lys Val Gly Leu Ala Leu Tyr Asn
    50                  55                  60

Gly Pro Ala Tyr Thr Glu Val Thr Tyr Gly Ala Phe Lys Ala Arg Ala
65                  70                  75                  80

Val Pro Phe Asn Val Asn Tyr Arg Tyr Arg Glu Ala Glu Leu Ala Tyr
                85                  90                  95

Leu Leu Asp Asn Ala Asp Cys Glu Val Val Val Ala His Pro Glu Leu
            100                 105                 110

Val Glu Arg Ile Glu Ala Val Arg Asp Gln Val Pro Ser Ile Arg Leu
        115                 120                 125

Leu Val Val Val Gly Gly Glu Thr Asp Ala Ser Pro Ser Pro Glu Pro
    130                 135                 140

Pro Asp Gly Trp Val His Tyr Glu Arg Leu Leu Ala Asp Ala Glu Pro
145                 150                 155                 160

Ala Arg Arg Ile Glu Arg Ser Gly Asp Asp Leu Trp Phe Leu Tyr Thr
                165                 170                 175

Gly Gly Thr Thr Gly Met Pro Lys Gly Val Met Trp Pro His Arg Ser
            180                 185                 190
```

```
Leu Leu Gly Val Phe Ala Pro Thr Trp Lys Gly Leu Lys Gln Pro Leu
        195                 200                 205

Pro Thr Thr Pro Val Glu Ala Ala Ala Thr Ala Arg Arg Leu Arg Asp
    210                 215                 220

Gln Ser Ala Glu Gln Arg Leu Ile Pro Ala Ala Pro Met Met His Gly
225                 230                 235                 240

Thr Ser Ser Gln Leu Thr Leu Gly Gly Leu Ser Ala Gly Ala His Val
                245                 250                 255

Ile Thr Leu Pro Ser Arg Ser Phe Asp Ala Ala Arg Leu Trp Ala Thr
            260                 265                 270

Val Glu Asp Arg Ser Ala Ser His Leu Cys Ile Val Gly Asp Ala Phe
        275                 280                 285

Cys Arg Pro Met Ile Ala Glu Leu Glu Ala Ala Glu Ala Ala Gly Thr
    290                 295                 300

Pro Tyr Asn Leu Ala Ser Leu Lys Val Val Thr Ser Ser Gly Ala Met
305                 310                 315                 320

Trp Ser Ser Ala Gln Lys Glu Ala Leu Leu Glu Arg Ala Pro Ala Leu
                325                 330                 335

Leu Ile Asp Leu Leu Gly Ser Ser Glu Gly Asn Gly Phe Gly Ala Ser
            340                 345                 350

Val Ala Arg Arg Gly Arg Ser Ala Gly Thr Ala Arg Phe Gln Leu Gly
        355                 360                 365

Asp His Ala Ala Val Phe Thr Glu Asp Gly Arg Arg Val Glu Pro Gly
    370                 375                 380

Ser Gly Glu Arg Gly Met Leu Ala Thr Gly Gly His Leu Pro Leu Gly
385                 390                 395                 400

Tyr Tyr Lys Asp Pro Val Lys Thr Ala Ala Thr Tyr Pro Val Tyr Glu
                405                 410                 415

Gly Arg Arg Trp Ala Val Pro Gly Asp Tyr Ala Thr Val Glu Ser Asp
            420                 425                 430

Asn Thr Ile Thr Leu Leu Gly Arg Gly Ser Val Cys Ile Asn Thr Ala
        435                 440                 445

Gly Glu Lys Val Phe Pro Glu Glu Val Glu Glu Ala Thr Lys Ser Leu
    450                 455                 460

Asp Trp Val Ile Asp Ala Thr Val Val Gly Val Pro Asp Lys Lys Trp
465                 470                 475                 480

Gly Ser Ala Val Thr Ala Val Val Ser Leu Gly Ser Asn Arg Pro Ala
                485                 490                 495

Gly Val Ala Ser Pro Pro Ala Gly Ser Gly Thr Leu Ala Ala Ser Asp
            500                 505                 510

Leu Leu Gly Gln Val Arg Glu His Val Lys Asp Gln Leu Ala Ala Tyr
        515                 520                 525

Lys Ala Pro Arg His Val Val Val Val Asp Ala Val Lys Arg Gly Pro
    530                 535                 540

Asn Gly Lys Ala Asp Tyr Arg Trp Ala Thr Glu Ile Ala Glu Val Ala
545                 550                 555                 560

Leu Gly His Gly Thr Ser Ala Pro Ser Ala Glu Pro Val Arg Ser Gly
                565                 570                 575

Arg Pro
```

<210> SEQ ID NO 15
<211> LENGTH: 1593
<212> TYPE: DNA
<213> ORGANISM: Candidatus Microthrix parvicella

<400> SEQUENCE: 15

```
gtgagcacac cggagaccgc cgacacgatc tgggaactgg ttgaggcacg ggcgcaggcc      60
acacccgacg ccgtaatgct catcgacgag gcggatacca agctcacctg tgtccaactg     120
cgcgacgcgg cactgagcac cgccgccggg ctggccgcga tgggcatcgg cgaaaacacg     180
ccggtcacct ggcagttgcc gaccacgatc gatgccgttg tcacctcgct ggcactggcc     240
cgcctcggtg cgctgcagaa cccgatcctg cacatctacc gggagcgcga gctgggggtg     300
gccatcaggc gtacccgtcc cgagttggtg atcgtgcccg gcgagtggat gggtaccgac     360
tttgaggcga tgaccgccgg ggtgctcgac agcctggaag gtgacgacgt ggacggtgca     420
gcccgcccgt gcgtgctcag cctggccgac ggtcgcccta cgggcgatgc cgctactctg     480
gcgccttttg cgccgcctga cgacccggcc accgcggtgc gctggatcta ttacacgtcg     540
ggcaccacgt ccgagcccaa gggcgtgcgc cacaccgacg ccacgttgtt ggccggtggg     600
cgaggcctgg cggcagcggt cgacctgggc gccgacgatg tcgggtcgat ggcgtttccg     660
tatgcccaca tcgcaggacc cgactacctg atcatgtgtc tgcactccgg gtttccgttt     720
gtactcatcg ggcattcaa cccgcccgcc gccgtcgaga cgtacaaccg ctatggcgtg     780
acgatgatcg gcggctcgac ggcgttctac cagatgttcc tggccgagca ggccaagacc     840
ccggggacga agttcattcc cacgttgaag ctgatctccg gcggaggcgc ccccaagccg     900
cccgagttgg ccgcccgcat tcgcgatgag atcggtgtac cggtgtgcca cggatacggc     960
atgaccgagg tgccgatgat tgcacagggg tcgccccgcg acaccgagga gcaattggcc    1020
aacaccgagg gggccccggt gcctggatgc gaggttcgca tcgtcaccga ggacggctcg    1080
gtggcatcga ccgggcagga gggcgaggtt cgcctcaagg gccccatggt gtgcttgggc    1140
tacaccgacg cggaggcaac cgcagccgcg ttcgacgacg agggttggtt ccgcaccggc    1200
gacctgggca tcctgcgaga cgatggccac cttgcgctga ccgggcgcct gaaggatgtg    1260
atcatccgca agggtgagaa catctcggcg aaggaggtgg aggatctgct cttcacccac    1320
cccaaagtgg ccgatgttgc cgtcatcggc ttgccggacg aggatcgcgg cgaacgcgtt    1380
gccgccgtcg tggaacgggc tgagggcgtt gacgacctga catttgccga aatgtctgct    1440
catctcaacg ccgcagggct gatgacccgc aagatccccg agcagcttga ggtcgtcgag    1500
gccctgccgc gaaacgaaac gttgcgcaag gtgctgaagt tcaagctgcg ggagacctac    1560
gcggatgtac cgtggacccc ggaaccccgc tga                                 1593
```

<210> SEQ ID NO 16
<211> LENGTH: 530
<212> TYPE: PRT
<213> ORGANISM: Candidatus Microthrix parvicella

<400> SEQUENCE: 16

```
Met Ser Thr Pro Glu Thr Ala Asp Thr Ile Trp Glu Leu Val Glu Ala
1               5                   10                  15

Arg Ala Gln Ala Thr Pro Asp Ala Val Met Leu Ile Asp Glu Ala Asp
            20                  25                  30

Thr Lys Leu Thr Cys Val Gln Leu Arg Asp Ala Ala Leu Ser Thr Ala
        35                  40                  45

Ala Gly Leu Ala Ala Met Gly Ile Gly Glu Asn Thr Pro Val Thr Trp
    50                  55                  60

Gln Leu Pro Thr Thr Ile Asp Ala Val Val Thr Ser Leu Ala Leu Ala
65                  70                  75                  80
```

```
Arg Leu Gly Ala Leu Gln Asn Pro Ile Leu His Ile Tyr Arg Glu Arg
                85                  90                  95

Glu Leu Gly Val Ala Ile Arg Arg Thr Arg Pro Glu Leu Val Ile Val
            100                 105                 110

Pro Gly Glu Trp Met Gly Thr Asp Phe Glu Ala Met Thr Ala Gly Val
        115                 120                 125

Leu Asp Ser Leu Glu Gly Asp Asp Val Asp Gly Ala Ala Arg Pro Cys
    130                 135                 140

Val Leu Ser Leu Ala Asp Gly Arg Pro Thr Gly Asp Ala Ala Thr Leu
145                 150                 155                 160

Ala Pro Phe Ala Pro Pro Asp Asp Pro Ala Thr Ala Val Arg Trp Ile
                165                 170                 175

Tyr Tyr Thr Ser Gly Thr Thr Ser Glu Pro Lys Gly Val Arg His Thr
            180                 185                 190

Asp Ala Thr Leu Leu Ala Gly Gly Arg Gly Leu Ala Ala Ala Val Asp
        195                 200                 205

Leu Gly Ala Asp Asp Val Gly Ser Met Ala Phe Pro Tyr Ala His Ile
    210                 215                 220

Ala Gly Pro Asp Tyr Leu Ile Met Cys Leu His Ser Gly Phe Pro Phe
225                 230                 235                 240

Val Leu Ile Gly Ala Phe Asn Pro Pro Ala Ala Val Glu Thr Tyr Asn
                245                 250                 255

Arg Tyr Gly Val Thr Met Ile Gly Gly Ser Thr Ala Phe Tyr Gln Met
            260                 265                 270

Phe Leu Ala Glu Gln Ala Lys Thr Pro Gly Thr Lys Phe Ile Pro Thr
        275                 280                 285

Leu Lys Leu Ile Ser Gly Gly Gly Ala Pro Lys Pro Pro Glu Leu Ala
    290                 295                 300

Ala Arg Ile Arg Asp Glu Ile Gly Val Pro Val Cys His Gly Tyr Gly
305                 310                 315                 320

Met Thr Glu Val Pro Met Ile Ala Gln Gly Ser Pro Arg Asp Thr Glu
                325                 330                 335

Glu Gln Leu Ala Asn Thr Glu Gly Ala Pro Val Pro Gly Cys Glu Val
            340                 345                 350

Arg Ile Val Thr Glu Asp Gly Ser Val Ala Ser Thr Gly Gln Glu Gly
        355                 360                 365

Glu Val Arg Leu Lys Gly Pro Met Val Cys Leu Gly Tyr Thr Asp Ala
    370                 375                 380

Glu Ala Thr Ala Ala Ala Phe Asp Asp Glu Gly Trp Phe Arg Thr Gly
385                 390                 395                 400

Asp Leu Gly Ile Leu Arg Asp Asp Gly His Leu Ala Leu Thr Gly Arg
                405                 410                 415

Leu Lys Asp Val Ile Ile Arg Lys Gly Glu Asn Ile Ser Ala Lys Glu
            420                 425                 430

Val Glu Asp Leu Leu Phe Thr His Pro Lys Val Ala Asp Val Ala Val
        435                 440                 445

Ile Gly Leu Pro Asp Glu Asp Arg Gly Glu Arg Val Ala Ala Val Val
    450                 455                 460

Glu Arg Ala Glu Gly Val Asp Asp Leu Thr Phe Ala Glu Met Ser Ala
465                 470                 475                 480

His Leu Asn Ala Ala Gly Leu Met Thr Arg Lys Ile Pro Glu Gln Leu
                485                 490                 495
```

```
Glu Val Val Glu Ala Leu Pro Arg Asn Glu Thr Leu Arg Lys Val Leu
            500                 505                 510

Lys Phe Lys Leu Arg Glu Thr Tyr Ala Asp Val Pro Trp Thr Pro Glu
        515                 520                 525

Pro Arg
    530
```

<210> SEQ ID NO 17
<211> LENGTH: 1758
<212> TYPE: DNA
<213> ORGANISM: Candidatus Microthrix parvicella

<400> SEQUENCE: 17

```
atggacccgc acgttccgac gctgttcgac gcgatcgcct cgcaccgccc aaccgccgcc      60

gccattcgaa cacgcaacca caccaccacg tgggcggact tggcgtcccg taccgatgcg     120

ctcgcggcgg cactggcggc caccgggatc ggtcgtcgct ccacagcaga cgatggtccg     180

gcccaaccgt gggagtgccc caacccacgc gtggccctgt acctccacaa tcacccggcc     240

tacctggagg ccatggtcgg tgcgtggaag gccggggcaa cagcgatgaa cgtcaactac     300

cgctaccgcg ccaccgaact tgtcgacctc ctcaatgacg gcacaccgga ggcgatcgtg     360

taccaccggt gcttcacacc aacgctgcac gaggtactga cccggctgca gatcgtgccc     420

aggttgctgg tgtgtgtgcc tgacgagtcc gaccacgacc ttctgccggg tgcgatcctg     480

tacgaggacc tgctgagggc ggccgggccg ctggacaacg aggtgcgacg ccaatggagt     540

cacgaggacc ggtacctggt gtacaccggc ggcaccaccg gcacgccaaa gggggtgctg     600

tggcgccaga gcgattttgc ggtctcggcg ctgggtttcg ccccggcagc gctcagccgg     660

ggggtcaccg agtgggcacg ccggttgccg ccggacggcc cggccacgtt gcctgctccc     720

ccgttcatgc acggtgccgc ccattggaac gcactggccg catggctcaa gggcggcacc     780

gtcgtcctgc cggaacatcc tgagcgattc gatcccgacg cggtgctcga tgccgtggag     840

tggggtgccg cgtcggcgct gatcatcgtg gggatgcct tcgctcgtcc cctgctggag     900

gccgaccgag ggcgtcaccg cgagctggcc tcgctgcgtc acctgctgac cggcggcgca     960

accctgtcgc cggcggtcaa ggcacagctc atcgaacggt ggccgcacct caccgtggtg    1020

gacgtgctcg gcagctcgga gtcggggaga caagccgtgc acaggcatcg tgcagtcaca    1080

gccgtgcaca ggcatcgtgc agtcacagcc gtgcacaggc atcgtgcagt cacagccgtg    1140

cacaggcatc gtgcagtcac agctcgtgag gccgtaccgg acgcccgggt ctttcagccc    1200

gacgacgcca cggtcatcct caacgaatcg gtttcggcga tcatcgagcc accggccgcc    1260

ggcgagcagt cggaggtcgg atggttggcc cggcggggtc gggttccgct ggggtacctc    1320

ggccatccac aacgcacggc ggcaacgttc ccggtactcg acgggcagca cctggccgtc    1380

accggggacc gggcccggta caccctcgcc ggcgacgacc aactgcggat cgaactgctg    1440

ggtcgcgaat cggcctgtat caacaccgga ggcgaaaagg tgtttgccga ggaggttgag    1500

gtctgcctca accggcaccc ggcggtggtc gacctgctgg ttgccccggc cgtcgacgag    1560

cagttcggtc aggcggtcgg agtcgtggcg gccctgaggc ccggtgcctc ggtgaacctg    1620

gacgaccttc ggcagtttgg acgcctgtcg ttggccgact acaagctgcc tcgacgcctg    1680

gtggtggtgg acgaggtggt gcgctctcca agtggcaaac ccgactatcg ctgggctcgg    1740

agccaactcg accgatga                                                  1758
```

<210> SEQ ID NO 18

<211> LENGTH: 585
<212> TYPE: PRT
<213> ORGANISM: Candidatus Microthrix parvicella

<400> SEQUENCE: 18

```
Met Asp Pro His Val Pro Thr Leu Phe Asp Ala Ile Ala Ser His Arg
1               5                   10                  15

Pro Thr Ala Ala Ala Ile Arg Thr Arg Asn His Thr Thr Thr Trp Ala
            20                  25                  30

Asp Leu Ala Ser Arg Thr Asp Ala Leu Ala Ala Ala Leu Ala Ala Thr
        35                  40                  45

Gly Ile Gly Arg Arg Ser Thr Ala Asp Asp Gly Pro Ala Gln Pro Trp
    50                  55                  60

Glu Cys Pro Asn Pro Arg Val Ala Leu Tyr Leu His Asn His Pro Ala
65                  70                  75                  80

Tyr Leu Glu Ala Met Val Gly Ala Trp Lys Ala Gly Ala Thr Ala Met
                85                  90                  95

Asn Val Asn Tyr Arg Tyr Arg Ala Thr Glu Leu Val Asp Leu Leu Asn
            100                 105                 110

Asp Gly Thr Pro Glu Ala Ile Val Tyr His Arg Cys Phe Thr Pro Thr
        115                 120                 125

Leu His Glu Val Leu Thr Arg Leu Gln Ile Val Pro Arg Leu Leu Val
    130                 135                 140

Cys Val Pro Asp Glu Ser Asp His Asp Leu Leu Pro Gly Ala Ile Leu
145                 150                 155                 160

Tyr Glu Asp Leu Leu Arg Ala Ala Gly Pro Leu Asp Asn Glu Val Arg
                165                 170                 175

Arg Gln Trp Ser His Glu Asp Arg Tyr Leu Val Tyr Thr Gly Gly Thr
            180                 185                 190

Thr Gly Thr Pro Lys Gly Val Leu Trp Arg Gln Ser Asp Phe Ala Val
        195                 200                 205

Ser Ala Leu Gly Phe Ala Pro Ala Ala Leu Ser Arg Gly Val Thr Glu
    210                 215                 220

Trp Ala Arg Arg Leu Pro Pro Asp Gly Pro Ala Thr Leu Pro Ala Pro
225                 230                 235                 240

Pro Phe Met His Gly Ala Ala His Trp Asn Ala Leu Ala Ala Trp Leu
                245                 250                 255

Lys Gly Gly Thr Val Val Leu Pro Glu His Pro Glu Arg Phe Asp Pro
            260                 265                 270

Asp Ala Val Leu Asp Ala Val Glu Trp Gly Ala Ala Ser Ala Leu Ile
        275                 280                 285

Ile Val Gly Asp Ala Phe Ala Arg Pro Leu Leu Glu Ala Asp Arg Gly
    290                 295                 300

Arg His Arg Glu Leu Ala Ser Leu Arg His Leu Leu Thr Gly Gly Ala
305                 310                 315                 320

Thr Leu Ser Pro Ala Val Lys Ala Gln Leu Ile Glu Arg Trp Pro His
                325                 330                 335

Leu Thr Val Val Asp Val Leu Gly Ser Ser Glu Ser Gly Arg Gln Ala
            340                 345                 350

Val His Arg His Arg Ala Val Thr Ala Val His Arg His Arg Ala Val
        355                 360                 365

Thr Ala Val His Arg His Arg Ala Val Thr Ala Val His Arg His Arg
    370                 375                 380

Ala Val Thr Ala Arg Glu Ala Val Pro Asp Ala Arg Val Phe Gln Pro
```

```
385                 390                 395                 400

Asp Asp Ala Thr Val Ile Leu Asn Glu Ser Val Ser Ala Ile Ile Glu
                405                 410                 415

Pro Pro Ala Ala Gly Glu Gln Ser Glu Val Gly Trp Leu Ala Arg Arg
            420                 425                 430

Gly Arg Val Pro Leu Gly Tyr Leu Gly His Pro Gln Arg Thr Ala Ala
        435                 440                 445

Thr Phe Pro Val Leu Asp Gly Gln His Leu Ala Val Thr Gly Asp Arg
    450                 455                 460

Ala Arg Tyr Thr Leu Ala Gly Asp Asp Gln Leu Arg Ile Glu Leu Leu
465                 470                 475                 480

Gly Arg Glu Ser Ala Cys Ile Asn Thr Gly Gly Glu Lys Val Phe Ala
                485                 490                 495

Glu Glu Val Glu Val Cys Leu Asn Arg His Pro Ala Val Val Asp Leu
            500                 505                 510

Leu Val Ala Pro Ala Val Asp Glu Gln Phe Gly Gln Ala Val Gly Val
        515                 520                 525

Val Ala Ala Leu Arg Pro Gly Ala Ser Val Asn Leu Asp Asp Leu Arg
    530                 535                 540

Gln Phe Gly Arg Leu Ser Leu Ala Asp Tyr Lys Leu Pro Arg Arg Leu
545                 550                 555                 560

Val Val Val Asp Glu Val Val Arg Ser Pro Ser Gly Lys Pro Asp Tyr
                565                 570                 575

Arg Trp Ala Arg Ser Gln Leu Asp Arg
            580                 585


<210> SEQ ID NO 19
<211> LENGTH: 1710
<212> TYPE: DNA
<213> ORGANISM: Candidatus Microthrix parvicella

<400> SEQUENCE: 19

gtgacctcgc cgattcccgc cggaggtgag tctccgtcga ccttgatcga actcattgag      60

gtggcatctt cctcacgtct cagcttcatc ggtgaaaccg gctcggttga ggcagggacg     120

gaaacctggt ctgccgcgga aacgcacgag cgttcggact tcgtagcggg gcaactgctg     180

gcgtgtgggc tagagcccgg acaggcggtc ggcctacttc tcgttgacca tcgaagcacg     240

gtcccggcct tccttgggtc gctccgagcg ggtctcattc cgacgctgat cgcaccaccc     300

catccaggtg cagacctgtc ggaatggaca catcagctca agcacctggc tgcaatcggt     360

tcgtttgttt cggtgatcac cacaaattcg atcgcggcgc tcctgccgca cgattcgttg     420

ggtaccccaa cgctcaccct ggagttcgtc gcggagcacg aaagcgtcag cgaccgacca     480

gggatcgtcc ccggtgctga tgcatttcga caacggacgt ccggaacaac cggacttccc     540

aaactcatcc gggtgacaca tgcagcagcg gtcgcgaaca tcaaggcgat catcaaccac     600

ggcgtccggg cagggagcaa tgaccgttcg gtgagctggc tgcccttcta ccatgacatg     660

ggcctggtag ggcagcttct cgctcccttg gcctctggta ctccaacctg gtacctaccc     720

accacctcgt ttgcgcgccg tcccgcttct tgggggtcgc tcatgtcgca agtggcagcg     780

accgtctcgt tcgcgcccaa cttcgcttac gaggcgctgg ttcggcggac gaaaccggcc     840

aaggtggccg gctgggacct ctccagttgg aaggtagccg gatgcggggc cgaacccatc     900

caacccgcca cgcttgagca ggttgccacc caacttgcgc ccgccggctt tcgacccgag     960

gcgttcctgc cgtgttacgg attggccgag acggtccttg cagcgagctt cggccgactt    1020
```

```
gatgccgttc caaccatcat cgaagcagat attgatgcct tcgagggtgg tgggatgatc   1080

aggtccgccc agccaggcgc cggagcaaga agatttgtca gctgtgggct gccgttggcc   1140

gaccatgaga ttcacatcac cgaacccaat tccggtcagg aactagagga cgggctcgtc   1200

ggggagatca cgctgtcggg gccatcaatc acagccggtt accttggcga cccagacgag   1260

aatgcggcac gttttaccga ggccggcctc cgaaccggcg acctgggcgc cctcgttgat   1320

ggcgagttgg ttgtgacagg aagatcgaag gacctgatca tcgttgcggg ccgcaacatc   1380

tgtccttatc aaatcgagca aacgatcacc gacgcatgtc ggttgccgtt cggaagggcg   1440

gtggtcgtcg cccgatcaaa caacctcggg acggaggagg ccgtcctcgt gacagatcta   1500

cccaagacca atctcgacga catgctggac gcgtcgcgtg acgcagtcac aggagctcac   1560

ggcatctcga ttgccgaagc gctgcgatgg ccggcgggtc gctttccacg caccacgagc   1620

ggtaagactc gacgggtcgt ggttgagcaa tgggctgcgc accaagacgc aagtacagcc   1680

accgcccaaa tcaactctga tgagccctaa                                    1710
```

```
<210> SEQ ID NO 20
<211> LENGTH: 569
<212> TYPE: PRT
<213> ORGANISM: Candidatus Microthrix parvicella

<400> SEQUENCE: 20

Met Thr Ser Pro Ile Pro Ala Gly Gly Glu Ser Pro Ser Thr Leu Ile
1               5                   10                  15

Glu Leu Ile Glu Val Ala Ser Ser Ser Arg Leu Ser Phe Ile Gly Glu
            20                  25                  30

Thr Gly Ser Val Glu Ala Gly Thr Glu Thr Trp Ser Ala Ala Glu Thr
        35                  40                  45

His Glu Arg Ser Asp Phe Val Ala Gly Gln Leu Leu Ala Cys Gly Leu
    50                  55                  60

Glu Pro Gly Gln Ala Val Gly Leu Leu Leu Val Asp His Arg Ser Thr
65                  70                  75                  80

Val Pro Ala Phe Leu Gly Ser Leu Arg Ala Gly Leu Ile Pro Thr Leu
                85                  90                  95

Ile Ala Pro Pro His Pro Gly Ala Asp Leu Ser Glu Trp Thr His Gln
            100                 105                 110

Leu Lys His Leu Ala Ala Ile Gly Ser Phe Val Ser Val Ile Thr Thr
        115                 120                 125

Asn Ser Ile Ala Ala Leu Leu Pro His Asp Ser Leu Gly Thr Pro Thr
    130                 135                 140

Leu Thr Leu Glu Phe Val Ala Glu His Glu Ser Val Ser Asp Arg Pro
145                 150                 155                 160

Gly Ile Val Pro Gly Ala Asp Ala Phe Arg Gln Arg Thr Ser Gly Thr
                165                 170                 175

Thr Gly Leu Pro Lys Leu Ile Arg Val Thr His Ala Ala Ala Val Ala
            180                 185                 190

Asn Ile Lys Ala Ile Ile Asn His Gly Val Arg Ala Gly Ser Asn Asp
        195                 200                 205

Arg Ser Val Ser Trp Leu Pro Phe Tyr His Asp Met Gly Leu Val Gly
    210                 215                 220

Gln Leu Leu Ala Pro Leu Ala Ser Gly Thr Pro Thr Trp Tyr Leu Pro
225                 230                 235                 240

Thr Thr Ser Phe Ala Arg Arg Pro Ala Ser Trp Gly Ser Leu Met Ser
```

```
                245                 250                 255

Gln Val Ala Ala Thr Val Ser Phe Ala Pro Asn Phe Ala Tyr Glu Ala
            260                 265                 270

Leu Val Arg Arg Thr Lys Pro Ala Lys Val Ala Gly Trp Asp Leu Ser
        275                 280                 285

Ser Trp Lys Val Ala Gly Cys Gly Ala Glu Pro Ile Gln Pro Ala Thr
    290                 295                 300

Leu Glu Gln Val Ala Thr Gln Leu Ala Pro Ala Gly Phe Arg Pro Glu
305                 310                 315                 320

Ala Phe Leu Pro Cys Tyr Gly Leu Ala Glu Thr Val Leu Ala Ala Ser
                325                 330                 335

Phe Gly Arg Leu Asp Ala Val Pro Thr Ile Ile Glu Ala Asp Ile Asp
            340                 345                 350

Ala Phe Glu Gly Gly Gly Met Ile Arg Ser Ala Gln Pro Gly Ala Gly
        355                 360                 365

Ala Arg Arg Phe Val Ser Cys Gly Leu Pro Leu Ala Asp His Glu Ile
    370                 375                 380

His Ile Thr Glu Pro Asn Ser Gly Gln Glu Leu Glu Asp Gly Leu Val
385                 390                 395                 400

Gly Glu Ile Thr Leu Ser Gly Pro Ser Ile Thr Ala Gly Tyr Leu Gly
                405                 410                 415

Asp Pro Asp Glu Asn Ala Ala Arg Phe Thr Glu Ala Gly Leu Arg Thr
            420                 425                 430

Gly Asp Leu Gly Ala Leu Val Asp Gly Glu Leu Val Val Thr Gly Arg
        435                 440                 445

Ser Lys Asp Leu Ile Ile Val Ala Gly Arg Asn Ile Cys Pro Tyr Gln
    450                 455                 460

Ile Glu Gln Thr Ile Thr Asp Ala Cys Arg Leu Pro Phe Gly Arg Ala
465                 470                 475                 480

Val Val Val Ala Arg Ser Asn Asn Leu Gly Thr Glu Glu Ala Val Leu
                485                 490                 495

Val Thr Asp Leu Pro Lys Thr Asn Leu Asp Asp Met Leu Asp Ala Ser
            500                 505                 510

Arg Asp Ala Val Thr Gly Ala His Gly Ile Ser Ile Ala Glu Ala Leu
        515                 520                 525

Arg Trp Pro Ala Gly Arg Phe Pro Arg Thr Thr Ser Gly Lys Thr Arg
    530                 535                 540

Arg Val Val Val Glu Gln Trp Ala Ala His Gln Asp Ala Ser Thr Ala
545                 550                 555                 560

Thr Ala Gln Ile Asn Ser Asp Glu Pro
                565
```

<210> SEQ ID NO 21
<211> LENGTH: 1944
<212> TYPE: DNA
<213> ORGANISM: Candidatus Microthrix parvicella

<400> SEQUENCE: 21

```
atgccggtgg tgagcttctc caacgatgga gttggggtgc cgatggttga agacagtttg      60

ccgattatgg atgggcgcca gttcgaaatc cactggcttg gcgccgatgc tgagtcggta     120

ccggccgagt tcggcgggcg actaccggcg ccggggaagg ggttcgtgtc tccgggcctg     180

ttggaggctt ctggtggcgt ttcgggtttc cacgagcggt ttggtgttgg ggtggatgaa     240

cacagtgggg atgtccgttg ggatcgggta acggcctttg ctgaggagtt tctggcgttt     300
```

```
gcgacgcttc cggaaggcct ggtgcttccg gaagcgcgcg tcgcagggca gcagcgcttc    360

ctggtgggtt tcgatgctga ggaactgggc gccggcttgc cgacaggatt tcagacacca    420

agcggtctcg tggcggtgcc acattcgctc gacgaacgtt tgccttctcc ttcacaggcg    480

ctgacgggcg ctctatttgg gctgttgata cctggtctgt tggtgctggg tcttggcttg    540

tctgcccatt cgacgctgcg cgcgcaacgg agcgacgcgt tggtctacct cggggctggc    600

cccaattcgt tggatgtgtt cgatgctgcg gaggccgccg tcctgagcgt gccggtcgct    660

ttggtcgttt cggcgatgat gtggggcgtc ctgggtgtgc cgacaacgtt gccgtccggc    720

tcggttgagt acctgcccgg agacttgcgg ccgggtgcgg gtccttcggg cgtcgctctg    780

gtcctcgttc tgctggtgcc ggtggcggtc ggggcgctga tgccaaaggt gaccgcttgg    840

cgaacgcggc gtaagcagcg caccgtcaag ttgggcggcc ttgtcttgtt gctcgtaccc    900

gtcgcggtat ctgccgcgag caccctgatc ccaccccagg cgagggctct gcgttttgtg    960

gcggtactgg cgtcggtcgt ctcggtggtt cctctcgtcg ccgttgctgt tcttccgtgg   1020

ctcggaacgc tgttggtggt gcctgaccgc gtggcgagac tgcttgccgg tcgccggttc   1080

cagtggggcg acaagcgggg atctgatctc attcgaatca cgacgctgac cgtcgtggcc   1140

gtcgtcgtgg tttcgtcgat caatctcctt gccgacagcg ccgccctgga ggagtcgagt   1200

tcgcggtcgg gtatcgtgac catcgacacc ttcgcagaag tggatcaagc ggcattcacc   1260

gaattcgatg cacgcgtgcc cggggctcca atcggggctg tggtcgatgg gcaagtgttc   1320

gttgccaact gcgaacaact ggcggctctt gtcgacgtca gcgcgcaggg gtgcgcaacg   1380

aaccccgaac ggttcatgaa cgaggtcaat cgctcggagt ctcgccgctt cgagacgtac   1440

acgatcggca acccgccacc agatcggccg gtcggccaga tgattgcccg agtcgattcg   1500

gacagccgag cccatgcgct tcaagccaac gccaacgcca tgttcggtcc ttcaagcgtg   1560

ttgggttggg agtatctggg gccaaacccc atcaccgggt ggatctcgcc cctcggtgct   1620

gcagcggtcg gcctgttcgg cgttgcggtg gccttgctga ttgcgaacac gatcaggttc   1680

ccatcccaga gcgaccaatc gttggtctgg ctcgccgcgc cggctccaac ccgccgcgca   1740

gtattgcgct ggggccttca ttccgcggtg ttattcggtg tgctgctcgg aagcggatac   1800

ggcatcatcg cagtaagtgc gggaacacca ggcgaaatca cccaactgga ccatgtctcg   1860

ctggccatca cagcgatcac ctgcgggatc gcaatttcgg ccatcgtcga aacatccctc   1920

tgggcccgtg ccaggaagcc gtag                                          1944
```

<210> SEQ ID NO 22
<211> LENGTH: 647
<212> TYPE: PRT
<213> ORGANISM: Candidatus Microthrix parvicella

<400> SEQUENCE: 22

```
Met Pro Val Val Ser Phe Ser Asn Asp Gly Val Gly Val Pro Met Val
1               5                   10                  15

Glu Asp Ser Leu Pro Ile Met Asp Gly Arg Gln Phe Glu Ile His Trp
            20                  25                  30

Leu Gly Ala Asp Ala Glu Ser Val Pro Ala Glu Phe Gly Gly Arg Leu
        35                  40                  45

Pro Ala Pro Gly Lys Gly Phe Val Ser Pro Gly Leu Leu Glu Ala Ser
    50                  55                  60

Gly Gly Val Ser Gly Phe His Glu Arg Phe Gly Val Gly Val Asp Glu
65                  70                  75                  80
```

```
His Ser Gly Asp Val Arg Trp Asp Arg Val Thr Ala Phe Ala Glu Glu
                85                  90                  95

Phe Leu Ala Phe Ala Thr Leu Pro Glu Gly Leu Val Leu Pro Glu Ala
            100                 105                 110

Arg Val Ala Gly Gln Gln Arg Phe Leu Val Gly Phe Asp Ala Glu Glu
        115                 120                 125

Leu Gly Ala Gly Leu Pro Thr Gly Phe Gln Thr Pro Ser Gly Leu Val
    130                 135                 140

Ala Val Pro His Ser Leu Asp Glu Arg Leu Pro Ser Pro Ser Gln Ala
145                 150                 155                 160

Leu Thr Gly Ala Leu Phe Gly Leu Leu Ile Pro Gly Leu Leu Val Leu
                165                 170                 175

Gly Leu Gly Leu Ser Ala His Ser Thr Leu Arg Ala Gln Arg Ser Asp
            180                 185                 190

Ala Leu Val Tyr Leu Gly Ala Gly Pro Asn Ser Leu Asp Val Phe Asp
        195                 200                 205

Ala Ala Glu Ala Ala Val Leu Ser Val Pro Val Ala Leu Val Val Ser
    210                 215                 220

Ala Met Met Trp Gly Val Leu Gly Val Pro Thr Thr Leu Pro Ser Gly
225                 230                 235                 240

Ser Val Glu Tyr Leu Pro Gly Asp Leu Arg Pro Gly Ala Gly Pro Ser
                245                 250                 255

Gly Val Ala Leu Val Leu Val Leu Leu Val Pro Val Ala Val Gly Ala
            260                 265                 270

Leu Met Pro Lys Val Thr Ala Trp Arg Thr Arg Arg Lys Gln Arg Thr
        275                 280                 285

Val Lys Leu Gly Gly Leu Val Leu Leu Leu Val Pro Val Ala Val Ser
    290                 295                 300

Ala Ala Ser Thr Leu Ile Pro Pro Gln Ala Arg Ala Leu Arg Phe Val
305                 310                 315                 320

Ala Val Leu Ala Ser Val Val Ser Val Val Pro Leu Val Ala Val Ala
                325                 330                 335

Val Leu Pro Trp Leu Gly Thr Leu Leu Val Val Pro Asp Arg Val Ala
            340                 345                 350

Arg Leu Leu Ala Gly Arg Arg Phe Gln Trp Gly Asp Lys Arg Gly Ser
        355                 360                 365

Asp Leu Ile Arg Ile Thr Thr Leu Thr Val Val Ala Val Val Val Val
    370                 375                 380

Ser Ser Ile Asn Leu Leu Ala Asp Ser Ala Ala Leu Glu Glu Ser Ser
385                 390                 395                 400

Ser Arg Ser Gly Ile Val Thr Ile Asp Thr Phe Ala Glu Val Asp Gln
                405                 410                 415

Ala Ala Phe Thr Glu Phe Asp Ala Arg Val Pro Gly Ala Pro Ile Gly
            420                 425                 430

Ala Val Val Asp Gly Gln Val Phe Val Ala Asn Cys Glu Gln Leu Ala
        435                 440                 445

Ala Leu Val Asp Val Ser Ala Gln Gly Cys Ala Thr Asn Pro Glu Arg
    450                 455                 460

Phe Met Asn Glu Val Asn Arg Ser Glu Ser Arg Arg Phe Glu Thr Tyr
465                 470                 475                 480

Thr Ile Gly Asn Pro Pro Pro Asp Arg Pro Val Gly Gln Met Ile Ala
                485                 490                 495
```

```
Arg Val Asp Ser Asp Ser Arg Ala His Ala Leu Gln Ala Asn Ala Asn
            500                 505                 510

Ala Met Phe Gly Pro Ser Ser Val Leu Gly Trp Glu Tyr Leu Gly Pro
        515                 520                 525

Asn Pro Ile Thr Gly Trp Ile Ser Pro Leu Gly Ala Ala Ala Val Gly
    530                 535                 540

Leu Phe Gly Val Ala Val Ala Leu Leu Ile Ala Asn Thr Ile Arg Phe
545                 550                 555                 560

Pro Ser Gln Ser Asp Gln Ser Leu Val Trp Leu Ala Ala Pro Ala Pro
                565                 570                 575

Thr Arg Arg Ala Val Leu Arg Trp Gly Leu His Ser Ala Val Leu Phe
            580                 585                 590

Gly Val Leu Leu Gly Ser Gly Tyr Gly Ile Ile Ala Val Ser Ala Gly
        595                 600                 605

Thr Pro Gly Glu Ile Thr Gln Leu Asp His Val Ser Leu Ala Ile Thr
    610                 615                 620

Ala Ile Thr Cys Gly Ile Ala Ile Ser Ala Ile Val Glu Thr Ser Leu
625                 630                 635                 640

Trp Ala Arg Ala Arg Lys Pro
                645
```

<210> SEQ ID NO 23
<211> LENGTH: 1608
<212> TYPE: DNA
<213> ORGANISM: Candidatus Microthrix parvicella

<400> SEQUENCE: 23

```
gtgctgctgg gcgacgaact ggatgcagcc tcacgccacg cgcccgacac cccggcgctg      60

gcatgtggcg accgcagttg gaccttcacc gagtggaacc gcgcctcgtt ggcgctggca     120

gccagggtgg ccgattcggt cgcccccgacc gggcgggtgg cggtgcttgc aaccaaccac     180

cccacggtgg cactggcgct cagcgccgtg ccccgggccg gacgggtgct gtcgatgccc     240

aactggcgcc tgcatcccgc cgagatcgca gacgtgatcg aggacgtggg cgccgaactg     300

atcatcggca ctgccgattt ggtcgacccg gtgatgaaac ttctcgccga gcgtggcctc     360

atgccacagc gctggggtct cttcgagatc gacgaactgc ttggcgacca acccgtcgag     420

caaccctccc cccgacaacc ggacgcaacc gcgcctgctc ccagtcccac gccgggcgat     480

ccggcgtgga tcatccacac gtcgggcacc accggcaccc ccaaaggcgt ggtgctgacc     540

cacgcctccc tgctggctgg tgcgaccacc gccctgttcg gccgtccggt gggtccagcc     600

gacacctacc tgtacccgtt ccccctgtgt cacgtgtcgg cccacaacgt gttggcgttg     660

cacctggcac gtcggcccgt ggtgctcacc gagcgctttg agccggcgct cctgtgggag     720

cagacccggc gctggggcgt caccatggtc agcctggccc ccacgatgct tgccatgctg     780

ctcgatgatc cggccaccga ctcggcgggt cgcggcgccc ttcgagcgat cggctacggc     840

gcctctgcga tcactccaga actgctcacc gaggcctccc agcggctggg gtgcgaattc     900

tccggcggat acggcatgac cgaggcatcg ggcaacgccg tgttcctcga cgccgccgcc     960

caccggctgg ctctccacgg cgacgcgcgg ccgctgacct ccgccgggtt cccagggccg    1020

ctgacacggg cccggatcac ccccgtcccc gccgatggcc cagaccacag ccccatcgcc    1080

gggcccatcg ccgggaccgt agctgcggcc gtgcgtgggg cggaggtgcg aaccggcgag    1140

gtgggccaga tcgagctggc cggtcctcag gtggcggccg ggtactgggg tcgaccggac    1200

gccaccgccg acacgtttgg cagcgacggc tggctgcgca ccggcgacct cggccgtctc    1260
```

```
gacgacgatg ggcggctctg ggtcaccgac cgcctgaagg acctggtgat ctccggtggt   1320

gagaacgtgt cggcccgcga ggtggagttg gtgttggcca cacatccggc cgtcaaagcg   1380

gtggccgtcg tcggctcgcc ggacgcacgc tggggcgagg tggtcaccgc ggtcgtcgtc   1440

gcccgcgatg ggcggaccat cgaccatgcc gaactccagg ctcacgttcg atcgtcgctg   1500

gcgccgttca aggtgccaaa gcgcatcgag atggtggagg ccctgcccca gaacgccacc   1560

ggcaaggtcg acaaggtggc cctgcgggca accctgggcc ggttctga                 1608


<210> SEQ ID NO 24
<211> LENGTH: 535
<212> TYPE: PRT
<213> ORGANISM: Candidatus Microthrix parvicella

<400> SEQUENCE: 24

Met Leu Leu Gly Asp Glu Leu Asp Ala Ala Ser Arg His Ala Pro Asp
1               5                   10                  15

Thr Pro Ala Leu Ala Cys Gly Asp Arg Ser Trp Thr Phe Thr Glu Trp
            20                  25                  30

Asn Arg Ala Ser Leu Ala Leu Ala Ala Arg Val Ala Asp Ser Val Ala
        35                  40                  45

Pro Thr Gly Arg Val Ala Val Leu Ala Thr Asn His Pro Thr Val Ala
    50                  55                  60

Leu Ala Leu Ser Ala Val Pro Arg Ala Gly Arg Val Leu Ser Met Pro
65                  70                  75                  80

Asn Trp Arg Leu His Pro Ala Glu Ile Ala Asp Val Ile Glu Asp Val
                85                  90                  95

Gly Ala Glu Leu Ile Ile Gly Thr Ala Asp Leu Val Asp Pro Val Met
            100                 105                 110

Lys Leu Leu Ala Glu Arg Gly Leu Met Pro Gln Arg Trp Gly Leu Phe
        115                 120                 125

Glu Ile Asp Glu Leu Leu Gly Asp Gln Pro Val Glu Gln Pro Ser Pro
    130                 135                 140

Arg Gln Pro Asp Ala Thr Ala Pro Ala Pro Ser Pro Thr Pro Gly Asp
145                 150                 155                 160

Pro Ala Trp Ile Ile His Thr Ser Gly Thr Thr Gly Thr Pro Lys Gly
                165                 170                 175

Val Val Leu Thr His Ala Ser Leu Leu Ala Gly Ala Thr Thr Ala Leu
            180                 185                 190

Phe Gly Arg Pro Val Gly Pro Ala Asp Thr Tyr Leu Tyr Pro Phe Pro
        195                 200                 205

Leu Cys His Val Ser Ala His Asn Val Leu Ala Leu His Leu Ala Arg
    210                 215                 220

Arg Pro Val Val Leu Thr Glu Arg Phe Glu Pro Ala Leu Leu Trp Glu
225                 230                 235                 240

Gln Thr Arg Arg Trp Gly Val Thr Met Val Ser Leu Ala Pro Thr Met
                245                 250                 255

Leu Ala Met Leu Leu Asp Asp Pro Ala Thr Asp Ser Ala Gly Arg Gly
            260                 265                 270

Ala Leu Arg Ala Ile Gly Tyr Gly Ala Ser Ala Ile Thr Pro Glu Leu
        275                 280                 285

Leu Thr Glu Ala Ser Gln Arg Leu Gly Cys Glu Phe Ser Gly Gly Tyr
    290                 295                 300

Gly Met Thr Glu Ala Ser Gly Asn Ala Val Phe Leu Asp Ala Ala Ala
```

305 310 315 320

His Arg Leu Ala Leu His Gly Asp Ala Arg Pro Leu Thr Ser Ala Gly
325 330 335

Phe Pro Gly Pro Leu Thr Arg Ala Arg Ile Thr Pro Val Pro Ala Asp
340 345 350

Gly Pro Asp His Ser Pro Ile Ala Gly Pro Ile Ala Gly Thr Val Ala
355 360 365

Ala Ala Val Arg Gly Ala Glu Val Arg Thr Gly Glu Val Gly Gln Ile
370 375 380

Glu Leu Ala Gly Pro Gln Val Ala Ala Gly Tyr Trp Gly Arg Pro Asp
385 390 395 400

Ala Thr Ala Asp Thr Phe Gly Ser Asp Gly Trp Leu Arg Thr Gly Asp
405 410 415

Leu Gly Arg Leu Asp Asp Asp Gly Arg Leu Trp Val Thr Asp Arg Leu
420 425 430

Lys Asp Leu Val Ile Ser Gly Gly Glu Asn Val Ser Ala Arg Glu Val
435 440 445

Glu Leu Val Leu Ala Thr His Pro Ala Val Lys Ala Val Ala Val Val
450 455 460

Gly Ser Pro Asp Ala Arg Trp Gly Glu Val Val Thr Ala Val Val Val
465 470 475 480

Ala Arg Asp Gly Arg Thr Ile Asp His Ala Glu Leu Gln Ala His Val
485 490 495

Arg Ser Ser Leu Ala Pro Phe Lys Val Pro Lys Arg Ile Glu Met Val
500 505 510

Glu Ala Leu Pro Gln Asn Ala Thr Gly Lys Val Asp Lys Val Ala Leu
515 520 525

Arg Ala Thr Leu Gly Arg Phe
530 535

<210> SEQ ID NO 25
<211> LENGTH: 1554
<212> TYPE: DNA
<213> ORGANISM: Candidatus Microthrix parvicella

<400> SEQUENCE: 25
ttgacccagc tgcgatttcc cggagttcac gcccaggctg accccggccg tgtggccatc 60
accatggccg gcaccggcga acaggtcacc ttcggcgagc tcgacgcaat ttccaaccgg 120
ctggcccgca cctttcggtc cttggggctg gaggcgggtg gacacgtggc aacctgcatg 180
gaaaaccggg tcgaggtgct ggaagtggcc tggggcgccc attacgccgg gctgcactac 240
accttcatct ccacccggct caccccggac gaagctgcgt tcatcatcgg agactccggc 300
tccaaggtgg tcgtgctcac gccccagctg ggccgggtac tgatgcctgc cctcgccggg 360
ttggtcgacg acgacgtcac cttcgtgtcg atcggcggcg aggtcgacgg cgctgacgat 420
ctgatggcgc tggcggcgga acggtcaccc gacccgattc ccgacgccac cgagggcgcc 480
gacatgctgt attcctcggg caccaccggc cgccccaagg gcgtgcttcg agccctttca 540
ggcgaaccgc tgggcaccac tgcgggtttg gcgttgttgg gcgagttcct catggggatg 600
agcccggaga gcgtgtacct ctccccccgcc ccgatgtatc acgcggcccc gctcaagtgg 660
agcctcgaga gcctggcgct gggcgcgtcg gtggtgctga tggagcgctt cgagcccgag 720
gcgttgctgt cggccatcga gactcacggg gtgacgcacg gccagttcgt acccaccatg 780
ttcgtgcgca tgctgaagct gcccgaagag gtgcgcaacc ggtacgacgt ctccagcctg 840

```
caggcgatca tccacgccgc ggccccatgc ccagaggacg tgaagcgggc gatgatcgcc    900

tggatgggtc cgatcatcaa cgagtactac gccggtaccg aggggtcggg tttctgctgg    960

gcctcggcgg aggactggct gacccaccct ggcacggttg gaaagccgct ggtcggtgtg   1020

atccacatcg tcgatcccga cggtgaggag ctgccggtcg gcgaggaggg ggtcgtgtac   1080

ttcggtgagg gcccccagtt cgaataccac aacgatcccg aaaagaccgc cgaggcctac   1140

aacgaacggg gctggtccac cctgggcgac atcggcaaag tcgacgagga cggcttcctg   1200

tacctcaccg accgtcagag caacatgatc atttccggcg gcgtcaacgt gtacccccag   1260

gaggcggaga acgtgctcgc ctcgcatccc gacatttacg acgtggccgt gatcggcatc   1320

ccaaacgagg acttcggcga ggaggtcaag gcggtggtgc aggtgacgga cggcgtcgag   1380

acgtccgacg agacggccgg ggcgctcatc gcgtactgcc gggagcggtt ggccgacatc   1440

aagtgcccgc gcagcgtgga cttcgtcgat gagttgcccc gcctaccaac gggcaagctg   1500

ctgaaacgcc tgctcaagga caagtactgg gagggccacg gctcccgcat ctga         1554
```

```
<210> SEQ ID NO 26
<211> LENGTH: 517
<212> TYPE: PRT
<213> ORGANISM: Candidatus Microthrix parvicella

<400> SEQUENCE: 26

Met Thr Gln Leu Arg Phe Pro Gly Val His Ala Gln Ala Asp Pro Gly
1               5                   10                  15

Arg Val Ala Ile Thr Met Ala Gly Thr Gly Glu Gln Val Thr Phe Gly
            20                  25                  30

Glu Leu Asp Ala Ile Ser Asn Arg Leu Ala Arg Thr Phe Arg Ser Leu
        35                  40                  45

Gly Leu Glu Ala Gly Gly His Val Ala Thr Cys Met Glu Asn Arg Val
    50                  55                  60

Glu Val Leu Glu Val Ala Trp Gly Ala His Tyr Ala Gly Leu His Tyr
65                  70                  75                  80

Thr Phe Ile Ser Thr Arg Leu Thr Pro Asp Glu Ala Ala Phe Ile Ile
                85                  90                  95

Gly Asp Ser Gly Ser Lys Val Val Val Leu Thr Pro Gln Leu Gly Arg
            100                 105                 110

Val Leu Met Pro Ala Leu Ala Gly Leu Val Asp Asp Asp Val Thr Phe
        115                 120                 125

Val Ser Ile Gly Gly Glu Val Asp Gly Ala Asp Asp Leu Met Ala Leu
    130                 135                 140

Ala Ala Glu Arg Ser Pro Asp Pro Ile Pro Asp Ala Thr Glu Gly Ala
145                 150                 155                 160

Asp Met Leu Tyr Ser Ser Gly Thr Thr Gly Arg Pro Lys Gly Val Leu
                165                 170                 175

Arg Ala Leu Ser Gly Glu Pro Leu Gly Thr Thr Ala Gly Leu Ala Leu
            180                 185                 190

Leu Gly Glu Phe Leu Met Gly Met Ser Pro Glu Ser Val Tyr Leu Ser
        195                 200                 205

Pro Ala Pro Met Tyr His Ala Ala Pro Leu Lys Trp Ser Leu Glu Ser
    210                 215                 220

Leu Ala Leu Gly Ala Ser Val Val Leu Met Glu Arg Phe Glu Pro Glu
225                 230                 235                 240

Ala Leu Leu Ser Ala Ile Glu Thr His Gly Val Thr His Gly Gln Phe
```

```
                245                 250                 255

Val Pro Thr Met Phe Val Arg Met Leu Lys Leu Pro Glu Glu Val Arg
            260                 265                 270

Asn Arg Tyr Asp Val Ser Ser Leu Gln Ala Ile Ile His Ala Ala Ala
        275                 280                 285

Pro Cys Pro Glu Asp Val Lys Arg Ala Met Ile Ala Trp Met Gly Pro
    290                 295                 300

Ile Ile Asn Glu Tyr Tyr Ala Gly Thr Glu Gly Ser Gly Phe Cys Trp
305                 310                 315                 320

Ala Ser Ala Glu Asp Trp Leu Thr His Pro Gly Thr Val Gly Lys Pro
                325                 330                 335

Leu Val Gly Val Ile His Ile Val Asp Pro Asp Gly Glu Glu Leu Pro
            340                 345                 350

Val Gly Glu Glu Gly Val Val Tyr Phe Gly Glu Gly Pro Gln Phe Glu
        355                 360                 365

Tyr His Asn Asp Pro Glu Lys Thr Ala Glu Ala Tyr Asn Glu Arg Gly
    370                 375                 380

Trp Ser Thr Leu Gly Asp Ile Gly Lys Val Asp Glu Asp Gly Phe Leu
385                 390                 395                 400

Tyr Leu Thr Asp Arg Gln Ser Asn Met Ile Ile Ser Gly Gly Val Asn
                405                 410                 415

Val Tyr Pro Gln Glu Ala Glu Asn Val Leu Ala Ser His Pro Asp Ile
            420                 425                 430

Tyr Asp Val Ala Val Ile Gly Ile Pro Asn Glu Asp Phe Gly Glu Glu
        435                 440                 445

Val Lys Ala Val Val Gln Val Thr Asp Gly Val Glu Thr Ser Asp Glu
    450                 455                 460

Thr Ala Gly Ala Leu Ile Ala Tyr Cys Arg Glu Arg Leu Ala Asp Ile
465                 470                 475                 480

Lys Cys Pro Arg Ser Val Asp Phe Val Asp Glu Leu Pro Arg Leu Pro
                485                 490                 495

Thr Gly Lys Leu Leu Lys Arg Leu Leu Lys Asp Lys Tyr Trp Glu Gly
            500                 505                 510

His Gly Ser Arg Ile
        515


<210> SEQ ID NO 27
<211> LENGTH: 1638
<212> TYPE: DNA
<213> ORGANISM: Candidatus Microthrix parvicella

<400> SEQUENCE: 27

atgctgggca cgatgcagga acgtcaactg accttggacc atttcgtcaa ccgggctgag      60

acgtacttcc cggaccgcga gatcgtcaca aacacggcgg cgggcctgca gcgaaccacc     120

tatggggcgt gggcggaccg tacccacagg ttggcgggag tgctggacaa cctgggcatc     180

tccgccgagg gtcgcgttgc cacctttgca tggaacaccg cccgtcacct ggagttgtat     240

ttcgccgccc cgtgcagcgg tcgggtgctg cacaccctca acctgcggct ctttcccgag     300

cagttgacct acatcgtcaa ccacgctgag gacgaggtga tcttcgttga tcgcagcctg     360

ttgggtctgc tcgtgcctcg ggtcggcgag ttcaacaccg tgaagcacat cgtcgtcatg     420

gacgatggcg tgcccaacga gatccccagc ttcgacggag gccccgaggt gcacgactac     480

gaggaactgc tggcaggtgc cgagcgcacc gagttccgct gcgacgacga gtgggccgcc     540
```

```
gcctcgatgt gttacacctc cggcacgacg ggtaacccca agggcgtcac ctacacccat    600

cggtccacct acctgcacac gatggctgcc atgttggccg acacgatcgg ggtgaccgag    660

gccgacgtca tcctgcccgt ggtgcccatg ttccatgcca atgcgtgggg tctggcccat    720

gccgcggtgg cgagcggggc gaagctggtc cagcccgggc cggacctgtc gccgggcacg    780

ctggcacgtc tcattgagga ggagaaggtc acgcttgccg ccggcgtgcc caccatctgg    840

atgggcgtgg tcgaggagct ggaggggcgc gacacctcgg cgttgcgggt ggtcccatgt    900

gggggttctg cggtaccgac ctcactgtcg aaacgatttg aagaggtcac aggcctaccg    960

atcctgcagg cttgggggat gaccgaaacc tcgccggtcg gctcggtcgc caaggtgatc   1020

tcctcgctgg aggactcgtc cgaggagaag ctggacgagt tgcgggcgtc gcagggtctt   1080

cctgtgctgg gcgtcgagct tcgcgtggtg acgcccgacg gcgagcaggt gccgtgggac   1140

ggtgagaccc agggcgagct tcaagccgcg ggcccctgga tcaccaacgg ctattacaac   1200

gatgagcgct cggccgaggc gatgaccgag gacggctggt gccgaaccgg tgacgtggcc   1260

gtgatgctgc ccgagggcta cctgaagctg gtggatcgca ccaaggacgt catcaagacc   1320

ggtggcgagt ggatcagctc ggtcgagctc gaaaacgaga tcatggccca tccggcggtg   1380

gccgaagccg ccgtgatcgc cgtggcgcac cccaagtggg ccgaacgtcc gctggcctgc   1440

gttgtcctgc gggacggcgc tgaggcgacc agggacgaga tcctggcctt tctcgacggc   1500

cgggtggcca agtggtggat tcccgacgac gtggtgttca tcgacgaggt gcccaagacg   1560

tcggttggca agttctccaa aaagaccctg cgggagcagt tcgccgacta cgaactcccc   1620

ggcgtcgccg acgcctga                                                 1638
```

<210> SEQ ID NO 28
<211> LENGTH: 545
<212> TYPE: PRT
<213> ORGANISM: Candidatus Microthrix parvicella

<400> SEQUENCE: 28

```
Met Leu Gly Thr Met Gln Glu Arg Gln Leu Thr Leu Asp His Phe Val
1               5                   10                  15

Asn Arg Ala Glu Thr Tyr Phe Pro Asp Arg Glu Ile Val Thr Asn Thr
            20                  25                  30

Ala Ala Gly Leu Gln Arg Thr Thr Tyr Gly Ala Trp Ala Asp Arg Thr
        35                  40                  45

His Arg Leu Ala Gly Val Leu Asp Asn Leu Gly Ile Ser Ala Glu Gly
    50                  55                  60

Arg Val Ala Thr Phe Ala Trp Asn Thr Ala Arg His Leu Glu Leu Tyr
65                  70                  75                  80

Phe Ala Ala Pro Cys Ser Gly Arg Val Leu His Thr Leu Asn Leu Arg
                85                  90                  95

Leu Phe Pro Glu Gln Leu Thr Tyr Ile Val Asn His Ala Glu Asp Glu
            100                 105                 110

Val Ile Phe Val Asp Arg Ser Leu Leu Gly Leu Leu Val Pro Arg Val
        115                 120                 125

Gly Glu Phe Asn Thr Val Lys His Ile Val Val Met Asp Asp Gly Val
    130                 135                 140

Pro Asn Glu Ile Pro Ser Phe Asp Gly Gly Pro Glu Val His Asp Tyr
145                 150                 155                 160

Glu Glu Leu Leu Ala Gly Ala Glu Arg Thr Glu Phe Arg Cys Asp Asp
                165                 170                 175
```

```
Glu Trp Ala Ala Ala Ser Met Cys Tyr Thr Ser Gly Thr Thr Gly Asn
            180                 185                 190

Pro Lys Gly Val Thr Tyr Thr His Arg Ser Thr Tyr Leu His Thr Met
        195                 200                 205

Ala Ala Met Leu Ala Asp Thr Ile Gly Val Thr Glu Ala Asp Val Ile
    210                 215                 220

Leu Pro Val Val Pro Met Phe His Ala Asn Ala Trp Gly Leu Ala His
225                 230                 235                 240

Ala Ala Val Ala Ser Gly Ala Lys Leu Val Gln Pro Gly Pro Asp Leu
                245                 250                 255

Ser Pro Gly Thr Leu Ala Arg Leu Ile Glu Glu Glu Lys Val Thr Leu
            260                 265                 270

Ala Ala Gly Val Pro Thr Ile Trp Met Gly Val Val Glu Glu Leu Glu
        275                 280                 285

Gly Arg Asp Thr Ser Ala Leu Arg Val Val Pro Cys Gly Gly Ser Ala
    290                 295                 300

Val Pro Thr Ser Leu Ser Lys Arg Phe Glu Glu Val Thr Gly Leu Pro
305                 310                 315                 320

Ile Leu Gln Ala Trp Gly Met Thr Glu Thr Ser Pro Val Gly Ser Val
                325                 330                 335

Ala Lys Val Ile Ser Ser Leu Glu Asp Ser Ser Glu Glu Lys Leu Asp
            340                 345                 350

Glu Leu Arg Ala Ser Gln Gly Leu Pro Val Leu Gly Val Glu Leu Arg
        355                 360                 365

Val Val Thr Pro Asp Gly Glu Gln Val Pro Trp Asp Gly Glu Thr Gln
    370                 375                 380

Gly Glu Leu Gln Ala Ala Gly Pro Trp Ile Thr Asn Gly Tyr Tyr Asn
385                 390                 395                 400

Asp Glu Arg Ser Ala Glu Ala Met Thr Glu Asp Gly Trp Cys Arg Thr
                405                 410                 415

Gly Asp Val Ala Val Met Leu Pro Glu Gly Tyr Leu Lys Leu Val Asp
            420                 425                 430

Arg Thr Lys Asp Val Ile Lys Thr Gly Gly Glu Trp Ile Ser Ser Val
        435                 440                 445

Glu Leu Glu Asn Glu Ile Met Ala His Pro Ala Val Ala Glu Ala Ala
    450                 455                 460

Val Ile Ala Val Ala His Pro Lys Trp Ala Glu Arg Pro Leu Ala Cys
465                 470                 475                 480

Val Val Leu Arg Asp Gly Ala Glu Ala Thr Arg Asp Glu Ile Leu Ala
                485                 490                 495

Phe Leu Asp Gly Arg Val Ala Lys Trp Trp Ile Pro Asp Asp Val Val
            500                 505                 510

Phe Ile Asp Glu Val Pro Lys Thr Ser Val Gly Lys Phe Ser Lys Lys
        515                 520                 525

Thr Leu Arg Glu Gln Phe Ala Asp Tyr Glu Leu Pro Gly Val Ala Asp
    530                 535                 540

Ala
545


<210> SEQ ID NO 29
<211> LENGTH: 1620
<212> TYPE: DNA
<213> ORGANISM: Candidatus Microthrix parvicella

<400> SEQUENCE: 29
```

```
atggccggat ggaactttgc cgagttgtgg gaacggattg catcaaaaca accggatgcc      60
gaggcccagg tccaaggcga ccgccgaatc agctggagcg agttcgaccg acgtgccgat     120
gggctggccc gtcacctgct ggaccaaggg gcccagcacc aggacaaggt cgccgtttat     180
ctgtacaact gcccggagta tctagaaacc acgtttgcgt gttacaaggc cgggctggtt     240
ccggtgaaca ccaactaccg gtacgtcgag gacgagctcg cctacctttg ggacaacgcc     300
gatgccgtcg ccatcgtgtt tcacggctgt ttcaccgacc gcgtcgcagc ggtacgcaac     360
cgcgttccca ccgcacggac ctggctgtgg gtggacgacg gctcgggccc ctgccccgat     420
tgggcgtttc cctacgaggt ggcggcggca accgaaaccg atggccacac cgtggccccc     480
tgggggcgca gcggggacga cattctgatg atctacaccg gtggcaccac cggcatgccc     540
aagggcacca tgtggcgcca ggacgacctg atccgcgccc tgtgcgccac cggtaacccg     600
gttttgggcg aggagtgcga gaccgccgga tacgacgccg cgctggagac gatcggcgcc     660
tccgcggctc ccgggctgcc ggcctgcccg ctgatgcacg gcaccggctg gttcaccgcc     720
aacatgtacc tgaccaatgg cgggtcggtg gtgtgccttc ccagccgaca tctggacatc     780
cccgagctgc tcgacgtcgt cgagcaggag aagatcgccg cagtcaccat cgtcggtgat     840
gcgttcgcca agccgattgt ggccgcgctg gacgccgagc cggatcgttg ggacatcagc     900
tcgatcgtgc tgatcacctc gtcgggggtg atgtggtcgg agtcggccaa gttgggtctg     960
ctggcacatc acccgaacat gatgctgatc gacagcttca gctcatcgga ggccatcggg    1020
ctgggccagt cggtctccgc cggcgactca gccgccgaca cagcctcgtt tgcactcggg    1080
gtggccgccc gagtggtccg tgacgacggt agcgacgtag aaccaggttc gggagagcgg    1140
ggccgagtgg ccgtcggcgg ccacgtgccg atcggctact acaaggaccc cgaaaagtcg    1200
gcctcaacgt tcatccaaat cgacggaaag agctacagct gcccaggtga ctgggccacc    1260
gtggaggcgg acgggtcgat caccctgctg ggccgcgggt cggtgtgcat caacacggcg    1320
ggcgagaagg tgtttcccga agaggtggag gaggcgctga agacccatgc cagcgtgtac    1380
gacgccgtgg tcgttggcgt gcccgacgac cgcttcggcg agacgatcgc cgcccgttgtt    1440
caaccaaccg aaggcagctc gatcgacgcc gacgagttgg tggcgcacac caaacactcg    1500
ctggccggtt acaaggcccc ccgcacggtg ctggtggtgg acagtatcgg cagagcgccc    1560
aacgcaaagg tggattacaa gcgttggaag tcctacgccg ctgagcacgt cggggcctga    1620
```

<210> SEQ ID NO 30
<211> LENGTH: 539
<212> TYPE: PRT
<213> ORGANISM: Candidatus Microthrix parvicella

<400> SEQUENCE: 30

```
Met Ala Gly Trp Asn Phe Ala Glu Leu Trp Glu Arg Ile Ala Ser Lys
1               5                   10                  15

Gln Pro Asp Ala Glu Ala Gln Val Gln Gly Asp Arg Arg Ile Ser Trp
            20                  25                  30

Ser Glu Phe Asp Arg Arg Ala Asp Gly Leu Ala Arg His Leu Leu Asp
        35                  40                  45

Gln Gly Ala Gln His Gln Asp Lys Val Ala Val Tyr Leu Tyr Asn Cys
    50                  55                  60

Pro Glu Tyr Leu Glu Thr Thr Phe Ala Cys Tyr Lys Ala Gly Leu Val
65                  70                  75                  80

Pro Val Asn Thr Asn Tyr Arg Tyr Val Glu Asp Glu Leu Ala Tyr Leu
```

-continued

```
                85                  90                  95

Trp Asp Asn Ala Asp Ala Val Ala Ile Val Phe His Gly Cys Phe Thr
            100                 105                 110

Asp Arg Val Ala Ala Val Arg Asn Arg Val Pro Thr Ala Arg Thr Trp
        115                 120                 125

Leu Trp Val Asp Asp Gly Ser Gly Pro Cys Pro Asp Trp Ala Phe Pro
    130                 135                 140

Tyr Glu Val Ala Ala Ala Thr Glu Thr Asp Gly His Thr Val Ala Pro
145                 150                 155                 160

Trp Gly Arg Ser Gly Asp Asp Ile Leu Met Ile Tyr Thr Gly Gly Thr
                165                 170                 175

Thr Gly Met Pro Lys Gly Thr Met Trp Arg Gln Asp Asp Leu Ile Arg
            180                 185                 190

Ala Leu Cys Ala Thr Gly Asn Pro Val Leu Gly Glu Glu Cys Glu Thr
        195                 200                 205

Ala Gly Tyr Asp Ala Ala Leu Glu Thr Ile Gly Ala Ser Ala Ala Pro
    210                 215                 220

Gly Leu Pro Ala Cys Pro Leu Met His Gly Thr Gly Trp Phe Thr Ala
225                 230                 235                 240

Asn Met Tyr Leu Thr Asn Gly Gly Ser Val Val Cys Leu Pro Ser Arg
                245                 250                 255

His Leu Asp Ile Pro Glu Leu Leu Asp Val Val Glu Gln Glu Lys Ile
            260                 265                 270

Ala Ala Val Thr Ile Val Gly Asp Ala Phe Ala Lys Pro Ile Val Ala
        275                 280                 285

Ala Leu Asp Ala Glu Pro Asp Arg Trp Asp Ile Ser Ser Ile Val Leu
    290                 295                 300

Ile Thr Ser Ser Gly Val Met Trp Ser Glu Ser Ala Lys Leu Gly Leu
305                 310                 315                 320

Leu Ala His His Pro Asn Met Met Leu Ile Asp Ser Phe Ser Ser Ser
                325                 330                 335

Glu Ala Ile Gly Leu Gly Gln Ser Val Ser Ala Gly Asp Ser Ala Ala
            340                 345                 350

Asp Thr Ala Ser Phe Ala Leu Gly Val Ala Ala Arg Val Val Arg Asp
        355                 360                 365

Asp Gly Ser Asp Val Glu Pro Gly Ser Gly Glu Arg Gly Arg Val Ala
    370                 375                 380

Val Gly Gly His Val Pro Ile Gly Tyr Tyr Lys Asp Pro Glu Lys Ser
385                 390                 395                 400

Ala Ser Thr Phe Ile Gln Ile Asp Gly Lys Ser Tyr Ser Cys Pro Gly
                405                 410                 415

Asp Trp Ala Thr Val Glu Ala Asp Gly Ser Ile Thr Leu Leu Gly Arg
            420                 425                 430

Gly Ser Val Cys Ile Asn Thr Ala Gly Glu Lys Val Phe Pro Glu Glu
        435                 440                 445

Val Glu Glu Ala Leu Lys Thr His Ala Ser Val Tyr Asp Ala Val Val
    450                 455                 460

Val Gly Val Pro Asp Asp Arg Phe Gly Glu Thr Ile Ala Ala Val Val
465                 470                 475                 480

Gln Pro Thr Glu Gly Ser Ser Ile Asp Ala Asp Glu Leu Val Ala His
                485                 490                 495

Thr Lys His Ser Leu Ala Gly Tyr Lys Ala Pro Arg Thr Val Leu Val
            500                 505                 510
```

```
Val Asp Ser Ile Gly Arg Ala Pro Asn Ala Lys Val Asp Tyr Lys Arg
        515                 520                 525

Trp Lys Ser Tyr Ala Ala Glu His Val Gly Ala
    530                 535


<210> SEQ ID NO 31
<211> LENGTH: 1809
<212> TYPE: DNA
<213> ORGANISM: Candidatus Microthrix parvicella

<400> SEQUENCE: 31

atgacacatg gagtcgagca gccaggcgac ggggaccccg ctcgaaacaa ggtctcgacc     60

cccacgacga ccgagatcat cgcggaggta cggtcccaac tgatcggtcc cggcggggcc    120

ttcgaggtgg tcaccgagcc ggtcgggggc atcggtcaac cgggccccat cgacatgctg    180

gtgtacgcca atcggctcgc acatctacgc gaggtctttg cattcgccgc agcacacggc    240

gacgccacct tcatcgtcta cggcgagcga cgcatcacgt tctcccagtt cgtcgccgat    300

gccaaccggg tggcagccaa cctggccacc ctcggggtgg gacacggcga ccgggttgcc    360

gtgctcagcc aaaacaaccc cgagtggtgc ctcaccttct gggccacggt caacctcggc    420

gcgatcctgg tggggctcaa cggatggtgg aacaccgacg agattctctt cggtttatcc    480

gatagcggcg ccaagatttt ggtggcggac cccaaacggc tggcccgggt gtcgggctcg    540

ctcgacggcc tgcccgacct gcaacaggtg gtggtgatcg gagcgcgtga cccaaacgac    600

cagagcgact cagtgccggt tcgcccattt gccgatctgt tggcagggga ggatccagca    660

cctccggcca caccattggc cgaagccgac cccgccgtca tcttctacac ctcggggacc    720

acaggccgcc ccaagggtgc catctcgaca caccgcggca tggtggccaa cctgcaaaac    780

accgtgtttt cattgaccgc caacggcatg gtgctcgatc ggcttggtga acccagctcg    840

accgcacccg gcggcccccc gacggcactc ttcacctctc cgttgttcca tgtgtccggc    900

tgccactcca ccctggtggt tggtctgctc ggcgggctga aactggtgat gatggaggat    960

cgcttcaccc cggaggcggc gttggccctg atccaggacg agcaggtcac catctggtcc   1020

accgtcccca ccatgatctg gcgcacgtgt gagtacccgg ggcgagccga ctacaacacg   1080

tcatcgatca cctcggtggc ctttgggggt tcaccctcgg cagctgaact gcagcgcatg   1140

attcgggaga catttcccaa tgtccgggca acgtccaatg catacggcct gactgaatcg   1200

tcgtcggtgg ccaccctgca tctggccggt gcaacgctcg accgtccgga ttcggtaggc   1260

ctgcccatgc ctgtggtcga gttggctatt gccgatgccg acggaagtca ccttggaccg   1320

aacgttcagg gtgaggtgct gatccggggg ccgatcatca tgcccggata ctggaaccgc   1380

cccgatgcca cagcgacgac acttcgggat ggttggctgc acaccggcga cctcggacat   1440

gtggatgagg acggctacct gttcatcacc gaccgtgcca aggacatgat catccgaggt   1500

ggtgaaaacg tgtattgcgt ggagattgaa cagcgtctgg tggagcaccc acaagtggcc   1560

gacgccgcag tggtgggggt accgcacgcc gaactgggcg aacaggtgaa ggcggtcgtc   1620

gaattggtcg ccgacgccga catcgacgac gcccagcttc ggtcatgggt gggcgacgca   1680

ctcgcaacgt tcaaggtgcc ggcgatcatc gaacgatggc cgggcaagct gccgcgcaac   1740

gcctccggca agctgctcaa gaacgtccta cgcggctccg gcccggtcag cttcgccgaa   1800

acgatgtaa                                                           1809


<210> SEQ ID NO 32
```

<211> LENGTH: 602
<212> TYPE: PRT
<213> ORGANISM: Candidatus Microthrix parvicella

<400> SEQUENCE: 32

```
Met Thr His Gly Val Glu Gln Pro Gly Asp Gly Asp Pro Ala Arg Asn
1               5                   10                  15

Lys Val Ser Thr Pro Thr Thr Thr Glu Ile Ile Ala Glu Val Arg Ser
            20                  25                  30

Gln Leu Ile Gly Pro Gly Gly Ala Phe Glu Val Val Thr Glu Pro Val
        35                  40                  45

Gly Gly Ile Gly Gln Pro Gly Pro Ile Asp Met Leu Val Tyr Ala Asn
    50                  55                  60

Arg Leu Ala His Leu Arg Glu Val Phe Ala Phe Ala Ala Ala His Gly
65                  70                  75                  80

Asp Ala Thr Phe Ile Val Tyr Gly Glu Arg Arg Ile Thr Phe Ser Gln
                85                  90                  95

Phe Val Ala Asp Ala Asn Arg Val Ala Ala Asn Leu Ala Thr Leu Gly
            100                 105                 110

Val Gly His Gly Asp Arg Val Ala Val Leu Ser Gln Asn Asn Pro Glu
        115                 120                 125

Trp Cys Leu Thr Phe Trp Ala Thr Val Asn Leu Gly Ala Ile Leu Val
    130                 135                 140

Gly Leu Asn Gly Trp Trp Asn Thr Asp Glu Ile Leu Phe Gly Leu Ser
145                 150                 155                 160

Asp Ser Gly Ala Lys Ile Leu Val Ala Asp Pro Lys Arg Leu Ala Arg
                165                 170                 175

Val Ser Gly Ser Leu Asp Gly Leu Pro Asp Leu Gln Gln Val Val Val
            180                 185                 190

Ile Gly Ala Arg Asp Pro Asn Asp Gln Ser Asp Ser Val Pro Val Arg
        195                 200                 205

Pro Phe Ala Asp Leu Leu Ala Gly Glu Asp Pro Ala Pro Pro Ala Thr
    210                 215                 220

Pro Leu Ala Glu Ala Asp Pro Ala Val Ile Phe Tyr Thr Ser Gly Thr
225                 230                 235                 240

Thr Gly Arg Pro Lys Gly Ala Ile Ser Thr His Arg Gly Met Val Ala
                245                 250                 255

Asn Leu Gln Asn Thr Val Phe Ser Leu Thr Ala Asn Gly Met Val Leu
            260                 265                 270

Asp Arg Leu Gly Glu Pro Ser Ser Thr Ala Pro Gly Gly Pro Pro Thr
        275                 280                 285

Ala Leu Phe Thr Ser Pro Leu Phe His Val Ser Gly Cys His Ser Thr
    290                 295                 300

Leu Val Val Gly Leu Leu Gly Gly Leu Lys Leu Val Met Met Glu Asp
305                 310                 315                 320

Arg Phe Thr Pro Glu Ala Ala Leu Ala Leu Ile Gln Asp Glu Gln Val
                325                 330                 335

Thr Ile Trp Ser Thr Val Pro Thr Met Ile Trp Arg Thr Cys Glu Tyr
            340                 345                 350

Pro Gly Arg Ala Asp Tyr Asn Thr Ser Ser Ile Thr Ser Val Ala Phe
        355                 360                 365

Gly Gly Ser Pro Ser Ala Ala Glu Leu Gln Arg Met Ile Arg Glu Thr
    370                 375                 380

Phe Pro Asn Val Arg Ala Thr Ser Asn Ala Tyr Gly Leu Thr Glu Ser
```

```
385                 390                 395                 400

Ser Ser Val Ala Thr Leu His Leu Ala Gly Ala Thr Leu Asp Arg Pro
                405                 410                 415

Asp Ser Val Gly Leu Pro Met Pro Val Val Glu Leu Ala Ile Ala Asp
            420                 425                 430

Ala Asp Gly Ser His Leu Gly Pro Asn Val Gln Gly Glu Val Leu Ile
        435                 440                 445

Arg Gly Pro Ile Ile Met Pro Gly Tyr Trp Asn Arg Pro Asp Ala Thr
    450                 455                 460

Ala Thr Thr Leu Arg Asp Gly Trp Leu His Thr Gly Asp Leu Gly His
465                 470                 475                 480

Val Asp Glu Asp Gly Tyr Leu Phe Ile Thr Asp Arg Ala Lys Asp Met
                485                 490                 495

Ile Ile Arg Gly Gly Glu Asn Val Tyr Cys Val Glu Ile Glu Gln Arg
            500                 505                 510

Leu Val Glu His Pro Gln Val Ala Asp Ala Ala Val Val Gly Val Pro
        515                 520                 525

His Ala Glu Leu Gly Glu Gln Val Lys Ala Val Val Glu Leu Val Ala
    530                 535                 540

Asp Ala Asp Ile Asp Asp Ala Gln Leu Arg Ser Trp Val Gly Asp Ala
545                 550                 555                 560

Leu Ala Thr Phe Lys Val Pro Ala Ile Ile Glu Arg Trp Pro Gly Lys
                565                 570                 575

Leu Pro Arg Asn Ala Ser Gly Lys Leu Leu Lys Asn Val Leu Arg Gly
            580                 585                 590

Ser Gly Pro Val Ser Phe Ala Glu Thr Met
        595                 600
```

<210> SEQ ID NO 33
<211> LENGTH: 1662
<212> TYPE: DNA
<213> ORGANISM: Candidatus Microthrix parvicella

<400> SEQUENCE: 33

```
atgaacgaac agagcacgac cgcagcgacc tcaccggttc cttggaacct ggccgatctt      60

tgggagctga ccaccgatca gtatccagac cgcgaagcgc tcgtggtggg ggagcagcgg     120

gtctcctacc ggcagattga ggagcgggcc aatgcgctgg cacacgtcct gaccgacgcg     180

ggggtggggc cgggcgacca cgtggcctgc tacctgcaga actgcgcgga gtatgtcgag     240

acgatgctgg ccgcgttcaa gatccgtgca gttccgctca acgtcaacta ccgctatgtg     300

gctgccgagc tgtcgcatct gcttcgggat ggcgacgcgg tggcggttgt cttccaccgg     360

cgcttcagcg attccctggc cgaggtggca cccgaactcg acgaccttcg catcagcctg     420

gtggttgacg acatcgaccc ccgggcggac gtgcccacca ccgacccgac cacgttcggg     480

gcgctcgact acgacgacgc ggtgggggcg gcctcgaccg atcgggactt cccggctcga     540

agcggcgacg acgtctacct gatgtacacc ggcggcacca ccggtatgcc caagggcgtc     600

gagtggcgca tggaggatgc cttcttcgcc tgtgtcggtg gaggcgaccc gatgcggctc     660

gtgggcccgg tgtccacggc cgaggaactg accgagcgaa tccttgatga cgccgtggtg     720

acgatggcct gcgcgccgct gatccacgcc gcagcccagt ggacctcgat gtcctggtgg     780

ctgtgcggcg gacggatggt gctgctgccc ggcagcttcg acggtgccga ggtgtggcgg     840

caggttgccg ccgaaggggt caacatcctg atcctcatcg gtgatgcgat ggcccgcccg     900
```

```
ctgctggacg cgtgggaggc cgaggggccc ttcgaggtgc cctcgctgta cacgatttcc    960

tccggtgggg cgccgcttca ccccactaac aagacccgtc ttcaggagat tctccccaac   1020

ctgatcctgg ccgacggcta cggcagttcc gagaccggat cacacgccac ccagcggctc   1080

atgccgggcg aggatgccag caagggcact cgttttgcga tggacccggc ggtgacctgc   1140

gtgctcgacg agaacctgca gccggtcgag ccggggtcgg gcaacatggg cagggttgcc   1200

cgcaccgggc gaatgccgct gaggtactac ggcgacccca agaagaccgc agagacgttt   1260

gtcgaggtcg gcggcgtccg ttgggcggtc accggcgatc aggccaccgt cgacaccgac   1320

ggcaccatca ccgtgctggg ccgtggctcg gtcagcatca acaccggcgg ggaaaaggtg   1380

tttcccgagg aggtcgaggc ggcgctgaaa acccacccgg gcgttttcga caccgtggtg   1440

gtgggcgtgc ccgacgaacg ctggggcgag acggtagccg ccgtcgttgc gcccagggag   1500

ggcaccgagc tgacccttga cgacctgaaa gcacacgtga aaggcacgat cgccgggtac   1560

aaggcccctc gcaagctggt gctggttgac gaggtggtgc gctcgccgac cggcaaggcc   1620

gactacccgt gggccaagga gcgggcatcc tcggaggcgt ga                      1662


<210> SEQ ID NO 34
<211> LENGTH: 553
<212> TYPE: PRT
<213> ORGANISM: Candidatus Microthrix parvicella

<400> SEQUENCE: 34

Met Asn Glu Gln Ser Thr Thr Ala Ala Thr Ser Pro Val Pro Trp Asn
1               5                   10                  15

Leu Ala Asp Leu Trp Glu Leu Thr Thr Asp Gln Tyr Pro Asp Arg Glu
            20                  25                  30

Ala Leu Val Val Gly Glu Gln Arg Val Ser Tyr Arg Gln Ile Glu Glu
        35                  40                  45

Arg Ala Asn Ala Leu Ala His Val Leu Thr Asp Ala Gly Val Gly Pro
    50                  55                  60

Gly Asp His Val Ala Cys Tyr Leu Gln Asn Cys Ala Glu Tyr Val Glu
65                  70                  75                  80

Thr Met Leu Ala Ala Phe Lys Ile Arg Ala Val Pro Leu Asn Val Asn
                85                  90                  95

Tyr Arg Tyr Val Ala Ala Glu Leu Ser His Leu Leu Arg Asp Gly Asp
            100                 105                 110

Ala Val Ala Val Val Phe His Arg Arg Phe Ser Asp Ser Leu Ala Glu
        115                 120                 125

Val Ala Pro Glu Leu Asp Asp Leu Arg Ile Ser Leu Val Val Asp Asp
    130                 135                 140

Ile Asp Pro Arg Ala Asp Val Pro Thr Thr Asp Pro Thr Thr Phe Gly
145                 150                 155                 160

Ala Leu Asp Tyr Asp Asp Ala Val Gly Ala Ala Ser Thr Asp Arg Asp
                165                 170                 175

Phe Pro Ala Arg Ser Gly Asp Asp Val Tyr Leu Met Tyr Thr Gly Gly
            180                 185                 190

Thr Thr Gly Met Pro Lys Gly Val Glu Trp Arg Met Glu Asp Ala Phe
        195                 200                 205

Phe Ala Cys Val Gly Gly Gly Asp Pro Met Arg Leu Val Gly Pro Val
    210                 215                 220

Ser Thr Ala Glu Glu Leu Thr Glu Arg Ile Leu Asp Asp Ala Val Val
225                 230                 235                 240
```

```
Thr Met Ala Cys Ala Pro Leu Ile His Ala Ala Ala Gln Trp Thr Ser
            245                 250                 255

Met Ser Trp Trp Leu Cys Gly Gly Arg Met Val Leu Leu Pro Gly Ser
            260                 265                 270

Phe Asp Gly Ala Glu Val Trp Arg Gln Val Ala Ala Glu Gly Val Asn
        275                 280                 285

Ile Leu Ile Leu Ile Gly Asp Ala Met Ala Arg Pro Leu Leu Asp Ala
    290                 295                 300

Trp Glu Ala Glu Gly Pro Phe Glu Val Pro Ser Leu Tyr Thr Ile Ser
305                 310                 315                 320

Ser Gly Gly Ala Pro Leu His Pro Thr Asn Lys Thr Arg Leu Gln Glu
            325                 330                 335

Ile Leu Pro Asn Leu Ile Leu Ala Asp Gly Tyr Gly Ser Ser Glu Thr
            340                 345                 350

Gly Ser His Ala Thr Gln Arg Leu Met Pro Gly Glu Asp Ala Ser Lys
        355                 360                 365

Gly Thr Arg Phe Ala Met Asp Pro Ala Val Thr Cys Val Leu Asp Glu
    370                 375                 380

Asn Leu Gln Pro Val Glu Pro Gly Ser Gly Asn Met Gly Arg Val Ala
385                 390                 395                 400

Arg Thr Gly Arg Met Pro Leu Arg Tyr Tyr Gly Asp Pro Lys Lys Thr
            405                 410                 415

Ala Glu Thr Phe Val Glu Val Gly Gly Val Arg Trp Ala Val Thr Gly
            420                 425                 430

Asp Gln Ala Thr Val Asp Thr Asp Gly Thr Ile Thr Val Leu Gly Arg
        435                 440                 445

Gly Ser Val Ser Ile Asn Thr Gly Gly Glu Lys Val Phe Pro Glu Glu
    450                 455                 460

Val Glu Ala Ala Leu Lys Thr His Pro Gly Val Phe Asp Thr Val Val
465                 470                 475                 480

Val Gly Val Pro Asp Glu Arg Trp Gly Glu Thr Val Ala Ala Val Val
            485                 490                 495

Ala Pro Arg Glu Gly Thr Glu Leu Thr Leu Asp Asp Leu Lys Ala His
            500                 505                 510

Val Lys Gly Thr Ile Ala Gly Tyr Lys Ala Pro Arg Lys Leu Val Leu
        515                 520                 525

Val Asp Glu Val Val Arg Ser Pro Thr Gly Lys Ala Asp Tyr Pro Trp
    530                 535                 540

Ala Lys Glu Arg Ala Ser Ser Glu Ala
545                 550
```

<210> SEQ ID NO 35
<211> LENGTH: 1656
<212> TYPE: DNA
<213> ORGANISM: Candidatus Microthrix parvicella

<400> SEQUENCE: 35

```
gtgtcagagc acccaacaaa tgacccgctt gcaggcgatg taaccgctcc gcagaccacc      60

ccggcgctgc tcgcccaggt ggcgtcgcgc tatggcgacg acccgggggt ggtcgacggc     120

gacgtcgccc tcacctgggc gcagctggcc ggccgcgccg cagagttggc gagggcggtg     180

gcagcacacg gcatcgaggc gggcgaccgg gtggccatct gggcgccgaa ctgttgggag     240

tgggtggtgg ccgtcctggg tctgcactcg gccggtgcgg tgctggtgcc gatcaacacg     300

aggtatcggg gggaggaggc ggcccatctg ctcgagcgtt cgcaggcacg gttgcttttt     360
```

```
acggtgggcg agtttttggg caccgactat ctggcgttgt tgggcgaccg tcgcccggcg    420

gtgaccgaca cggtggtggt gcttcgcagc gatgccgaca cgaacgatct cacgaccggt    480

gagactcagg gcggcgccgt gctcgacctg gcgacgttcc tgggtcgagc cggggaggtg    540

gccgacgcgg agatcgacgc tcgcattgca gcgcttgacg gcgacagtcc ctcggacatc    600

ctcttcacct ccggcaccac cgggcagccg aagggggcgg tctgcacgca cggccaggtg    660

gtgcgggcct atgccgcctg ggccaacgtg gtcgggttga cccatgacga ccgctacctg    720

gtggtcagcc cgttctttca cgcctttggc tacaaggcgg gcatcatcgc cgccatgacg    780

gtgggttcgc ccatctaccc cgagccggtg ttcgacgtga acaaggtgat ggagcgggtt    840

gcggccgaac agatctcgat gctgcccggc ccgccgacgc tgtaccagag catgctgaac    900

catccggatc tggatacaga ggcgctggcc ggcctgcgcc tggcggtcac gggtgccgcg    960

tcggtgcccg tcgagctgat cgaggcgatg ggtgacacgc tcggcttcga gacggtgatc   1020

accgggtacg ggctgaccga ggcctgcggc atcgccacga tgtgtcgcga cggcgacgat   1080

ccgatgacca tcgccaccac ctcgggacgc gcgatccccg gcgtggaggt ggtcacgttc   1140

gacgaggcag gcaacccgac cgcagcgggt gtgccgggtg aggtgcgcat acgtggctac   1200

aacgtcatgg tcgggtacct ggacgacccg gaggcgactg ccgagaccat cgacgccgat   1260

ggatggctgg ccaccggcga catcggggtg ctcgatgctg acggcaacct ggccatcacc   1320

gaccggttga aggacatgtt catcgtgggt gggttcaacg cgtaccccgc cgagatcgaa   1380

cgccaactgc tgttgcaccc ggacgtggcc caggccgcgg tgatcggggt gcccgacggc   1440

cggctgggtg aggtcggata cgcctttgtg gtgccgactg ccggcgtgtc gatcgacggc   1500

gccgccatca tcgcctggtg ccgcgaacac ctggccaact tcaaagtgcc ccggtatgtg   1560

gagtcgatcg acgagttgcc gttcaacgct ggtggcaagg tgatgaagtt ccagttgcgg   1620

gatcgagcgg cggagacgct gggcgaccac tcgtga                             1656
```

<210> SEQ ID NO 36
<211> LENGTH: 551
<212> TYPE: PRT
<213> ORGANISM: Candidatus Microthrix parvicella

<400> SEQUENCE: 36

```
Met Ser Glu His Pro Thr Asn Asp Pro Leu Ala Gly Asp Val Thr Ala
1               5                   10                  15

Pro Gln Thr Thr Pro Ala Leu Leu Ala Gln Val Ala Ser Arg Tyr Gly
            20                  25                  30

Asp Asp Pro Gly Val Val Asp Gly Asp Val Ala Leu Thr Trp Ala Gln
        35                  40                  45

Leu Ala Gly Arg Ala Ala Glu Leu Ala Arg Ala Val Ala Ala His Gly
    50                  55                  60

Ile Glu Ala Gly Asp Arg Val Ala Ile Trp Ala Pro Asn Cys Trp Glu
65                  70                  75                  80

Trp Val Val Ala Val Leu Gly Leu His Ser Ala Gly Ala Val Leu Val
                85                  90                  95

Pro Ile Asn Thr Arg Tyr Arg Gly Glu Glu Ala Ala His Leu Leu Glu
            100                 105                 110

Arg Ser Gln Ala Arg Leu Leu Phe Thr Val Gly Glu Phe Leu Gly Thr
        115                 120                 125

Asp Tyr Leu Ala Leu Leu Gly Asp Arg Arg Pro Ala Val Thr Asp Thr
    130                 135                 140
```

```
Val Val Val Leu Arg Ser Asp Ala Asp Thr Asn Asp Leu Thr Thr Gly
145                 150                 155                 160

Glu Thr Gln Gly Gly Ala Val Leu Asp Leu Ala Thr Phe Leu Gly Arg
                165                 170                 175

Ala Gly Glu Val Ala Asp Ala Glu Ile Asp Ala Arg Ile Ala Ala Leu
            180                 185                 190

Asp Gly Asp Ser Pro Ser Asp Ile Leu Phe Thr Ser Gly Thr Thr Gly
        195                 200                 205

Gln Pro Lys Gly Ala Val Cys Thr His Gly Gln Val Val Arg Ala Tyr
    210                 215                 220

Ala Ala Trp Ala Asn Val Val Gly Leu Thr His Asp Asp Arg Tyr Leu
225                 230                 235                 240

Val Val Ser Pro Phe Phe His Ala Phe Gly Tyr Lys Ala Gly Ile Ile
                245                 250                 255

Ala Ala Met Thr Val Gly Ser Pro Ile Tyr Pro Glu Pro Val Phe Asp
            260                 265                 270

Val Asn Lys Val Met Glu Arg Val Ala Ala Glu Gln Ile Ser Met Leu
        275                 280                 285

Pro Gly Pro Pro Thr Leu Tyr Gln Ser Met Leu Asn His Pro Asp Leu
    290                 295                 300

Asp Thr Glu Ala Leu Ala Gly Leu Arg Leu Ala Val Thr Gly Ala Ala
305                 310                 315                 320

Ser Val Pro Val Glu Leu Ile Glu Ala Met Gly Asp Thr Leu Gly Phe
                325                 330                 335

Glu Thr Val Ile Thr Gly Tyr Gly Leu Thr Glu Ala Cys Gly Ile Ala
            340                 345                 350

Thr Met Cys Arg Asp Gly Asp Asp Pro Met Thr Ile Ala Thr Thr Ser
        355                 360                 365

Gly Arg Ala Ile Pro Gly Val Glu Val Val Thr Phe Asp Glu Ala Gly
    370                 375                 380

Asn Pro Thr Ala Ala Gly Val Pro Gly Glu Val Arg Ile Arg Gly Tyr
385                 390                 395                 400

Asn Val Met Val Gly Tyr Leu Asp Asp Pro Glu Ala Thr Ala Glu Thr
                405                 410                 415

Ile Asp Ala Asp Gly Trp Leu Ala Thr Gly Asp Ile Gly Val Leu Asp
            420                 425                 430

Ala Asp Gly Asn Leu Ala Ile Thr Asp Arg Leu Lys Asp Met Phe Ile
        435                 440                 445

Val Gly Gly Phe Asn Ala Tyr Pro Ala Glu Ile Glu Arg Gln Leu Leu
    450                 455                 460

Leu His Pro Asp Val Ala Gln Ala Ala Val Ile Gly Val Pro Asp Gly
465                 470                 475                 480

Arg Leu Gly Glu Val Gly Tyr Ala Phe Val Val Pro Thr Ala Gly Val
                485                 490                 495

Ser Ile Asp Gly Ala Ala Ile Ile Ala Trp Cys Arg Glu His Leu Ala
            500                 505                 510

Asn Phe Lys Val Pro Arg Tyr Val Glu Ser Ile Asp Glu Leu Pro Phe
        515                 520                 525

Asn Ala Gly Gly Lys Val Met Lys Phe Gln Leu Arg Asp Arg Ala Ala
    530                 535                 540

Glu Thr Leu Gly Asp His Ser
545                 550
```

<210> SEQ ID NO 37
<211> LENGTH: 1530
<212> TYPE: DNA
<213> ORGANISM: Candidatus Microthrix parvicella

<400> SEQUENCE: 37

```
atgaaggttg acctgagcgt catcgatttc ctcgatcggg ccgagaccgt gtttccggac     60
cgggtggtgt tcgtggacga acccgatcaa atcgccgagt cgtggggcga ggtgaccggc    120
gccgagttcg cccgtcgggc ccgcaaccag gccgctcacc tggacgcgct tggcatcggg    180
gtgggggaac gggtggcgat catctcgcag aactcggccc gcctggcctg tggattcttc    240
ggggtgtcgg gctggggacg cgtctacgtg ccggtcaact tccgcctcag cccggccgag    300
gtcgcctaca tcgtcgacca ctgcggggcc acggtgttgt tgtacgaccc ggaactggcc    360
gacaccgttg ccgaccttga cgtcgcccac aaggtgatgc tgggcaccga cagcgatgtc    420
gaatggtttt tcaccgacgg cgagcccgca ccctgggagc ccgacgagga cgccaccgcc    480
accatcaact acacgtcggg caccaccgcc cgccccaagg gggtggagca gacccaccgc    540
tcgctgtggc tcaacgcctc cacctttggc tggcacgccg gggtgaacga gcgggacgtc    600
tacctgcaca cgctgccgat gtttcactgc aacgggtggg gcatggtgta cgcctcgctg    660
ggcatgggcg tgaaacaggt ggtgctgcgc aaggtggacg gtgccgagat cctgcgacgg    720
atcgaccgcc acggtgtcac gtttgcctgc gccgccccgg cggtcgtcgc ggccgccctc    780
gaagctgcgc ccgagttcga cccggtgccc ggccgtgacc gcatgcgggt gatcgtggcc    840
ggtgcgcccc caccaacgca gaccatcgaa cgggtggagg ccgagcttgg ttgggagttc    900
atccagatct acgggctgac cgagaccgcc ccgctgatga cgatgaaccg ctgccggagc    960
gaatgggacg acctcgcacc atcggagcgg gcgtccaacc tggcggccgc cggatcacca   1020
acgatcggca tgcgggtgag cgtggacgcc tacggggagg tgctcgcccg gggcaaccac   1080
gtgctcgagg ggtactgggc tcagccggag gccaccgccg cggccatcgt cgacggttgg   1140
ttccacaccg gcgacggcgg cacggtcgag ggtggcgtgg tcaccatctc ggatcgcaag   1200
aaggacgtga tcatctcggg cggcgagaac gtctcgtcga tcgaggtgga ggacgcggtg   1260
ttcagccatc ccgaggtggc cgaagtggcg gtgatcgggg tgccgtcgga caagtggggc   1320
gaaacggtga tggccctggt ggtgcgcacg gacggctcca ccctcaccga ggaggcactg   1380
atcgcccaca cccggcagcg gctggcgggt tacaagtgcc ccaagacgat cgagtttcgt   1440
gaggagttgg tgcggaccgc caccggcaag ctgcagaagt tcaagctgcg tgcgccctac   1500
tgggagggcc tcgaccgtca ggtgaactga                                    1530
```

<210> SEQ ID NO 38
<211> LENGTH: 509
<212> TYPE: PRT
<213> ORGANISM: Candidatus Microthrix parvicella

<400> SEQUENCE: 38

```
Met Lys Val Asp Leu Ser Val Ile Asp Phe Leu Asp Arg Ala Glu Thr
1               5                   10                  15

Val Phe Pro Asp Arg Val Val Phe Val Asp Glu Pro Asp Gln Ile Ala
            20                  25                  30

Glu Ser Trp Gly Glu Val Thr Gly Ala Glu Phe Ala Arg Arg Ala Arg
        35                  40                  45

Asn Gln Ala Ala His Leu Asp Ala Leu Gly Ile Gly Val Gly Glu Arg
    50                  55                  60
```

```
Val Ala Ile Ile Ser Gln Asn Ser Ala Arg Leu Ala Cys Gly Phe Phe
65                  70                  75                  80

Gly Val Ser Gly Trp Gly Arg Val Tyr Val Pro Val Asn Phe Arg Leu
                85                  90                  95

Ser Pro Ala Glu Val Ala Tyr Ile Val Asp His Cys Gly Ala Thr Val
            100                 105                 110

Leu Leu Tyr Asp Pro Glu Leu Ala Asp Thr Val Ala Asp Leu Asp Val
        115                 120                 125

Ala His Lys Val Met Leu Gly Thr Asp Ser Asp Val Glu Trp Phe Phe
    130                 135                 140

Thr Asp Gly Glu Pro Ala Pro Trp Glu Pro Asp Glu Asp Ala Thr Ala
145                 150                 155                 160

Thr Ile Asn Tyr Thr Ser Gly Thr Thr Ala Arg Pro Lys Gly Val Glu
                165                 170                 175

Gln Thr His Arg Ser Leu Trp Leu Asn Ala Ser Thr Phe Gly Trp His
            180                 185                 190

Ala Gly Val Asn Glu Arg Asp Val Tyr Leu His Thr Leu Pro Met Phe
        195                 200                 205

His Cys Asn Gly Trp Gly Met Val Tyr Ala Ser Leu Gly Met Gly Val
    210                 215                 220

Lys Gln Val Val Leu Arg Lys Val Asp Gly Ala Glu Ile Leu Arg Arg
225                 230                 235                 240

Ile Asp Arg His Gly Val Thr Phe Ala Cys Ala Ala Pro Ala Val Val
                245                 250                 255

Ala Ala Ala Leu Glu Ala Ala Pro Glu Phe Asp Pro Val Pro Gly Arg
            260                 265                 270

Asp Arg Met Arg Val Ile Val Ala Gly Ala Pro Pro Pro Thr Gln Thr
        275                 280                 285

Ile Glu Arg Val Glu Ala Glu Leu Gly Trp Glu Phe Ile Gln Ile Tyr
    290                 295                 300

Gly Leu Thr Glu Thr Ala Pro Leu Met Thr Met Asn Arg Cys Arg Ser
305                 310                 315                 320

Glu Trp Asp Asp Leu Ala Pro Ser Glu Arg Ala Ser Asn Leu Ala Ala
                325                 330                 335

Ala Gly Ser Pro Thr Ile Gly Met Arg Val Ser Val Asp Ala Tyr Gly
            340                 345                 350

Glu Val Leu Ala Arg Gly Asn His Val Leu Glu Gly Tyr Trp Ala Gln
        355                 360                 365

Pro Glu Ala Thr Ala Ala Ala Ile Val Asp Gly Trp Phe His Thr Gly
    370                 375                 380

Asp Gly Gly Thr Val Glu Gly Gly Val Val Thr Ile Ser Asp Arg Lys
385                 390                 395                 400

Lys Asp Val Ile Ile Ser Gly Gly Glu Asn Val Ser Ser Ile Glu Val
                405                 410                 415

Glu Asp Ala Val Phe Ser His Pro Glu Val Ala Glu Val Ala Val Ile
            420                 425                 430

Gly Val Pro Ser Asp Lys Trp Gly Glu Thr Val Met Ala Leu Val Val
        435                 440                 445

Arg Thr Asp Gly Ser Thr Leu Thr Glu Glu Ala Leu Ile Ala His Thr
    450                 455                 460

Arg Gln Arg Leu Ala Gly Tyr Lys Cys Pro Lys Thr Ile Glu Phe Arg
465                 470                 475                 480
```

```
Glu Glu Leu Val Arg Thr Ala Thr Gly Lys Leu Gln Lys Phe Lys Leu
                485                 490                 495

Arg Ala Pro Tyr Trp Glu Gly Leu Asp Arg Gln Val Asn
            500                 505
```

<210> SEQ ID NO 39
<211> LENGTH: 1614
<212> TYPE: DNA
<213> ORGANISM: Candidatus Microthrix parvicella

<400> SEQUENCE: 39

```
gtggtagtca cccaaaccct gggcccggcg gtcagcctgg cagccacgct ggccgaggcc      60

gcagttcgct ttggcgacgc gccggcggtg gtccgctggg atgacgagcc gctgggttac     120

gcaggctggt ggcaacaggc gctggcggtc gcccggtgga tggcccggcg gggtgtcagc     180

gagggcgacc gggtggcatt gatcctgcca tcgggcctgg agtatctggt ggcctacgct     240

gccgcgtcgg cgctgggcgc cgtcacggcg gggtcaacc cgtcgctcgc cccggccgaa      300

cgcgccgcgc tggtggagct ggtcgatccc gtcctggtgg tctccgatcc gaccctgacc     360

gacggccttc cggccgaccg caacgtggag ctggtcacgc cctgcgagcc gggtcgtgcg     420

ccgtgggcgg cacagctgga ggcggaccga tgtgcgttcc agggtggcgg cgtggcaggc     480

cctccgccgc tcgacggcgc ccctcaaccg ttacccggcc gcgctgcggc gctggtgttc     540

acctcgggta ccaccggcct gcccaaggcc gcgcggttca ccgagggtgc gctctcggcg     600

gtggccgccc tcgatctcgg cgccatcgcc caccggtggg gcggcggtgg gccgatgttc     660

gtgtccaccc agtttgccca tgtgggtctg atgaccaagc ttccgtggta cctccgaacc     720

ggtaccaggc ttcacctggt caaccgttgg cgggccgacg acgtgctcga gctggtcgca     780

cgggagcgca tgggcgtgat cggtgcggtg gcgccgcaag tggcgctgat gttgcgttcc     840

gcgcagatgg acgccctcga cctctcggcg gtgaacctgc tgatcgtggg aggcgccgcc     900

agcccgaccc ccctggtgag ggaggcccgc gagcgcttcg ccgccgggta caccattcgc     960

tactcgtcca ctgagaccgg cggctgcggg ttggccacac cgccgtggcc ggagcacccg    1020

ggcgacgatc gcaccatcgg gcggccacgt ccgggcatcg aagcctcgat tcgagacgac    1080

gacggcgccg aggtaccgga cgactcgctc ggcgaactct ggatccgaac accgagtgcc    1140

atgtccgggt actgggaggc gccggaggcc accgccgtcg ccctctccga cggctgggtt    1200

cgcaccggtg acctggccgt tcgggagccg gcaaccccgg aacgacctgg ccgttaccgg    1260

ttggcgggac ggcgaggcga catgtacatc cgcggcgggt acaacgtgtt tcccgccgag    1320

gtggaggcag ttcttgccga tcaccccgcc gtcgcacagg tggcggtcgt gccgagggtc    1380

gacgaggtga tgggcgaggt gggggtggcc gtcgtggtgc cacgaccggg gctcgctgca    1440

ccaacgctcg aatcgctgcg acggcacggc gaagccttga tcgcccgata caaactgccc    1500

gaggcgatga tcatgctgga ggcacttccg ctggggacca ccggcaaggt cgaccggcgg    1560

ctcctcatcg agcttggcgg gcgaccggac cgccgggaag gctccggggc atga          1614
```

<210> SEQ ID NO 40
<211> LENGTH: 537
<212> TYPE: PRT
<213> ORGANISM: Candidatus Microthrix parvicella

<400> SEQUENCE: 40

```
Met Val Val Thr Gln Thr Leu Gly Pro Ala Val Ser Leu Ala Ala Thr
1               5                   10                  15
```

```
Leu Ala Glu Ala Ala Val Arg Phe Gly Asp Ala Pro Ala Val Val Arg
            20                  25                  30

Trp Asp Asp Glu Pro Leu Gly Tyr Ala Gly Trp Trp Gln Gln Ala Leu
        35                  40                  45

Ala Val Ala Arg Trp Met Ala Arg Arg Gly Val Ser Glu Gly Asp Arg
    50                  55                  60

Val Ala Leu Ile Leu Pro Ser Gly Leu Glu Tyr Leu Val Ala Tyr Ala
65                  70                  75                  80

Ala Ala Ser Ala Leu Gly Ala Val Thr Ala Gly Val Asn Pro Ser Leu
                85                  90                  95

Ala Pro Ala Glu Arg Ala Ala Leu Val Glu Leu Val Asp Pro Val Leu
            100                 105                 110

Val Val Ser Asp Pro Thr Leu Thr Asp Gly Leu Pro Ala Asp Arg Asn
        115                 120                 125

Val Glu Leu Val Thr Pro Cys Glu Pro Gly Arg Ala Pro Trp Ala Ala
    130                 135                 140

Gln Leu Glu Ala Asp Arg Cys Ala Phe Gln Gly Gly Gly Val Ala Gly
145                 150                 155                 160

Pro Pro Pro Leu Asp Gly Ala Pro Gln Pro Leu Pro Gly Arg Ala Ala
                165                 170                 175

Ala Leu Val Phe Thr Ser Gly Thr Thr Gly Leu Pro Lys Ala Ala Arg
            180                 185                 190

Phe Thr Glu Gly Ala Leu Ser Ala Val Ala Ala Leu Asp Leu Gly Ala
        195                 200                 205

Ile Ala His Arg Trp Gly Gly Gly Gly Pro Met Phe Val Ser Thr Gln
    210                 215                 220

Phe Ala His Val Gly Leu Met Thr Lys Leu Pro Trp Tyr Leu Arg Thr
225                 230                 235                 240

Gly Thr Arg Leu His Leu Val Asn Arg Trp Arg Ala Asp Asp Val Leu
                245                 250                 255

Glu Leu Val Ala Arg Glu Arg Met Gly Val Ile Gly Ala Val Ala Pro
            260                 265                 270

Gln Val Ala Leu Met Leu Arg Ser Ala Gln Met Asp Ala Leu Asp Leu
        275                 280                 285

Ser Ala Val Asn Leu Leu Ile Val Gly Gly Ala Ala Ser Pro Thr Pro
    290                 295                 300

Leu Val Arg Glu Ala Arg Glu Arg Phe Ala Ala Gly Tyr Thr Ile Arg
305                 310                 315                 320

Tyr Ser Ser Thr Glu Thr Gly Gly Cys Gly Leu Ala Thr Pro Pro Trp
                325                 330                 335

Pro Glu His Pro Gly Asp Asp Arg Thr Ile Gly Arg Pro Arg Pro Gly
            340                 345                 350

Ile Glu Ala Ser Ile Arg Asp Asp Asp Gly Ala Glu Val Pro Asp Asp
        355                 360                 365

Ser Leu Gly Glu Leu Trp Ile Arg Thr Pro Ser Ala Met Ser Gly Tyr
    370                 375                 380

Trp Glu Ala Pro Glu Ala Thr Ala Val Ala Leu Ser Asp Gly Trp Val
385                 390                 395                 400

Arg Thr Gly Asp Leu Ala Val Arg Glu Pro Ala Thr Pro Glu Arg Pro
                405                 410                 415

Gly Arg Tyr Arg Leu Ala Gly Arg Arg Gly Asp Met Tyr Ile Arg Gly
            420                 425                 430

Gly Tyr Asn Val Phe Pro Ala Glu Val Glu Ala Val Leu Ala Asp His
```

```
        435                 440                 445

Pro Ala Val Ala Gln Val Ala Val Val Pro Arg Val Asp Glu Val Met
    450                 455                 460

Gly Glu Val Gly Val Ala Val Val Val Pro Arg Pro Gly Leu Ala Ala
465                 470                 475                 480

Pro Thr Leu Glu Ser Leu Arg Arg His Gly Glu Ala Leu Ile Ala Arg
                485                 490                 495

Tyr Lys Leu Pro Glu Ala Met Ile Met Leu Glu Ala Leu Pro Leu Gly
            500                 505                 510

Thr Thr Gly Lys Val Asp Arg Arg Leu Leu Ile Glu Leu Gly Gly Arg
        515                 520                 525

Pro Asp Arg Arg Glu Gly Ser Gly Ala
    530                 535


<210> SEQ ID NO 41
<211> LENGTH: 1533
<212> TYPE: DNA
<213> ORGANISM: Candidatus Microthrix parvicella

<400> SEQUENCE: 41

gtgagtgcga cgcaccggcc tccgacatca aacgccacgc ctcacttcgt cgaggttgtc     60

gcggcgaccg tcgaacggtt cggccatcgg cccctccttt cggcccacgg atccggcgcg    120

gcgctgacct acgccgacgt ctggggctgg gccggagcga gcgcccaacg gctcgccggg    180

gtgggcgcca ccccgggcga acgggtggtg gttcgggcgc cgaagtcggt cgagatgctc    240

atcgcctacc ttgcggcgct ccgcctcggc gccgtctgga cccctgtggc accaacggcc    300

acgaccaccg agctgaatca ggtgatcgac gatgccgagc cgcgggtggt gatcgacggc    360

aaccgcgcac tctgcgacat ggtgggagcg gcacccgctg gggcaccaga gccccaacca    420

ggcgattggc ccaaccccac gccaggccca gaccaaatcg ccgccatgct ctacacctcg    480

ggcaccaccg gtcgccccaa gggcgtgccg atcaccggcg cggcgctgag cgccaacgcc    540

catgcactgg tggacgcgtg gcggttcacc gaacacgatg tgctggtgca cgctctgccc    600

atccatcatg cccacggcct gttcgtggcc gtgggctgcg tgctggcgtc tggctcgtcg    660

atgcggtgga tcgaccgatt tgatgccacc gaggtgatcg acgggcttcg gaaggccacg    720

atgttcatgg gggtacccac ccacttcgtg cgcctcttgg aggactccgg ctttgaccgc    780

gcaacatgcg catccgtcag attgctcatc tccgggtcgg ccccacttcc ggcggtcacg    840

tttcaacaca tcgccgaccg caccggcctt gaggtcgtgg agcgctacgg catgaccgaa    900

accctgatgc tcgcctccaa cccaatcgac ggcatccgca agcccgggtc ggtgggactg    960

cccctgcccg ggtggaggt gcgtctgggg tcgtttgacg atgccgaccg gccggggcgg   1020

gcgacggagg tcggcatggt ggaggtgcgc gggccaagcg tgtttgagca ctactggggt   1080

cgcccacccg acccggcgga tcgagcgtcg gcggccgatg acgaccatgc ggaagggccg   1140

gcccaacagc cctggtttcg caccggcgac ctgggtcgct tcgatgctga cggctacctc   1200

cacctggttg gacgctccaa ggacctgatc atctcgggag ggctcaacgt gtaccccgcc   1260

gaggtggaag ccgtcttgga aggccaaccc ggggtggccg aggtggcggt catcggcctg   1320

ccagacgacc actggggcca gcaggtcacc gccatcgtcg tgcccgacac cggccccgcc   1380

ccgtccgacg agttctgcga acagttggtg gcaccggccc gggaacggtt atcggcctac   1440

aagctccccc ggcaggttca cctgaccgat gccctgccgc gcaacacgat gggcaaggtg   1500

gacaaggcag cactgcggcg cagcttcggc tga                                 1533
```

<210> SEQ ID NO 42
<211> LENGTH: 510
<212> TYPE: PRT
<213> ORGANISM: Candidatus Microthrix parvicella

<400> SEQUENCE: 42

```
Met Ser Ala Thr His Arg Pro Pro Thr Ser Asn Ala Thr Pro His Phe
1               5                   10                  15

Val Glu Val Val Ala Ala Thr Val Glu Arg Phe Gly His Arg Pro Leu
            20                  25                  30

Leu Ser Ala His Gly Ser Gly Ala Ala Leu Thr Tyr Ala Asp Val Trp
        35                  40                  45

Gly Trp Ala Gly Ala Ser Ala Gln Arg Leu Ala Gly Val Gly Ala Thr
    50                  55                  60

Pro Gly Glu Arg Val Val Val Arg Ala Pro Lys Ser Val Glu Met Leu
65                  70                  75                  80

Ile Ala Tyr Leu Ala Ala Leu Arg Leu Gly Ala Val Trp Thr Pro Val
                85                  90                  95

Ala Pro Thr Ala Thr Thr Thr Glu Leu Asn Gln Val Ile Asp Asp Ala
            100                 105                 110

Glu Pro Arg Val Val Ile Asp Gly Asn Arg Ala Leu Cys Asp Met Val
        115                 120                 125

Gly Ala Ala Pro Ala Gly Ala Pro Glu Pro Gln Pro Gly Asp Trp Pro
    130                 135                 140

Asn Pro Thr Pro Gly Pro Asp Gln Ile Ala Ala Met Leu Tyr Thr Ser
145                 150                 155                 160

Gly Thr Thr Gly Arg Pro Lys Gly Val Pro Ile Thr Gly Ala Ala Leu
                165                 170                 175

Ser Ala Asn Ala His Ala Leu Val Asp Ala Trp Arg Phe Thr Glu His
            180                 185                 190

Asp Val Leu Val His Ala Leu Pro Ile His His Ala His Gly Leu Phe
        195                 200                 205

Val Ala Val Gly Cys Val Leu Ala Ser Gly Ser Ser Met Arg Trp Ile
    210                 215                 220

Asp Arg Phe Asp Ala Thr Glu Val Ile Asp Gly Leu Arg Lys Ala Thr
225                 230                 235                 240

Met Phe Met Gly Val Pro Thr His Phe Val Arg Leu Leu Glu Asp Ser
                245                 250                 255

Gly Phe Asp Arg Ala Thr Cys Ala Ser Val Arg Leu Leu Ile Ser Gly
            260                 265                 270

Ser Ala Pro Leu Pro Ala Val Thr Phe Gln His Ile Ala Asp Arg Thr
        275                 280                 285

Gly Leu Glu Val Val Glu Arg Tyr Gly Met Thr Glu Thr Leu Met Leu
    290                 295                 300

Ala Ser Asn Pro Ile Asp Gly Ile Arg Lys Pro Gly Ser Val Gly Leu
305                 310                 315                 320

Pro Leu Pro Gly Val Glu Val Arg Leu Gly Ser Phe Asp Asp Ala Asp
                325                 330                 335

Arg Pro Gly Arg Ala Thr Glu Val Gly Met Val Glu Val Arg Gly Pro
            340                 345                 350

Ser Val Phe Glu His Tyr Trp Gly Arg Pro Pro Asp Pro Ala Asp Arg
        355                 360                 365

Ala Ser Ala Ala Asp Asp Asp His Ala Glu Gly Pro Ala Gln Gln Pro
```

```
    370                 375                 380

Trp Phe Arg Thr Gly Asp Leu Gly Arg Phe Asp Ala Asp Gly Tyr Leu
385                 390                 395                 400

His Leu Val Gly Arg Ser Lys Asp Leu Ile Ile Ser Gly Gly Leu Asn
                405                 410                 415

Val Tyr Pro Ala Glu Val Glu Ala Val Leu Glu Gly Gln Pro Gly Val
            420                 425                 430

Ala Glu Val Ala Val Ile Gly Leu Pro Asp Asp His Trp Gly Gln Gln
        435                 440                 445

Val Thr Ala Ile Val Val Pro Asp Thr Gly Pro Ala Pro Ser Asp Glu
    450                 455                 460

Phe Cys Glu Gln Leu Val Ala Pro Ala Arg Glu Arg Leu Ser Ala Tyr
465                 470                 475                 480

Lys Leu Pro Arg Gln Val His Leu Thr Asp Ala Leu Pro Arg Asn Thr
                485                 490                 495

Met Gly Lys Val Asp Lys Ala Ala Leu Arg Arg Ser Phe Gly
            500                 505                 510


<210> SEQ ID NO 43
<211> LENGTH: 1689
<212> TYPE: DNA
<213> ORGANISM: Candidatus Microthrix parvicella

<400> SEQUENCE: 43

atgcaacagc ctgggggcaa cagcgcgatg actgcgacca acgatcagca gccaatcaac      60

gtcgacgtga gcggggcggc cgaagacgtg gcggtggagc tcgacgccga gaccgtcgcc     120

aggtttcaat ttcatggaca ggacgtcggg tggctgctcg accagcgggc gaccaaccgg     180

gccgatcacc cgtttttggt gtgggagccc aaggacggtc cgagccgaac ctggacctat     240

ggcgagttcg ccgtcgccac caggaaggtc gccgccgggc tggccgaacg gggtgttggc     300

gtgggggacg cggtcctgat ccatgccgag aactgtcccg aagcggcgat cgcctggtac     360

gcggtggccc gccttggcgg catcgcggtc accaccaaca cccgcagcgt ggccgccgag     420

ctcagctact tcatcgagca ctcgggcgct gtcggggcaa tcacccaacc caagttggcg     480

tcggtggtgg cagaggcggg tgccgacctg gcctgggtgg tcgtgaccga cgacaacgtg     540

ggcgagcctg ccgacgatga gcagttggcc catggaggtg agtcgttcga ctcgttgttc     600

ggcgacgccg acaccgtgcc ggcgctccac cccgatccgt tgcgcccggt gagcatcatg     660

ttcacgtcgg gcaccacctc caagcccaag gcggtggtgc acacgcacgg caacgtgctg     720

tggagcgcca aggtcaaccc gcccaacatc gacttcggcc ccgatgacac ctacctgtgt     780

tacctgccgt tcttccacat caacacgcag ggctgggcga tgtggacggt gcttggcgcc     840

ggcggcaccg tggtgttgca gccgaagttc tccaccagcc gcttctggca ggtcatcgcc     900

gcccaccgtg tcacgcacat ttcgttgatc ccgttcgtct tcaaggcaat cggcgccgag     960

ccgatccccg agcacacggt tcgggttggt gtgttcggcc tgatcatgcc gttcctggat    1020

gagtggcttg gtatgcgggt catggccgcc tacggcatga ccgagctggt gacccattgc    1080

gtccgctcgg tccccaacga ggcctacccc gacatggcca tgggtcgggt tgcacccggt    1140

tacgagatga tggtcgtcaa tcacgagacc aatcgcccag ccgaagtggg cgagatgggc    1200

gagttgtgga tccgcggcgt gcggggcatc tcggtgtttc aggagtacct caataatccc    1260

gaggccaacg ccaagatgtt ctcgaacgac gggtggtgcc gcaccgggga tgtggttcgc    1320

ctggaggccg acggcaacat cttctactgc gaccgcgaca aggatgcgct gaaggtgggc    1380
```

ggcgaaaacg tgtcggcccg cgaggtggag gacgtgtgcc gcacggtgcc gggtatcgac 1440
gacatcgcgg tcgtggccaa gagccacgac atgttggaca tggtgcccgt ggcgttcgtg 1500
atccgcaacg ccggcgccga gtcggaggag gtgatggccg ccgccatcat cgacgcctgc 1560
gccggcgctt tggccgactt caaggtgcct cgggcggtct attacctcga cgagtttccg 1620
actgctgaac tgggcaagat ctccaagaag gacttgcggg acctggccga cacgttcgca 1680
gcggtctga 1689

<210> SEQ ID NO 44
<211> LENGTH: 562
<212> TYPE: PRT
<213> ORGANISM: Candidatus Microthrix parvicella

<400> SEQUENCE: 44

Met Gln Gln Pro Gly Gly Asn Ser Ala Met Thr Ala Thr Asn Asp Gln
1 5 10 15

Gln Pro Ile Asn Val Asp Val Ser Gly Ala Ala Glu Asp Val Ala Val
20 25 30

Glu Leu Asp Ala Glu Thr Val Ala Arg Phe Gln Phe His Gly Gln Asp
35 40 45

Val Gly Trp Leu Leu Asp Gln Arg Ala Thr Asn Arg Ala Asp His Pro
50 55 60

Phe Leu Val Trp Glu Pro Lys Asp Gly Pro Ser Arg Thr Trp Thr Tyr
65 70 75 80

Gly Glu Phe Ala Val Ala Thr Arg Lys Val Ala Ala Gly Leu Ala Glu
85 90 95

Arg Gly Val Gly Val Gly Asp Ala Val Leu Ile His Ala Glu Asn Cys
100 105 110

Pro Glu Ala Ala Ile Ala Trp Tyr Ala Val Ala Arg Leu Gly Gly Ile
115 120 125

Ala Val Thr Thr Asn Thr Arg Ser Val Ala Ala Glu Leu Ser Tyr Phe
130 135 140

Ile Glu His Ser Gly Ala Val Gly Ala Ile Thr Gln Pro Lys Leu Ala
145 150 155 160

Ser Val Val Ala Glu Ala Gly Ala Asp Leu Ala Trp Val Val Val Thr
165 170 175

Asp Asp Asn Val Gly Glu Pro Ala Asp Asp Glu Gln Leu Ala His Gly
180 185 190

Gly Glu Ser Phe Asp Ser Leu Phe Gly Asp Ala Asp Thr Val Pro Ala
195 200 205

Leu His Pro Asp Pro Leu Arg Pro Val Ser Ile Met Phe Thr Ser Gly
210 215 220

Thr Thr Ser Lys Pro Lys Ala Val Val His Thr His Gly Asn Val Leu
225 230 235 240

Trp Ser Ala Lys Val Asn Pro Pro Asn Ile Asp Phe Gly Pro Asp Asp
245 250 255

Thr Tyr Leu Cys Tyr Leu Pro Phe Phe His Ile Asn Thr Gln Gly Trp
260 265 270

Ala Met Trp Thr Val Leu Gly Ala Gly Gly Thr Val Val Leu Gln Pro
275 280 285

Lys Phe Ser Thr Ser Arg Phe Trp Gln Val Ile Ala Ala His Arg Val
290 295 300

Thr His Ile Ser Leu Ile Pro Phe Val Phe Lys Ala Ile Gly Ala Glu

```
305                 310                 315                 320

Pro Ile Pro Glu His Thr Val Arg Val Gly Val Phe Gly Leu Ile Met
                325                 330                 335

Pro Phe Leu Asp Glu Trp Leu Gly Met Arg Val Met Ala Ala Tyr Gly
            340                 345                 350

Met Thr Glu Leu Val Thr His Cys Val Arg Ser Val Pro Asn Glu Ala
        355                 360                 365

Tyr Pro Asp Met Ala Met Gly Arg Val Ala Pro Gly Tyr Glu Met Met
    370                 375                 380

Val Val Asn His Glu Thr Asn Arg Pro Ala Glu Val Gly Glu Met Gly
385                 390                 395                 400

Glu Leu Trp Ile Arg Gly Val Arg Gly Ile Ser Val Phe Gln Glu Tyr
                405                 410                 415

Leu Asn Asn Pro Glu Ala Asn Ala Lys Met Phe Ser Asn Asp Gly Trp
            420                 425                 430

Cys Arg Thr Gly Asp Val Val Arg Leu Glu Ala Asp Gly Asn Ile Phe
        435                 440                 445

Tyr Cys Asp Arg Asp Lys Asp Ala Leu Lys Val Gly Gly Glu Asn Val
    450                 455                 460

Ser Ala Arg Glu Val Glu Asp Val Cys Arg Thr Val Pro Gly Ile Asp
465                 470                 475                 480

Asp Ile Ala Val Val Ala Lys Ser His Asp Met Leu Asp Met Val Pro
                485                 490                 495

Val Ala Phe Val Ile Arg Asn Ala Gly Ala Glu Ser Glu Glu Val Met
            500                 505                 510

Ala Ala Ala Ile Ile Asp Ala Cys Ala Gly Ala Leu Ala Asp Phe Lys
        515                 520                 525

Val Pro Arg Ala Val Tyr Tyr Leu Asp Glu Phe Pro Thr Ala Glu Leu
    530                 535                 540

Gly Lys Ile Ser Lys Lys Asp Leu Arg Asp Leu Ala Asp Thr Phe Ala
545                 550                 555                 560

Ala Val


<210> SEQ ID NO 45
<211> LENGTH: 1848
<212> TYPE: DNA
<213> ORGANISM: Candidatus Microthrix parvicella

<400> SEQUENCE: 45

gtgaccacga ccgatgctgt acctgaaccg gtggcgggta gaggcggcac tcatgggcag     60

cggcaggtga gcgggtcgca cctcgctccg ttggcgccga acgcccacct gctcgagccc    120

ctgatcgaac gggctgccat cgaccccgac cgggtcgttg ccgcagtgcg ggaggggtcg    180

ggcttccgca atgtgaccgc gtcggagttt catggtcggg ttcgagcgat ggcgaagggc    240

ctcatcgcct cggaggtggc gccaggcgac cgggtggcgt tgatgtcggg cacccgcctg    300

gaatggctga tggtggacta cgccatcctg gccgtcggcg cggcgaccgt accgatttac    360

gagacgtcgg ctgccgacca ggtgtcgtgg atcctggcgg acagcggagc ggtgctggcc    420

gttgccgaga cctcgaacat ggccgaactg atcgatggca gcgtcgtcga tcccgaggtg    480

gcctgtggcg aagtgctcgt catcgacggc gccgggttgg acgacctggc ggcgaagggg    540

agcgaggtcg cagatgaaga actcgacagg cgaatcgccg ccctgaccat cgacgacctg    600

gcaaccctcg tctacacatc ggggacgacg ggccggccca aagggtgcat gctcacccac    660
```

```
ggcaacctgc gggccaacgt gaaacagaac ctcgatgcgg tggcgtcgat gctcggcccc    720

gacgagcgca gtctgctgtt cctgccgctg gcccacacgt acgccaagat catcgccctg    780

gtgggttcgg aatacggaat caagggcacg ttctcgtcgg ggatcgccaa cctgcccgag    840

gaactcgccc tttcctcgcc cacgatggtg gtggcggtgc cgcgcgtgtt cgagaaggtg    900

ttcagcaccg cacaacaacg ggcggaggcg ggcaacgttg gccccatctt cgaccgggcg    960

accgaggtgg ccatccgcta ttcacggcaa cgggccgagg ggtcggtcgg ttggctcacc   1020

cgcgccgagc acgcactgtt cgatcggctc gtctatcgca aggttcgcga cgggttcggc   1080

ggctcgatgc gtttcgcttt cagcgggggc agcccgctgg gtgaacgtct ggctcacttc   1140

ttcgatgggg tcggtgtgcg catctttgag ggctacggcc tgaccgaaac cggaccggtg   1200

ctggcggtga accgcgtcga cgcctggcgt ccgggaacgg tgggccgacc ggtggcgggc   1260

accagcctgc gtctcgccga ggatggcgaa gttgaggcga aggggcccca ggtgttccgc   1320

ggctactgga acaacgagga ggccacccgc gaagtgctgg cagacgatgg ctggttcaat   1380

accggcgatg tcggccgaat tgaggacggg tttctgcgca tcgtcggccg gaagaaggaa   1440

ctgatcgtca ccgccggcgg caagaacgtg gctcccgaac cgatggagga ccagttgcgg   1500

gcgcattcac tgatcagcca ggcgatggtg gtgggcgaca atcgtcggtt catcgcagcc   1560

gtggtgacga tcgacgagga ggcgttcgac gcctggtggc cgggggaccc caaccacgag   1620

atcagcgtgg ccgaggcggt cgaccaccat gatctgctgg ccgaggtgca gcacgccgtc   1680

gatgcggtga acgcaaaggt gtcgcgtgcg gaatcgatcc gaaagttcgc aatcctcccg   1740

aaggacctca ccgtggagga tggcgagatc acgcccacgc tgaaggtgcg acgggcgatc   1800

gtggctcagc actacgagca cgtgatcgac gagatgtacg ccacctga                1848
```

<210> SEQ ID NO 46
<211> LENGTH: 615
<212> TYPE: PRT
<213> ORGANISM: Candidatus Microthrix parvicella

<400> SEQUENCE: 46

```
Met Thr Thr Thr Asp Ala Val Pro Glu Pro Val Ala Gly Arg Gly Gly
1               5                   10                  15

Thr His Gly Gln Arg Gln Val Ser Gly Ser His Leu Ala Pro Leu Ala
            20                  25                  30

Pro Asn Ala His Leu Leu Glu Pro Leu Ile Glu Arg Ala Ala Ile Asp
        35                  40                  45

Pro Asp Arg Val Val Ala Ala Val Arg Glu Gly Ser Gly Phe Arg Asn
    50                  55                  60

Val Thr Ala Ser Glu Phe His Gly Arg Val Arg Ala Met Ala Lys Gly
65                  70                  75                  80

Leu Ile Ala Ser Glu Val Ala Pro Gly Asp Arg Val Ala Leu Met Ser
                85                  90                  95

Gly Thr Arg Leu Glu Trp Leu Met Val Asp Tyr Ala Ile Leu Ala Val
            100                 105                 110

Gly Ala Ala Thr Val Pro Ile Tyr Glu Thr Ser Ala Ala Asp Gln Val
        115                 120                 125

Ser Trp Ile Leu Ala Asp Ser Gly Ala Val Leu Ala Val Ala Glu Thr
    130                 135                 140

Ser Asn Met Ala Glu Leu Ile Asp Gly Ser Val Val Asp Pro Glu Val
145                 150                 155                 160

Ala Cys Gly Glu Val Leu Val Ile Asp Gly Ala Gly Leu Asp Asp Leu
```

```
                165                 170                 175

Ala Ala Lys Gly Ser Glu Val Ala Asp Glu Glu Leu Asp Arg Arg Ile
            180                 185                 190

Ala Ala Leu Thr Ile Asp Asp Leu Ala Thr Leu Val Tyr Thr Ser Gly
        195                 200                 205

Thr Thr Gly Arg Pro Lys Gly Cys Met Leu Thr His Gly Asn Leu Arg
    210                 215                 220

Ala Asn Val Lys Gln Asn Leu Asp Ala Val Ala Ser Met Leu Gly Pro
225                 230                 235                 240

Asp Glu Arg Ser Leu Leu Phe Leu Pro Leu Ala His Thr Tyr Ala Lys
                245                 250                 255

Ile Ile Ala Leu Val Gly Ser Glu Tyr Gly Ile Lys Gly Thr Phe Ser
            260                 265                 270

Ser Gly Ile Ala Asn Leu Pro Glu Glu Leu Ala Leu Ser Ser Pro Thr
        275                 280                 285

Met Val Val Ala Val Pro Arg Val Phe Glu Lys Val Phe Ser Thr Ala
    290                 295                 300

Gln Gln Arg Ala Glu Ala Gly Asn Val Gly Pro Ile Phe Asp Arg Ala
305                 310                 315                 320

Thr Glu Val Ala Ile Arg Tyr Ser Arg Gln Arg Ala Glu Gly Ser Val
                325                 330                 335

Gly Trp Leu Thr Arg Ala Glu His Ala Leu Phe Asp Arg Leu Val Tyr
            340                 345                 350

Arg Lys Val Arg Asp Gly Phe Gly Gly Ser Met Arg Phe Ala Phe Ser
        355                 360                 365

Gly Gly Ser Pro Leu Gly Glu Arg Leu Ala His Phe Phe Asp Gly Val
    370                 375                 380

Gly Val Arg Ile Phe Glu Gly Tyr Gly Leu Thr Glu Thr Gly Pro Val
385                 390                 395                 400

Leu Ala Val Asn Arg Val Asp Ala Trp Arg Pro Gly Thr Val Gly Arg
                405                 410                 415

Pro Val Ala Gly Thr Ser Leu Arg Leu Ala Glu Asp Gly Glu Val Glu
            420                 425                 430

Ala Lys Gly Pro Gln Val Phe Arg Gly Tyr Trp Asn Asn Glu Glu Ala
        435                 440                 445

Thr Arg Glu Val Leu Ala Asp Asp Gly Trp Phe Asn Thr Gly Asp Val
    450                 455                 460

Gly Arg Ile Glu Asp Gly Phe Leu Arg Ile Val Gly Arg Lys Lys Glu
465                 470                 475                 480

Leu Ile Val Thr Ala Gly Gly Lys Asn Val Ala Pro Glu Pro Met Glu
                485                 490                 495

Asp Gln Leu Arg Ala His Ser Leu Ile Ser Gln Ala Met Val Val Gly
            500                 505                 510

Asp Asn Arg Arg Phe Ile Ala Ala Val Val Thr Ile Asp Glu Glu Ala
        515                 520                 525

Phe Asp Ala Trp Trp Pro Gly Asp Pro Asn His Glu Ile Ser Val Ala
    530                 535                 540

Glu Ala Val Asp His His Asp Leu Leu Ala Glu Val Gln His Ala Val
545                 550                 555                 560

Asp Ala Val Asn Ala Lys Val Ser Arg Ala Glu Ser Ile Arg Lys Phe
                565                 570                 575

Ala Ile Leu Pro Lys Asp Leu Thr Val Glu Asp Gly Glu Ile Thr Pro
            580                 585                 590
```

```
Thr Leu Lys Val Arg Arg Ala Ile Val Ala Gln His Tyr Glu His Val
        595                 600                 605

Ile Asp Glu Met Tyr Ala Thr
    610                 615


<210> SEQ ID NO 47
<211> LENGTH: 1572
<212> TYPE: DNA
<213> ORGANISM: Candidatus Microthrix parvicella

<400> SEQUENCE: 47

atgacccgtc cgctggttcg tatcgtgcgg cgtgaggcgg cccgtctggg catgttgcga      60

gcggggctga cgttgggctc gctgctggag cgtgctgccg ccgtgcacgg atcatcggtg     120

atggtcgatc aggcggcgga gcctcgcacc ggcgtaccgg cccgaattct caccgtcgcc     180

gcagcggccg agctggtcga cgtttgggcg ggtgcgctgg ttgcagatgg aaagctcggt     240

gccggcgatc gggtggtggt cgccacgcca aactcggtcg agatgttgct ggccaccctg     300

gcagtgtccc gtgcgggcgg tatcccggcc ccggtcaacg atgccatgcg tgacgacgag     360

attgcccacg tggttcggga cgctgacgct tcggtggtga tccgtggtgt tgacgagttg     420

gatgcgctgg ccttgcgcct gggggtgaac tccggcctgg gtgaagaccg gggggcgacc     480

gagcgggtgg ccgcgttgtt ctatacgtcc ggaaccaccg gaagccccaa gggtgctgcg     540

ttgacccatc gggcgttggt cggcgagctt ggccggctgg cggccctccc ggccgggctg     600

ctgatctccg agttggccct ggcgcttccg gtggcccata tctatgggtt tgcagctttg     660

gtggcagcct cggtgggagg gattccggtg cgtttccgcc cgcgttttcg gccgaccgag     720

gtactggacg acatcgagtc acgccgcagc tctgccttcg ccggggtacc cacgatgtac     780

cgcatgttgg aggaggcggg ggccgatgac cgtgacctgc ggtccgttcg cctctggatc     840

tccggtgcgg acgtgatgcc accggagttg gcccgtcgct tcaaacggcg cggcgccgca     900

ctgagcctgc ccggtctggg ggcggtgggc gaagcgacgt tcgccgaggg gtacggcatg     960

gtggagaccg gcgggggagc tgcggccaag gtgtcgccgc ccttcgtgcc cctgggcctg    1020

ggcgaccaat tgggtattcc gctgcccggc tattccttcc gagtggtgga cgagcacggc    1080

gacgaggtgc gtctcggtgc cgtcggacag ctgctcctgc gcggcccggg tgtactcgag    1140

gggtattggg gcgacgccga tgccaccaat gctgtgctcg acgacgaggg ttggctgtcg    1200

acaggggacc tggtccgtcg gggcccgatg ggcacgttct cctttcaggg gcgggagaag    1260

gcggtgatca aatctggggg gttttccgtg tatccacccg aggtggaacg ggtcatcgag    1320

cagcaccccg aggtcgtcga ggcgggtgtc gtgggcctcc ccgacgacaa gttcggcgag    1380

gtgcccgccg tggcggtgcg gctggtcgac agcgccacgg tgacgtctgc tcagcttctg    1440

gcctggatgg gcacgcgcct gtcggactac aagacaccgc gtcgcgtgtt catcgtggac    1500

gatctgcccc gtacgggaac caacaagttg cagcgctccg aattggtcga gcgcctccgc    1560

gaccgcgact ga                                                        1572


<210> SEQ ID NO 48
<211> LENGTH: 523
<212> TYPE: PRT
<213> ORGANISM: Candidatus Microthrix parvicella

<400> SEQUENCE: 48

Met Thr Arg Pro Leu Val Arg Ile Val Arg Arg Glu Ala Ala Arg Leu
1               5                   10                  15
```

```
Gly Met Leu Arg Ala Gly Leu Thr Leu Gly Ser Leu Leu Glu Arg Ala
            20                  25                  30

Ala Ala Val His Gly Ser Ser Val Met Val Asp Gln Ala Ala Glu Pro
        35                  40                  45

Arg Thr Gly Val Pro Ala Arg Ile Leu Thr Val Ala Ala Ala Ala Glu
    50                  55                  60

Leu Val Asp Val Trp Ala Gly Ala Leu Val Ala Asp Gly Lys Leu Gly
65                  70                  75                  80

Ala Gly Asp Arg Val Val Val Ala Thr Pro Asn Ser Val Glu Met Leu
                85                  90                  95

Leu Ala Thr Leu Ala Val Ser Arg Ala Gly Gly Ile Pro Ala Pro Val
            100                 105                 110

Asn Asp Ala Met Arg Asp Asp Glu Ile Ala His Val Val Arg Asp Ala
        115                 120                 125

Asp Ala Ser Val Val Ile Arg Gly Val Asp Glu Leu Asp Ala Leu Ala
    130                 135                 140

Leu Arg Leu Gly Val Asn Ser Gly Leu Gly Glu Asp Arg Gly Ala Thr
145                 150                 155                 160

Glu Arg Val Ala Ala Leu Phe Tyr Thr Ser Gly Thr Thr Gly Ser Pro
                165                 170                 175

Lys Gly Ala Ala Leu Thr His Arg Ala Leu Val Gly Glu Leu Gly Arg
            180                 185                 190

Leu Ala Ala Leu Pro Ala Gly Leu Leu Ile Ser Glu Leu Ala Leu Ala
        195                 200                 205

Leu Pro Val Ala His Ile Tyr Gly Phe Ala Ala Leu Val Ala Ala Ser
    210                 215                 220

Val Gly Gly Ile Pro Val Arg Phe Arg Pro Arg Phe Arg Pro Thr Glu
225                 230                 235                 240

Val Leu Asp Asp Ile Glu Ser Arg Arg Ser Ser Ala Phe Ala Gly Val
                245                 250                 255

Pro Thr Met Tyr Arg Met Leu Glu Glu Ala Gly Ala Asp Asp Arg Asp
            260                 265                 270

Leu Arg Ser Val Arg Leu Trp Ile Ser Gly Ala Asp Val Met Pro Pro
        275                 280                 285

Glu Leu Ala Arg Arg Phe Lys Arg Arg Gly Ala Ala Leu Ser Leu Pro
    290                 295                 300

Gly Leu Gly Ala Val Gly Glu Ala Thr Phe Ala Glu Gly Tyr Gly Met
305                 310                 315                 320

Val Glu Thr Gly Gly Gly Ala Ala Ala Lys Val Ser Pro Pro Phe Val
                325                 330                 335

Pro Leu Gly Leu Gly Asp Gln Leu Gly Ile Pro Leu Pro Gly Tyr Ser
            340                 345                 350

Phe Arg Val Val Asp Glu His Gly Asp Glu Val Arg Leu Gly Ala Val
        355                 360                 365

Gly Gln Leu Leu Leu Arg Gly Pro Gly Val Leu Glu Gly Tyr Trp Gly
    370                 375                 380

Asp Ala Asp Ala Thr Asn Ala Val Leu Asp Asp Glu Gly Trp Leu Ser
385                 390                 395                 400

Thr Gly Asp Leu Val Arg Arg Gly Pro Met Gly Thr Phe Ser Phe Gln
                405                 410                 415

Gly Arg Glu Lys Ala Val Ile Lys Ser Gly Gly Phe Ser Val Tyr Pro
            420                 425                 430
```

```
Pro Glu Val Glu Arg Val Ile Glu Gln His Pro Glu Val Val Glu Ala
        435                 440                 445

Gly Val Val Gly Leu Pro Asp Asp Lys Phe Gly Glu Val Pro Ala Val
    450                 455                 460

Ala Val Arg Leu Val Asp Ser Ala Thr Val Thr Ser Ala Gln Leu Leu
465                 470                 475                 480

Ala Trp Met Gly Thr Arg Leu Ser Asp Tyr Lys Thr Pro Arg Arg Val
                485                 490                 495

Phe Ile Val Asp Asp Leu Pro Arg Thr Gly Thr Asn Lys Leu Gln Arg
            500                 505                 510

Ser Glu Leu Val Glu Arg Leu Arg Asp Arg Asp
        515                 520


<210> SEQ ID NO 49
<211> LENGTH: 1530
<212> TYPE: DNA
<213> ORGANISM: Candidatus Microthrix parvicella

<400> SEQUENCE: 49

gtgaatctgg ccagcatcat cgacggacac gacgacgacc gggtggctgt gatcagccgc     60

ggtcgtccca ccacctatgg cgagttgcgg cgtcaggttg ctggtttgcg acggggattg    120

accgatctgg gcctcaccac cggtgattcc gtcgccatca tggcgtccaa caaccgctac    180

ttcgtcgtca gctacctggc gacgcttgga gcgggcctgg tggcggtgcc gctcaacccc    240

accactcctg ctttggcggt gaaagaggaa ctggaggccg tgaaggcgcg ggcgttgatc    300

gccggtccgt ccgctcgggc cctggtgacc ggcaacaccg agggcgcgct cgacagcatc    360

gagttcgtca tcgggtgcgg atttgagccg gacggcggaa cccaattcga gacgctgatc    420

gaatccgagt cggccgattg ggtggaactt gacgaggaca cgccggcggt cctggccttc    480

acctcgggta cggccgggct gcccaaacct gcagtgctca gccacgccaa cctgatggtc    540

aacgtccaac agcagctgtc ctcggccgag gaccgccagt gcgccgacga cgtgtcattg    600

gcggtggcgc cgttgagcca catcatgggg ttcaacctgg tgttggccac atcgctctcg    660

gtcggcgcgt cggtggtgct gatcgaacgg ttcgatccgg tgttggcgct ggaatcgatg    720

cagaaacacg gcgtcacggt ggtggtcggc cccccgacca tgtgggcggc ctggttgaac    780

ctgccggatc taccctccga cgtgttctcg tcggtccgca tcgcggcctc gggcgccgcc    840

cggctgccgg tggaggtgtc ggaggccttc gagcggcgat tcgggttgcg cctgtgggag    900

ggctatggcc tcaccgaggc atcgccgatg gtgtgttcgt cctatggcac cgacgctccc    960

cacggctcgg tgggctttcc cgcccccgga ctggaggtcc gcctggtgga ccgcgagggc   1020

gacgacgtgt tgatcggcga tccgggcgag ctgctggttc gcggccccaa catcttctcc   1080

gggtatctca acgaacccga ggccacagcc gatgcgctgg atggcgacgg ttggctgcac   1140

accggcgaca tcgccgtcgt cgacgagcac ggctacgtgt tcctcgtcga ccgcagtaaa   1200

gacctgatca tcgtctcggg cttcaacgtg tacccggccg aggtcgagac ggccatccgc   1260

tcgcatccgc tggtggagga ctgcgtggtg gtgggggtgc cccatccggg caccggcgag   1320

tcggtggtgg cctacgtcgt gcccgccgac aaggcgatgt tggaggagga aggcgtcatc   1380

cgccactgcc agacacgact ggcccgatac aagtgcccca agaagatttg gttcaccgat   1440

gaggtgcctc aggaccttgg aggcaaggtg ttacggcgaa tgttgcccgc ccgcccgtcg   1500

gcgcaaaaga cctcgtggga gcccaactga                                    1530
```

<210> SEQ ID NO 50
<211> LENGTH: 509
<212> TYPE: PRT
<213> ORGANISM: Candidatus Microthrix parvicella

<400> SEQUENCE: 50

```
Met Asn Leu Ala Ser Ile Ile Asp Gly His Asp Asp Asp Arg Val Ala
1               5                   10                  15

Val Ile Ser Arg Gly Arg Pro Thr Thr Tyr Gly Glu Leu Arg Arg Gln
            20                  25                  30

Val Ala Gly Leu Arg Arg Gly Leu Thr Asp Leu Gly Leu Thr Thr Gly
        35                  40                  45

Asp Ser Val Ala Ile Met Ala Ser Asn Asn Arg Tyr Phe Val Val Ser
    50                  55                  60

Tyr Leu Ala Thr Leu Gly Ala Gly Leu Val Ala Val Pro Leu Asn Pro
65                  70                  75                  80

Thr Thr Pro Ala Leu Ala Val Lys Glu Glu Leu Glu Ala Val Lys Ala
                85                  90                  95

Arg Ala Leu Ile Ala Gly Pro Ser Ala Arg Ala Leu Val Thr Gly Asn
            100                 105                 110

Thr Glu Gly Ala Leu Asp Ser Ile Glu Phe Val Ile Gly Cys Gly Phe
        115                 120                 125

Glu Pro Asp Gly Gly Thr Gln Phe Glu Thr Leu Ile Glu Ser Glu Ser
    130                 135                 140

Ala Asp Trp Val Glu Leu Asp Glu Asp Thr Pro Ala Val Leu Ala Phe
145                 150                 155                 160

Thr Ser Gly Thr Ala Gly Leu Pro Lys Pro Ala Val Leu Ser His Ala
                165                 170                 175

Asn Leu Met Val Asn Val Gln Gln Gln Leu Ser Ser Ala Glu Asp Arg
            180                 185                 190

Gln Cys Ala Asp Asp Val Ser Leu Ala Val Ala Pro Leu Ser His Ile
        195                 200                 205

Met Gly Phe Asn Leu Val Leu Ala Thr Ser Leu Ser Val Gly Ala Ser
    210                 215                 220

Val Val Leu Ile Glu Arg Phe Asp Pro Val Leu Ala Leu Glu Ser Met
225                 230                 235                 240

Gln Lys His Gly Val Thr Val Val Val Gly Pro Pro Thr Met Trp Ala
                245                 250                 255

Ala Trp Leu Asn Leu Pro Asp Leu Pro Ser Asp Val Phe Ser Ser Val
            260                 265                 270

Arg Ile Ala Ala Ser Gly Ala Ala Arg Leu Pro Val Glu Val Ser Glu
        275                 280                 285

Ala Phe Glu Arg Arg Phe Gly Leu Arg Leu Trp Glu Gly Tyr Gly Leu
    290                 295                 300

Thr Glu Ala Ser Pro Met Val Cys Ser Ser Tyr Gly Thr Asp Ala Pro
305                 310                 315                 320

His Gly Ser Val Gly Phe Pro Ala Pro Gly Leu Glu Val Arg Leu Val
                325                 330                 335

Asp Arg Glu Gly Asp Asp Val Leu Ile Gly Asp Pro Gly Glu Leu Leu
            340                 345                 350

Val Arg Gly Pro Asn Ile Phe Ser Gly Tyr Leu Asn Glu Pro Glu Ala
        355                 360                 365

Thr Ala Asp Ala Leu Asp Gly Asp Gly Trp Leu His Thr Gly Asp Ile
    370                 375                 380
```

```
Ala Val Val Asp Glu His Gly Tyr Val Phe Leu Val Asp Arg Ser Lys
385                 390                 395                 400

Asp Leu Ile Ile Val Ser Gly Phe Asn Val Tyr Pro Ala Glu Val Glu
                405                 410                 415

Thr Ala Ile Arg Ser His Pro Leu Val Glu Asp Cys Val Val Val Gly
            420                 425                 430

Val Pro His Pro Gly Thr Gly Glu Ser Val Val Ala Tyr Val Val Pro
        435                 440                 445

Ala Asp Lys Ala Met Leu Glu Glu Glu Gly Val Ile Arg His Cys Gln
    450                 455                 460

Thr Arg Leu Ala Arg Tyr Lys Cys Pro Lys Lys Ile Trp Phe Thr Asp
465                 470                 475                 480

Glu Val Pro Gln Asp Leu Gly Gly Lys Val Leu Arg Arg Met Leu Pro
                485                 490                 495

Ala Arg Pro Ser Ala Gln Lys Thr Ser Trp Glu Pro Asn
            500                 505


<210> SEQ ID NO 51
<211> LENGTH: 1797
<212> TYPE: DNA
<213> ORGANISM: Candidatus Microthrix parvicella

<400> SEQUENCE: 51

atgacgctga ccgacgacga gattcttgca agagtcgagg gccagactgt tcccaccgcc      60

ttcatggcca ccgttgccgc ctatggcgac catgtggcgc ttcggtcgat ggttggggac     120

ggctggaggc aactcacctt caaccagtac gccgaacagg tggccacagc ggccgccggc     180

ctgcgcgctg tcggtgtcgg caagggcgac cgcgtcgtca tcatgatgcg caacattccc     240

gagtttcaca tcgtcgacct ggcgaccacg tttctgggcg caactcccat ctcgatctac     300

aacagttcgt caccagacca ggtggcatac ctggtcggcg actgtgccgc caaggtcgcg     360

gtcgtggagg gcgagggctt cgcgtcgcgt ttccgagccg tgcgcgatca gcttcccgct     420

ctcgagagcc tggtgatgct gaacgacgcc gacgccgacg ccgacgccgt ggcgtgggat     480

gcgttcatgg cccacgatcc cctcgatctg accgttgagg tcaacaacgc ctcacccgag     540

gatctggcca ccgtcatcta cacctccggc accaccggta acccaaaggg cgtcatgttg     600

agtcacctca acatcgtgtg gaccggggag tcgctgcgtg agacgttccc atttcccgag     660

accgccgggg tcagggtgat gtcgtatctg ccgatggctc acatcgccga gcgcatgacg     720

tcgcactatg ccagtgcgat catggcctac gacgtgtgtt gttgcccaga gttctccgaa     780

ctcaccgccc acatcggggc ggtgcatccc aacctgatgt ttggcgtgcc ccgggtgtgg     840

gagaagatcc actccggcat cgccgcagtg ctctccgccg acccggaaaa agaacagaag     900

gtcgccgagg ccgtcgaggc ggcgctcccc atcatggaga agatggatgc cggtactgcg     960

agcgaagagg agatcgccac gtggcaattc ctcgacgacg tcgccttctc gaccatccgc    1020

aacctcctgg gtcttgagga actgcaactg gcggtcagcg gcgctgcgcc gatctccgcc    1080

gagctgttgt cttggttccg agccatcggt gtcaacctgt gcgaggttta cgggatgtcg    1140

gagtcaaccg gcccgatgac cttcaccgtc gaaaacccca aggcgggaac cgtcggcccg    1200

gcgattccgg gatccgaggt cgctctggcc gaggacggcg aggtgatctt ccgaggttcc    1260

aacgtgttcg tcggctacct gaaccagccc gaaaagaccg ccgagaccat catcgacggc    1320

tggctgcact ccggcgacat cggcacgctc gacgacgacg gttacctcac catcgtcgac    1380

cgcaagaagg agttgatcgt caccgccggc ggcaagaaca tcagcccggc caacctggag    1440
```

```
gctgagctga agatgattga catcgtcggc caggcggctg cgatcggtga ccagcgaaag   1500

ttcgtctccg ccctgttggt gctcgatccc gaggttgccc cgatctgggc gcagcgcaat   1560

ggcatcgagt tcgagtcgct cgacgaactc gccaaacacg atgcggttcg agcccatgtc   1620

gacgcaggcg tcgcgcaggc gatggaagga ttcaaccacg ccgaggcggt gaagcgctgg   1680

gtcatcctcg gcgacgagtg ggagcccgac tccgaggtac tgacgcccac ctcaaaactc   1740

aagcgccgcg gcatcctgac ccgctacgaa gtggaaatcg agtcgatgta cgcctga      1797
```

<210> SEQ ID NO 52
<211> LENGTH: 598
<212> TYPE: PRT
<213> ORGANISM: Candidatus Microthrix parvicella

<400> SEQUENCE: 52

```
Met Thr Leu Thr Asp Asp Glu Ile Leu Ala Arg Val Glu Gly Gln Thr
1               5                   10                  15

Val Pro Thr Ala Phe Met Ala Thr Val Ala Ala Tyr Gly Asp His Val
            20                  25                  30

Ala Leu Arg Ser Met Val Gly Asp Gly Trp Arg Gln Leu Thr Phe Asn
        35                  40                  45

Gln Tyr Ala Glu Gln Val Ala Thr Ala Ala Ala Gly Leu Arg Ala Val
    50                  55                  60

Gly Val Gly Lys Gly Asp Arg Val Val Ile Met Met Arg Asn Ile Pro
65                  70                  75                  80

Glu Phe His Ile Val Asp Leu Ala Thr Thr Phe Leu Gly Ala Thr Pro
                85                  90                  95

Ile Ser Ile Tyr Asn Ser Ser Ser Pro Asp Gln Val Ala Tyr Leu Val
            100                 105                 110

Gly Asp Cys Ala Ala Lys Val Ala Val Val Glu Gly Glu Gly Phe Ala
        115                 120                 125

Ser Arg Phe Arg Ala Val Arg Asp Gln Leu Pro Ala Leu Glu Ser Leu
    130                 135                 140

Val Met Leu Asn Asp Ala Asp Ala Asp Ala Asp Ala Val Ala Trp Asp
145                 150                 155                 160

Ala Phe Met Ala His Asp Pro Leu Asp Leu Thr Val Glu Val Asn Asn
                165                 170                 175

Ala Ser Pro Glu Asp Leu Ala Thr Val Ile Tyr Thr Ser Gly Thr Thr
            180                 185                 190

Gly Asn Pro Lys Gly Val Met Leu Ser His Leu Asn Ile Val Trp Thr
        195                 200                 205

Gly Glu Ser Leu Arg Glu Thr Phe Pro Phe Pro Glu Thr Ala Gly Val
    210                 215                 220

Arg Val Met Ser Tyr Leu Pro Met Ala His Ile Ala Glu Arg Met Thr
225                 230                 235                 240

Ser His Tyr Ala Ser Ala Ile Met Ala Tyr Asp Val Cys Cys Cys Pro
                245                 250                 255

Glu Phe Ser Glu Leu Thr Ala His Ile Gly Ala Val His Pro Asn Leu
            260                 265                 270

Met Phe Gly Val Pro Arg Val Trp Glu Lys Ile His Ser Gly Ile Ala
        275                 280                 285

Ala Val Leu Ser Ala Asp Pro Glu Lys Glu Gln Lys Val Ala Glu Ala
    290                 295                 300

Val Glu Ala Ala Leu Pro Ile Met Glu Lys Met Asp Ala Gly Thr Ala
```

```
305                 310                 315                 320

Ser Glu Glu Glu Ile Ala Thr Trp Gln Phe Leu Asp Asp Val Ala Phe
                325                 330                 335

Ser Thr Ile Arg Asn Leu Leu Gly Leu Glu Glu Leu Gln Leu Ala Val
            340                 345                 350

Ser Gly Ala Ala Pro Ile Ser Ala Glu Leu Leu Ser Trp Phe Arg Ala
        355                 360                 365

Ile Gly Val Asn Leu Cys Glu Val Tyr Gly Met Ser Glu Ser Thr Gly
    370                 375                 380

Pro Met Thr Phe Thr Val Glu Asn Pro Lys Ala Gly Thr Val Gly Pro
385                 390                 395                 400

Ala Ile Pro Gly Ser Glu Val Ala Leu Ala Glu Asp Gly Glu Val Ile
                405                 410                 415

Phe Arg Gly Ser Asn Val Phe Val Gly Tyr Leu Asn Gln Pro Glu Lys
            420                 425                 430

Thr Ala Glu Thr Ile Ile Asp Gly Trp Leu His Ser Gly Asp Ile Gly
        435                 440                 445

Thr Leu Asp Asp Asp Gly Tyr Leu Thr Ile Val Asp Arg Lys Lys Glu
    450                 455                 460

Leu Ile Val Thr Ala Gly Gly Lys Asn Ile Ser Pro Ala Asn Leu Glu
465                 470                 475                 480

Ala Glu Leu Lys Met Ile Asp Ile Val Gly Gln Ala Ala Ala Ile Gly
                485                 490                 495

Asp Gln Arg Lys Phe Val Ser Ala Leu Leu Val Leu Asp Pro Glu Val
            500                 505                 510

Ala Pro Ile Trp Ala Gln Arg Asn Gly Ile Glu Phe Glu Ser Leu Asp
        515                 520                 525

Glu Leu Ala Lys His Asp Ala Val Arg Ala His Val Asp Ala Gly Val
    530                 535                 540

Ala Gln Ala Met Glu Gly Phe Asn His Ala Glu Ala Val Lys Arg Trp
545                 550                 555                 560

Val Ile Leu Gly Asp Glu Trp Glu Pro Asp Ser Glu Val Leu Thr Pro
                565                 570                 575

Thr Ser Lys Leu Lys Arg Arg Gly Ile Leu Thr Arg Tyr Glu Val Glu
            580                 585                 590

Ile Glu Ser Met Tyr Ala
        595


<210> SEQ ID NO 53
<211> LENGTH: 1632
<212> TYPE: DNA
<213> ORGANISM: Candidatus Microthrix parvicella

<400> SEQUENCE: 53

atggggttca acatcgcaga tctgttcgag cgcgccgtgg acgcggtgcc cgatcggacc      60

gcagtcgtgt gcggtgacag gtcgctgacc ttcgccgagt tcgatgccga gtccaaccgg     120

ctggccaacc acctgctgtc cgaaggcatc gggaccggcg accacatcgg catctacgcc     180

cagaactcgg tggaatggct gatcgccatg atcgctgcgt tcaaggtgcg tggcgtgccg     240

atcaacatca actttcgcta cgtcgaagac gaactggtct acctgttcga caacgccgac     300

ctggtggcgt tggtgcacga ccggggctac gtcgaccgga tcgcgtcggt gaccgagcgc     360

gtgcccgggt tgcggcacct ggtgacgatc gaggatggga gtgatgccga ccccgccacg     420

atcggatcgg tcgcgtgggc agacgcagtt ggggcggcga gcaccgaccg tccgcaggtg     480
```

```
gaacgctccg gcgacgatca ctacgtgctc tacaccgggg gcaccaccgg catgcccaag    540

ggtgtcgtgt ggcgccatga ggatgtcttc tatgcgctgg gtggaggcgt ggacgcctac    600

accaacgaac gcatcaccca cgggcaggaa ctggccgaca aggcacgggc ctccgacgca    660

ccgatggtgg ccctgaacac accgccgctg atgcacggcg ccgcgcaatg gggtcgctg     720

cggtttctct tcgagggcaa caccgtggtg ttcgttcgca acttcagccc cgaagcggtg    780

tttgacgcca tcgaggccaa ccgggtgacc accatcgtca tcaccggcga cgccatggcc    840

cgcccgttgg tggaaaccct ggccgaacag cccgaccgtt gggacctgtc ctcgctgttc    900

gtcgtgtcct ccagcgcagt ggtgttcagc ccgtcgctga aggaacagat gttggatctg    960

ctgcccgaca tcatcatcgt tgacgccatc ggctcgtcgg agagcggcat gaacggcatg   1020

gtcgtgcaga ccaaaggcga gacagccacc cacggcgggg gagggccgac ggtgaaggcc   1080

gggcgcgacg cggcggtgtt ggacgacgat ctcaacccga tggaaccggg caccggcgtg   1140

atcggcaagc tggcccgggg cggcaacatc ccggtgggct actacaagga ccccgtgaag   1200

accgccgcca cgtttgtcac cgccgccgac ggcaaccgtt atgcggttgc cggggacttt   1260

gccaggttgg aggccgatgg caccatcacg ctgttggggc ggggctcggt ctgcatcaac   1320

tcgggcggcg aaaagatctt cccagaggag gtcgagggcg tgttgaaggc ccacccggcc   1380

gtgtacgaca ccattgtggt gggcgttccc gatgaccgct ggggccaggc ggtttgcgcc   1440

gtggtgcagc cgagggacct tgaggcgccg ccgtcgttgg cgtcgctggc cgaccactgc   1500

cgctcgcatc tcgccgggta caagctgccc cgccacctgg tgctgaccga cgaaatcgtg   1560

cgctcaccca gtggcaaacc cgactatccg tgggccagtg tgctggcaaa ggaggaactc   1620

ggcctcgatt ga                                                       1632
```

<210> SEQ ID NO 54
<211> LENGTH: 543
<212> TYPE: PRT
<213> ORGANISM: Candidatus Microthrix parvicella

<400> SEQUENCE: 54

```
Met Gly Phe Asn Ile Ala Asp Leu Phe Glu Arg Ala Val Asp Ala Val
1               5                   10                  15

Pro Asp Arg Thr Ala Val Val Cys Gly Asp Arg Ser Leu Thr Phe Ala
            20                  25                  30

Glu Phe Asp Ala Glu Ser Asn Arg Leu Ala Asn His Leu Leu Ser Glu
        35                  40                  45

Gly Ile Gly Thr Gly Asp His Ile Gly Ile Tyr Ala Gln Asn Ser Val
    50                  55                  60

Glu Trp Leu Ile Ala Met Ile Ala Ala Phe Lys Val Arg Gly Val Pro
65                  70                  75                  80

Ile Asn Ile Asn Phe Arg Tyr Val Glu Asp Glu Leu Val Tyr Leu Phe
                85                  90                  95

Asp Asn Ala Asp Leu Val Ala Leu Val His Asp Arg Gly Tyr Val Asp
            100                 105                 110

Arg Ile Ala Ser Val Thr Glu Arg Val Pro Gly Leu Arg His Leu Val
        115                 120                 125

Thr Ile Glu Asp Gly Ser Asp Ala Asp Pro Ala Thr Ile Gly Ser Val
    130                 135                 140

Ala Trp Ala Asp Ala Val Gly Ala Ala Ser Thr Asp Arg Pro Gln Val
145                 150                 155                 160
```

```
Glu Arg Ser Gly Asp Asp His Tyr Val Leu Tyr Thr Gly Gly Thr Thr
                165                 170                 175

Gly Met Pro Lys Gly Val Val Trp Arg His Glu Asp Val Phe Tyr Ala
            180                 185                 190

Leu Gly Gly Gly Val Asp Ala Tyr Thr Asn Glu Arg Ile Thr His Gly
        195                 200                 205

Gln Glu Leu Ala Asp Lys Ala Arg Ala Ser Asp Ala Pro Met Val Ala
    210                 215                 220

Leu Asn Thr Pro Pro Leu Met His Gly Ala Ala Gln Trp Gly Ser Leu
225                 230                 235                 240

Arg Phe Leu Phe Glu Gly Asn Thr Val Val Phe Val Arg Asn Phe Ser
                245                 250                 255

Pro Glu Ala Val Phe Asp Ala Ile Glu Ala Asn Arg Val Thr Thr Ile
            260                 265                 270

Val Ile Thr Gly Asp Ala Met Ala Arg Pro Leu Val Glu Thr Leu Ala
        275                 280                 285

Glu Gln Pro Asp Arg Trp Asp Leu Ser Ser Leu Phe Val Val Ser Ser
    290                 295                 300

Ser Ala Val Val Phe Ser Pro Ser Leu Lys Glu Gln Met Leu Asp Leu
305                 310                 315                 320

Leu Pro Asp Ile Ile Ile Val Asp Ala Ile Gly Ser Ser Glu Ser Gly
                325                 330                 335

Met Asn Gly Met Val Val Gln Thr Lys Gly Glu Thr Ala Thr His Gly
            340                 345                 350

Gly Gly Gly Pro Thr Val Lys Ala Gly Arg Asp Ala Ala Val Leu Asp
        355                 360                 365

Asp Asp Leu Asn Pro Met Glu Pro Gly Thr Gly Val Ile Gly Lys Leu
    370                 375                 380

Ala Arg Gly Gly Asn Ile Pro Val Gly Tyr Tyr Lys Asp Pro Val Lys
385                 390                 395                 400

Thr Ala Ala Thr Phe Val Thr Ala Ala Asp Gly Asn Arg Tyr Ala Val
                405                 410                 415

Ala Gly Asp Phe Ala Arg Leu Glu Ala Asp Gly Thr Ile Thr Leu Leu
            420                 425                 430

Gly Arg Gly Ser Val Cys Ile Asn Ser Gly Gly Glu Lys Ile Phe Pro
        435                 440                 445

Glu Glu Val Glu Gly Val Leu Lys Ala His Pro Ala Val Tyr Asp Thr
    450                 455                 460

Ile Val Val Gly Val Pro Asp Asp Arg Trp Gly Gln Ala Val Cys Ala
465                 470                 475                 480

Val Val Gln Pro Arg Asp Leu Glu Ala Pro Pro Ser Leu Ala Ser Leu
                485                 490                 495

Ala Asp His Cys Arg Ser His Leu Ala Gly Tyr Lys Leu Pro Arg His
            500                 505                 510

Leu Val Leu Thr Asp Glu Ile Val Arg Ser Pro Ser Gly Lys Pro Asp
        515                 520                 525

Tyr Pro Trp Ala Ser Val Leu Ala Lys Glu Glu Leu Gly Leu Asp
    530                 535                 540
```

<210> SEQ ID NO 55
<211> LENGTH: 2079
<212> TYPE: DNA
<213> ORGANISM: Candidatus Microthrix parvicella

<400> SEQUENCE: 55

```
gtggtgatcg ctgtaggcgt gttctcggca gcgacttggt gcgcagcggg tttctggtcc     60
gcgagccagc gaaacgagac cagggatctt gctcgtatgc cggtcgtgga cttcggtagc    120
ggcggtgcgg gggtgccgtt gcttggcaag agtttgccga ttctggatgg gcgccagttc    180
gaaatccact ggctgggtgc cgacgctcag tcgattccgg ccgagttcgg cgggcatcta    240
ccggagccag ggaaagggtt cgtttcgccg gccctgattg aggccgcagg tggacccggt    300
ggcttccagg aacggttcgg tatcgaggtt gatgaacaca atcgtgatgt ccggtgggag    360
catgtgacgg cgtttgctgg cgagtttttg gcgttcgcga cggttccgga gggacgacct    420
ccatcggtgg gagcatctgc aggtcctcag caaagtctgg tgggatttga tgcagaagaa    480
ctgggcgcga gcgtggcaag tgggccattt gagatgccga gcgggctcgt aacgattccc    540
cactcgctcg acgagcgtgt ccctactcca gcagcagctc agagcggagc catgttcggc    600
ctgttgcttc cgggactgtt ggtgctgggg atcggattgt ccgctcgctc ggcgttgcgt    660
acccaacgca gcgacgcgtt ggtctatcta ggagctggcc ctaacgcaca ggatgcgttc    720
gatgcgtcgg aagccgccac gctgagcgtg ccgattgcgc tcatcgtgtc ggcggtcatg    780
tgggggatct tgggtgtccc cacgtcgttg ccgttcggct cgatcgagta cttgtccggc    840
gacttgcggc cgagtgctgg catcgctgtc gtcgcactgc ttattgcgtt gctggtgccg    900
gtggcggtcg gagcgctgac acccaaggtg accgcgtgga gagcgcagcg caataagcgc    960
accatccgtt ggaccggacg cctcctgttg cttgttcccg tcgccgtttc cgtcgcgacg   1020
acccagttcc ctcctcagct gagagctctc cgacttgttg tagtgcttgc gtcggttgtc   1080
gcagtcgttc cgaccgtcgc cgttgctgtt ttaccggtgg ttggcgcgat actcactgcg   1140
cctgaccgag ttgcgaggct ggttgccggt cgtcggttcc aacggggcga ccagcgggga   1200
tctgatctca ttcgcatcac gaccctgacc gttgtggctg cagttgtatt gacctcgatg   1260
agtctcgctt cctacgccgg tgccctggag tcggaggggc cgcctggcat catgaccgtc   1320
agcgctgatt cggagattga tggtccgacg ttcgccgagt tcgctatgca gttccccaac   1380
gttccgttcg cgactgttgt cgatgggcaa gtgttcgtgg ccaattgcga agaactggca   1440
gtaccggcgg ggcccgggtc gcaagggtgc tcaacggacc ccgaacggtt tatgaacgag   1500
gtcgagcgct cgacagccgt tcgtcctggg gtcttcgtgc ttggcagccc gccgctcgac   1560
cggccggttg ttcagatgat tgcccgggtc gattcggcca gccaggccca cgctctcgaa   1620
gctgacgcca atgccatctt cggcccctca agcgtgagcg gttgggaccg cttgggtcca   1680
aacccgatca tcgggtgggt ccagccactc ggtgtgtcag cactcgcgct gtttggtgtg   1740
gcggtggtct tgctgctcgt gaacacgatc cggttcccgt cgcagagcga ccaggccctg   1800
gcctggctcg ctgcacccat ccgaacccga cgtgccgtgt tgcgttgggg ctttcactcc   1860
gcagtgtggg ttggggtcct gctcgggtgc ggctacggaa tcgtcgcggt taccgccggt   1920
caaccatcgg ggatcaccga actcgactac ctatcgctgg ccaattcggc aatcctctgc   1980
ggggcagcga catcggtcgt cattgaggcc gccctctggg cacatggcag acagcaagtt   2040
ggtgtgccag ctggcgccga gtcagtcgat atctattag                          2079
```

<210> SEQ ID NO 56
<211> LENGTH: 692
<212> TYPE: PRT
<213> ORGANISM: Candidatus Microthrix parvicella

<400> SEQUENCE: 56

```
Met Val Ile Ala Val Gly Val Phe Ser Ala Ala Thr Trp Cys Ala Ala
1               5                   10                  15

Gly Phe Trp Ser Ala Ser Gln Arg Asn Glu Thr Arg Asp Leu Ala Arg
            20                  25                  30

Met Pro Val Val Asp Phe Gly Ser Gly Gly Ala Gly Val Pro Leu Leu
        35                  40                  45

Gly Lys Ser Leu Pro Ile Leu Asp Gly Arg Gln Phe Glu Ile His Trp
    50                  55                  60

Leu Gly Ala Asp Ala Gln Ser Ile Pro Ala Glu Phe Gly Gly His Leu
65                  70                  75                  80

Pro Glu Pro Gly Lys Gly Phe Val Ser Pro Ala Leu Ile Glu Ala Ala
                85                  90                  95

Gly Gly Pro Gly Gly Phe Gln Glu Arg Phe Gly Ile Glu Val Asp Glu
            100                 105                 110

His Asn Arg Asp Val Arg Trp Glu His Val Thr Ala Phe Ala Gly Glu
        115                 120                 125

Phe Leu Ala Phe Ala Thr Val Pro Glu Gly Arg Pro Pro Ser Val Gly
    130                 135                 140

Ala Ser Ala Gly Pro Gln Gln Ser Leu Val Gly Phe Asp Ala Glu Glu
145                 150                 155                 160

Leu Gly Ala Ser Val Ala Ser Gly Pro Phe Glu Met Pro Ser Gly Leu
                165                 170                 175

Val Thr Ile Pro His Ser Leu Asp Glu Arg Val Pro Thr Pro Ala Ala
            180                 185                 190

Ala Gln Ser Gly Ala Met Phe Gly Leu Leu Leu Pro Gly Leu Leu Val
        195                 200                 205

Leu Gly Ile Gly Leu Ser Ala Arg Ser Ala Leu Arg Thr Gln Arg Ser
    210                 215                 220

Asp Ala Leu Val Tyr Leu Gly Ala Gly Pro Asn Ala Gln Asp Ala Phe
225                 230                 235                 240

Asp Ala Ser Glu Ala Ala Thr Leu Ser Val Pro Ile Ala Leu Ile Val
                245                 250                 255

Ser Ala Val Met Trp Gly Ile Leu Gly Val Pro Thr Ser Leu Pro Phe
            260                 265                 270

Gly Ser Ile Glu Tyr Leu Ser Gly Asp Leu Arg Pro Ser Ala Gly Ile
        275                 280                 285

Ala Val Val Ala Leu Leu Ile Ala Leu Leu Val Pro Val Ala Val Gly
    290                 295                 300

Ala Leu Thr Pro Lys Val Thr Ala Trp Arg Ala Gln Arg Asn Lys Arg
305                 310                 315                 320

Thr Ile Arg Trp Thr Gly Arg Leu Leu Leu Leu Val Pro Val Ala Val
                325                 330                 335

Ser Val Ala Thr Thr Gln Phe Pro Pro Gln Leu Arg Ala Leu Arg Leu
            340                 345                 350

Val Val Val Leu Ala Ser Val Val Ala Val Val Pro Thr Val Ala Val
        355                 360                 365

Ala Val Leu Pro Val Val Gly Ala Ile Leu Thr Ala Pro Asp Arg Val
    370                 375                 380

Ala Arg Leu Val Ala Gly Arg Arg Phe Gln Arg Gly Asp Gln Arg Gly
385                 390                 395                 400

Ser Asp Leu Ile Arg Ile Thr Thr Leu Thr Val Val Ala Ala Val Val
                405                 410                 415

Leu Thr Ser Met Ser Leu Ala Ser Tyr Ala Gly Ala Leu Glu Ser Glu
```

```
            420                 425                 430

Gly Pro Pro Gly Ile Met Thr Val Ser Ala Asp Ser Glu Ile Asp Gly
        435                 440                 445

Pro Thr Phe Ala Glu Phe Ala Met Gln Phe Pro Asn Val Pro Phe Ala
    450                 455                 460

Thr Val Val Asp Gly Gln Val Phe Val Ala Asn Cys Glu Glu Leu Ala
465                 470                 475                 480

Val Pro Ala Gly Pro Gly Ser Gln Gly Cys Ser Thr Asp Pro Glu Arg
                485                 490                 495

Phe Met Asn Glu Val Glu Arg Ser Thr Ala Val Arg Pro Gly Val Phe
            500                 505                 510

Val Leu Gly Ser Pro Pro Leu Asp Arg Pro Val Val Gln Met Ile Ala
        515                 520                 525

Arg Val Asp Ser Ala Ser Gln Ala His Ala Leu Glu Ala Asp Ala Asn
    530                 535                 540

Ala Ile Phe Gly Pro Ser Ser Val Ser Gly Trp Asp Arg Leu Gly Pro
545                 550                 555                 560

Asn Pro Ile Ile Gly Trp Val Gln Pro Leu Gly Val Ser Ala Leu Ala
                565                 570                 575

Leu Phe Gly Val Ala Val Val Leu Leu Leu Val Asn Thr Ile Arg Phe
            580                 585                 590

Pro Ser Gln Ser Asp Gln Ala Leu Ala Trp Leu Ala Ala Pro Ile Arg
        595                 600                 605

Thr Arg Arg Ala Val Leu Arg Trp Gly Phe His Ser Ala Val Trp Val
    610                 615                 620

Gly Val Leu Leu Gly Cys Gly Tyr Gly Ile Val Ala Val Thr Ala Gly
625                 630                 635                 640

Gln Pro Ser Gly Ile Thr Glu Leu Asp Tyr Leu Ser Leu Ala Asn Ser
                645                 650                 655

Ala Ile Leu Cys Gly Ala Ala Thr Ser Val Val Ile Glu Ala Ala Leu
            660                 665                 670

Trp Ala His Gly Arg Gln Gln Val Gly Val Pro Ala Gly Ala Glu Ser
        675                 680                 685

Val Asp Ile Tyr
    690
```

<210> SEQ ID NO 57
<211> LENGTH: 807
<212> TYPE: DNA
<213> ORGANISM: Candidatus Microthrix parvicella

<400> SEQUENCE: 57

```
atgaacctgg gtatccgcac cgtcgaccgc acgctggtgg tcaccatcaa ccggcccgag     60

cgccgcaacg ccatcgatgg cccgacggcg gacgatttgc atcggacgtt cgtcggcttc    120

gatgccgacg acacactcga tgtggcggtg ttggccggtg cgaacggaac gttctgcgca    180

ggcgccgacc tgcacgccat cgccgagggc aacggcaacc gggtcgccgg agacctgtcg    240

gaaccggctc cgctgggctg cacccggctg gagctgaaca agccggtgat cgcggcggtg    300

gagggctttg ccgtcgccgg agggttggag ctggccctgt ggtgcgacct gcgggtggcg    360

gcgagcgacg ccaccttcgg ggtgtactgc cgacgcttcg gcgtgccgct gatcgatggc    420

gggacggttc gccttccccg gctggtcggg cacagccgcg ccatggacat gattctcacc    480

ggtcggagcg tgtccggcag cgaggccggc gcgtggggtc tcgccaaccg ggtctgcgag    540
```

```
ccgggtgagg cgttggacga ggcgatcgag ctggccacgt cgttgtcggc gttgcctcag    600

acatgtctga ggaacgaccg aaggtcgtgc aacgaacaat ggggcctcgg gcttggagct    660

gccctggcca acgagactcg gctggggttg gacacgttgc gcagcggcga gtcgttggcg    720

ggtgccggtc gcttcgccgc cggcgccggc cgaggaggga ctcccgccgg ggcagccgaa    780

cgaggtgagg cccaacccaa gcggtag                                         807
```

```
<210> SEQ ID NO 58
<211> LENGTH: 268
<212> TYPE: PRT
<213> ORGANISM: Candidatus Microthrix parvicella

<400> SEQUENCE: 58

Met Asn Leu Gly Ile Arg Thr Val Asp Arg Thr Leu Val Val Thr Ile
1               5                   10                  15

Asn Arg Pro Glu Arg Arg Asn Ala Ile Asp Gly Pro Thr Ala Asp Asp
            20                  25                  30

Leu His Arg Thr Phe Val Gly Phe Asp Ala Asp Asp Thr Leu Asp Val
        35                  40                  45

Ala Val Leu Ala Gly Ala Asn Gly Thr Phe Cys Ala Gly Ala Asp Leu
    50                  55                  60

His Ala Ile Ala Glu Gly Asn Gly Asn Arg Val Ala Gly Asp Leu Ser
65                  70                  75                  80

Glu Pro Ala Pro Leu Gly Cys Thr Arg Leu Glu Leu Asn Lys Pro Val
                85                  90                  95

Ile Ala Ala Val Glu Gly Phe Ala Val Ala Gly Gly Leu Glu Leu Ala
            100                 105                 110

Leu Trp Cys Asp Leu Arg Val Ala Ala Ser Asp Ala Thr Phe Gly Val
        115                 120                 125

Tyr Cys Arg Arg Phe Gly Val Pro Leu Ile Asp Gly Gly Thr Val Arg
    130                 135                 140

Leu Pro Arg Leu Val Gly His Ser Arg Ala Met Asp Met Ile Leu Thr
145                 150                 155                 160

Gly Arg Ser Val Ser Gly Ser Glu Ala Gly Ala Trp Gly Leu Ala Asn
                165                 170                 175

Arg Val Cys Glu Pro Gly Glu Ala Leu Asp Glu Ala Ile Glu Leu Ala
            180                 185                 190

Thr Ser Leu Ser Ala Leu Pro Gln Thr Cys Leu Arg Asn Asp Arg Arg
        195                 200                 205

Ser Cys Asn Glu Gln Trp Gly Leu Gly Leu Gly Ala Ala Leu Ala Asn
    210                 215                 220

Glu Thr Arg Leu Gly Leu Asp Thr Leu Arg Ser Gly Glu Ser Leu Ala
225                 230                 235                 240

Gly Ala Gly Arg Phe Ala Ala Gly Ala Gly Arg Gly Gly Thr Pro Ala
                245                 250                 255

Gly Ala Ala Glu Arg Gly Glu Ala Gln Pro Lys Arg
            260                 265
```

```
<210> SEQ ID NO 59
<211> LENGTH: 822
<212> TYPE: DNA
<213> ORGANISM: Candidatus Microthrix parvicella

<400> SEQUENCE: 59

atggccgagg ccgacgctcc gcttcttgtg gagcgaaccg acgacgacgt ggtgatcgcc     60
```

```
accccttcgca atggcaaagt gaacgcgttg tccaaccggg tgctggacgc cattggcgac    120

gccgccgcgg aatgggccaa ggatccaccc ggcgcggtcg tgctgacggg cgggcccaag    180

ctctttgctg ccggtgccga tatcgaccag ttcgtcgcct ccgacgaagg ggctgacgac    240

gcggtgacct tggtggacac cgatgccgtg cggtcgattg ctcaggcgtt tcgtcgagcg    300

agccgggcat tggaggccct cccctgcgca gtactggcgg aggtttccgg ctacgcactg    360

ggcggcgggt gcgagctggc gctggcggcc gatctgcgca tcgcgtcgga acgggcgcgg    420

ttcggacagc ccgagatcct gctgggcatc atccccggcg gcggcggcac gcagcggctg    480

gcccggctga tcgggccgtc aagggcaaag gacctggtgt tcaccggacg tcaggtggac    540

gcatccgagg cgcttggcat ggggttggtc aacgaggtgg tgccccacga tcacctgcgt    600

caacgcacgt tggaattggc cacctcgttt gcgtgcgggc cccgtcgggc catcgccctg    660

tccaagctgg ccatctccaa ggggatggag ggcaccctcg agcgaggact cgacgtggag    720

gaagatgcct tcgctgcggt gttctcaacc agcgacgcgg ccatcggcgt cgggtcgttt    780

caacaacacg gccccggcca ggcccacttc agcggccgct ga                        822
```

<210> SEQ ID NO 60
<211> LENGTH: 273
<212> TYPE: PRT
<213> ORGANISM: Candidatus Microthrix parvicella

<400> SEQUENCE: 60

```
Met Ala Glu Ala Asp Ala Pro Leu Leu Val Glu Arg Thr Asp Asp Asp
1               5                   10                  15

Val Val Ile Ala Thr Leu Arg Asn Gly Lys Val Asn Ala Leu Ser Asn
            20                  25                  30

Arg Val Leu Asp Ala Ile Gly Asp Ala Ala Ala Glu Trp Ala Lys Asp
        35                  40                  45

Pro Pro Gly Ala Val Val Leu Thr Gly Gly Pro Lys Leu Phe Ala Ala
    50                  55                  60

Gly Ala Asp Ile Asp Gln Phe Val Ala Ser Asp Glu Gly Ala Asp Asp
65                  70                  75                  80

Ala Val Thr Leu Val Asp Thr Asp Ala Val Arg Ser Ile Ala Gln Ala
                85                  90                  95

Phe Arg Arg Ala Ser Arg Ala Leu Glu Ala Leu Pro Cys Ala Val Leu
            100                 105                 110

Ala Glu Val Ser Gly Tyr Ala Leu Gly Gly Gly Cys Glu Leu Ala Leu
        115                 120                 125

Ala Ala Asp Leu Arg Ile Ala Ser Glu Arg Ala Arg Phe Gly Gln Pro
    130                 135                 140

Glu Ile Leu Leu Gly Ile Ile Pro Gly Gly Gly Gly Thr Gln Arg Leu
145                 150                 155                 160

Ala Arg Leu Ile Gly Pro Ser Arg Ala Lys Asp Leu Val Phe Thr Gly
                165                 170                 175

Arg Gln Val Asp Ala Ser Glu Ala Leu Gly Met Gly Leu Val Asn Glu
            180                 185                 190

Val Val Pro His Asp His Leu Arg Gln Arg Thr Leu Glu Leu Ala Thr
        195                 200                 205

Ser Phe Ala Cys Gly Pro Arg Arg Ala Ile Ala Leu Ser Lys Leu Ala
    210                 215                 220

Ile Ser Lys Gly Met Glu Gly Thr Leu Glu Arg Gly Leu Asp Val Glu
225                 230                 235                 240
```

```
Glu Asp Ala Phe Ala Ala Val Phe Ser Thr Ser Asp Ala Ala Ile Gly
                245                 250                 255

Val Gly Ser Phe Gln Gln His Gly Pro Gly Gln Ala His Phe Ser Gly
            260                 265                 270

Arg


<210> SEQ ID NO 61
<211> LENGTH: 798
<212> TYPE: DNA
<213> ORGANISM: Candidatus Microthrix parvicella

<400> SEQUENCE: 61

atggcgcctg aaagccggcc cgcaacgacg ggtgaccccc actcgctggc acggctggag      60

gttcacgaag gggcgtcgc cgtgctcacg ctggatgacc ccaggcgggc caacgccttc      120

accctggaca tgtgccacca catcaccgct gcggtcgacc gaatcgaggc agattcaggc     180

gtctcatccc tggtcgtgac cggcgccgga tcggtgttct gcgccggagc cgatctgtca     240

tcgctgggaa cctcacgcga agccggtctc cgggccatct acgacgggtt cctgcgcgtc     300

gcccgctgct cgctgcccac ggtggcggcg gtgaacggcg ccgccgtcgg tgccggcatg     360

aacctggcgc tggccgccga cgtgcggttg gccgcccgtt cagcccggtt cgacacgcgg     420

ttcttgtcgc tcggcatcca cccgggggt ggccacagct ggatgctgag gcgggcggtc      480

ggccaccaga ccgctgccgc catgatgctg ttcggtgagg tgctcgacgg cgtccaggcc     540

gaccaacgcg gcctcgctca tcgctgcgta cccgacgacg acctgctgga gaacgccatc     600

gacctggcgg ccggcgcagc ccaggccccc cgagagctcc tgattcgggc caccgaaaca     660

ctccgcacca tcgacacggc ggccacccac gacgaggcgg tcgaccgtga actcatcacc     720

cagctgtggt cgatggacca gggggatttt gccgagcgac tggcggcgat gtcccgaaaa     780

atcagctcca agggctga                                                   798


<210> SEQ ID NO 62
<211> LENGTH: 265
<212> TYPE: PRT
<213> ORGANISM: Candidatus Microthrix parvicella

<400> SEQUENCE: 62

Met Ala Pro Glu Ser Arg Pro Ala Thr Thr Gly Asp Pro His Ser Leu
1               5                   10                  15

Ala Arg Leu Glu Val His Glu Gly Gly Val Ala Val Leu Thr Leu Asp
            20                  25                  30

Asp Pro Arg Arg Ala Asn Ala Phe Thr Leu Asp Met Cys His His Ile
        35                  40                  45

Thr Ala Ala Val Asp Arg Ile Glu Ala Asp Ser Gly Val Ser Ser Leu
    50                  55                  60

Val Val Thr Gly Ala Gly Ser Val Phe Cys Ala Gly Ala Asp Leu Ser
65                  70                  75                  80

Ser Leu Gly Thr Ser Arg Glu Ala Gly Leu Arg Ala Ile Tyr Asp Gly
                85                  90                  95

Phe Leu Arg Val Ala Arg Cys Ser Leu Pro Thr Val Ala Ala Val Asn
            100                 105                 110

Gly Ala Ala Val Gly Ala Gly Met Asn Leu Ala Leu Ala Ala Asp Val
        115                 120                 125

Arg Leu Ala Ala Arg Ser Ala Arg Phe Asp Thr Arg Phe Leu Ser Leu
    130                 135                 140
```

```
Gly Ile His Pro Gly Gly Gly His Ser Trp Met Leu Arg Arg Ala Val
145                 150                 155                 160

Gly His Gln Thr Ala Ala Ala Met Met Leu Phe Gly Glu Val Leu Asp
                165                 170                 175

Gly Val Gln Ala Asp Gln Arg Gly Leu Ala His Arg Cys Val Pro Asp
            180                 185                 190

Asp Asp Leu Leu Glu Asn Ala Ile Asp Leu Ala Ala Gly Ala Ala Gln
        195                 200                 205

Ala Pro Arg Glu Leu Leu Ile Arg Ala Thr Glu Thr Leu Arg Thr Ile
    210                 215                 220

Asp Thr Ala Ala Thr His Asp Glu Ala Val Asp Arg Glu Leu Ile Thr
225                 230                 235                 240

Gln Leu Trp Ser Met Asp Gln Gly Asp Phe Ala Glu Arg Leu Ala Ala
                245                 250                 255

Met Ser Arg Lys Ile Ser Ser Lys Gly
            260                 265


<210> SEQ ID NO 63
<211> LENGTH: 840
<212> TYPE: DNA
<213> ORGANISM: Candidatus Microthrix parvicella

<400> SEQUENCE: 63

atggccgagg ccagcagcac cgaccgcccc cttgacgagc aggttcggct ggagatcgtc     60

gaccaggtgg cctggatcac catcgatcgg cccgagaagg gcaatgcact ctcgccgccg    120

tgtcgcgacc gcatccgcga cctgatcaat gagctcaacg gcagctacgc cgcccgcgcc    180

atcgtgctga ccgccgcagg tgacaagctc ttttgccccg gcgcagacct gagccaccgg    240

gttccttcgg agcgccccga aggtgtgccc gagcgagcgg ttggcgacgc acgccggatg    300

atgctcgacg ggcagtacac gctgtttccc gccatcctcg acagcgagct gccgatcatc    360

gccgcggtca acggaacggc tgccggcatg ggcgcacacc tggcattcgc ctgcgacctg    420

gtgatcgccg cagaaggcac caagttcatc gaggtgttca gccgtcgggg cttggtggtc    480

gacgccctgg gtgcctacct cctgccccgc accatcggcc tccacaaggc gaaggaattg    540

gtgttgttcg ccgacgacct gccggtggcc gaagctgagc ggctgggtct ggtcaacaag    600

gtggtgcccc gagacgagtt ggcggcgacc gcgggggagt gggccgggcg gcttgcatcc    660

gggcccacca aggcacttgg cctgtcgaag tggctgttga accagagctt cgacgtggat    720

cgcgccacga tgatgagcaa cgaggccatc gccgtggagc tcaataccca ctcggaagac    780

ttcgccgagg gcatggcgtc gttccgcgag cgacgcgatc cggtctggcg cggctactga    840


<210> SEQ ID NO 64
<211> LENGTH: 279
<212> TYPE: PRT
<213> ORGANISM: Candidatus Microthrix parvicella

<400> SEQUENCE: 64

Met Ala Glu Ala Ser Ser Thr Asp Arg Pro Leu Asp Glu Gln Val Arg
1               5                   10                  15

Leu Glu Ile Val Asp Gln Val Ala Trp Ile Thr Ile Asp Arg Pro Glu
            20                  25                  30

Lys Gly Asn Ala Leu Ser Pro Pro Cys Arg Asp Arg Ile Arg Asp Leu
        35                  40                  45

Ile Asn Glu Leu Asn Gly Ser Tyr Ala Ala Arg Ala Ile Val Leu Thr
    50                  55                  60
```

```
Ala Ala Gly Asp Lys Leu Phe Cys Pro Gly Ala Asp Leu Ser His Arg
65                  70                  75                  80

Val Pro Ser Glu Arg Pro Glu Gly Val Pro Glu Arg Ala Val Gly Asp
                85                  90                  95

Ala Arg Arg Met Met Leu Asp Gly Gln Tyr Thr Leu Phe Pro Ala Ile
            100                 105                 110

Leu Asp Ser Glu Leu Pro Ile Ile Ala Ala Val Asn Gly Thr Ala Ala
        115                 120                 125

Gly Met Gly Ala His Leu Ala Phe Ala Cys Asp Leu Val Ile Ala Ala
    130                 135                 140

Glu Gly Thr Lys Phe Ile Glu Val Phe Ser Arg Arg Gly Leu Val Val
145                 150                 155                 160

Asp Ala Leu Gly Ala Tyr Leu Leu Pro Arg Thr Ile Gly Leu His Lys
                165                 170                 175

Ala Lys Glu Leu Val Leu Phe Ala Asp Asp Leu Pro Val Ala Glu Ala
            180                 185                 190

Glu Arg Leu Gly Leu Val Asn Lys Val Val Pro Arg Asp Glu Leu Ala
        195                 200                 205

Ala Thr Ala Gly Glu Trp Ala Gly Arg Leu Ala Ser Gly Pro Thr Lys
    210                 215                 220

Ala Leu Gly Leu Ser Lys Trp Leu Leu Asn Gln Ser Phe Asp Val Asp
225                 230                 235                 240

Arg Ala Thr Met Met Ser Asn Glu Ala Ile Ala Val Glu Leu Asn Thr
                245                 250                 255

His Ser Glu Asp Phe Ala Glu Gly Met Ala Ser Phe Arg Glu Arg Arg
            260                 265                 270

Asp Pro Val Trp Arg Gly Tyr
        275


<210> SEQ ID NO 65
<211> LENGTH: 792
<212> TYPE: DNA
<213> ORGANISM: Candidatus Microthrix parvicella

<400> SEQUENCE: 65

atgggtgaca gcctcgacca accactggta cttcgctccg acctcgacca cgtcgccacg      60

ctgacgctga accggccggc agcacgcaac gccctgtccg agcccatgct ggatgcgctc     120

gccgcccggc tcgacgaggt ggacgccgac cccacggtgc acgtggtggt gctgaccggg     180

gccggacctg cgttctgtgc cggacacgac ctgcgcgagg ttcgttccaa cgaagaaccc     240

gagtttcgcg aacgcctctt tgcccgctgc tccaacgtga tgatgcaact cacccgcctg     300

cgccggccgg tgatcgcaca ggtggcgggc gtggccaccg cagccgggtg ccagctggtt     360

gccagctgcg acctggcggt cgcaggcgag tcgtcccgct tcgccacccc aggtgtgaac     420

atcggcctgt tctgctcgac accgatggtt gcccttaccc gcacggttgc tcccaagcac     480

gcccttgaaa tgttgctgac cggcgacatg atcgatgcca ccgaggccca ccgcatcggg     540

ctgatcaacc gggtcgttcc cgacccgcgg ctggcagatg ccaccgagga gctggcgcgg     600

accatcgcct ccaaatcacc catgaccgtg gccctcggca aggccgcata ctggaaacag     660

cgcgacctac ccttggccga cgcttacgcg cacacctcac gcgtgatggt ggacaacctg     720

gcaaccaacg acgccgcaga aggcatcgga gcgttcctcg acaagcgatc tcccacctgg     780

atcgggtcct ga                                                         792
```

<210> SEQ ID NO 66
<211> LENGTH: 263
<212> TYPE: PRT
<213> ORGANISM: Candidatus Microthrix parvicella

<400> SEQUENCE: 66

```
Met Gly Asp Ser Leu Asp Gln Pro Leu Val Leu Arg Ser Asp Leu Asp
1               5                   10                  15

His Val Ala Thr Leu Thr Leu Asn Arg Pro Ala Ala Arg Asn Ala Leu
            20                  25                  30

Ser Glu Pro Met Leu Asp Ala Leu Ala Ala Arg Leu Asp Glu Val Asp
        35                  40                  45

Ala Asp Pro Thr Val His Val Val Val Leu Thr Gly Ala Gly Pro Ala
    50                  55                  60

Phe Cys Ala Gly His Asp Leu Arg Glu Val Arg Ser Asn Glu Glu Pro
65                  70                  75                  80

Glu Phe Arg Glu Arg Leu Phe Ala Arg Cys Ser Asn Val Met Met Gln
                85                  90                  95

Leu Thr Arg Leu Arg Arg Pro Val Ile Ala Gln Val Ala Gly Val Ala
            100                 105                 110

Thr Ala Ala Gly Cys Gln Leu Val Ala Ser Cys Asp Leu Ala Val Ala
        115                 120                 125

Gly Glu Ser Ser Arg Phe Ala Thr Pro Gly Val Asn Ile Gly Leu Phe
    130                 135                 140

Cys Ser Thr Pro Met Val Ala Leu Thr Arg Thr Val Ala Pro Lys His
145                 150                 155                 160

Ala Leu Glu Met Leu Leu Thr Gly Asp Met Ile Asp Ala Thr Glu Ala
                165                 170                 175

His Arg Ile Gly Leu Ile Asn Arg Val Val Pro Asp Pro Arg Leu Ala
            180                 185                 190

Asp Ala Thr Glu Glu Leu Ala Arg Thr Ile Ala Ser Lys Ser Pro Met
        195                 200                 205

Thr Val Ala Leu Gly Lys Ala Ala Tyr Trp Lys Gln Arg Asp Leu Pro
    210                 215                 220

Leu Ala Asp Ala Tyr Ala His Thr Ser Arg Val Met Val Asp Asn Leu
225                 230                 235                 240

Ala Thr Asn Asp Ala Ala Glu Gly Ile Gly Ala Phe Leu Asp Lys Arg
                245                 250                 255

Ser Pro Thr Trp Ile Gly Ser
            260
```

<210> SEQ ID NO 67
<211> LENGTH: 918
<212> TYPE: DNA
<213> ORGANISM: Candidatus Microthrix parvicella

<400> SEQUENCE: 67

```
gtgctcgatc aaaatgtggg gtcggtcaca gcggcacccg agaacccgca ccccgtcccg      60

gtcgagtttg gtcgcggctc cacccgcccg gtgccgtcgg cgacggtacg gtggcggccg     120

ctacgaaggg agctgcacat gtcggacctg gtcagcgtgg agcgtcaggg atacgtgttg     180

gtgatcggcg tcgatcgcca ggccaaggcc aacgcgtgga acgtcgagat catcgcggcg     240

gtcgcggcgg cctacaccga actgcacgac gatccggacc tccgggtcgg ggtggtgcac     300

ggggccggca aacacttcag tgccgggctc gacctgcccg acgtgcttcc ggcggttcag     360
```

```
agcggcgaca tcgccgacgt cctccccgag gggatgcgcg acccgtggga cttcttcggt    420

gagccgtgcg ccaaaccgat cgtgctcgcg gttcagggcc gttgctacac gttgggtatc    480

gagttggcgc tggcatctca ggcgacgatc gccgcgaacg acaccgtctt cgcccagctc    540

gaggtggccc gggcgatcgt gccgttgggt ggggcatcgc tgaggcttcc gcaactgggc    600

gcgatcggca cgaagtggct gttgggtgcc gagccgttct cggcgtcgga ggcgcttctc    660

gccggcatgg tcaccgaggt ggtcgagccg gggacccagc tggatcgggc gatcgaggtg    720

gcccagcaga tcgccaccaa cgccccgctg gcggtgcaga gtgcgctggc ggccacccgg    780

gccggtcagc gggcggcccg cgatgcggcc tgtgcgcaga tgcgccagag catgccgcag    840

ctgctggaaa cggccgacgt tgccgagggc gtcgccgcca tgatggagcg acgcccaccc    900

aagttcaccg gcacctga                                                  918


<210> SEQ ID NO 68
<211> LENGTH: 305
<212> TYPE: PRT
<213> ORGANISM: Candidatus Microthrix parvicella

<400> SEQUENCE: 68

Met Leu Asp Gln Asn Val Gly Ser Val Thr Ala Ala Pro Glu Asn Pro
1               5                   10                  15

His Pro Val Pro Val Glu Phe Gly Arg Gly Ser Thr Arg Pro Val Pro
            20                  25                  30

Ser Ala Thr Val Arg Trp Arg Pro Leu Arg Arg Glu Leu His Met Ser
        35                  40                  45

Asp Leu Val Ser Val Glu Arg Gln Gly Tyr Val Leu Val Ile Gly Val
    50                  55                  60

Asp Arg Gln Ala Lys Ala Asn Ala Trp Asn Val Glu Ile Ile Ala Ala
65                  70                  75                  80

Val Ala Ala Ala Tyr Thr Glu Leu His Asp Asp Pro Asp Leu Arg Val
                85                  90                  95

Gly Val Val His Gly Ala Gly Lys His Phe Ser Ala Gly Leu Asp Leu
            100                 105                 110

Pro Asp Val Leu Pro Ala Val Gln Ser Gly Asp Ile Ala Asp Val Leu
        115                 120                 125

Pro Glu Gly Met Arg Asp Pro Trp Asp Phe Phe Gly Glu Pro Cys Ala
    130                 135                 140

Lys Pro Ile Val Leu Ala Val Gln Gly Arg Cys Tyr Thr Leu Gly Ile
145                 150                 155                 160

Glu Leu Ala Leu Ala Ser Gln Ala Thr Ile Ala Ala Asn Asp Thr Val
                165                 170                 175

Phe Ala Gln Leu Glu Val Ala Arg Ala Ile Val Pro Leu Gly Gly Ala
            180                 185                 190

Ser Leu Arg Leu Pro Gln Leu Gly Ala Ile Gly Thr Lys Trp Leu Leu
        195                 200                 205

Gly Ala Glu Pro Phe Ser Ala Ser Glu Ala Leu Leu Ala Gly Met Val
    210                 215                 220

Thr Glu Val Val Glu Pro Gly Thr Gln Leu Asp Arg Ala Ile Glu Val
225                 230                 235                 240

Ala Gln Gln Ile Ala Thr Asn Ala Pro Leu Ala Val Gln Ser Ala Leu
                245                 250                 255

Ala Ala Thr Arg Ala Gly Gln Arg Ala Ala Arg Asp Ala Ala Cys Ala
            260                 265                 270
```

```
Gln Met Arg Gln Ser Met Pro Gln Leu Leu Glu Thr Ala Asp Val Ala
        275                 280                 285

Glu Gly Val Ala Ala Met Met Glu Arg Arg Pro Pro Lys Phe Thr Gly
    290                 295                 300

Thr
305


<210> SEQ ID NO 69
<211> LENGTH: 870
<212> TYPE: DNA
<213> ORGANISM: Candidatus Microthrix parvicella

<400> SEQUENCE: 69

ttgatcctca aggtcacatc gtgggagacg gtcggccgcg tcgcggtgat tcggctgaac      60

cgtccgcatc gcaacaacgc ctggaccggg cgcatgcacc acgagtaccg ggcactgatc     120

gagcgggccg agaccgaccc cgatatccgc tgcatcgtcg tcaccgggga gggccgatcg     180

ttctgcgtgg gggccgacag tgatgcgctt gccggtcatg ccgatagggg tggttacgac     240

ccggggttgc ccgccgagtt gccgatgccc ggctacggcg tgcgggacga ctacgacgac     300

gacttcgtct ttcactatgg cctgagaacg ccggtgatcg cgtccatcaa cggcccgtgt     360

gcgggcgtcg gattcgtgct ggcctgctac gcggacctcc gattcgccgc caagggcgct     420

cggctggcca cggccaacgc ccggctcgga ctcccggcgg agttcggtct cagttgggtg     480

ctaccccgcc tggtcggggt cacccgagcg gctgagctgc tgatgaccgg ccgaaagttc     540

cgggccgagg aggccgaggg ttggggcctg ttcaacgagg tgatcgagcc caaccaactc     600

atggcgcacg tcatggaggt ggcccgaggc ctggccgagg acgtggaccc caaggcggtc     660

gctaccacta agtaccagct gtaccgggat gccgaccgca gcgtcgggcc ggccgtgtcc     720

gacgcccaac ggttcatgcg tgaaaccatg gccggacccg agttcgccga gggcgtgaaa     780

gccttccggg agggcgtccc gcccgacttc ccgaatgcgg ccgtggagcc agccggtccg     840

ggctctaaca tgggcgatac gcccggatag                                      870


<210> SEQ ID NO 70
<211> LENGTH: 289
<212> TYPE: PRT
<213> ORGANISM: Candidatus Microthrix parvicella

<400> SEQUENCE: 70

Met Ile Leu Lys Val Thr Ser Trp Glu Thr Val Gly Arg Val Ala Val
1               5                   10                  15

Ile Arg Leu Asn Arg Pro His Arg Asn Asn Ala Trp Thr Gly Arg Met
            20                  25                  30

His His Glu Tyr Arg Ala Leu Ile Glu Arg Ala Glu Thr Asp Pro Asp
        35                  40                  45

Ile Arg Cys Ile Val Val Thr Gly Glu Gly Arg Ser Phe Cys Val Gly
    50                  55                  60

Ala Asp Ser Asp Ala Leu Ala Gly His Ala Asp Arg Gly Gly Tyr Asp
65                  70                  75                  80

Pro Gly Leu Pro Ala Glu Leu Pro Met Pro Gly Tyr Gly Val Arg Asp
                85                  90                  95

Asp Tyr Asp Asp Asp Phe Val Phe His Tyr Gly Leu Arg Thr Pro Val
            100                 105                 110

Ile Ala Ser Ile Asn Gly Pro Cys Ala Gly Val Gly Phe Val Leu Ala
        115                 120                 125
```

```
Cys Tyr Ala Asp Leu Arg Phe Ala Ala Lys Gly Ala Arg Leu Ala Thr
    130                 135                 140

Ala Asn Ala Arg Leu Gly Leu Pro Ala Glu Phe Gly Leu Ser Trp Val
145                 150                 155                 160

Leu Pro Arg Leu Val Gly Val Thr Arg Ala Ala Glu Leu Leu Met Thr
                165                 170                 175

Gly Arg Lys Phe Arg Ala Glu Glu Ala Glu Gly Trp Gly Leu Phe Asn
            180                 185                 190

Glu Val Ile Glu Pro Asn Gln Leu Met Ala His Val Met Glu Val Ala
        195                 200                 205

Arg Gly Leu Ala Glu Asp Val Asp Pro Lys Ala Val Ala Thr Thr Lys
    210                 215                 220

Tyr Gln Leu Tyr Arg Asp Ala Asp Arg Ser Val Gly Pro Ala Val Ser
225                 230                 235                 240

Asp Ala Gln Arg Phe Met Arg Glu Thr Met Ala Gly Pro Glu Phe Ala
                245                 250                 255

Glu Gly Val Lys Ala Phe Arg Glu Gly Val Pro Pro Asp Phe Pro Asn
            260                 265                 270

Ala Ala Val Glu Pro Ala Gly Pro Gly Ser Asn Met Gly Asp Thr Pro
        275                 280                 285

Gly


<210> SEQ ID NO 71
<211> LENGTH: 843
<212> TYPE: DNA
<213> ORGANISM: Candidatus Microthrix parvicella

<400> SEQUENCE: 71

gtggcggtcg ttgttcgtga tgaatgccag actcgaacca tgaaggatgc ggacggtctc      60

tacggcgatt tcactgggtt cggggtggac cggccggccg acggggtgct gcgcctcacg     120

ctcgacgcgc cgggcctcaa cgcggtcgac gccgacgctc accgcagcct ggctgacgtg     180

tggcgggtga tcgaccgcga tccggacacc cgggtggcgc tgatccgcgg cgcaggcaaa     240

gggttttccg ccgggggaag cttcgaactg ctcgacgaga tcatggccga tcgtgcggcc     300

cgcacccggg tgttgaacga ggcgcgcgac ctggtgtggg gcatcatcga ctgctccaag     360

ccggtggtgt cggcaattca cggccctgcg gttggcgccg gtttggtggc ggcgctgctg     420

gccgacgtgt cggttgcggc gcgcagcgca aagatcatcg acggtcacac ccgcctgggg     480

gtggcggccg gcgaccatgc ggcggtggcg tggccgctgc tgtgcggcat ggccaaggcc     540

aagtaccacc tgctgaccaa ccgtccgctc agcggcgagg aggccgagcg cattgggctg     600

gtgtcgctgt gcgtcgacga cgacgccgtg caggacgagg cgatgagcat cgccaccgac     660

ctggccgccg gatcggccga ggcgatcgcc ttcaccaagc acacgctcaa ccaccactac     720

cgctcggccg gccccgcatt cgacgcctcg ctgtacgccg agttctacgg cttcggtggc     780

ccggacgccc gcgaggggct ggcctcccac cgcgagaagc gatcgcccaa cttcgggggt     840

tga                                                                   843


<210> SEQ ID NO 72
<211> LENGTH: 280
<212> TYPE: PRT
<213> ORGANISM: Candidatus Microthrix parvicella

<400> SEQUENCE: 72

Met Ala Val Val Val Arg Asp Glu Cys Gln Thr Arg Thr Met Lys Asp
```

```
1               5                   10                  15

Ala Asp Gly Leu Tyr Gly Asp Phe Thr Gly Phe Gly Val Asp Arg Pro
            20                  25                  30

Ala Asp Gly Val Leu Arg Leu Thr Leu Asp Ala Pro Gly Leu Asn Ala
        35                  40                  45

Val Asp Ala Asp Ala His Arg Ser Leu Ala Asp Val Trp Arg Val Ile
    50                  55                  60

Asp Arg Asp Pro Asp Thr Arg Val Ala Leu Ile Arg Gly Ala Gly Lys
65                  70                  75                  80

Gly Phe Ser Ala Gly Gly Ser Phe Glu Leu Leu Asp Glu Ile Met Ala
                85                  90                  95

Asp Arg Ala Ala Arg Thr Arg Val Leu Asn Glu Ala Arg Asp Leu Val
            100                 105                 110

Trp Gly Ile Ile Asp Cys Ser Lys Pro Val Val Ser Ala Ile His Gly
        115                 120                 125

Pro Ala Val Gly Ala Gly Leu Val Ala Ala Leu Leu Ala Asp Val Ser
    130                 135                 140

Val Ala Ala Arg Ser Ala Lys Ile Ile Asp Gly His Thr Arg Leu Gly
145                 150                 155                 160

Val Ala Ala Gly Asp His Ala Ala Val Ala Trp Pro Leu Leu Cys Gly
                165                 170                 175

Met Ala Lys Ala Lys Tyr His Leu Leu Thr Asn Arg Pro Leu Ser Gly
            180                 185                 190

Glu Glu Ala Glu Arg Ile Gly Leu Val Ser Leu Cys Val Asp Asp Asp
        195                 200                 205

Ala Val Gln Asp Glu Ala Met Ser Ile Ala Thr Asp Leu Ala Ala Gly
    210                 215                 220

Ser Ala Glu Ala Ile Ala Phe Thr Lys His Thr Leu Asn His His Tyr
225                 230                 235                 240

Arg Ser Ala Gly Pro Ala Phe Asp Ala Ser Leu Tyr Ala Glu Phe Tyr
                245                 250                 255

Gly Phe Gly Gly Pro Asp Ala Arg Glu Gly Leu Ala Ser His Arg Glu
            260                 265                 270

Lys Arg Ser Pro Asn Phe Gly Gly
        275                 280
```

<210> SEQ ID NO 73
<211> LENGTH: 762
<212> TYPE: DNA
<213> ORGANISM: Candidatus Microthrix parvicella

<400> SEQUENCE: 73

```
atgatcagcc cggtcgagcc caccgatgcc ccaaccgtgc tcagcgagcg tctcgtcgac     60

gttgcggtga tcaccatcaa tcggcctcgg cggcgcaacg ccttggacgg tgccaccgtt    120

gctgcgctgc accaggcgat ctccgacgcg gcgtcggggg ccccccgggt cctggtgctc    180

accggagccg atggccactt ctgcgccggt gccgatatca ccaccaccga ggatcccgac    240

tacacgatcg ggctgcgggc catgctggat gcactcgccg gtctcgcctt tccaacgatt    300

gccgccatcg aggggtcctg catggggttg ggtgtgcaac tggccctgtc ggtcgacctg    360

cgggtggccg ccgaggatgt ccgatttgcc gtgccggtgg cccgcttggg cctgttgacc    420

gatcatcgaa ccctgcaacg actggccctg gcggttggat ggggcatggc ccgctcgatg    480

gtgctcgccg gtgatgtgtt gaacttcgac gacgcctggc ggctgggcct ggtgcagcgt    540
```

```
cgagggggag tgaacacggc gctggagtgg gccgaggaca tcgccaagct ggcgccgctc    600

tcccaggccg gagcgaagct ggggcttgat ctgctggagg agccggtggc cgacgatccg    660

cgctatcgcg aggcattcct gcgggcctgg gcgtcagatg acctggccga aggtcgcgcc    720

gcattcgccg aaaggcgctc gcccacattc cgcggccgct ga                       762


<210> SEQ ID NO 74
<211> LENGTH: 253
<212> TYPE: PRT
<213> ORGANISM: Candidatus Microthrix parvicella

<400> SEQUENCE: 74

Met Ile Ser Pro Val Glu Pro Thr Asp Ala Pro Thr Val Leu Ser Glu
1               5                   10                  15

Arg Leu Val Asp Val Ala Val Ile Thr Ile Asn Arg Pro Arg Arg Arg
            20                  25                  30

Asn Ala Leu Asp Gly Ala Thr Val Ala Ala Leu His Gln Ala Ile Ser
        35                  40                  45

Asp Ala Ala Ser Gly Ala Pro Arg Val Leu Val Leu Thr Gly Ala Asp
    50                  55                  60

Gly His Phe Cys Ala Gly Ala Asp Ile Thr Thr Thr Glu Asp Pro Asp
65                  70                  75                  80

Tyr Thr Ile Gly Leu Arg Ala Met Leu Asp Ala Leu Ala Gly Leu Ala
                85                  90                  95

Phe Pro Thr Ile Ala Ala Ile Glu Gly Ser Cys Met Gly Leu Gly Val
            100                 105                 110

Gln Leu Ala Leu Ser Val Asp Leu Arg Val Ala Ala Glu Asp Val Arg
        115                 120                 125

Phe Ala Val Pro Val Ala Arg Leu Gly Leu Leu Thr Asp His Arg Thr
    130                 135                 140

Leu Gln Arg Leu Ala Leu Ala Val Gly Trp Gly Met Ala Arg Ser Met
145                 150                 155                 160

Val Leu Ala Gly Asp Val Leu Asn Phe Asp Asp Ala Trp Arg Leu Gly
                165                 170                 175

Leu Val Gln Arg Arg Gly Gly Val Asn Thr Ala Leu Glu Trp Ala Glu
            180                 185                 190

Asp Ile Ala Lys Leu Ala Pro Leu Ser Gln Ala Gly Ala Lys Leu Gly
        195                 200                 205

Leu Asp Leu Leu Glu Glu Pro Val Ala Asp Asp Pro Arg Tyr Arg Glu
    210                 215                 220

Ala Phe Leu Arg Ala Trp Ala Ser Asp Asp Leu Ala Glu Gly Arg Ala
225                 230                 235                 240

Ala Phe Ala Glu Arg Arg Ser Pro Thr Phe Arg Gly Arg
                245                 250


<210> SEQ ID NO 75
<211> LENGTH: 909
<212> TYPE: DNA
<213> ORGANISM: Candidatus Microthrix parvicella

<400> SEQUENCE: 75

gtggcaaccg tgaccgaatc gccccactcg tcgagcaccg tccccgcgtc cccgcctcaa     60

gcggcaacct ccggtggccg gccgcccgac ggtgacgtgc cggcggcgcc gatcagggcc    120

ctgccgggcg aaggggtgga cggcctggcc gtggcgttgt cgggccgggt gctgcgggtc    180

acgttgaacc gtcccgatca gcgcaactcc ctgacctggg cgatgatcga tgggctgcgt    240
```

```
cggatcttcg tcgaggtgcg aggtgatgat cgggtgggag cagtggtgct gaccggggcc    300

ggtgaccggg ccttcagcgc cggcgcggac ctgtcgggca tgacgggggg ctcggccctg    360

gccatgcatg aggcgcgggg ccaacttccg gcgctgtttg aggccatgtg ggccgccgga    420

acgccgacgg tggcgtcggt gcggggatac tgccttgccg ggggcatggg cctggccttg    480

gcgtgcgacc tggtggtggc ggccgacgac gccgtgttcg gcacgcccga gatcaatgtg    540

ggtctgtggc cctatgtcat cacggtgccg ctgctccggt cgatgccgcc gaagcgggcc    600

ctggagttga tgatgaccgg ccgtcgtatc gacgccgccg aggccgaccg gtttggcttc    660

ttggcccgca cggtgccggt cgaggagttg gaggcgacga ccgacgagtt ggcggccggc    720

ctgtcacggg cgccgagcgg ggtgatggcc ttgggtcgcg actcgttcta ccgggcggtc    780

gacgcgacgg ccgccgacgc actgtctcac ctgcaggcca tgctgagcct gggatcatcg    840

ttggacgacg ccgccgaggg caccacggcg ttccttgaaa agcgtcaacc gaattggagc    900

ggatcatga                                                            909
```

```
<210> SEQ ID NO 76
<211> LENGTH: 302
<212> TYPE: PRT
<213> ORGANISM: Candidatus Microthrix parvicella

<400> SEQUENCE: 76

Met Ala Thr Val Thr Glu Ser Pro His Ser Ser Ser Thr Val Pro Ala
1               5                   10                  15

Ser Pro Pro Gln Ala Ala Thr Ser Gly Gly Arg Pro Pro Asp Gly Asp
            20                  25                  30

Val Pro Ala Ala Pro Ile Arg Ala Leu Pro Gly Glu Gly Val Asp Gly
        35                  40                  45

Leu Ala Val Ala Leu Ser Gly Arg Val Leu Arg Val Thr Leu Asn Arg
    50                  55                  60

Pro Asp Gln Arg Asn Ser Leu Thr Trp Ala Met Ile Asp Gly Leu Arg
65                  70                  75                  80

Arg Ile Phe Val Glu Val Arg Gly Asp Asp Arg Val Gly Ala Val Val
                85                  90                  95

Leu Thr Gly Ala Gly Asp Arg Ala Phe Ser Ala Gly Ala Asp Leu Ser
            100                 105                 110

Gly Met Thr Gly Gly Ser Ala Leu Ala Met His Glu Ala Arg Gly Gln
        115                 120                 125

Leu Pro Ala Leu Phe Glu Ala Met Trp Ala Ala Gly Thr Pro Thr Val
    130                 135                 140

Ala Ser Val Arg Gly Tyr Cys Leu Ala Gly Gly Met Gly Leu Ala Leu
145                 150                 155                 160

Ala Cys Asp Leu Val Val Ala Ala Asp Asp Ala Val Phe Gly Thr Pro
                165                 170                 175

Glu Ile Asn Val Gly Leu Trp Pro Tyr Val Ile Thr Val Pro Leu Leu
            180                 185                 190

Arg Ser Met Pro Pro Lys Arg Ala Leu Glu Leu Met Met Thr Gly Arg
        195                 200                 205

Arg Ile Asp Ala Ala Glu Ala Asp Arg Phe Gly Phe Leu Ala Arg Thr
    210                 215                 220

Val Pro Val Glu Glu Leu Glu Ala Thr Thr Asp Glu Leu Ala Ala Gly
225                 230                 235                 240

Leu Ser Arg Ala Pro Ser Gly Val Met Ala Leu Gly Arg Asp Ser Phe
```

```
                245                 250                 255

Tyr Arg Ala Val Asp Ala Thr Ala Ala Asp Ala Leu Ser His Leu Gln
            260                 265                 270

Ala Met Leu Ser Leu Gly Ser Ser Leu Asp Asp Ala Ala Glu Gly Thr
        275                 280                 285

Thr Ala Phe Leu Glu Lys Arg Gln Pro Asn Trp Ser Gly Ser
    290                 295                 300


<210> SEQ ID NO 77
<211> LENGTH: 897
<212> TYPE: DNA
<213> ORGANISM: Candidatus Microthrix parvicella

<400> SEQUENCE: 77

atgagccccg atgtcgcgga gaattcgccc cagagcccgg tgtccccggc cgactcgacc      60

tgggagtgct tcgacgtcga tctgagcgac ggggtcgccc acgtccggtt gaaccgtccg     120

gaggcctaca actcgatggt cccggcgttc tggaccgagc tccccgccat cgtggagggg     180

ctcgatgccg caggcaccac ccgcgtgatg gtgctgtcgt cgaccggcaa gcacttctcg     240

gccggaatgg acctggcggt gttcaccgag ggcggccttg gtggtgcgtc gggcgtgtcc     300

gagcaggggc gccgcaacgc aggcctgtgg ctcatggtgc agcacctcca gcgcagcttc     360

accgccctgg cgaacgcccg gtttcccgtg ctcgcagcgg tgcagggcgg ctgtatcggg     420

ggcgcggtcg acatggtcgc ggcggccgat tgccgctatg gcaccgagga cagcttcgtc     480

tgcattcagg agatcaacat cgccatgacg gccgacgtcg gcacgctgca gcgcctgggc     540

aggctggtgc ccgagggcgt ggcccgcgag tgggcctaca ccggcgaccg aatcccggcc     600

ggacgcgtcc gtgaggttgg gtttttcaac gagacctttg ccgaccatga agcgctcgtc     660

gccggcgtgc tcgaaatcgc acggcgtatc gccacccagt cgccgctggc gatctggggc     720

accaaagagg ccatcagcta tgcccgggac cactccactg ccgacgccct gcatcagatg     780

gccgggtggc agtcgggcat gttccagcct ggcgacatga tggaggcctt caccgccaaa     840

ggcgaaaagc gtgcgcccgt gttcgagggg ctgccgccac tccccggagc ccgctga        897


<210> SEQ ID NO 78
<211> LENGTH: 298
<212> TYPE: PRT
<213> ORGANISM: Candidatus Microthrix parvicella

<400> SEQUENCE: 78

Met Ser Pro Asp Val Ala Glu Asn Ser Pro Gln Ser Pro Val Ser Pro
1               5                   10                  15

Ala Asp Ser Thr Trp Glu Cys Phe Asp Val Asp Leu Ser Asp Gly Val
            20                  25                  30

Ala His Val Arg Leu Asn Arg Pro Glu Ala Tyr Asn Ser Met Val Pro
        35                  40                  45

Ala Phe Trp Thr Glu Leu Pro Ala Ile Val Glu Gly Leu Asp Ala Ala
    50                  55                  60

Gly Thr Thr Arg Val Met Val Leu Ser Ser Thr Gly Lys His Phe Ser
65                  70                  75                  80

Ala Gly Met Asp Leu Ala Val Phe Thr Glu Gly Gly Leu Gly Gly Ala
                85                  90                  95

Ser Gly Val Ser Glu Gln Gly Arg Arg Asn Ala Gly Leu Trp Leu Met
            100                 105                 110

Val Gln His Leu Gln Arg Ser Phe Thr Ala Leu Ala Asn Ala Arg Phe
```

```
        115                 120                 125

Pro Val Leu Ala Ala Val Gln Gly Gly Cys Ile Gly Gly Ala Val Asp
    130                 135                 140

Met Val Ala Ala Ala Asp Cys Arg Tyr Gly Thr Glu Asp Ser Phe Val
145                 150                 155                 160

Cys Ile Gln Glu Ile Asn Ile Ala Met Thr Ala Asp Val Gly Thr Leu
                165                 170                 175

Gln Arg Leu Gly Arg Leu Val Pro Glu Gly Val Ala Arg Glu Trp Ala
            180                 185                 190

Tyr Thr Gly Asp Arg Ile Pro Ala Gly Arg Val Arg Glu Val Gly Phe
        195                 200                 205

Phe Asn Glu Thr Phe Ala Asp His Glu Ala Leu Val Ala Gly Val Leu
    210                 215                 220

Glu Ile Ala Arg Arg Ile Ala Thr Gln Ser Pro Leu Ala Ile Trp Gly
225                 230                 235                 240

Thr Lys Glu Ala Ile Ser Tyr Ala Arg Asp His Ser Thr Ala Asp Ala
                245                 250                 255

Leu His Gln Met Ala Gly Trp Gln Ser Gly Met Phe Gln Pro Gly Asp
            260                 265                 270

Met Met Glu Ala Phe Thr Ala Lys Gly Glu Lys Arg Ala Pro Val Phe
        275                 280                 285

Glu Gly Leu Pro Pro Leu Pro Gly Ala Arg
    290                 295
```

<210> SEQ ID NO 79
<211> LENGTH: 798
<212> TYPE: DNA
<213> ORGANISM: Candidatus Microthrix parvicella

<400> SEQUENCE: 79

```
gtgagcgact accagacctt gctgttggac atctccgacg gggtggccac cctgacgctg      60

aaccgccccg accgctacaa cgcgttcgac gccaccatgt tggaggagtt gccgcaggcg     120

tgggcccgcc tgcgcgacga cggcgaggtg cgtgcggtcg tcctgaccgg cgccggcgat     180

gcggcgttct gcaccggtat cgaccgggat gccgtgccca ccaccgaggg cgactacagc     240

ttcgacccct acacctacca ggatccgggc gaggcgctgg ggcccaaaac ccacggcatg     300

tggaagccgg tgatcgcagc ggtcaacggc atggcctgtg gcggcgcgtt ctatctgctg     360

ggcgaggtgg agtttctgat cgccgccgag ggcgccacct tcttcgatcc ccacgtcacc     420

tacggcatgg cggcggtgct cgaacccacg ctgttggcac ccgcatgcc cttcggcgac     480

ctgatgcgga tgatgctgtt gggtgcccac gagcggctct cggcggcccg cgcgctggag     540

gtggggctgg tcagcgaagt gacccctgcc gatcggttgg ccgagcgggc ccgttgggcg     600

gccgaggcga tcgcctccca gccggctgat gccgttgttg cgacggtccg caacctgtgg     660

atggcccagg agctgtcgcg ccgtcaggcc ctcgacctcg gcagctttct gctggctgcc     720

ggcaactcgg tggaggcgct ggccgagggc caggcgttct tcgcctccgg caaacgcgtg     780

aagcccaacg ttcgataa                                                   798
```

<210> SEQ ID NO 80
<211> LENGTH: 265
<212> TYPE: PRT
<213> ORGANISM: Candidatus Microthrix parvicella

<400> SEQUENCE: 80

```
Met Ser Asp Tyr Gln Thr Leu Leu Leu Asp Ile Ser Asp Gly Val Ala
1               5                   10                  15

Thr Leu Thr Leu Asn Arg Pro Asp Arg Tyr Asn Ala Phe Asp Ala Thr
            20                  25                  30

Met Leu Glu Glu Leu Pro Gln Ala Trp Ala Arg Leu Arg Asp Asp Gly
        35                  40                  45

Glu Val Arg Ala Val Val Leu Thr Gly Ala Gly Asp Ala Ala Phe Cys
    50                  55                  60

Thr Gly Ile Asp Arg Asp Ala Val Pro Thr Thr Glu Gly Asp Tyr Ser
65                  70                  75                  80

Phe Asp Pro Tyr Thr Tyr Gln Asp Pro Gly Glu Ala Leu Gly Pro Lys
                85                  90                  95

Thr His Gly Met Trp Lys Pro Val Ile Ala Ala Val Asn Gly Met Ala
            100                 105                 110

Cys Gly Gly Ala Phe Tyr Leu Leu Gly Glu Val Glu Phe Leu Ile Ala
        115                 120                 125

Ala Glu Gly Ala Thr Phe Phe Asp Pro His Val Thr Tyr Gly Met Ala
    130                 135                 140

Ala Val Leu Glu Pro Thr Leu Leu Ala Pro Arg Met Pro Phe Gly Asp
145                 150                 155                 160

Leu Met Arg Met Met Leu Leu Gly Ala His Glu Arg Leu Ser Ala Ala
                165                 170                 175

Arg Ala Leu Glu Val Gly Leu Val Ser Glu Val Thr Pro Ala Asp Arg
            180                 185                 190

Leu Ala Glu Arg Ala Arg Trp Ala Ala Glu Ala Ile Ala Ser Gln Pro
        195                 200                 205

Ala Asp Ala Val Val Ala Thr Val Arg Asn Leu Trp Met Ala Gln Glu
    210                 215                 220

Leu Ser Arg Arg Gln Ala Leu Asp Leu Gly Ser Phe Leu Leu Ala Ala
225                 230                 235                 240

Gly Asn Ser Val Glu Ala Leu Ala Glu Gly Gln Ala Phe Phe Ala Ser
                245                 250                 255

Gly Lys Arg Val Lys Pro Asn Val Arg
            260                 265
```

<210> SEQ ID NO 81
<211> LENGTH: 780
<212> TYPE: DNA
<213> ORGANISM: Candidatus Microthrix parvicella

<400> SEQUENCE: 81

```
atgacatctt caggtgcaac cttctccacg ctcaccgtcg agttgtccgg cggcatcggc     60

cggctgacgc tcaaccagcc tgaccagctg aacccgctgg ggtccgacgc gctgaccgaa    120

atcgccaagg ccgcgcgctg gttcgacgat gagggcgccc gggtggtcgt catcacctct    180

gccggtgatc gggcgttctc ggccggtttc gatctgcggg aactcacccg gggttccgac    240

gaggcaccgg acgtcgacct tggttacctg atggtcgacg cggtcgaggc catggatgcc    300

atcaccatcg cagccatcca cgggcactgc gtcggcggag gaatcctgct ggcggttggt    360

tgcgacctgc gcatcgccgc cgacaacacc cggtttgcca tccccgagat cgatctgggc    420

attcctctgg cctggggcgg catcccgcgt ttggtccgcg aggtgggcgc agcgtccacc    480

agggagttgg tcatgacgtg ccgtccgttc gacgcaatcg aggcgcagcg cctggggatg    540

atcaaccgag tggtgccact cgatcggctg cgcgctgaga ccgacgagct ggcggcgtca    600
```

```
ttggcggcca agccggtctc gctgctgcgc atgaccaaac gtcaggttca cgaggcggcc     660

gaggacctgc tgaccaccag atcggggtgg gcggcctctg cgcacctggc ggtggctctc     720

gccgacccgg aggcacgcgg cgcggcggcc ggctacctgg cctcgcgatc caaggactga     780


<210> SEQ ID NO 82
<211> LENGTH: 259
<212> TYPE: PRT
<213> ORGANISM: Candidatus Microthrix parvicella

<400> SEQUENCE: 82

Met Thr Ser Ser Gly Ala Thr Phe Ser Thr Leu Thr Val Glu Leu Ser
1               5                   10                  15

Gly Gly Ile Gly Arg Leu Thr Leu Asn Gln Pro Asp Gln Leu Asn Pro
            20                  25                  30

Leu Gly Ser Asp Ala Leu Thr Glu Ile Ala Lys Ala Ala Arg Trp Phe
        35                  40                  45

Asp Asp Glu Gly Ala Arg Val Val Val Ile Thr Ser Ala Gly Asp Arg
    50                  55                  60

Ala Phe Ser Ala Gly Phe Asp Leu Arg Glu Leu Thr Arg Gly Ser Asp
65                  70                  75                  80

Glu Ala Pro Asp Val Asp Leu Gly Tyr Leu Met Val Asp Ala Val Glu
                85                  90                  95

Ala Met Asp Ala Ile Thr Ile Ala Ala Ile His Gly His Cys Val Gly
            100                 105                 110

Gly Gly Ile Leu Leu Ala Val Gly Cys Asp Leu Arg Ile Ala Ala Asp
        115                 120                 125

Asn Thr Arg Phe Ala Ile Pro Glu Ile Asp Leu Gly Ile Pro Leu Ala
    130                 135                 140

Trp Gly Gly Ile Pro Arg Leu Val Arg Glu Val Gly Ala Ala Ser Thr
145                 150                 155                 160

Arg Glu Leu Val Met Thr Cys Arg Pro Phe Asp Ala Ile Glu Ala Gln
                165                 170                 175

Arg Leu Gly Met Ile Asn Arg Val Val Pro Leu Asp Arg Leu Arg Ala
            180                 185                 190

Glu Thr Asp Glu Leu Ala Ala Ser Leu Ala Ala Lys Pro Val Ser Leu
        195                 200                 205

Leu Arg Met Thr Lys Arg Gln Val His Glu Ala Ala Glu Asp Leu Leu
    210                 215                 220

Thr Thr Arg Ser Gly Trp Ala Ala Ser Ala His Leu Ala Val Ala Leu
225                 230                 235                 240

Ala Asp Pro Glu Ala Arg Gly Ala Ala Ala Gly Tyr Leu Ala Ser Arg
                245                 250                 255

Ser Lys Asp


<210> SEQ ID NO 83
<211> LENGTH: 837
<212> TYPE: DNA
<213> ORGANISM: Candidatus Microthrix parvicella

<400> SEQUENCE: 83

gtgaccaacc ccgcccaacc atccccagcc ggctcagccg gcgctgatga cctgaacgac      60

tgccccaata tcaaggtgag cgacgccaac cggatccgta cggtcacgat cgatcggccg     120

gaggccaagg gtgcaatgcg gggtgacatg tggaacgccc tcgccaacgc aatggtggat     180

gcgcaggaca acccggcggt cgccgtcgtg ttgttgaccg ggaccggcga tgcgttctgc     240
```

```
gccggggtcg acctcgccga aatggccgag atcgcccttg gcaccggtga tgccgatgtc    300

catgcgttcc cccgtctcgc cgacacgatg gcgacctttg ccaagccgct gatcgtggcg    360

gtcaacggca ttggggtggg ttttggggcc acggtgctgg gcttcgccga cctggcgttc    420

atgtcgtcga ccgcccgggt gaaatgcccg ttcacccgtc tcggcgtggc tcccgagttg    480

gcgagcagct acacgtttcc ggcgctcctc gggcgccagc aggcttcgtg ggccttgctc    540

agctccgagt ggctcgacgc cgaggagtgc gcacggatgg gtctggtgtt tcgtgtgtgt    600

gagcccgacg atctgctttc cgtcacgatg gaccacgccc gggttctcgc cgccaagccg    660

atcagctcgc tggtggaatc caagacggcg atcctggcgg cgatggcacc gcagatcgcc    720

gccgcccgcc aacgcgagga cgaggccttc caacgcctgc tcggcacgcc ggagaacctg    780

gaggccatga ccgccttcgc cgagaagcgc gaacccgact tctccaacct cggctga       837
```

<210> SEQ ID NO 84
<211> LENGTH: 278
<212> TYPE: PRT
<213> ORGANISM: Candidatus Microthrix parvicella

<400> SEQUENCE: 84

```
Met Thr Asn Pro Ala Gln Pro Ser Pro Ala Gly Ser Ala Gly Ala Asp
1               5                   10                  15

Asp Leu Asn Asp Cys Pro Asn Ile Lys Val Ser Asp Ala Asn Arg Ile
            20                  25                  30

Arg Thr Val Thr Ile Asp Arg Pro Glu Ala Lys Gly Ala Met Arg Gly
        35                  40                  45

Asp Met Trp Asn Ala Leu Ala Asn Ala Met Val Asp Ala Gln Asp Asn
    50                  55                  60

Pro Ala Val Ala Val Val Leu Leu Thr Gly Thr Gly Asp Ala Phe Cys
65                  70                  75                  80

Ala Gly Val Asp Leu Ala Glu Met Ala Glu Ile Ala Leu Gly Thr Gly
                85                  90                  95

Asp Ala Asp Val His Ala Phe Pro Arg Leu Ala Asp Thr Met Ala Thr
            100                 105                 110

Phe Ala Lys Pro Leu Ile Val Ala Val Asn Gly Ile Gly Val Gly Phe
        115                 120                 125

Gly Ala Thr Val Leu Gly Phe Ala Asp Leu Ala Phe Met Ser Ser Thr
    130                 135                 140

Ala Arg Val Lys Cys Pro Phe Thr Arg Leu Gly Val Ala Pro Glu Leu
145                 150                 155                 160

Ala Ser Ser Tyr Thr Phe Pro Ala Leu Leu Gly Arg Gln Gln Ala Ser
                165                 170                 175

Trp Ala Leu Leu Ser Ser Glu Trp Leu Asp Ala Glu Glu Cys Ala Arg
            180                 185                 190

Met Gly Leu Val Phe Arg Val Cys Glu Pro Asp Asp Leu Leu Ser Val
        195                 200                 205

Thr Met Asp His Ala Arg Val Leu Ala Ala Lys Pro Ile Ser Ser Leu
    210                 215                 220

Val Glu Ser Lys Thr Ala Ile Leu Ala Ala Met Ala Pro Gln Ile Ala
225                 230                 235                 240

Ala Ala Arg Gln Arg Glu Asp Glu Ala Phe Gln Arg Leu Leu Gly Thr
                245                 250                 255

Pro Glu Asn Leu Glu Ala Met Thr Ala Phe Ala Glu Lys Arg Glu Pro
            260                 265                 270
```

Asp Phe Ser Asn Leu Gly
        275

<210> SEQ ID NO 85
<211> LENGTH: 930
<212> TYPE: DNA
<213> ORGANISM: Candidatus Microthrix parvicella

<400> SEQUENCE: 85
gtgagcgaca cccccgacga ccagaggatc gctgcggtgg aatcgacgta cggcacggtg 60
gcgccgcagg ccgcgagctc cgacaacgtc ccggcgctcg gctcggcgcc cgaggtgctg 120
atcgtcgacg acccggcacc gttcgtgcgc cgcctcaccc tcaaccggcc cgagaagcgc 180
aacgcgctca gccaccagct gcgcgccgag atcatggctg cgctccagca ggccgaccag 240
gatcccgacg tgcgggtgat gatcgtgcgc ggagccggca gctgcttctc cgccggatac 300
gagctgggcg gtgccaacga gggcgtcgac atgccccact tcaccgccga gggcgagggt 360
cagtggcccc gccacgtcac cgagacgtgg atgagcatct gggacctggc caagccggtg 420
atcgcccagg tgcacggcta ctgcctggcc gggggcagcg agctggccac cggttgcgac 480
ctggtctacg tcgcccacga cgccaagatg ggctacccgg ccgtgcgctt cggcgtgccc 540
gacatgcact ttcacgcatg gatgctcggt atgcgggcgg cgatggagat gatggtcacc 600
ggcgactcga tctcgggcga cgaggcggtg cgcctcggct gggccaaccg ggccttcgac 660
gaggccaacc tggacgacga ggtgctcgcc gtcgccgggc gggtcgccaa catccccacc 720
gacatcgtgt cgctcaacaa gcgggcggtg catcggggca tggacacgat gggcatgcgc 780
accgccatcc gacagggcac cgagctgtgc gcgatgggta ccaaggcggc cacgttcacc 840
gagttcatcg acaagatgcg agatgagggc ctgaccaagg cgctgtccga acgagacgca 900
gccttcggcg actaccgcac cggcgggtga 930

<210> SEQ ID NO 86
<211> LENGTH: 309
<212> TYPE: PRT
<213> ORGANISM: Candidatus Microthrix parvicella

<400> SEQUENCE: 86

Met Ser Asp Thr Pro Asp Asp Gln Arg Ile Ala Ala Val Glu Ser Thr
1               5                   10                  15

Tyr Gly Thr Val Ala Pro Gln Ala Ala Ser Ser Asp Asn Val Pro Ala
            20                  25                  30

Leu Gly Ser Ala Pro Glu Val Leu Ile Val Asp Asp Pro Ala Pro Phe
        35                  40                  45

Val Arg Arg Leu Thr Leu Asn Arg Pro Glu Lys Arg Asn Ala Leu Ser
    50                  55                  60

His Gln Leu Arg Ala Glu Ile Met Ala Ala Leu Gln Gln Ala Asp Gln
65                  70                  75                  80

Asp Pro Asp Val Arg Val Met Ile Val Arg Gly Ala Gly Ser Cys Phe
                85                  90                  95

Ser Ala Gly Tyr Glu Leu Gly Gly Ala Asn Glu Gly Val Asp Met Pro
            100                 105                 110

His Phe Thr Ala Glu Gly Glu Gly Gln Trp Pro Arg His Val Thr Glu
        115                 120                 125

Thr Trp Met Ser Ile Trp Asp Leu Ala Lys Pro Val Ile Ala Gln Val
    130                 135                 140

```
His Gly Tyr Cys Leu Ala Gly Gly Ser Glu Leu Ala Thr Gly Cys Asp
145                 150                 155                 160

Leu Val Tyr Val Ala His Asp Ala Lys Met Gly Tyr Pro Ala Val Arg
                165                 170                 175

Phe Gly Val Pro Asp Met His Phe His Ala Trp Met Leu Gly Met Arg
            180                 185                 190

Ala Ala Met Glu Met Met Val Thr Gly Asp Ser Ile Ser Gly Asp Glu
        195                 200                 205

Ala Val Arg Leu Gly Trp Ala Asn Arg Ala Phe Asp Glu Ala Asn Leu
    210                 215                 220

Asp Asp Glu Val Leu Ala Val Ala Gly Arg Val Ala Asn Ile Pro Thr
225                 230                 235                 240

Asp Ile Val Ser Leu Asn Lys Arg Ala Val His Arg Gly Met Asp Thr
                245                 250                 255

Met Gly Met Arg Thr Ala Ile Arg Gln Gly Thr Glu Leu Cys Ala Met
            260                 265                 270

Gly Thr Lys Ala Ala Thr Phe Thr Glu Phe Ile Asp Lys Met Arg Asp
        275                 280                 285

Glu Gly Leu Thr Lys Ala Leu Ser Glu Arg Asp Ala Ala Phe Gly Asp
    290                 295                 300

Tyr Arg Thr Gly Gly
305


<210> SEQ ID NO 87
<211> LENGTH: 819
<212> TYPE: DNA
<213> ORGANISM: Candidatus Microthrix parvicella

<400> SEQUENCE: 87

atggccgacg atcacgaacc ggcggtgctg accgaacggg tgggccacgt gctggtggtc      60

accctcaacc gtccggaccg catgaacacc attaatggcg aggtgctggt gcgcttctac     120

gacgccatgt tggaggcgga cagcaacccg gacattcggg tggcgatcat caccggcgca     180

ggcaagaact tctgcgccgg tgccgacctg aaagaaatgg ccggtggcca tcagggcgag     240

gacaccagcg gtgtcgacgt gcagggccgt ctggccgccg accccgattt accgtggaag     300

gcgctcctgc gcacctggcg gcccaacgtt ccgctgatca ccgcagccga ggggcaggcg     360

atcgccggcg gcaccgaact gaccggcgcc accgagattc gcgtggcggg ggagtccgca     420

aagttcggca tctccgaagt gcgctggtcg ctctatgcga tgggcgggtc ggtggtgcgc     480

atcccacgcc agatcccgta caccgtggcc gctgaattgt tgctgaccgg cgaccacatc     540

gacgctcagc gagcgctgca gttgggcctt gtcggtcacg tggtgcccga cggcgaagca     600

ctgaccaagg cgttggagat cgctgagcgc atcgccgcca atggtcccct tgccgtgaag     660

gcgatcctgc gcaccctgcg ggagaccaac ggtatgcagg agaccgaggc actcgaccac     720

gagttcacct acgggtggga tgtgttcgcc tctgaggacg cacgggaggg tccacgggcc     780

ttcaaggaaa aacgcacccc caacttcaag ggaagtag                             819


<210> SEQ ID NO 88
<211> LENGTH: 272
<212> TYPE: PRT
<213> ORGANISM: Candidatus Microthrix parvicella

<400> SEQUENCE: 88

Met Ala Asp Asp His Glu Pro Ala Val Leu Thr Glu Arg Val Gly His
1               5                   10                  15
```

```
Val Leu Val Val Thr Leu Asn Arg Pro Asp Arg Met Asn Thr Ile Asn
            20                  25                  30

Gly Glu Val Leu Val Arg Phe Tyr Asp Ala Met Leu Glu Ala Asp Ser
        35                  40                  45

Asn Pro Asp Ile Arg Val Ala Ile Ile Thr Gly Ala Gly Lys Asn Phe
    50                  55                  60

Cys Ala Gly Ala Asp Leu Lys Glu Met Ala Gly Gly His Gln Gly Glu
65                  70                  75                  80

Asp Thr Ser Gly Val Asp Val Gln Gly Arg Leu Ala Ala Asp Pro Asp
                85                  90                  95

Leu Pro Trp Lys Ala Leu Leu Arg Thr Trp Arg Pro Asn Val Pro Leu
            100                 105                 110

Ile Thr Ala Ala Glu Gly Gln Ala Ile Ala Gly Gly Thr Glu Leu Thr
        115                 120                 125

Gly Ala Thr Glu Ile Arg Val Ala Gly Glu Ser Ala Lys Phe Gly Ile
    130                 135                 140

Ser Glu Val Arg Trp Ser Leu Tyr Ala Met Gly Gly Ser Val Val Arg
145                 150                 155                 160

Ile Pro Arg Gln Ile Pro Tyr Thr Val Ala Ala Glu Leu Leu Leu Thr
                165                 170                 175

Gly Asp His Ile Asp Ala Gln Arg Ala Leu Gln Leu Gly Leu Val Gly
            180                 185                 190

His Val Val Pro Asp Gly Glu Ala Leu Thr Lys Ala Leu Glu Ile Ala
        195                 200                 205

Glu Arg Ile Ala Ala Asn Gly Pro Leu Ala Val Lys Ala Ile Leu Arg
    210                 215                 220

Thr Leu Arg Glu Thr Asn Gly Met Gln Glu Thr Glu Ala Leu Asp His
225                 230                 235                 240

Glu Phe Thr Tyr Gly Trp Asp Val Phe Ala Ser Glu Asp Ala Arg Glu
                245                 250                 255

Gly Pro Arg Ala Phe Lys Glu Lys Arg Thr Pro Asn Phe Lys Gly Lys
            260                 265                 270
```

<210> SEQ ID NO 89
<211> LENGTH: 822
<212> TYPE: DNA
<213> ORGANISM: Candidatus Microthrix parvicella

<400> SEQUENCE: 89

```
atgacgaacg aggaaaccac agccagtccg gtgatcgagg gcaacaacaa ggtgctcatg      60

gagcgccgcg gccacgtcgc aatcatcacg atcaaccgtc ccgaggcacg caacgccgtc     120

aacggcgacg tggctcaggg catcgaggcc gcaatcgacc agttggaagc tgatgacgac     180

ctgtgggtcg gagtgctcac cggtgcgcgc accgaaaagg gctggatctt ctcggccgga     240

gccgacctga aggccatgag caccgacccg ggcgccatga tgaccgagaa gggcggattc     300

gccgggttcg tcgcacgtga gcgcaccaag ccggtgatcg ccgcggtcga cggtccggca     360

ctcgccgggg gaaccgagat cgtgttggcc tgcgacatgg tcgttgcgtc ggagacggcc     420

gtgttcggcg tacccgaggt gctgcgcaat ctcgtcgccg ccggcggcgg gctgttcagg     480

cttccccgcg tgttgccccg caacgtggcc atggaactgg tgctcaccgg gcgcctggac     540

ttcccggccg agcgggctca tcacttcggt tgggtgaatg ccctgaccga ggaggccgat     600

gcgttggacg gtgccgtcca attggccgag caggtggcca aggctgctcc gctggccgtc     660
```

```
cgcgagagtc gcaagatcgt gcttgagtcg gccctggccg atgaggagac cggctggcgg    720

ctgtccaacg agggaatcgc caagatgttc ggcgccgaag acttcggtga aggtctcacg    780

gccttcttcg agaagcgcga ccccgtatgg aagggccgct ga                       822


<210> SEQ ID NO 90
<211> LENGTH: 273
<212> TYPE: PRT
<213> ORGANISM: Candidatus Microthrix parvicella

<400> SEQUENCE: 90

Met Thr Asn Glu Glu Thr Thr Ala Ser Pro Val Ile Glu Gly Asn Asn
1               5                   10                  15

Lys Val Leu Met Glu Arg Arg Gly His Val Ala Ile Ile Thr Ile Asn
            20                  25                  30

Arg Pro Glu Ala Arg Asn Ala Val Asn Gly Asp Val Ala Gln Gly Ile
        35                  40                  45

Glu Ala Ala Ile Asp Gln Leu Glu Ala Asp Asp Asp Leu Trp Val Gly
    50                  55                  60

Val Leu Thr Gly Ala Arg Thr Glu Lys Gly Trp Ile Phe Ser Ala Gly
65                  70                  75                  80

Ala Asp Leu Lys Ala Met Ser Thr Asp Pro Gly Ala Met Met Thr Glu
                85                  90                  95

Lys Gly Gly Phe Ala Gly Phe Val Ala Arg Glu Arg Thr Lys Pro Val
            100                 105                 110

Ile Ala Ala Val Asp Gly Pro Ala Leu Ala Gly Gly Thr Glu Ile Val
        115                 120                 125

Leu Ala Cys Asp Met Val Val Ala Ser Glu Thr Ala Val Phe Gly Val
    130                 135                 140

Pro Glu Val Leu Arg Asn Leu Val Ala Ala Gly Gly Gly Leu Phe Arg
145                 150                 155                 160

Leu Pro Arg Val Leu Pro Arg Asn Val Ala Met Glu Leu Val Leu Thr
                165                 170                 175

Gly Arg Leu Asp Phe Pro Ala Glu Arg Ala His His Phe Gly Trp Val
            180                 185                 190

Asn Ala Leu Thr Glu Glu Ala Asp Ala Leu Asp Gly Ala Val Gln Leu
        195                 200                 205

Ala Glu Gln Val Ala Lys Ala Ala Pro Leu Ala Val Arg Glu Ser Arg
    210                 215                 220

Lys Ile Val Leu Glu Ser Ala Leu Ala Asp Glu Glu Thr Gly Trp Arg
225                 230                 235                 240

Leu Ser Asn Glu Gly Ile Ala Lys Met Phe Gly Ala Glu Asp Phe Gly
                245                 250                 255

Glu Gly Leu Thr Ala Phe Phe Glu Lys Arg Asp Pro Val Trp Lys Gly
            260                 265                 270

Arg


<210> SEQ ID NO 91
<211> LENGTH: 870
<212> TYPE: DNA
<213> ORGANISM: Candidatus Microthrix parvicella

<400> SEQUENCE: 91

atgaacgagc acatcttcac cttcgccggg agcgacgggc tcccgatcca cacgtaccgc     60

tggagcggcg acggaacccc gcgggccatc gtccaggtgg cgcacggcat gggcgagcac    120
```

-continued gccgcccgct accgcaggtt tgcggaggcg ctcgtcgacg ccggatgtgt ggtgtatgcc 180
aacgaccatc gcggtcacgg acggaccgcc ggaggcgctg agcgtcacgg cgacctcgga 240
gaggccggct gggcgggcct cgtcgccgac ctgggcaccc tcggacgacg ggcacgtgag 300
gagcatcccg acatcccgct ggtgctgttt ggtcattcga tggggtcctt cgccgtccaa 360
cagttcttga tcgaacactc cggtgacgtc gacgccgccg tcctgtcggg cacttcggcg 420
ctcgacgtga tcggtgccgg catcgacccc gacgcggagg tcgacctcag cgccttcaat 480
gcaccattcg agccggcgcc gaccgagtac gaatggctca gccgggaccg tgccgaggtc 540
gacgcctacg tcgccgatga ggactgcggt ttcggcctga atgcaacggc cgcccgcggg 600
atgctcgaag ggacagcgac caccgccgat ccggaagcga tcgccaggat ccgcagcgac 660
cttccaatcc acctcatgtc cggcgacgcc gacccgttgg cgggtggcgg ggaactgatc 720
gagttggtgg cgacgcggta ccgggaggcc ggggtcaccg acgtcaccgt tgcccgttac 780
cccgaggcgc gtcacgagat cctcaacgag accaaccgcg gcgaggtcac cgccgatctc 840
atcgcgtggc ttgacaccgt tctggtctga 870

<210> SEQ ID NO 92
<211> LENGTH: 289
<212> TYPE: PRT
<213> ORGANISM: Candidatus Microthrix parvicella

<400> SEQUENCE: 92

Met Asn Glu His Ile Phe Thr Phe Ala Gly Ser Asp Gly Leu Pro Ile
1 5 10 15

His Thr Tyr Arg Trp Ser Gly Asp Gly Thr Pro Arg Ala Ile Val Gln
20 25 30

Val Ala His Gly Met Gly Glu His Ala Ala Arg Tyr Arg Arg Phe Ala
35 40 45

Glu Ala Leu Val Asp Ala Gly Cys Val Val Tyr Ala Asn Asp His Arg
50 55 60

Gly His Gly Arg Thr Ala Gly Gly Ala Glu Arg His Gly Asp Leu Gly
65 70 75 80

Glu Ala Gly Trp Ala Gly Leu Val Ala Asp Leu Gly Thr Leu Gly Arg
85 90 95

Arg Ala Arg Glu Glu His Pro Asp Ile Pro Leu Val Leu Phe Gly His
100 105 110

Ser Met Gly Ser Phe Ala Val Gln Gln Phe Leu Ile Glu His Ser Gly
115 120 125

Asp Val Asp Ala Ala Val Leu Ser Gly Thr Ser Ala Leu Asp Val Ile
130 135 140

Gly Ala Gly Ile Asp Pro Asp Ala Glu Val Asp Leu Ser Ala Phe Asn
145 150 155 160

Ala Pro Phe Glu Pro Ala Pro Thr Glu Tyr Glu Trp Leu Ser Arg Asp
165 170 175

Arg Ala Glu Val Asp Ala Tyr Val Ala Asp Glu Asp Cys Gly Phe Gly
180 185 190

Leu Asn Ala Thr Ala Ala Arg Gly Met Leu Glu Gly Thr Ala Thr Thr
195 200 205

Ala Asp Pro Glu Ala Ile Ala Arg Ile Arg Ser Asp Leu Pro Ile His
210 215 220

Leu Met Ser Gly Asp Ala Asp Pro Leu Ala Gly Gly Gly Glu Leu Ile
225 230 235 240

```
Glu Leu Val Ala Thr Arg Tyr Arg Glu Ala Gly Val Thr Asp Val Thr
                245                 250                 255

Val Ala Arg Tyr Pro Glu Ala Arg His Glu Ile Leu Asn Glu Thr Asn
            260                 265                 270

Arg Gly Glu Val Thr Ala Asp Leu Ile Ala Trp Leu Asp Thr Val Leu
        275                 280                 285

Val


<210> SEQ ID NO 93
<211> LENGTH: 840
<212> TYPE: DNA
<213> ORGANISM: Candidatus Microthrix parvicella

<400> SEQUENCE: 93

gtgaacaccg agacctccac caagcccggc acaggcggcg tcacgctgca caccatccgc      60

tggacacccg atgctcagcc caccgcacgg ccaaccgccg agatcctgct ggtgcacggt     120

tacgccgagc actccggccg gtacgaacag gtcgcccgac gattctgcga cgccggcttc     180

gcggtcacgt ccctggacca ccggggccac ggccaaacca ccggggtgaa gcgaggcacg     240

atcgactcct tcccggctct ggtcgacgac ctggtggcga tggtcgatgg catcggcacc     300

gacacaccgc tgttcgtcta cggccactcg atgggcggcc tggccaccgt ccggctggcc     360

gagcgcgacg actcgaggtt tgccggcgtg atcatcaccg gggcgtccct gcaggcggcg     420

gcgagcgtac ccaggccggt gctggccgct gccaacctgg tcggcaggtt cgcacccaat     480

ctgcccacca tccagctgga cggcgacgcc atctcccggg tacctgaggt gcgggccgac     540

tacgacgccg acccgctgaa cttccggggc aaggtcacca ccggcacggc ccggcagttg     600

tcggtggcga tggatgccgc gatggacgag gccgccaaca tcacggcgcc gatcctgatc     660

atgcatggaa gcgacgacac cctggccgat cctgccggtt cggtgcggtt ctcgtccaag     720

gtcgggtcga ccgaccgcac ggtcagcatc tggcccggct gtttccacga actgcacaat     780

gagccggaag ccgacgcggt gctcgccacc gtgatcgact ggatcaacgg gcaccgatag     840


<210> SEQ ID NO 94
<211> LENGTH: 279
<212> TYPE: PRT
<213> ORGANISM: Candidatus Microthrix parvicella

<400> SEQUENCE: 94

Met Asn Thr Glu Thr Ser Thr Lys Pro Gly Thr Gly Gly Val Thr Leu
1               5                   10                  15

His Thr Ile Arg Trp Thr Pro Asp Ala Gln Pro Thr Ala Arg Pro Thr
            20                  25                  30

Ala Glu Ile Leu Leu Val His Gly Tyr Ala Glu His Ser Gly Arg Tyr
        35                  40                  45

Glu Gln Val Ala Arg Arg Phe Cys Asp Ala Gly Phe Ala Val Thr Ser
    50                  55                  60

Leu Asp His Arg Gly His Gly Gln Thr Thr Gly Val Lys Arg Gly Thr
65                  70                  75                  80

Ile Asp Ser Phe Pro Ala Leu Val Asp Asp Leu Val Ala Met Val Asp
                85                  90                  95

Gly Ile Gly Thr Asp Thr Pro Leu Phe Val Tyr Gly His Ser Met Gly
            100                 105                 110

Gly Leu Ala Thr Val Arg Leu Ala Glu Arg Asp Asp Ser Arg Phe Ala
        115                 120                 125
```

```
Gly Val Ile Ile Thr Gly Ala Ser Leu Gln Ala Ala Ala Ser Val Pro
    130                 135                 140

Arg Pro Val Leu Ala Ala Ala Asn Leu Val Gly Arg Phe Ala Pro Asn
145                 150                 155                 160

Leu Pro Thr Ile Gln Leu Asp Gly Asp Ala Ile Ser Arg Val Pro Glu
                165                 170                 175

Val Arg Ala Asp Tyr Asp Ala Asp Pro Leu Asn Phe Arg Gly Lys Val
            180                 185                 190

Thr Thr Gly Thr Ala Arg Gln Leu Ser Val Ala Met Asp Ala Ala Met
        195                 200                 205

Asp Glu Ala Ala Asn Ile Thr Ala Pro Ile Leu Ile Met His Gly Ser
    210                 215                 220

Asp Asp Thr Leu Ala Asp Pro Ala Gly Ser Val Arg Phe Ser Ser Lys
225                 230                 235                 240

Val Gly Ser Thr Asp Arg Thr Val Ser Ile Trp Pro Gly Cys Phe His
                245                 250                 255

Glu Leu His Asn Glu Pro Glu Ala Asp Ala Val Leu Ala Thr Val Ile
            260                 265                 270

Asp Trp Ile Asn Gly His Arg
        275
```

<210> SEQ ID NO 95
<211> LENGTH: 1158
<212> TYPE: DNA
<213> ORGANISM: Candidatus Microthrix parvicella

<400> SEQUENCE: 95

```
atggctgacg tagtgatcgc aagcgctgtt cgtacccccca tcggcacctc ctacaagggc      60

accctggcgg cgacgaccgc ccagcagctc tccgaggtgg ccgtcggggc cgcccttgag     120

cgctccggtg tgcccgccga ggcgatcgaa gacctcgtga tgggcgagtc gatgcagggt     180

ggcggcaaca tcgcccgcta cacggccatc gagttgggtc tcgacagcgt gcccggtgcg     240

gcgattcagc gctggtgcgc ctcgggcatg tcggcggtca actacctggc cgccaacatc     300

gcctcgggca tggtcgagtg cggtatcgcg ggtggtaccg agtcgatgtc gacggcaccg     360

gccaccatga agccgggtcc cgatgggtca cagcagagtt ggctgcccgc cgcccacccc     420

gagaccgaca tcacgccggc cttcaatatg gcgatgacgg tgggggagaa caccgcccgt     480

atcgccggcg tcactcgtga gcaggctgac gagtgggcat ttcactccca tcagcgggca     540

atcgcagcca tcgacaacgg ctacttcgac gccgagttgg tgcccgttcc gctcggcgac     600

ggcaacaact tcagcgtcga cgaacacccg cgtcgcacct cgtcgctcga gaaactggcg     660

tctctgccgg tgatcaaccc gatgttggag ggtgccatcg tcacccccgg caacagctcg     720

ggcctcaacg acggcgctgc cgccatggtg ctgtgcagcc gcgagttcgc caccagtcat     780

ggtctgaccc cgctggcgac gatccgctcc tgggcatcgg cggccgacat ggtggagcga     840

aacggtctgg cccccacgct ggcgatccca aaggcgctca agctggccgg tatcggtatc     900

gacgacgtcg atgcggtgga gatcaatgag gcgttctcgt cgatggctgt ggcatcgtcc     960

cgcgagctgg gccttgacca cgcgatcacc aaccaggtgg gctcgggctg ttcgctgggc    1020

caccccatcg cctgcaccgg cgcgcgcatg ctcgtcacga tggcccatca gttggctcgc    1080

accgacaccc agtggggcgt tgccgccatg tgcgccgccg gtggcatggg cgccgcgacg    1140

gtgatcgagc ggctctga                                                 1158
```

<210> SEQ ID NO 96
<211> LENGTH: 385
<212> TYPE: PRT
<213> ORGANISM: Candidatus Microthrix parvicella

<400> SEQUENCE: 96

```
Met Ala Asp Val Val Ile Ala Ser Ala Val Arg Thr Pro Ile Gly Thr
1               5                   10                  15

Ser Tyr Lys Gly Thr Leu Ala Ala Thr Thr Ala Gln Gln Leu Ser Glu
            20                  25                  30

Val Ala Val Gly Ala Ala Leu Glu Arg Ser Gly Val Pro Ala Glu Ala
        35                  40                  45

Ile Glu Asp Leu Val Met Gly Glu Ser Met Gln Gly Gly Gly Asn Ile
    50                  55                  60

Ala Arg Tyr Thr Ala Ile Glu Leu Gly Leu Asp Ser Val Pro Gly Ala
65                  70                  75                  80

Ala Ile Gln Arg Trp Cys Ala Ser Gly Met Ser Ala Val Asn Tyr Leu
                85                  90                  95

Ala Ala Asn Ile Ala Ser Gly Met Val Glu Cys Gly Ile Ala Gly Gly
            100                 105                 110

Thr Glu Ser Met Ser Thr Ala Pro Ala Thr Met Lys Pro Gly Pro Asp
        115                 120                 125

Gly Ser Gln Gln Ser Trp Leu Pro Ala Ala His Pro Glu Thr Asp Ile
    130                 135                 140

Thr Pro Ala Phe Asn Met Ala Met Thr Val Gly Glu Asn Thr Ala Arg
145                 150                 155                 160

Ile Ala Gly Val Thr Arg Glu Gln Ala Asp Glu Trp Ala Phe His Ser
                165                 170                 175

His Gln Arg Ala Ile Ala Ala Ile Asp Asn Gly Tyr Phe Asp Ala Glu
            180                 185                 190

Leu Val Pro Val Pro Leu Gly Asp Gly Asn Asn Phe Ser Val Asp Glu
        195                 200                 205

His Pro Arg Arg Thr Ser Ser Leu Glu Lys Leu Ala Ser Leu Pro Val
    210                 215                 220

Ile Asn Pro Met Leu Glu Gly Ala Ile Val Thr Pro Gly Asn Ser Ser
225                 230                 235                 240

Gly Leu Asn Asp Gly Ala Ala Ala Met Val Leu Cys Ser Arg Glu Phe
                245                 250                 255

Ala Thr Ser His Gly Leu Thr Pro Leu Ala Thr Ile Arg Ser Trp Ala
            260                 265                 270

Ser Ala Ala Asp Met Val Glu Arg Asn Gly Leu Ala Pro Thr Leu Ala
        275                 280                 285

Ile Pro Lys Ala Leu Lys Leu Ala Gly Ile Gly Ile Asp Asp Val Asp
    290                 295                 300

Ala Val Glu Ile Asn Glu Ala Phe Ser Ser Met Ala Val Ala Ser Ser
305                 310                 315                 320

Arg Glu Leu Gly Leu Asp His Ala Ile Thr Asn Gln Val Gly Ser Gly
                325                 330                 335

Cys Ser Leu Gly His Pro Ile Ala Cys Thr Gly Ala Arg Met Leu Val
            340                 345                 350

Thr Met Ala His Gln Leu Ala Arg Thr Asp Thr Gln Trp Gly Val Ala
        355                 360                 365

Ala Met Cys Ala Ala Gly Gly Met Gly Ala Ala Thr Val Ile Glu Arg
    370                 375                 380
```

Leu
385

<210> SEQ ID NO 97
<211> LENGTH: 1203
<212> TYPE: DNA
<213> ORGANISM: Candidatus Microthrix parvicella

<400> SEQUENCE: 97
atgagcaagc acaacgagcg ggtcttcgtg atcggcgtcg ggatgaccaa gtttgagaag 60
cccggagccc gcgagggctg ggactacccg cagatggtga aggagtcggg aaccgaagcg 120
cttgaggacg cgggcgtcgg ctacgaccgg gtcgagcagg tgcacgccgg ctacgtgtac 180
ggcgactcca cctgcggtga acgggccgtc tacgagctgg gcatgaccgg catcccaatc 240
accaacgtca acaacaactg ctccaccggg tcgaccgccc tgtatctgag cgccgaagcg 300
atccgcggcg gtcgtgccga ctgcgtgatg gcggtgggct tcgagaagat ggagaagggc 360
tcgttggcga tcggcgcgga ggaccgcgag cagccgctga tgaagcacat gatggccctc 420
ggcgaactgt acgagttcgc catgccgccg gcgccctaca tgttcggcgc tgccggtcgc 480
gagcacatgg agaagtacgg ctcgacaccg gagcacttcg ccaagatcgg cgagaagaac 540
catcgacact cggccaacaa cccctacgcc cagttccagg acgtctacac gctccaggag 600
atcctcgacg ccaagatggt gtacccgccg ctcacccggc tgcagtgctc ccccacctcc 660
gatggctccg gcgctgcggt gctcgccagc gaggaggtcg tcgacgtcaa cggcctggcc 720
gaccaggcgg tcgagatcgt cgggcagacc atcgtcaccg acctggccag cacgttcgaa 780
gccggcaccg cggctgccct cgtcggctac gacatgacca aggaggccgg ccgtcaggtg 840
ttcgagcagg ccggcctggg catcgacgac ttccaggtga tcgaactgca cgactgcttc 900
cccactaacg agctgctcac ctacgaggca ctgggcctgg ccgccgaggg cgaaggccac 960
aagctgatcg acaacgacga caccacctac ggcggccgct gggtggtcaa cccctccggc 1020
gggctgatct ccaaaggcca cccgctgggc gccaccgggc tggcccaggg ctcagaactg 1080
gtctggcaac tgcgcggcac cgccgaagca cggcaggtcg acgacgtcac ggccggcctg 1140
caacacaaca tcggcctggg cggcgccgcc gtcgtcaccg cctaccaacg cgccgaccgc 1200
tga 1203

<210> SEQ ID NO 98
<211> LENGTH: 400
<212> TYPE: PRT
<213> ORGANISM: Candidatus Microthrix parvicella

<400> SEQUENCE: 98

Met Ser Lys His Asn Glu Arg Val Phe Val Ile Gly Val Gly Met Thr
1 5 10 15

Lys Phe Glu Lys Pro Gly Ala Arg Glu Gly Trp Asp Tyr Pro Gln Met
20 25 30

Val Lys Glu Ser Gly Thr Glu Ala Leu Glu Asp Ala Gly Val Gly Tyr
35 40 45

Asp Arg Val Glu Gln Val His Ala Gly Tyr Val Tyr Gly Asp Ser Thr
50 55 60

Cys Gly Glu Arg Ala Val Tyr Glu Leu Gly Met Thr Gly Ile Pro Ile
65 70 75 80

Thr Asn Val Asn Asn Asn Cys Ser Thr Gly Ser Thr Ala Leu Tyr Leu
85 90 95

```
Ser Ala Glu Ala Ile Arg Gly Gly Arg Ala Asp Cys Val Met Ala Val
            100                 105                 110

Gly Phe Glu Lys Met Glu Lys Gly Ser Leu Ala Ile Gly Ala Glu Asp
        115                 120                 125

Arg Glu Gln Pro Leu Met Lys His Met Met Ala Leu Gly Glu Leu Tyr
    130                 135                 140

Glu Phe Ala Met Pro Pro Ala Pro Tyr Met Phe Gly Ala Ala Gly Arg
145                 150                 155                 160

Glu His Met Glu Lys Tyr Gly Ser Thr Pro Glu His Phe Ala Lys Ile
                165                 170                 175

Gly Glu Lys Asn His Arg His Ser Ala Asn Asn Pro Tyr Ala Gln Phe
            180                 185                 190

Gln Asp Val Tyr Thr Leu Gln Glu Ile Leu Asp Ala Lys Met Val Tyr
        195                 200                 205

Pro Pro Leu Thr Arg Leu Gln Cys Ser Pro Thr Ser Asp Gly Ser Gly
    210                 215                 220

Ala Ala Val Leu Ala Ser Glu Glu Val Val Asp Val Asn Gly Leu Ala
225                 230                 235                 240

Asp Gln Ala Val Glu Ile Val Gly Gln Thr Ile Val Thr Asp Leu Ala
                245                 250                 255

Ser Thr Phe Glu Ala Gly Thr Ala Ala Ala Leu Val Gly Tyr Asp Met
            260                 265                 270

Thr Lys Glu Ala Gly Arg Gln Val Phe Glu Gln Ala Gly Leu Gly Ile
        275                 280                 285

Asp Asp Phe Gln Val Ile Glu Leu His Asp Cys Phe Pro Thr Asn Glu
    290                 295                 300

Leu Leu Thr Tyr Glu Ala Leu Gly Leu Ala Ala Glu Gly Glu Gly His
305                 310                 315                 320

Lys Leu Ile Asp Asn Asp Asp Thr Thr Tyr Gly Gly Arg Trp Val Val
                325                 330                 335

Asn Pro Ser Gly Gly Leu Ile Ser Lys Gly His Pro Leu Gly Ala Thr
            340                 345                 350

Gly Leu Ala Gln Gly Ser Glu Leu Val Trp Gln Leu Arg Gly Thr Ala
        355                 360                 365

Glu Ala Arg Gln Val Asp Asp Val Thr Ala Gly Leu Gln His Asn Ile
    370                 375                 380

Gly Leu Gly Gly Ala Ala Val Val Thr Ala Tyr Gln Arg Ala Asp Arg
385                 390                 395                 400
```

<210> SEQ ID NO 99
<211> LENGTH: 1260
<212> TYPE: DNA
<213> ORGANISM: Candidatus Microthrix parvicella

<400> SEQUENCE: 99

```
gtggtgctgg gcgccctcat tggcccggtt tctgacgagg cgtcagactg gggcaaacca      60

ggagcaggtt ggccgttgtg caacctgccg atcgggagga tcaccatggc cgaggcctac     120

atcgtcgacg cagtccgaac cccggtgggg cgacggggag ggggcctctc ggccgtgcac     180

ccggccgacc tgggtgccca ctcgctcaag gcgctgatgg agcgcaccgg cgtggacccg     240

ggggcagtcg aggatgtgat cttcgggtgt gtcgacacga tcggtggcca ggccggcgac     300

atcgcccgca cctgctggct ggcggccggg ctgccggacc acgtgccggg caccaccatc     360

gaccgccagt gcgggtcgtc acaacaggcc gtgcattttg ccgcccaggg ggtcatgtcg     420
```

```
ggcacgtcgg acctgatcgt ggccggcggg gtgcagcaaa tgtccaccat tccgatcagc    480

tcgtccatgt tggtcggcga ccagttcggc tacccggacc cgttcagtgg ctcgttgggt    540

tggcaggagc gatacggcga ccaggaggtc agccagtttc gttcggcgca gatgatcgcc    600

gacaagtggg actgcagccg cgacgagatg gagtccttcg cggtggagag ccacgagcgg    660

gccatccggg cacgggcaga aggccgtttc gatgccgaga tcgccccgtt tggcgaggtg    720

atggcggacg aaggaccccg cgaacccaat tgggacaaga tccgcagcct ccggcccttg    780

gaggagggag gcacgatcac tgcggcggtg gccagccaga tctcggacgc gtcggcggcg    840

ttgctgatcg cctccgagca ggcggtggag gaccacggcc ttacgcctcg ggcccgtatc    900

caccacctgt cggtgcgcgc cgacgacccc gtgtggatgc tgacagcgcc catcccggcc    960

acccgttacg cccttcagaa gtccggcctc accatggacg acatcgacct ggttgagatc   1020

aacgaggcgt ttgcctcggt ggtgctggcg tggatgaagg acctggaagt gccccacgac   1080

aaagtgaacg tcaacggcgg agccattgcg ctggggcacc ccctcggcgc caccggtgcc   1140

cgcctgatga ccaccctgct cggcgagctg gagcgcaccg gtggccggta cgggctgcag   1200

accatgtgtg agggtggcgg tcaggccaac gtgaccatca tcgaacgcct tggttcgtga   1260
```

<210> SEQ ID NO 100
<211> LENGTH: 419
<212> TYPE: PRT
<213> ORGANISM: Candidatus Microthrix parvicella

<400> SEQUENCE: 100

```
Met Val Leu Gly Ala Leu Ile Gly Pro Val Ser Asp Glu Ala Ser Asp
1               5                   10                  15

Trp Gly Lys Pro Gly Ala Gly Trp Pro Leu Cys Asn Leu Pro Ile Gly
            20                  25                  30

Arg Ile Thr Met Ala Glu Ala Tyr Ile Val Asp Ala Val Arg Thr Pro
        35                  40                  45

Val Gly Arg Arg Gly Gly Gly Leu Ser Ala Val His Pro Ala Asp Leu
    50                  55                  60

Gly Ala His Ser Leu Lys Ala Leu Met Glu Arg Thr Gly Val Asp Pro
65                  70                  75                  80

Gly Ala Val Glu Asp Val Ile Phe Gly Cys Val Asp Thr Ile Gly Gly
                85                  90                  95

Gln Ala Gly Asp Ile Ala Arg Thr Cys Trp Leu Ala Ala Gly Leu Pro
            100                 105                 110

Asp His Val Pro Gly Thr Thr Ile Asp Arg Gln Cys Gly Ser Ser Gln
        115                 120                 125

Gln Ala Val His Phe Ala Ala Gln Gly Val Met Ser Gly Thr Ser Asp
    130                 135                 140

Leu Ile Val Ala Gly Gly Val Gln Gln Met Ser Thr Ile Pro Ile Ser
145                 150                 155                 160

Ser Ser Met Leu Val Gly Asp Gln Phe Gly Tyr Pro Asp Pro Phe Ser
                165                 170                 175

Gly Ser Leu Gly Trp Gln Glu Arg Tyr Gly Asp Gln Glu Val Ser Gln
            180                 185                 190

Phe Arg Ser Ala Gln Met Ile Ala Asp Lys Trp Asp Cys Ser Arg Asp
        195                 200                 205

Glu Met Glu Ser Phe Ala Val Glu Ser His Glu Arg Ala Ile Arg Ala
    210                 215                 220

Arg Ala Glu Gly Arg Phe Asp Ala Glu Ile Ala Pro Phe Gly Glu Val
```

```
225                 230                 235                 240

Met Ala Asp Glu Gly Pro Arg Glu Pro Asn Trp Asp Lys Ile Arg Ser
                245                 250                 255

Leu Arg Pro Leu Glu Glu Gly Gly Thr Ile Thr Ala Ala Val Ala Ser
            260                 265                 270

Gln Ile Ser Asp Ala Ser Ala Ala Leu Leu Ile Ala Ser Glu Gln Ala
        275                 280                 285

Val Glu Asp His Gly Leu Thr Pro Arg Ala Arg Ile His His Leu Ser
    290                 295                 300

Val Arg Ala Asp Asp Pro Val Trp Met Leu Thr Ala Pro Ile Pro Ala
305                 310                 315                 320

Thr Arg Tyr Ala Leu Gln Lys Ser Gly Leu Thr Met Asp Asp Ile Asp
                325                 330                 335

Leu Val Glu Ile Asn Glu Ala Phe Ala Ser Val Val Leu Ala Trp Met
            340                 345                 350

Lys Asp Leu Glu Val Pro His Asp Lys Val Asn Val Asn Gly Gly Ala
        355                 360                 365

Ile Ala Leu Gly His Pro Leu Gly Ala Thr Gly Ala Arg Leu Met Thr
    370                 375                 380

Thr Leu Leu Gly Glu Leu Glu Arg Thr Gly Gly Arg Tyr Gly Leu Gln
385                 390                 395                 400

Thr Met Cys Glu Gly Gly Gly Gln Ala Asn Val Thr Ile Ile Glu Arg
                405                 410                 415

Leu Gly Ser


<210> SEQ ID NO 101
<211> LENGTH: 1182
<212> TYPE: DNA
<213> ORGANISM: Candidatus Microthrix parvicella

<400> SEQUENCE: 101

atggcaggtt cagtcatcct cggcggagca cgcactccgt tcggcaagtt ctccggctcg      60

ctcgccgggt tctccggcgc agagctgggg ggcaaggcca tcgctggcgc cctcgagcgc     120

accggcatct cagccgatca ggtcgactac gtactgatgg gccaggtgct ccaggcaggc     180

gcaggccaga tcacggcccg ccaggcagca gtcgccgccg gcatcggcct cgatgtgccc     240

gcgaccacca tcaacaaggt gtgtctctcc ggcatcaaca cgatcatgct ggccgacctc     300

ctcatccagg cgggagaggc agagattgtc gtcgccgggg gcatggagtc gatgaccaat     360

gctccgtacc tgctgcgcga ggcccgctcg ggcatgcgaa tgggtgacaa gaccgtcgtc     420

gactcgatga tgcacgactc cctcttctgc gccatcgatg agctggccat gggcgcatcc     480

accgaaaagt acgccgccgc agccggcctg aaccgcgacg tccaggacaa tctgtcggcc     540

cagagccacg aacgcgccgc cgccgcccaa aaggacggca agttcgacaa cgagatcatc     600

ccggtggcga ttcctcagcg taagggcgac ccgatcttgt tggaggccga cgagggcgtg     660

cgtcctggca ccaccgccga gtcgctgggc aagctgcgcc cggcattcgc caaggacggc     720

aacatcacgg cgggcaacgc ctcacagatc tccgacggcg gcgccgccgt catcgtgtgc     780

tcggctgcca aggccaagga gttgggcctc accccgttgg gcgagatcgt gtcgatcggc     840

caggttgcag gccccgatgc ctcgctgatc tcccagcccg cccaggcgat caaggccgca     900

ctggccaagg ccaacctggc ggttgaggac gtcgatctgt tcgagctcaa cgaggccttc     960

gccgccgtcg gttgtcagtc gatgaacgac ctgggtatct ccgacgacat cgtcaacgtc    1020
```

```
aacggcgggg cgatcgccat tggccacccg gtgggcgtgt ccggcacccg aatcgttttg   1080

acgctgctca acgagttgca gcggcgtggc ggtggcactg gtgccgctgc gctgtgcggc   1140

ggtggcggcc agggcgacgc catgatcgtc cgcaccgtct ga                      1182


<210> SEQ ID NO 102
<211> LENGTH: 393
<212> TYPE: PRT
<213> ORGANISM: Candidatus Microthrix parvicella

<400> SEQUENCE: 102

Met Ala Gly Ser Val Ile Leu Gly Gly Ala Arg Thr Pro Phe Gly Lys
1               5                   10                  15

Phe Ser Gly Ser Leu Ala Gly Phe Ser Gly Ala Glu Leu Gly Gly Lys
            20                  25                  30

Ala Ile Ala Gly Ala Leu Glu Arg Thr Gly Ile Ser Ala Asp Gln Val
        35                  40                  45

Asp Tyr Val Leu Met Gly Gln Val Leu Gln Ala Gly Ala Gly Gln Ile
    50                  55                  60

Thr Ala Arg Gln Ala Ala Val Ala Ala Gly Ile Gly Leu Asp Val Pro
65                  70                  75                  80

Ala Thr Thr Ile Asn Lys Val Cys Leu Ser Gly Ile Asn Thr Ile Met
                85                  90                  95

Leu Ala Asp Leu Leu Ile Gln Ala Gly Glu Ala Glu Ile Val Val Ala
            100                 105                 110

Gly Gly Met Glu Ser Met Thr Asn Ala Pro Tyr Leu Leu Arg Glu Ala
        115                 120                 125

Arg Ser Gly Met Arg Met Gly Asp Lys Thr Val Val Asp Ser Met Met
    130                 135                 140

His Asp Ser Leu Phe Cys Ala Ile Asp Glu Leu Ala Met Gly Ala Ser
145                 150                 155                 160

Thr Glu Lys Tyr Ala Ala Ala Ala Gly Leu Asn Arg Asp Val Gln Asp
                165                 170                 175

Asn Leu Ser Ala Gln Ser His Glu Arg Ala Ala Ala Ala Gln Lys Asp
            180                 185                 190

Gly Lys Phe Asp Asn Glu Ile Ile Pro Val Ala Ile Pro Gln Arg Lys
        195                 200                 205

Gly Asp Pro Ile Leu Leu Glu Ala Asp Glu Gly Val Arg Pro Gly Thr
    210                 215                 220

Thr Ala Glu Ser Leu Gly Lys Leu Arg Pro Ala Phe Ala Lys Asp Gly
225                 230                 235                 240

Asn Ile Thr Ala Gly Asn Ala Ser Gln Ile Ser Asp Gly Gly Ala Ala
                245                 250                 255

Val Ile Val Cys Ser Ala Ala Lys Ala Lys Glu Leu Gly Leu Thr Pro
            260                 265                 270

Leu Gly Glu Ile Val Ser Ile Gly Gln Val Ala Gly Pro Asp Ala Ser
        275                 280                 285

Leu Ile Ser Gln Pro Ala Gln Ala Ile Lys Ala Ala Leu Ala Lys Ala
    290                 295                 300

Asn Leu Ala Val Glu Asp Val Asp Leu Phe Glu Leu Asn Glu Ala Phe
305                 310                 315                 320

Ala Ala Val Gly Cys Gln Ser Met Asn Asp Leu Gly Ile Ser Asp Asp
                325                 330                 335

Ile Val Asn Val Asn Gly Gly Ala Ile Ala Ile Gly His Pro Val Gly
            340                 345                 350
```

```
Val Ser Gly Thr Arg Ile Val Leu Thr Leu Leu Asn Glu Leu Gln Arg
        355                 360                 365

Arg Gly Gly Gly Thr Gly Ala Ala Ala Leu Cys Gly Gly Gly Gly Gln
    370                 375                 380

Gly Asp Ala Met Ile Val Arg Thr Val
385                 390


<210> SEQ ID NO 103
<211> LENGTH: 1203
<212> TYPE: DNA
<213> ORGANISM: Candidatus Microthrix parvicella

<400> SEQUENCE: 103

atgcccgaag cagtcatcgt cgccaccgcc cgcagcccca tcggtcgggc catgaagggc      60

tccctgaagg acatgcgccc ggacgacctg tccgcccagg tgctgaccga cctgatgagc     120

aaggtcccgc agatcacccc cgaccacatc gacgacctga tcatgggctg tggtcagccg     180

gccggcgagt ccggtcacaa catcggtcgg gccaccgccg tgctcatggg ctggaaccag     240

gtccccggtg tcaccgtcaa ccgctactgc tcctcgtccc tgatgacgat ccgcatggcc     300

gcacacgcca tcaaggccgg cgagggcgac tgctttgtcg cagccggggt cgagacggtc     360

agccggttca tctacggcat ggccgatggt ccccacaacc cgctcttcgc cgacgccgag     420

gcacgcaccg ccacgctggc cgaaggcaac gaagccgact gggcgcccca cgacaacctg     480

cccgacgtgt acatcgccat gggccagacc gccgagaacg tggccgagta caagcaggtc     540

agccgcgagg cgcaggacga gttcgccgcc cgcagccaga acctgtccga gcaaagcctg     600

gacgagggct actgggcgga cgagatcacc ccgatcacgc tgccagacgg caccgtcgtc     660

aaggacgatg acggcatccg tcgtggcacc accgccgaga agctgtccgg ccttcagccc     720

gtgttccgcc caggcggcac cgtgacggcc ggcaatgcct gcccgctcaa cgatggcgct     780

gccggcgtcg tcgtcatgtc ggacaccctg gccaaggagt tggggctgac cccgctggcc     840

cgcatcgtgt cttccggcgt gtccggcctg aaccccgaga tcatgggcct cggcccggtc     900

gaggcgatca agcaggcgct cgggcgagcc aacatgtcga tcgacgatat cgacctggtc     960

gagatcaacg aggcgttcgc cgcacaggtg ctgccgtccg ccgacgagtt gggcatcccg    1020

atggacaagc tgaacacccg cggcggctca atcgcactgg gccacccgtt cggcatgacc    1080

ggcgcccgca tcatgaccac cctcatccac aacctccaga ccgcagacaa gaccttcggt    1140

gtggaaagca tgtgcgtcgg cggcggtcag ggcatggcca tggtggtcga gcgtctgagc    1200

tga                                                                  1203


<210> SEQ ID NO 104
<211> LENGTH: 400
<212> TYPE: PRT
<213> ORGANISM: Candidatus Microthrix parvicella

<400> SEQUENCE: 104

Met Pro Glu Ala Val Ile Val Ala Thr Ala Arg Ser Pro Ile Gly Arg
1               5                   10                  15

Ala Met Lys Gly Ser Leu Lys Asp Met Arg Pro Asp Asp Leu Ser Ala
            20                  25                  30

Gln Val Leu Thr Asp Leu Met Ser Lys Val Pro Gln Ile Thr Pro Asp
        35                  40                  45

His Ile Asp Asp Leu Ile Met Gly Cys Gly Gln Pro Ala Gly Glu Ser
    50                  55                  60
```

```
Gly His Asn Ile Gly Arg Ala Thr Ala Val Leu Met Gly Trp Asn Gln
65                  70                  75                  80

Val Pro Gly Val Thr Val Asn Arg Tyr Cys Ser Ser Ser Leu Met Thr
                85                  90                  95

Ile Arg Met Ala Ala His Ala Ile Lys Ala Gly Glu Gly Asp Cys Phe
            100                 105                 110

Val Ala Ala Gly Val Glu Thr Val Ser Arg Phe Ile Tyr Gly Met Ala
        115                 120                 125

Asp Gly Pro His Asn Pro Leu Phe Ala Asp Ala Glu Ala Arg Thr Ala
    130                 135                 140

Thr Leu Ala Glu Gly Asn Glu Ala Asp Trp Ala Pro His Asp Asn Leu
145                 150                 155                 160

Pro Asp Val Tyr Ile Ala Met Gly Gln Thr Ala Glu Asn Val Ala Glu
                165                 170                 175

Tyr Lys Gln Val Ser Arg Glu Ala Gln Asp Glu Phe Ala Ala Arg Ser
            180                 185                 190

Gln Asn Leu Ser Glu Gln Ser Leu Asp Glu Gly Tyr Trp Ala Asp Glu
        195                 200                 205

Ile Thr Pro Ile Thr Leu Pro Asp Gly Thr Val Val Lys Asp Asp Asp
    210                 215                 220

Gly Ile Arg Arg Gly Thr Thr Ala Glu Lys Leu Ser Gly Leu Gln Pro
225                 230                 235                 240

Val Phe Arg Pro Gly Gly Thr Val Thr Ala Gly Asn Ala Cys Pro Leu
                245                 250                 255

Asn Asp Gly Ala Ala Gly Val Val Val Met Ser Asp Thr Leu Ala Lys
            260                 265                 270

Glu Leu Gly Leu Thr Pro Leu Ala Arg Ile Val Ser Ser Gly Val Ser
        275                 280                 285

Gly Leu Asn Pro Glu Ile Met Gly Leu Gly Pro Val Glu Ala Ile Lys
    290                 295                 300

Gln Ala Leu Gly Arg Ala Asn Met Ser Ile Asp Asp Ile Asp Leu Val
305                 310                 315                 320

Glu Ile Asn Glu Ala Phe Ala Ala Gln Val Leu Pro Ser Ala Asp Glu
                325                 330                 335

Leu Gly Ile Pro Met Asp Lys Leu Asn Thr Arg Gly Gly Ser Ile Ala
            340                 345                 350

Leu Gly His Pro Phe Gly Met Thr Gly Ala Arg Ile Met Thr Thr Leu
        355                 360                 365

Ile His Asn Leu Gln Thr Ala Asp Lys Thr Phe Gly Val Glu Ser Met
    370                 375                 380

Cys Val Gly Gly Gly Gln Gly Met Ala Met Val Val Glu Arg Leu Ser
385                 390                 395                 400
```

<210> SEQ ID NO 105
<211> LENGTH: 1260
<212> TYPE: DNA
<213> ORGANISM: Candidatus Microthrix parvicella

<400> SEQUENCE: 105

```
gtgagttcga cgtggattct cggcgggtac cagagcgact tcgcccgctc gttgggtcgc      60

gagggcctgg gcatctccga cctcacgcag gagatcgtgg agggaaccct cgaggcggcg     120

ggcgttgacg ccgacgaggt cgactcggtc cacgtcgcta acgcgttcgg gcagctctac     180

accggccagg gtcacctggg ggccatgccg gccagcgtgg tgcccgaact gtggggcgtg     240
```

```
ccggcgatga gccacgaggc ggcatgcgcg tccagctcga tcgcggtgct ggcggcgatg    300

gccgagatcg aggcgggtcg ctatgactgt gtgctcgtgc tgggcgtcga ggtggagcga    360

accatgcccg gcgccgccgc cgcccgcacc cagcaggcgg cggcatgggt gggccacgag    420

accgacgggg tcgacttcat ctggcccgcg acgttcgacc ggatcgcgga cgagtacgac    480

cgtcgcttcg gcctggacga tgcccacctg cgggccatcg gcgagctgaa cctgaccaac    540

gccaaggaca acccgctggc acaaacccgg gactggcgct tgaacgagcg cagcttcggt    600

accgacgatc gatccaaccc tccggtggcc ggacggctgc gtcgcaacga ctgcacccag    660

atcaccgacg gtggcgccgg ggtggtgttg gtctcggatc gctggcttgc cgaccggcag    720

ggcgctgcaa cacctggcgg tgcctccggt ccgctcgggc gcatcgcggg gtggggccac    780

accacggtca gcctcggcct cgaagccaag ctgcggcgca gcgccgacgg cggcgccgat    840

ccgagcccct tcgtgatggg ccacgttcgg cgtgcgatca ccgacgccca tcggcgggcc    900

cggattgcgg gtatcgacga cgtcgactgc gtcgagaccc acgattgcat gacgccgtcg    960

gagtacctgg ccatcgacca cctgggcatc accggccccg gtgagtgctg gaaggcgatc   1020

gaagacgggc gcatccggcg aggtgggtcg atcccggtca acccgggcgg tggtttgatc   1080

ggtggtggcc atccggtggg tgccaccggc gtccgcatgc tgttcgacgt cgccaagcag   1140

gtgagcggta ccgccggtga gccgcaggtg gacggggcgc agcgggccca gacgctcaac   1200

atcggtggat cgaccgccac cacggtctca ttcgtcgttg aatcggcggt gtctcggtga   1260
```

<210> SEQ ID NO 106
<211> LENGTH: 419
<212> TYPE: PRT
<213> ORGANISM: Candidatus Microthrix parvicella

<400> SEQUENCE: 106

```
Met Ser Ser Thr Trp Ile Leu Gly Gly Tyr Gln Ser Asp Phe Ala Arg
1               5                   10                  15

Ser Leu Gly Arg Glu Gly Leu Gly Ile Ser Asp Leu Thr Gln Glu Ile
            20                  25                  30

Val Glu Gly Thr Leu Glu Ala Ala Gly Val Asp Ala Asp Glu Val Asp
        35                  40                  45

Ser Val His Val Ala Asn Ala Phe Gly Gln Leu Tyr Thr Gly Gln Gly
    50                  55                  60

His Leu Gly Ala Met Pro Ala Ser Val Val Pro Glu Leu Trp Gly Val
65                  70                  75                  80

Pro Ala Met Ser His Glu Ala Ala Cys Ala Ser Ser Ser Ile Ala Val
                85                  90                  95

Leu Ala Ala Met Ala Glu Ile Glu Ala Gly Arg Tyr Asp Cys Val Leu
            100                 105                 110

Val Leu Gly Val Glu Val Glu Arg Thr Met Pro Gly Ala Ala Ala Ala
        115                 120                 125

Arg Thr Gln Gln Ala Ala Ala Trp Val Gly His Glu Thr Asp Gly Val
    130                 135                 140

Asp Phe Ile Trp Pro Ala Thr Phe Asp Arg Ile Ala Asp Glu Tyr Asp
145                 150                 155                 160

Arg Arg Phe Gly Leu Asp Asp Ala His Leu Arg Ala Ile Gly Glu Leu
                165                 170                 175

Asn Leu Thr Asn Ala Lys Asp Asn Pro Leu Ala Gln Thr Arg Asp Trp
            180                 185                 190
```

-continued

```
Arg Leu Asn Glu Arg Ser Phe Gly Thr Asp Asp Arg Ser Asn Pro Pro
        195                 200                 205

Val Ala Gly Arg Leu Arg Arg Asn Asp Cys Thr Gln Ile Thr Asp Gly
    210                 215                 220

Gly Ala Gly Val Val Leu Val Ser Asp Arg Trp Leu Ala Asp Arg Gln
225                 230                 235                 240

Gly Ala Ala Thr Pro Gly Gly Ala Ser Gly Pro Leu Gly Arg Ile Ala
                245                 250                 255

Gly Trp Gly His Thr Thr Val Ser Leu Gly Leu Glu Ala Lys Leu Arg
            260                 265                 270

Arg Ser Ala Asp Gly Gly Ala Asp Pro Ser Pro Phe Val Met Gly His
        275                 280                 285

Val Arg Arg Ala Ile Thr Asp Ala His Arg Arg Ala Arg Ile Ala Gly
    290                 295                 300

Ile Asp Asp Val Asp Cys Val Glu Thr His Asp Cys Met Thr Pro Ser
305                 310                 315                 320

Glu Tyr Leu Ala Ile Asp His Leu Gly Ile Thr Gly Pro Gly Glu Cys
                325                 330                 335

Trp Lys Ala Ile Glu Asp Gly Arg Ile Arg Arg Gly Gly Ser Ile Pro
            340                 345                 350

Val Asn Pro Gly Gly Gly Leu Ile Gly Gly Gly His Pro Val Gly Ala
        355                 360                 365

Thr Gly Val Arg Met Leu Phe Asp Val Ala Lys Gln Val Ser Gly Thr
    370                 375                 380

Ala Gly Glu Pro Gln Val Asp Gly Ala Gln Arg Ala Gln Thr Leu Asn
385                 390                 395                 400

Ile Gly Gly Ser Thr Ala Thr Thr Val Ser Phe Val Val Glu Ser Ala
                405                 410                 415

Val Ser Arg
```

<210> SEQ ID NO 107
<211> LENGTH: 1224
<212> TYPE: DNA
<213> ORGANISM: Candidatus Microthrix parvicella

<400> SEQUENCE: 107

```
atggccgacg cattcatcat cgacgcgtgc cgcacgccga ggggcatcgg caagcccggc      60

aagggggcgc ttgcccacct tcacccccag cacctgggcg ccaccgtgct ggcggcgctg     120

cgcgaccgta acgacctcga caccagcgac gtcgacgaca tcgtctgggg aaccagctcg     180

caggtctcgg agcagagcgg cgacctgggc cgcatggccg ccctcgacgc cggctacgac     240

gtgaaggcca gcggggtcac gctcgaccgg ttctgcggct cgggcatcac cagcaccaac     300

atcgccgcca acgccatcat ggcgggcatg gaagacctgg tgatctccgg tggcaccgag     360

atgatgtcgc taccgaagac gggcatgttg cccatcggcg ccaacaacgc acatctccag     420

gagctccatc cacaaccgca ccagggcgtg tgcgccgacg ccatcgccac gctggacggc     480

atcggccgcg acgcgctcga cgcgcacgcc gccacctccc aggcccgggc cggccaggca     540

attgcggagg gtcgcttcga ccgcagcctg gtgcccgtct acaacctggg cggcagcctt     600

gcgctcgatc acgaggagtt tccgcggccc ggcaccaccg ccgagtcgct cgccaagctg     660

cggccctcgt tcgaggttgt cgccgactac cgccacaccg aagattccaa gacctaccgc     720

gagctggtcg cacagaagtt ccccgatctc acgatcgagc acgttcacca cgccggcaac     780

tcctccggtg tggtcgacgg cgccgccgcc atcctgctgg caagcgaggc ctacgccacg     840
```

```
gcccacacgc tcaagcctcg ggcccgagtg gtggccaccg ccaacatggg cgacgacccc    900

acgctgatgc tgaacgcacc cgtccccgcc gcccgcaagg tgctcgcgcg agccggcatg    960

acgctggacg acatcgacct gttcgagatc aacgaggcat tcgctgtggt gtccgagaag   1020

tttcagcgcg acctcaacct cgaccgcgac aaggtgaacg tcaacggtgg cgccatggcc   1080

ctcggccacc caatcggtgc aaccggctcg atcctgattg gcacggtgct cgatgagctg   1140

gagcggcgcg acctccagac cggcctggtc accatgtgtg cgggcggagg catggcaccc   1200

gccatcatca tcgaacgcgt ctga                                          1224
```

<210> SEQ ID NO 108
<211> LENGTH: 407
<212> TYPE: PRT
<213> ORGANISM: Candidatus Microthrix parvicella

<400> SEQUENCE: 108

```
Met Ala Asp Ala Phe Ile Ile Asp Ala Cys Arg Thr Pro Arg Gly Ile
1               5                   10                  15

Gly Lys Pro Gly Lys Gly Ala Leu Ala His Leu His Pro Gln His Leu
            20                  25                  30

Gly Ala Thr Val Leu Ala Ala Leu Arg Asp Arg Asn Asp Leu Asp Thr
        35                  40                  45

Ser Asp Val Asp Asp Ile Val Trp Gly Thr Ser Ser Gln Val Ser Glu
    50                  55                  60

Gln Ser Gly Asp Leu Gly Arg Met Ala Ala Leu Asp Ala Gly Tyr Asp
65                  70                  75                  80

Val Lys Ala Ser Gly Val Thr Leu Asp Arg Phe Cys Gly Ser Gly Ile
                85                  90                  95

Thr Ser Thr Asn Ile Ala Ala Asn Ala Ile Met Ala Gly Met Glu Asp
            100                 105                 110

Leu Val Ile Ser Gly Gly Thr Glu Met Met Ser Leu Pro Lys Thr Gly
        115                 120                 125

Met Leu Pro Ile Gly Ala Asn Asn Ala His Leu Gln Glu Leu His Pro
    130                 135                 140

Gln Pro His Gln Gly Val Cys Ala Asp Ala Ile Ala Thr Leu Asp Gly
145                 150                 155                 160

Ile Gly Arg Asp Ala Leu Asp Ala His Ala Ala Thr Ser Gln Ala Arg
                165                 170                 175

Ala Gly Gln Ala Ile Ala Glu Gly Arg Phe Asp Arg Ser Leu Val Pro
            180                 185                 190

Val Tyr Asn Leu Gly Gly Ser Leu Ala Leu Asp His Glu Glu Phe Pro
        195                 200                 205

Arg Pro Gly Thr Thr Ala Glu Ser Leu Ala Lys Leu Arg Pro Ser Phe
    210                 215                 220

Glu Val Val Ala Asp Tyr Arg His Thr Glu Asp Ser Lys Thr Tyr Arg
225                 230                 235                 240

Glu Leu Val Ala Gln Lys Phe Pro Asp Leu Thr Ile Glu His Val His
                245                 250                 255

His Ala Gly Asn Ser Ser Gly Val Val Asp Gly Ala Ala Ala Ile Leu
            260                 265                 270

Leu Ala Ser Glu Ala Tyr Ala Thr Ala His Thr Leu Lys Pro Arg Ala
        275                 280                 285

Arg Val Val Ala Thr Ala Asn Met Gly Asp Asp Pro Thr Leu Met Leu
    290                 295                 300
```

```
Asn Ala Pro Val Pro Ala Ala Arg Lys Val Leu Ala Arg Ala Gly Met
305                 310                 315                 320

Thr Leu Asp Asp Ile Asp Leu Phe Glu Ile Asn Glu Ala Phe Ala Val
                325                 330                 335

Val Ser Glu Lys Phe Gln Arg Asp Leu Asn Leu Asp Arg Asp Lys Val
            340                 345                 350

Asn Val Asn Gly Gly Ala Met Ala Leu Gly His Pro Ile Gly Ala Thr
        355                 360                 365

Gly Ser Ile Leu Ile Gly Thr Val Leu Asp Glu Leu Glu Arg Arg Asp
    370                 375                 380

Leu Gln Thr Gly Leu Val Thr Met Cys Ala Gly Gly Gly Met Ala Pro
385                 390                 395                 400

Ala Ile Ile Ile Glu Arg Val
                405
```

<210> SEQ ID NO 109
<211> LENGTH: 1209
<212> TYPE: DNA
<213> ORGANISM: Candidatus Microthrix parvicella

<400> SEQUENCE: 109

```
atgccgaacg ccgtgatcgt cgatgttgtc cgcaccgcag gggggaggcg caacggcgtc     60

ctttcgggat ggcatccagt ggacctggcg gccgaggtgc tgatggcgct ccagaagcgc    120

aacaacctgg acccgtcgct ggtggacgac gtgatcatgg ggtgcgtcat gcaggtgggc    180

gcgcaggggc tcaacatcgg ccgtaacgct gtgctggcgg ccggctggcc ggactccgtg    240

cccgccacca ccatcgaccg tcagtgcggt tcctcccagc aggcctatac cttcgcagcc    300

caggggggtta tggccggcgc ctacgacgtg gtcgtcgctg cgggggttga ggagatgagc    360

ctggtgccga tgggtgcctc ggtttccaag ggtgtcgggt ttcccttcac cgagggcatg    420

aacgaccgct acatcgacca gggtggcctg gtgccccaag gcatctccgc tgaaatgatc    480

gccgatcagt ggggcctcag ccgagaggac ctggacgcct tcggtgctcg gtcccagcag    540

ttcgccgaac gggctcgcga cgagggccgc ttcgacaacg agatcattcc ggttcagggt    600

cgccgccgcg acaaggagac cggcgaggtc accatcgagg atgcgccggt cacccaggac    660

gaggggatcc gccccgggac cactgccgag ggtctcgcca agttgaagcc cgccttcaag    720

cccgacgtcg gcaaggtgac agcggccaac agctcacaga tcaccgacgg tgcctccgct    780

gcactgatca tgtccgagga aaaggcggcc gagttgggcc tcaccccccg tgctcgcttc    840

catgcgttct cgctggccgg tgtgaacccg gtgaccatgc tgaccggccc gatcccctcc    900

acccagaagg tgctggctcg tgccgggatg agcgtggacg acatcgacct gttcgaggtg    960

aacgaggcgt tcgcctcggt tgtgttggca tggaaggcgg acatgggcct ggatgacgac   1020

accttcgacg ccaaggtcaa cgtcaacggc ggcgccattg ccctgggtca cccgctgggc   1080

gcctccggca ccaaactgct ggccaccctg ctgaacgagt tggagcgcac cggcggccgc   1140

tacgggctgc agaccatgtg cgagggcggc ggcttggcga acgccgccat catcgaacgt   1200

ctgggctga                                                            1209
```

<210> SEQ ID NO 110
<211> LENGTH: 402
<212> TYPE: PRT
<213> ORGANISM: Candidatus Microthrix parvicella

<400> SEQUENCE: 110

```
Met Pro Asn Ala Val Ile Val Asp Val Val Arg Thr Ala Gly Gly Arg
1               5                   10                  15

Arg Asn Gly Val Leu Ser Gly Trp His Pro Val Asp Leu Ala Ala Glu
            20                  25                  30

Val Leu Met Ala Leu Gln Lys Arg Asn Asn Leu Asp Pro Ser Leu Val
        35                  40                  45

Asp Asp Val Ile Met Gly Cys Val Met Gln Val Gly Ala Gln Gly Leu
    50                  55                  60

Asn Ile Gly Arg Asn Ala Val Leu Ala Ala Gly Trp Pro Asp Ser Val
65                  70                  75                  80

Pro Ala Thr Thr Ile Asp Arg Gln Cys Gly Ser Ser Gln Gln Ala Tyr
                85                  90                  95

Thr Phe Ala Ala Gln Gly Val Met Ala Gly Ala Tyr Asp Val Val Val
            100                 105                 110

Ala Ala Gly Val Glu Glu Met Ser Leu Val Pro Met Gly Ala Ser Val
        115                 120                 125

Ser Lys Gly Val Gly Phe Pro Phe Thr Glu Gly Met Asn Asp Arg Tyr
    130                 135                 140

Ile Asp Gln Gly Gly Leu Val Pro Gln Gly Ile Ser Ala Glu Met Ile
145                 150                 155                 160

Ala Asp Gln Trp Gly Leu Ser Arg Glu Asp Leu Asp Ala Phe Gly Ala
                165                 170                 175

Arg Ser Gln Gln Phe Ala Glu Arg Ala Arg Asp Glu Gly Arg Phe Asp
            180                 185                 190

Asn Glu Ile Ile Pro Val Gln Gly Arg Arg Arg Asp Lys Glu Thr Gly
        195                 200                 205

Glu Val Thr Ile Glu Asp Ala Pro Val Thr Gln Asp Glu Gly Ile Arg
    210                 215                 220

Pro Gly Thr Thr Ala Glu Gly Leu Ala Lys Leu Lys Pro Ala Phe Lys
225                 230                 235                 240

Pro Asp Val Gly Lys Val Thr Ala Ala Asn Ser Ser Gln Ile Thr Asp
                245                 250                 255

Gly Ala Ser Ala Ala Leu Ile Met Ser Glu Glu Lys Ala Ala Glu Leu
            260                 265                 270

Gly Leu Thr Pro Arg Ala Arg Phe His Ala Phe Ser Leu Ala Gly Val
        275                 280                 285

Asn Pro Val Thr Met Leu Thr Gly Pro Ile Pro Ser Thr Gln Lys Val
    290                 295                 300

Leu Ala Arg Ala Gly Met Ser Val Asp Asp Ile Asp Leu Phe Glu Val
305                 310                 315                 320

Asn Glu Ala Phe Ala Ser Val Val Leu Ala Trp Lys Ala Asp Met Gly
                325                 330                 335

Leu Asp Asp Asp Thr Phe Asp Ala Lys Val Asn Val Asn Gly Gly Ala
            340                 345                 350

Ile Ala Leu Gly His Pro Leu Gly Ala Ser Gly Thr Lys Leu Leu Ala
        355                 360                 365

Thr Leu Leu Asn Glu Leu Glu Arg Thr Gly Gly Arg Tyr Gly Leu Gln
    370                 375                 380

Thr Met Cys Glu Gly Gly Gly Leu Ala Asn Ala Ala Ile Ile Glu Arg
385                 390                 395                 400

Leu Gly
```

<210> SEQ ID NO 111
<211> LENGTH: 819
<212> TYPE: DNA
<213> ORGANISM: Candidatus Microthrix parvicella

<400> SEQUENCE: 111
atgggggagg gtggccgcat ggattttgcc cagatgatgg ccttggaggc acacgggccc 60
gacgtgtacg tcggcgcagg cccgcgatat ccgtggggcg gattgtacgg tggccagatc 120
gtcgcccagg ggttgcgttc ggcccagttg accgtcgacg aggccttcac gctgcactcg 180
atccacgcct atttcattcg catgggcgac cacaccgaac ccgttcgatt cgaggtggat 240
cgcattcgca acggccgatc gttctgcacg cggcgggtgg tggcccgcca ggccaccggg 300
gcgatcctca acctggcgtg ttcgtttcag cgacccgaac caggggagac gattcagagc 360
gtcaccatgc ccgacgtgcc cggccccgac gcctttgagg gcgactcgtg gtcgtccatg 420
ttcgagcggc gaaccgtggg gcccgacgca gcgtccgggc aaccgggggc gtgggccggg 480
ttgtggatgc gcacgccagg cgcggtcggg cctgaacttg cccatgcggc tttggcctac 540
ctgtctgatg acgtgcccac cgatgcggtg cttccacagc acccggaggc gctcccgacc 600
ggtgagaatc atgatcggtt catggtggcc agcctggatc atgccatctg gtttcaccgt 660
gggttcgacc cggccgagtg gcacctcttc gatgccacgt cccaggggtt cggcaacgga 720
aggggtctct cggtcggaca cgtgttctcg gccgacggtg tgcacgtggc cacggtgacc 780
caggaggtgc tgatccgtcg ggcccgcccc gccggatga 819

<210> SEQ ID NO 112
<211> LENGTH: 272
<212> TYPE: PRT
<213> ORGANISM: Candidatus Microthrix parvicella

<400> SEQUENCE: 112

Met Gly Glu Gly Gly Arg Met Asp Phe Ala Gln Met Met Ala Leu Glu
1 5 10 15

Ala His Gly Pro Asp Val Tyr Val Gly Ala Gly Pro Arg Tyr Pro Trp
20 25 30

Gly Gly Leu Tyr Gly Gly Gln Ile Val Ala Gln Gly Leu Arg Ser Ala
35 40 45

Gln Leu Thr Val Asp Glu Ala Phe Thr Leu His Ser Ile His Ala Tyr
50 55 60

Phe Ile Arg Met Gly Asp His Thr Glu Pro Val Arg Phe Glu Val Asp
65 70 75 80

Arg Ile Arg Asn Gly Arg Ser Phe Cys Thr Arg Arg Val Val Ala Arg
85 90 95

Gln Ala Thr Gly Ala Ile Leu Asn Leu Ala Cys Ser Phe Gln Arg Pro
100 105 110

Glu Pro Gly Glu Thr Ile Gln Ser Val Thr Met Pro Asp Val Pro Gly
115 120 125

Pro Asp Ala Phe Glu Gly Asp Ser Trp Ser Ser Met Phe Glu Arg Arg
130 135 140

Thr Val Gly Pro Asp Ala Ala Ser Gly Gln Pro Gly Ala Trp Ala Gly
145 150 155 160

Leu Trp Met Arg Thr Pro Gly Ala Val Gly Pro Glu Leu Ala His Ala
165 170 175

Ala Leu Ala Tyr Leu Ser Asp Asp Val Pro Thr Asp Ala Val Leu Pro
180 185 190

```
Gln His Pro Glu Ala Leu Pro Thr Gly Glu Asn His Asp Arg Phe Met
        195                 200                 205

Val Ala Ser Leu Asp His Ala Ile Trp Phe His Arg Gly Phe Asp Pro
    210                 215                 220

Ala Glu Trp His Leu Phe Asp Ala Thr Ser Gln Gly Phe Gly Asn Gly
225                 230                 235                 240

Arg Gly Leu Ser Val Gly His Val Phe Ser Ala Asp Gly Val His Val
                245                 250                 255

Ala Thr Val Thr Gln Glu Val Leu Ile Arg Arg Ala Arg Pro Ala Gly
            260                 265                 270


<210> SEQ ID NO 113
<211> LENGTH: 816
<212> TYPE: DNA
<213> ORGANISM: Candidatus Microthrix parvicella

<400> SEQUENCE: 113

atgggctcag gcatcgccga ggtggcgagc cgggcgggct acgaggtgat cctgcgctca      60

cgcaagcagg aatcggcgga tgccacgctg gccaagatgg actccaatct gaagcgtgcg     120

gtcgacaagg gtcggctttc cgaggaggac cacgccgcca tcctgggtcg ggtcaccgcc     180

acggccgacc tgtcggccgt cgccgactgc gacctggtga tcgaatcggt cgtcgaggat     240

ctcgccacca agtccgccct gttcaccgaa ctcgatcagg tgtgcggacc cgacacgatc     300

ctggcaacca acacctcgac cctggcggtc accgagttgg cggttgccac cgggcgcccg     360

gacaaggtct gcggcattca ctttttcaac cccgcgacgg cgatgaagct ggtcgagatc     420

gtgacgccga tgacggcgag cgacgagacg atcgaggccg cggtcgcctt cgccaccaag     480

tgcggcaagg atccggtcaa ggtggccgac cgggccgggt tcatcgtcaa ccacctgctg     540

ttcccgtacc tcaacaacgc cgtacgcatg ctggagaacg gcaccgccag ccgcgagcac     600

atcgaccagg cgatgatggg cggttgcaac ttcccgatgg gcccccctggc gctgctcgat     660

ctggtgggcc tggacacgtc cgtcgccatt ctcgatgccc tgtatgacga gtttggcgac     720

caccattacc gggtggtgcc gctgctgcgt cgcatggtga ccgccggata cctgggtcga     780

aagtccggtc agggcttcta cgactacagc aggtag                               816


<210> SEQ ID NO 114
<211> LENGTH: 271
<212> TYPE: PRT
<213> ORGANISM: Candidatus Microthrix parvicella

<400> SEQUENCE: 114

Met Gly Ser Gly Ile Ala Glu Val Ala Ser Arg Ala Gly Tyr Glu Val
1               5                   10                  15

Ile Leu Arg Ser Arg Lys Gln Glu Ser Ala Asp Ala Thr Leu Ala Lys
            20                  25                  30

Met Asp Ser Asn Leu Lys Arg Ala Val Asp Lys Gly Arg Leu Ser Glu
        35                  40                  45

Glu Asp His Ala Ala Ile Leu Gly Arg Val Thr Ala Thr Ala Asp Leu
    50                  55                  60

Ser Ala Val Ala Asp Cys Asp Leu Val Ile Glu Ser Val Val Glu Asp
65                  70                  75                  80

Leu Ala Thr Lys Ser Ala Leu Phe Thr Glu Leu Asp Gln Val Cys Gly
                85                  90                  95

Pro Asp Thr Ile Leu Ala Thr Asn Thr Ser Thr Leu Ala Val Thr Glu
            100                 105                 110
```

-continued

```
Leu Ala Val Ala Thr Gly Arg Pro Asp Lys Val Cys Gly Ile His Phe
        115                 120                 125

Phe Asn Pro Ala Thr Ala Met Lys Leu Val Glu Ile Val Thr Pro Met
    130                 135                 140

Thr Ala Ser Asp Glu Thr Ile Glu Ala Ala Val Ala Phe Ala Thr Lys
145                 150                 155                 160

Cys Gly Lys Asp Pro Val Lys Val Ala Asp Arg Ala Gly Phe Ile Val
                165                 170                 175

Asn His Leu Leu Phe Pro Tyr Leu Asn Asn Ala Val Arg Met Leu Glu
            180                 185                 190

Asn Gly Thr Ala Ser Arg Glu His Ile Asp Gln Ala Met Met Gly Gly
        195                 200                 205

Cys Asn Phe Pro Met Gly Pro Leu Ala Leu Leu Asp Leu Val Gly Leu
    210                 215                 220

Asp Thr Ser Val Ala Ile Leu Asp Ala Leu Tyr Asp Glu Phe Gly Asp
225                 230                 235                 240

His His Tyr Arg Val Val Pro Leu Leu Arg Arg Met Val Thr Ala Gly
                245                 250                 255

Tyr Leu Gly Arg Lys Ser Gly Gln Gly Phe Tyr Asp Tyr Ser Arg
            260                 265                 270
```